(12) United States Patent
Kwong et al.

(10) Patent No.: US 9,537,106 B2
(45) Date of Patent: Jan. 3, 2017

(54) ORGANIC ELECTROLUMINESCENT MATERIALS AND DEVICES

(71) Applicant: Universal Display Corporation, Ewing, NJ (US)

(72) Inventors: Raymond Kwong, Fo Tan (HK); Sui Tung Lam, Apleichau (HK); Chi Hang Lee, Chaiwan (HK)

(73) Assignee: Universal Display Corporation, Ewing, NJ (US)

( * ) Notice: Subject to any disclaimer, the term of this patent is extended or adjusted under 35 U.S.C. 154(b) by 543 days.

(21) Appl. No.: 13/890,437

(22) Filed: May 9, 2013

(65) Prior Publication Data

US 2014/0332758 A1    Nov. 13, 2014

(51) Int. Cl.
   *H01L 51/50*   (2006.01)
   *H01L 51/00*   (2006.01)
   (Continued)

(52) U.S. Cl.
   CPC ......... *H01L 51/0061* (2013.01); *C07D 471/14* (2013.01); *C09K 11/06* (2013.01);
   (Continued)

(58) Field of Classification Search
   None
   See application file for complete search history.

(56) References Cited

U.S. PATENT DOCUMENTS 4,769,292 A    9/1988    Tang et al.
5,061,569 A    10/1991   VanSlyke et al.
(Continued)

FOREIGN PATENT DOCUMENTS

EP    0650955    5/1995
EP    1725079    11/2006
(Continued)

OTHER PUBLICATIONS

Ma et al., Highly-efficient solution-processed OLEDs based on new bipolar emitters, 2010, Chem. Commun., vol. 46, pp. 3923-3925.*
(Continued)

*Primary Examiner* — Gregory Clark
(74) *Attorney, Agent, or Firm* — Duane Morris LLP

(57) ABSTRACT

Donor-acceptor compounds with nitrogen containing polyaromatics as the acceptor with emission originated from the charge transfer (CT) state is disclosed. The donor-acceptor compound is provided that has the structure of Formula 1 shown below:

Formula 1

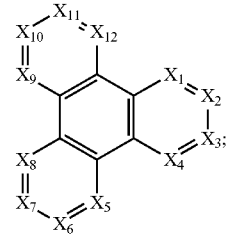

wherein $X_1$ to $X_{12}$ is independently selected from the group consisting of C—R and N, wherein at least one of $X_1$ to $X_{12}$ is N, wherein each R is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and com-
(Continued)

binations thereof; and at least one of the R comprises a donor group with at least two electron-donating nitrogens.

25 Claims, 3 Drawing Sheets

(51) Int. Cl.
  *C09K 11/06* (2006.01)
  *C07D 471/14* (2006.01)

(52) U.S. Cl.
  CPC ...... *H01L 51/0072* (2013.01); *H01L 51/5012* (2013.01); *H01L 51/5016* (2013.01)

(56) References Cited

U.S. PATENT DOCUMENTS

| | | | |
|---|---|---|---|
| 5,247,190 | A | 9/1993 | Friend et al. |
| 5,703,436 | A | 12/1997 | Forrest et al. |
| 5,707,745 | A | 1/1998 | Forrest et al. |
| 5,834,893 | A | 11/1998 | Bulovic et al. |
| 5,844,363 | A | 12/1998 | Gu et al. |
| 6,013,982 | A | 1/2000 | Thompson et al. |
| 6,087,196 | A | 7/2000 | Sturm et al. |
| 6,091,195 | A | 7/2000 | Forrest et al. |
| 6,097,147 | A | 8/2000 | Baldo et al. |
| 6,294,398 | B1 | 9/2001 | Kim et al. |
| 6,303,238 | B1 | 10/2001 | Thompson et al. |
| 6,337,102 | B1 | 1/2002 | Forrest et al. |
| 6,468,819 | B1 | 10/2002 | Kim et al. |
| 6,528,187 | B1 | 3/2003 | Okada |
| 6,687,266 | B1 | 2/2004 | Ma et al. |
| 6,835,469 | B2 | 12/2004 | Kwong et al. |
| 6,921,915 | B2 | 7/2005 | Takiguchi et al. |
| 7,087,321 | B2 | 8/2006 | Kwong et al. |
| 7,090,928 | B2 | 8/2006 | Thompson et al. |
| 7,154,114 | B2 | 12/2006 | Brooks et al. |
| 7,250,226 | B2 | 7/2007 | Tokito et al. |
| 7,279,704 | B2 | 10/2007 | Walters et al. |
| 7,332,232 | B2 | 2/2008 | Ma et al. |
| 7,338,722 | B2 | 3/2008 | Thompson et al. |
| 7,393,599 | B2 | 7/2008 | Thompson et al. |
| 7,396,598 | B2 | 7/2008 | Takeuchi et al. |
| 7,431,968 | B1 | 10/2008 | Shtein et al. |
| 7,445,855 | B2 | 11/2008 | Mackenzie et al. |
| 7,534,505 | B2 | 5/2009 | Lin et al. |
| 2002/0034656 | A1 | 3/2002 | Thompson et al. |
| 2002/0134984 | A1 | 9/2002 | Igarashi |
| 2002/0158242 | A1 | 10/2002 | Son et al. |
| 2003/0138657 | A1 | 7/2003 | Li et al. |
| 2003/0138662 | A1* | 7/2003 | Li et al. .......... 428/690 |
| 2003/0151042 | A1 | 8/2003 | Hueschen |
| 2003/0152802 | A1 | 8/2003 | Tsuboyama et al. |
| 2003/0170491 | A1* | 9/2003 | Liao et al. .......... 428/690 |
| 2003/0175553 | A1 | 9/2003 | Thompson et al. |
| 2003/0230980 | A1 | 12/2003 | Forrest et al. |
| 2004/0036077 | A1 | 2/2004 | Ise |
| 2004/0137267 | A1 | 7/2004 | Igarashi et al. |
| 2004/0137268 | A1 | 7/2004 | Igarashi et al. |
| 2004/0164292 | A1* | 8/2004 | Tung .......... G02F 1/133603 257/40 |
| 2004/0170863 | A1* | 9/2004 | Kim .......... C07C 13/72 428/690 |
| 2004/0174116 | A1 | 9/2004 | Lu et al. |
| 2005/0025993 | A1 | 2/2005 | Thompson et al. |
| 2005/0112407 | A1 | 5/2005 | Ogasawara et al. |
| 2005/0238919 | A1 | 10/2005 | Ogasawara |
| 2005/0244673 | A1 | 11/2005 | Satoh et al. |
| 2005/0260441 | A1 | 11/2005 | Thompson et al. |
| 2005/0260449 | A1 | 11/2005 | Walters et al. |
| 2006/0008670 | A1 | 1/2006 | Lin et al. |
| 2006/0202194 | A1 | 9/2006 | Jeong et al. |
| 2006/0240279 | A1 | 10/2006 | Adamovich et al. |
| 2006/0251923 | A1 | 11/2006 | Lin et al. |
| 2006/0263635 | A1 | 11/2006 | Ise |
| 2006/0280965 | A1 | 12/2006 | Kwong et al. |
| 2007/0190359 | A1 | 8/2007 | Knowles et al. |
| 2007/0278938 | A1 | 12/2007 | Yabunouchi et al. |
| 2008/0015355 | A1 | 1/2008 | Schafer et al. |
| 2008/0018221 | A1 | 1/2008 | Egen et al. |
| 2008/0106190 | A1 | 5/2008 | Yabunouchi et al. |
| 2008/0124572 | A1 | 5/2008 | Mizuki et al. |
| 2008/0220265 | A1 | 9/2008 | Xia et al. |
| 2008/0297033 | A1 | 12/2008 | Knowles et al. |
| 2009/0008605 | A1 | 1/2009 | Kawamura et al. |
| 2009/0009065 | A1 | 1/2009 | Nishimura et al. |
| 2009/0017330 | A1 | 1/2009 | Iwakuma et al. |
| 2009/0030202 | A1 | 1/2009 | Iwakuma et al. |
| 2009/0039776 | A1 | 2/2009 | Yamada et al. |
| 2009/0045730 | A1 | 2/2009 | Nishimura et al. |
| 2009/0045731 | A1 | 2/2009 | Nishimura et al. |
| 2009/0101870 | A1 | 4/2009 | Prakash et al. |
| 2009/0108737 | A1 | 4/2009 | Kwong et al. |
| 2009/0115316 | A1 | 5/2009 | Zheng et al. |
| 2009/0165846 | A1 | 7/2009 | Johannes et al. |
| 2009/0167162 | A1 | 7/2009 | Lin et al. |
| 2009/0179554 | A1 | 7/2009 | Kuma et al. |
| 2013/0134395 | A1* | 5/2013 | Kitano .......... H01L 51/0032 257/40 |

FOREIGN PATENT DOCUMENTS

| | | |
|---|---|---|
| EP | 2034538 | 3/2009 |
| JP | 200511610 | 1/2005 |
| JP | 2007123392 | 5/2007 |
| JP | 2007254297 | 10/2007 |
| JP | 2008074939 | 4/2008 |
| WO | 0139234 | 5/2001 |
| WO | 0202714 | 1/2002 |
| WO | 0215645 | 2/2002 |
| WO | 03040257 | 5/2003 |
| WO | 03060956 | 7/2003 |
| WO | 2004093207 | 10/2004 |
| WO | 2004107822 | 12/2004 |
| WO | 2005014551 | 2/2005 |
| WO | 2005019373 | 3/2005 |
| WO | 2005030900 | 4/2005 |
| WO | 2005089025 | 9/2005 |
| WO | 2005123873 | 12/2005 |
| WO | 2006009024 | 1/2006 |
| WO | 2006056418 | 6/2006 |
| WO | 2006072002 | 7/2006 |
| WO | 2006082742 | 8/2006 |
| WO | 2006098120 | 9/2006 |
| WO | 2006100298 | 9/2006 |
| WO | 2006103874 | 10/2006 |
| WO | 2006114966 | 11/2006 |
| WO | 2006132173 | 12/2006 |
| WO | 2007002683 | 1/2007 |
| WO | 2007004380 | 1/2007 |
| WO | 2007063754 | 6/2007 |
| WO | 2007063796 | 6/2007 |
| WO | 2008056746 | 5/2008 |
| WO | 2008101842 | 8/2008 |
| WO | 2008132085 | 11/2008 |
| WO | 2009000673 | 12/2008 |
| WO | 2009003898 | 1/2009 |
| WO | 2009008311 | 1/2009 |
| WO | 2009018009 | 2/2009 |
| WO | 2009050290 | 4/2009 |
| WO | 2009021126 | 5/2009 |
| WO | 2009062578 | 5/2009 |
| WO | 2009063833 | 5/2009 |
| WO | 2009066778 | 5/2009 |
| WO | 2009066779 | 5/2009 |
| WO | 2009086028 | 7/2009 |
| WO | 2009100991 | 8/2009 |

OTHER PUBLICATIONS

Uoyama, Hiroki et al., Highly efficient organic light-emitting diodes from delayed fluorescence, Nature, vol. 492, Dec. 13, 2012, p. 234-240, 2012 Macmillan Publishers Limited.

(56) References Cited

OTHER PUBLICATIONS

Zhang, Qisheng et al., Design of Efficient Thermally Activated Delayed Fluorescence Materials for Pure Blue Organic Light Emitting Diodes, Journal of the American Chemical Society, 2012, 134, pp. 14706-14709.
Tanaka, Hiroyuki et al., Efficient green thermally activated delayed fluorescense (TADF) from a phenoxazine-triphenyltriazine (PXZ-TRZ) derivative, Chemical Communications, 2012, 49, pp. 11392-11394.
Nakagawa, Tetsuya et al., Electroluminescence based on thermally activated delayed fluorescence generated by spirobifluorene donor-acceptor structure, Chemical Communications, 2012, 48, pp. 9580-9582.
Méhes, Gábor et al., Enhanced Electroluminescence Efficiency in a Spiro-Acidine Derivative through Thermally Activated Delayed Fluorescence, Angew. Chem. Int. Ed., 2012, 51, pp. 11311-11315.
Campos, Pedro J., et al. A Simple Synthesis of Aminoazapolycyclic Compounds via a Photochemically Induced Cyclization Reaction of 3-Amino-2-alkene Imines in an Acid Medium, Tetrahedron, 54, (1998), pp. 14113-14122.
Luo, Jiann-Kuan, et al., The Synthesis of Novel Polycyclic Heterocyclic Ring Systems via Photocyclization. 22 [1,2]. Dibenzo[f,h]benzothieno[2,3-c]quinoline, Dibenzo[f,h]benzothieno[2,3-c][1,2,4]triazolo[4,3-a]quinoline and Dibenzo[f, h]naphtho[2',1':4,5]thieno[2,3-c]quinoline, J. Heterocyclic Chem., 37, (2000), pp. 997-1001.
Adachi, Chihaya et al., "Organic Electroluminescent Device Having a Hole Conductor as an Emitting Layer," Appl. Phys. Lett., 55(15): 1489-1491 (1989).
Adachi, Chihaya et al., "Nearly 100% Internal Phosphorescence Efficiency in an Organic Light Emitting Device," J. Appl. Phys., 90(10): 5048-5051 (2001).
Adachi, Chihaya et al., "High-Efficiency Red Electrophosphorescence Devices," Appl. Phys. Lett., 78(11)1622-1624 (2001).
Aonuma, Masaki et al., "Material Design of Hole Transport Materials Capable of Thick-Film Formation in Organic Light Emitting Diodes," Appl. Phys. Lett., 90:183503-1-183503-3, 2007.
Baldo et al., Highly Efficient Phosphorescent Emission from Organic Electroluminescent Devices, Nature, vol. 395, 151-154, (1998).
Baldo et al., Very high-efficiency green organic light-emitting devices based on electrophosphorescence, Appl. Phys. Lett, vol. 75, No. 3, 4-6 (1999).
Gao, Zhiqiang et al., "Bright-Blue Electroluminescence From a Silyl-Substituted ter-(phenylene-vinylene) derivative," Appl. Phys. Lett., 74(6): 865-867 (1999).
Guo, Tzung-Fang et al., "Highly Efficient Electrophosphorescent Polymer Light-Emitting Devices," Organic Electronics, 115-20 (2000).
Hamada, Yuji et al., "High Luminance in Organic Electroluminescent Devices with Bis(10-hydroxybenzo[h]quinolinato) beryllium as an Emitter," Chem. Lett., 905-906 (1993).
Holmes, R.J. et al., "Blue Organic Electrophosphorescence Using Exothermic Host-Guest Energy Transfer," Appl. Phys. Lett., 82(15):2422-2424 (2003).
Hu, Nan-Xing et al., "Novel High Tg Hole-Transport Molecules Based on Indolo[3,2-b]carbazoles for Organic Light Emitting Devices," Synthetic Metals, 111-112:421-424 (2000).
Huang, Jinsong et al., "Highly Efficient Red-Emission Polymer Phosphorescent Light-Emitting Diodes Based on Two Novel Tris(1-phenylisoquinolinato-C2,N)iridium(III) Derivates," Adv. Mater, 19:739-743 (2007).
Huang, Wei-Sheng et al., "Highly Phosphorescent Bis-Cyclometalated Iridium Complexes Containing BenzoimidazoleBased Ligands," Chem. Mater, 16(12):2480-2488 (2004).
Hung, L.S. et al., "Anode Modification in Organic Light-Emitting Diodes by Low-Frequency Plasma Polymerization of CHF3," Appl. Phys. Lett, 78(5):673-675 (2001).

Ikai, Masamichi and Tokito, Shizuo, "Highly Efficient Phosphorescence From Organic Light-Emitting Devices with an Exciton-Block Layer," Appl. Phys. Lett., 79(2):156-158 (2001).
Ikeda, Hisao et al., "P-185 Low-Drive-Voltage OLEDs with a Buffer Layer Having Molybdenum Oxide," SID Symposium Digest, 37:923-926 (2006).
Inada, Hiroshi and Shirota, Yasuhiko, "1,3,5-Tris[4-(diphenylamino)phenyl]benzene and its Methylsubstituted Derivatives as a Novel Class of Amorphous Molecular Materials," J. Mater. Chem., 3(3):319-320 (1993).
Kanno, Hiroshi et al., "Highly Efficient and Stable Red Phosphorescent Organic Light-Emitting Device Using bis[2-(2-benzothiazoyl)phenolato]zinc(II) as host material," Appl. Phys. Lett., 90:123509-1-123509-3 (2007).
Kido, Junji et al., 1,2,4-Triazole Derivative as an Electron Transport Layer in Organic Electroluminescent Devices, Jpn. J. Appl. Phys., 32:L917-L920 (1993).
Kuwabara, Yoshiyuki et al., "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenyl-amino) triphenylamine (m-MTDATA), as Hole-Transport Materials," Adv. Mater., 6(9):677-679 (1994).
Kwong, Raymond C. et al., "High Operational Stability of Electrophosphorescent Devices," Appl. Phys. Lett., 81(1)162-164 (2002).
Lamansky, Sergey et al., "Synthesis and Characterization of Phosphorescent Cyclometalated Iridium Complexes," Inorg. Chem., 40(7):1704-1711 (2001).
Lee, Chang-Lyoul et al., "Polymer Phosphorescent Light-Emitting Devices Doped with Tris(2-phenylpyridine) Iridium as a Triplet Emitter," Appl. Phys. Lett., 77(15):2280-2282 (2000).
Lo, Shih-Chun et al., "Blue Phosphorescence from Iridium(III) Complexes at Room Temperature," Chem. Mater., 18(21)5119-5129 (2006).
Ma, Yuguang et al., "Triplet Luminescent Dinuclear-Gold(I) Complex-Based Light-Emitting Diodes with Low Turn-On voltage," Appl. Phys. Lett., 74(10):1361-1363 (1999).
Mi, Bao-Xiu et al., "Thermally Stable Hole-Transporting Material for Organic Light-Emitting Diode an Isoindole Derivative," Chem. Mater., 15(16):3148-3151 (2003).
Nishida, Jun-ichi et al., "Preparation, Characterization, and Electroluminescence Characteristics of α-Diimine-type Platinum(II) Complexes with Perfluorinated Phenyl Groups as Ligands," Chem. Lett., 34(4): 592-593 (2005).
Niu, Yu-Hua et al., "Highly Efficient Electrophosphorescent Devices with Saturated Red Emission from a Neutral Osmium Complex," Chem. Mater., 17(13):3532-3536 (2005).
Noda, Tetsuya and Shirota,Yasuhiko, "5,5'-Bis(dimesitylboryl)-2,2'-bithiophene and 5,5"-Bis(dimesitylboryl)-2,2'5',2"-terthiophene as a Novel Family of Electron-Transporting Amorphous Molecular Materials," J. Am. Chem. Soc., 120 (37):9714-9715 (1998).
Okumoto, Kenji et al., "Green Fluorescent Organic Light-Emitting Device with External Quantum Efficiency of Nearly 10%," Appl. Phys. Lett., 89:063504-1-063504-3 (2006).
Palilis, Leonidas C., "High Efficiency Molecular Organic Light-Emitting Diodes Based on Silole Derivatives and Their Exciplexes," Organic Electronics, 4:113-121 (2003).
Paulose, Betty Marie Jennifer S. et al., "First Examples of Alkenyl Pyridines as Organic Ligands for Phosphorescent Iridium Complexes," Adv. Mater., 16(22):2003-2007 (2004).
Ranjan, Sudhir et al., "Realizing Green Phosphorescent Light-Emitting Materials from Rhenium(I) Pyrazolato Diimine Complexes," Inorg. Chem., 42(4):1248-1255 (2003).
Sakamoto, Youichi et al., "Synthesis, Characterization, and Electron-Transport Property of Perfluorinated Phenylene Dendrimers," J. Am. Chem. Soc., 122(8):1832-1833 (2000).
Salbeck, J. et al., "Low Molecular Organic Glasses for Blue Electroluminescence," Synthetic Metals, 91209-215 (1997).
Shirota, Yasuhiko et al., "Starburst Molecules Based on p-Electron Systems as Materials for Organic Electroluminescent Devices," Journal of Luminescence, 72-74:985-991 (1997).

(56) References Cited

OTHER PUBLICATIONS

Sotoyama, Wataru et al., "Efficient Organic Light-Emitting Diodes with Phosphorescent Platinum Complexes Containing N^C^N-Co-ordinating Tridentate Ligand," Appl. Phys. Lett., 86:153505-1-153505-3 (2005).
Sun, Yiru and Forrest, Stephen R., "High-Efficiency White Organic Light Emitting Devices with Three Separate Phosphorescent Emission Layers," Appl. Phys. Lett., 91:263503-1-263503-3 (2007).
T. Östergård et al., "Langmuir-Blodgett Light-Emitting Diodes of Poly(3-Hexylthiophene) Electro-Optical Characteristics Related to Structure," Synthetic Metals, 87:171-177 (1997).
Takizawa, Shin-ya et al., "Phosphorescent Iridium Complexes Based on 2-Phenylimidazo[1,2-α]pyridine Ligands Tuning of Emission Color toward the Blue Region and Application to Polymer Light-Emitting Devices," Inorg. Chem., 46(10):4308-4319 (2007).
Tang, C.W. and VanSlyke, S.A., "Organic Electroluminescent Diodes," Appl. Phys. Lett., 51(12):913-915 (1987).
Tung, Yung-Liang et al., "Organic Light-Emitting Diodes Based on Charge-Neutral Ru II PHosphorescent Emitters," Adv. Mater., 17(8)1059-1064 (2005).
Van Slyke, S. A. et al., "Organic Electroluminescent Devices with Improved Stability," Appl. Phys. Lett, 69(15):2160-2162 (1996).
Wang, Y. et al., "Highly Efficient Electroluminescent Materials Based on Fluorinated Organometallic Iridium Compounds," Appl. Phys. Lett., 79(4):449-451 (2001).
Wong, Keith Man-Chung et al., A Novel Class of Phosphorescent Gold(III) Alkynyl-Based Organic Light-Emitting Devices with Tunable Colour, Chem. Commun., 2906-2908 (2005).
Wong, Wai-Yeung, "Multifunctional Iridium Complexes Based on Carbazole Modules as Highly Efficient Electrophosphors," Angew. Chem. Int. Ed., 45:7800-7803 (2006).

* cited by examiner

… … …

ORGANIC ELECTROLUMINESCENT MATERIALS AND DEVICES

PARTIES TO A JOINT RESEARCH AGREEMENT

The claimed invention was made by, on behalf of, and/or in connection with one or more of the following parties to a joint university corporation research agreement: Regents of the University of Michigan, Princeton University, University of Southern California, and the Universal Display Corporation. The agreement was in effect on and before the date the claimed invention was made, and the claimed invention was made as a result of activities undertaken within the scope of the agreement.

FIELD OF THE INVENTION

The present invention relates to organic light emitting devices. More specifically, the present disclosure pertains to luminescent materials comprising donor-acceptor compounds with nitrogen containing polyaromatics as the electron acceptor for use as emitters in organic light emitting diodes.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

One application for phosphorescent emissive molecules is a full color display. Industry standards for such a display call for pixels adapted to emit particular colors, referred to as "saturated" colors. In particular, these standards call for saturated red, green, and blue pixels. Color may be measured using CIE coordinates, which are well known to the art.

One example of a green emissive molecule is tris(2-phenylpyridine) iridium, denoted Ir(ppy)$_3$, which has the following structure:

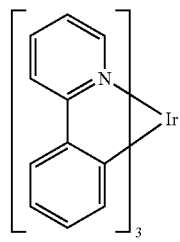

In this, and later figures herein, we depict the dative bond from nitrogen to metal (here, Ir) as a straight line.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher"

HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

As used herein, the phrase "electron acceptor" means a fragment that can accept electron density from an aromatic system, and the phrase "electron donor" means a fragment that donates electron density into an aromatic system.

More details on OLEDs, and the definitions described above, can be found in U.S. Pat. No. 7,279,704, which is incorporated herein by reference in its entirety.

SUMMARY OF THE INVENTION

Donor-acceptor compounds with nitrogen containing polyaromatics as the acceptor may be efficient emitters with emission originated from the charge transfer (CT) state. The emission can be tuned by varying the strength of the donor-acceptor interaction and the resulting energy of the CT state. The compounds may be used as emitters in OLED. According to an embodiment, a compound is provided that has the structure of Formula 1 shown below:

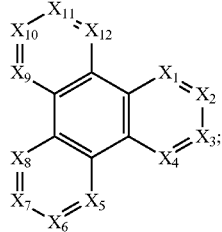

Formula 1 wherein $X_1$ to $X_{12}$ is independently selected from the group consisting of C—R and N;
wherein at least one of $X_1$ to $X_{12}$ is N;
wherein each R is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and at least one of the R comprises a donor group with at least two electron-donating nitrogens.

According to another embodiment, a first device comprising a first organic light emitting device is also provided. The first device can include an anode, a cathode, and an organic emissive layer disposed between the anode and the cathode. The organic emissive layer can include a compound of Formula 1, wherein $X_1$ to $X_{12}$ is independently selected from the group consisting of C—R and N; at least one of $X_1$ to $X_{12}$ is N; each R is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and wherein at least one of the R comprises a donor group with at least one electron-donating nitrogen.

The first device can be a consumer product, an organic light-emitting device, and/or a lighting panel.

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), which are incorporated by reference in their entireties. Phosphorescence is described in more detail in U.S. Pat. No. 7,279,704 at cols. 5-6, which are incorporated by reference.

Figure 1:
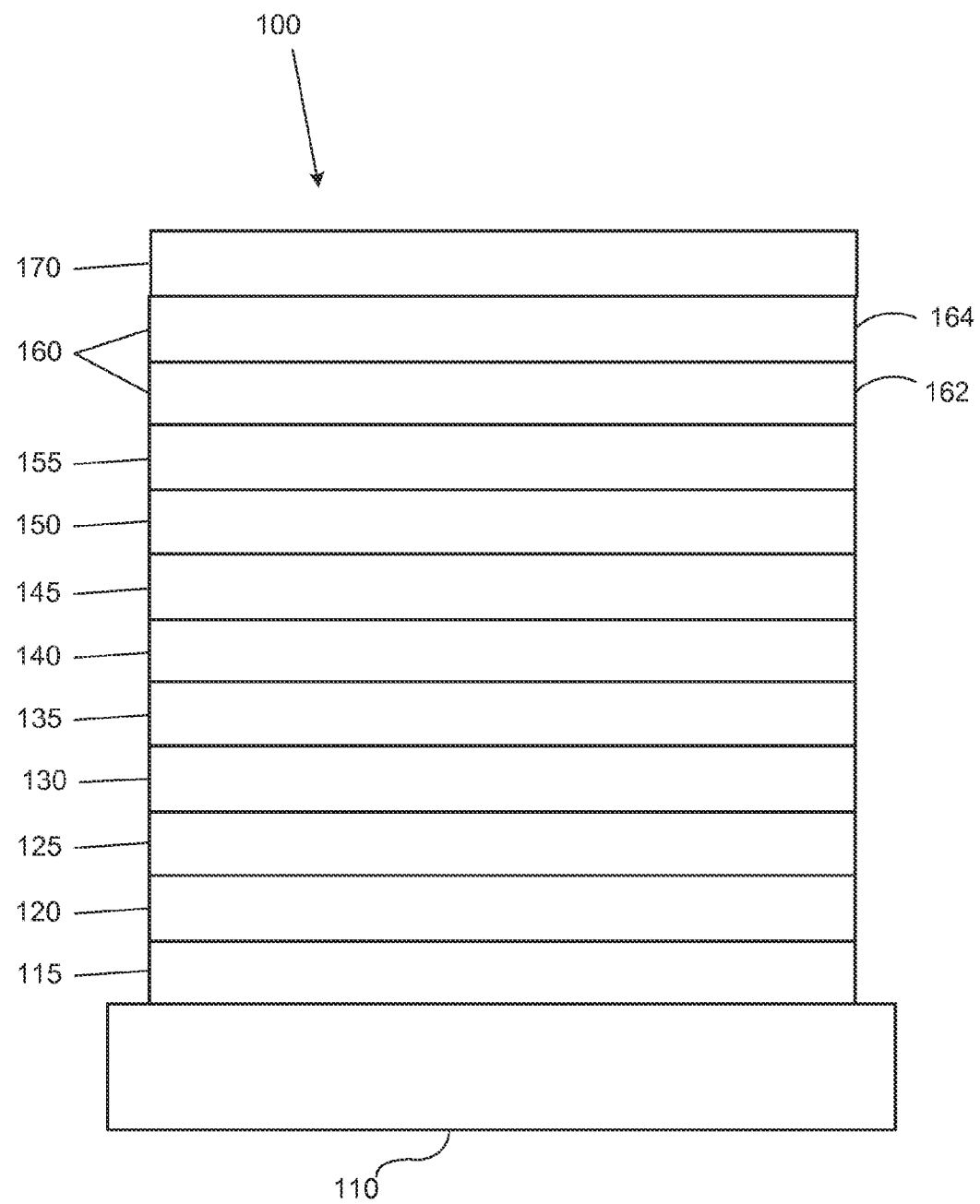
FIG. 1 shows an organic light emitting device.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, a cathode 160, and a barrier layer 170. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with $F_4$-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
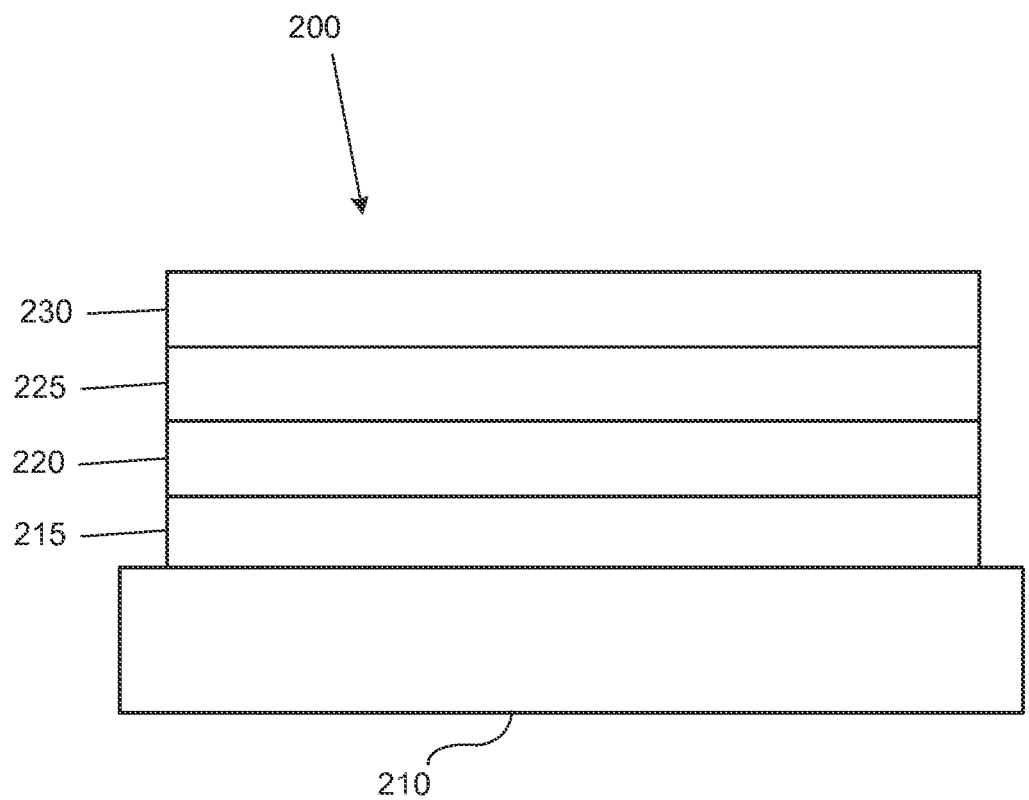
FIG. 2 shows an inverted organic light emitting device that does not have a separate electron transport layer.
Figure 3:
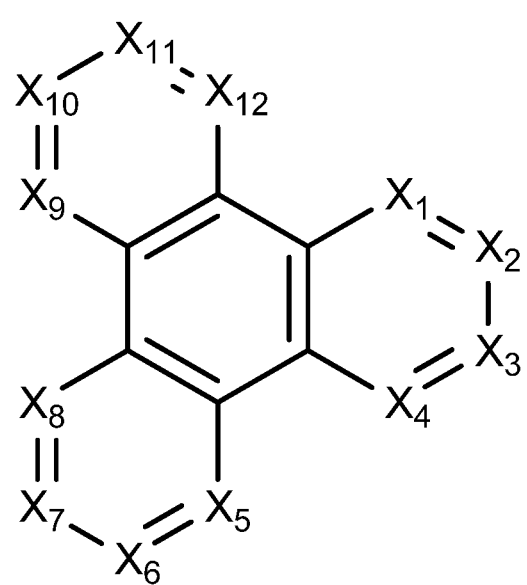
FIG. 3 shows Formula 1 as disclosed herein.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve out-coupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. Pat. No. 7,431,968, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processability than those having symmetric structures, because asymmetric materials may have a lower tendency to recrystallize. Dendrimer substituents may be used to enhance the ability of small molecules to undergo solution processing.

Devices fabricated in accordance with embodiments of the present invention may further optionally comprise a barrier layer. One purpose of the barrier layer is to protect the electrodes and organic layers from damaging exposure to harmful species in the environment including moisture, vapor and/or gases, etc. The barrier layer may be deposited over, under or next to a substrate, an electrode, or over any other parts of a device including an edge. The barrier layer may comprise a single layer, or multiple layers. The barrier layer may be formed by various known chemical vapor deposition techniques and may include compositions having a single phase as well as compositions having multiple phases. Any suitable material or combination of materials may be used for the barrier layer. The barrier layer may incorporate an inorganic or an organic compound or both. The preferred barrier layer comprises a mixture of a polymeric material and a non-polymeric material as described in U.S. Pat. No. 7,968,146, PCT Pat. Application Nos. PCT/US2007/023098 and PCT/US2009/042829, which are herein incorporated by reference in their entireties. To be considered a "mixture", the aforesaid polymeric and non-polymeric materials comprising the barrier layer should be deposited under the same reaction conditions and/or at the same time. The weight ratio of polymeric to non-polymeric material may be in the range of 95:5 to 5:95. The polymeric material and the non-polymeric material may be created from the same precursor material. In one example, the mixture of a polymeric material and a non-polymeric material consists essentially of polymeric silicon and inorganic silicon.

Devices fabricated in accordance with embodiments of the invention may be incorporated into a wide variety of consumer products, including flat panel displays, computer monitors, medical monitors, televisions, billboards, lights for interior or exterior illumination and/or signaling, heads up displays, fully transparent displays, flexible displays, laser printers, telephones, cell phones, personal digital assistants (PDAs), laptop computers, digital cameras, camcorders, viewfinders, micro-displays, 3-D displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.), but could be used outside this temperature range, for example, from −40 degree C. to +80 degree C.

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The terms halo, halogen, alkyl, cycloalkyl, alkenyl, alkynyl, aralkyl, heterocyclic group, aryl, aromatic group, and heteroaryl are known to the art, and are defined in U.S. Pat. No. 7,279,704 at cols. 31-32, which are incorporated herein by reference. As used herein, "substituted" indicates that a substituent other than H is bonded to the relevant carbon.

It is believed that the internal quantum efficiency (IQE) of fluorescent OLEDs can exceed the 25% spin statistics limit through delayed fluorescence. As used herein, there are two types of delayed fluorescence, i.e. P-type delayed fluorescence and E-type delayed fluorescence. P-type delayed fluorescence is generated from triplet-triplet annihilation (TTA).

On the other hand, E-type delayed fluorescence does not rely on the collision of two triplets, but rather on the thermal population between the triplet states and the singlet excited states. Compounds that are capable of generating E-type delayed fluorescence are required to have very small singlet-triplet gaps. Thermal energy can activate the transition from the triplet state back to the singlet state. This type of delayed fluorescence is also known as thermally activated delayed fluorescence (TADF). A distinctive feature of TADF is that the delayed component increases as temperature rises due to the increased thermal energy. If the reverse intersystem crossing rate is fast enough to minimize the non-radiative decay from the triplet state, the fraction of back populated singlet excited states can potentially reach 75%. The total singlet fraction can be 100%, far exceeding the spin statistics limit for electrically generated excitons.

It is believed that the internal quantum efficiency (IQE) of fluorescent OLEDs can exceed the 25% spin statistics limit through delayed fluorescence. As used herein, there are two types of delayed fluorescence, i.e. P-type delayed fluorescence and E-type delayed fluorescence. P-type delayed fluorescence is generated from triplet-triplet annihilation (TTA).

On the other hand, E-type delayed fluorescence does not rely on the collision of two triplets, but rather on the thermal population between the triplet states and the singlet excited states. Compounds that are capable of generating E-type delayed fluorescence are required to have very small singlet-triplet gaps. Thermal energy can activate the transition from the triplet state back to the singlet state. This type of delayed fluorescence is also known as thermally activated delayed fluorescence (TADF). A distinctive feature of TADF is that the delayed component increases as temperature rises due to the increased thermal energy. If the reverse intersystem crossing rate is fast enough to minimize the non-radiative decay from the triplet state, the fraction of back populated singlet excited states can potentially reach 75%. The total singlet fraction can be 100%, far exceeding the spin statistics limit for electrically generated excitons.

E-type delayed fluorescence characteristics can be found in an exciplex system or in a single compound. Without being bound by theory, it is believed that E-type delayed fluorescence requires the luminescent material to have a small singlet-triplet energy gap ($\Delta E_{S-T}$). Organic, non-metal containing, donor-acceptor luminescent materials may be able to achieve this. The emission in these materials is often characterized as a donor-acceptor charge-transfer (CT) type emission. The spatial separation of the HOMO and LUMO in these donor-acceptor type compounds often results in small $\Delta E_{S-T}$. These states may involve CT states. Often, donor-acceptor luminescent materials are constructed by connecting an electron donor moiety such as amino- or carbazole-derivatives and an electron acceptor moiety such as N-containing six-membered aromatic rings.

According to an embodiment, donor-acceptor compounds with unexpected CT emission properties are provided. The donor has two electron donating nitrogens. The acceptor moiety is based on electron deficient nitrogen containing triphenylene.

Donor-acceptor compounds with CT emissions may be useful in high efficiency delayed fluorescence OLED (Appl. Phys. Lett. 2012, 98, 083302; Nature Photonics, 2012, 6, 253; Nature 2012, 492, 234; Chem. Commun. 2012, 48, 11392; Angew. Chem. Int. Ed. 2012, 51, 11311; J. Am. Chem. Soc., 2012, 134, 14706; Chem. Commun. 2012, 48, 9580). The electron acceptors used are triazene or cyano groups. While these groups are strongly electron deficient, making the design of strong donor-acceptor strength easy, OLEDs incorporating them may not be very stable because of the lack of electron delocalization in these acceptors. In this invention, we use a high triplet energy polyaromatic system, namely, triphenylene with one or multiple nitrogens in the ring to render electron acceptor with high triplet energy. High triplet energy is important in order to obtain blue emission.

Triphenylene is a high triplet energy polyaromatic compound. Triphenylene with one or multiple nitrogens is electron deficient and can be used as an acceptor. We observed donor-acceptor emissions from a series of donor-acceptor compounds using azatriphenylene as the acceptor. The results are shown in Table 2 below.

According to a preferred embodiment, a donor-acceptor compounds having triphenylene with one or more nitrogens in the ring as an electron acceptor that are unexpectedly suited as delayed fluorescence emitters are disclosed. Such a compound has the structure according to Formula 1 shown below:

Formula 1

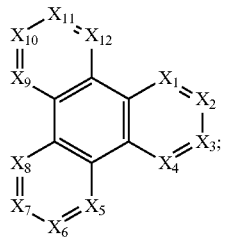

wherein $X_1$ to $X_{12}$ is independently selected from the group consisting of C—R and N;
wherein at least one of $X_1$ to $X_{12}$ is N;
wherein each R is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and
at least one of the R comprises a donor group with at least two electron-donating nitrogens.

In some embodiments, the donor-acceptor compound is selected from the group consisting of Formula 2

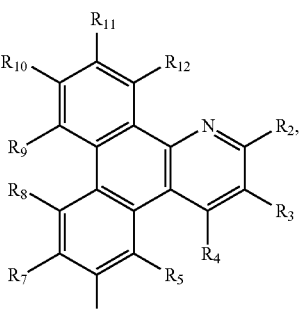

Formula 3

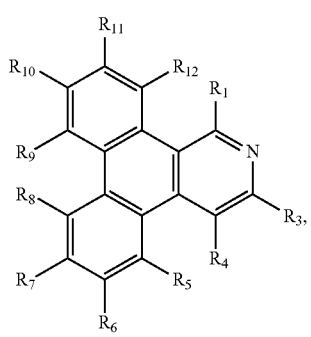

Formula 4

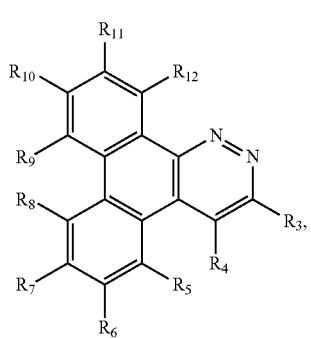

Formula 5

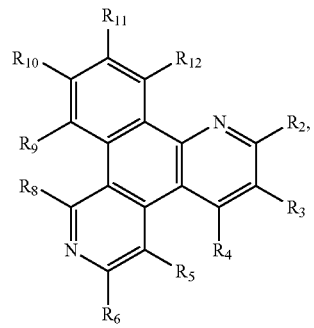

Formula 6

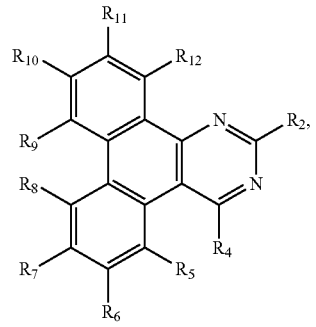

Formula 7

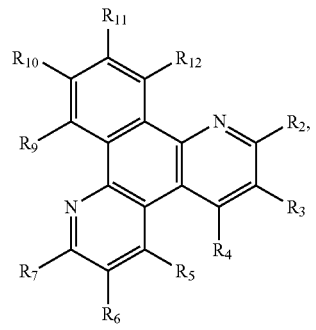

Formula 8

Formula 9

-continued
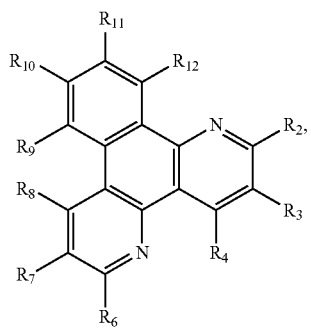
Formula 10
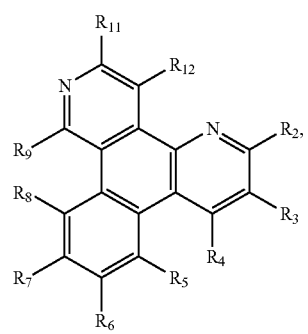
Formula 11
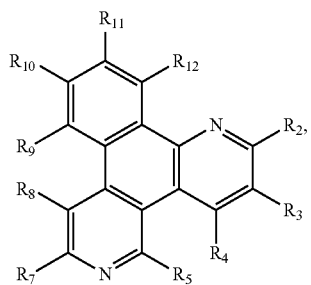
Formula 12
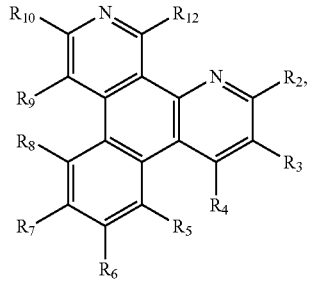
Formula 13
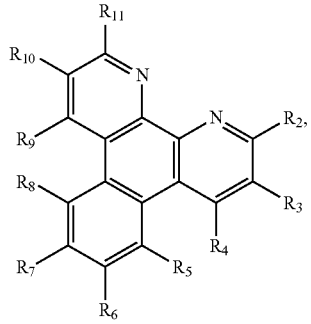
Formula 14
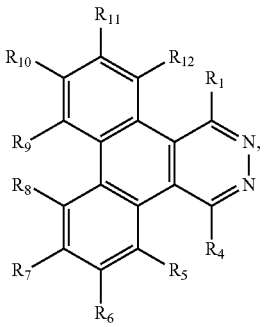
Formula 15
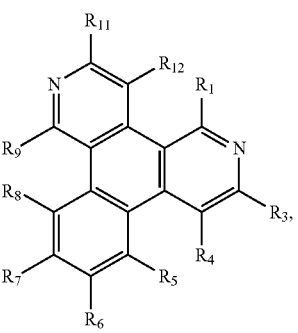
Formula 16
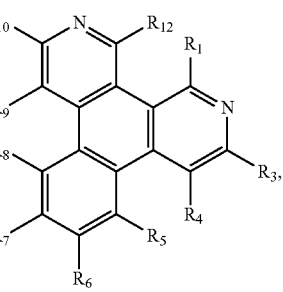
Formula 17
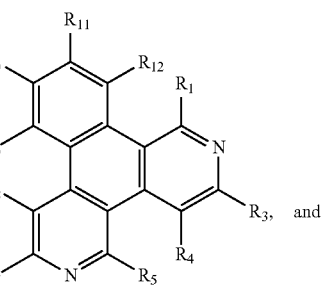
Formula 18
and
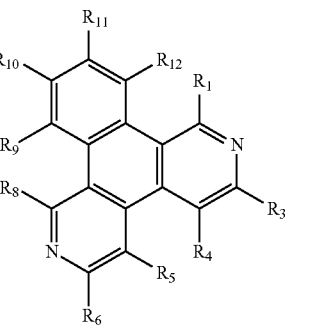
Formula 19
wherein $R_1$ to $R_{12}$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;

at least one of $R_1$ to $R_{12}$ is $$(L)_{m}(Donor)_{n};$$

wherein L is a linker, m is 1 or 0, n≥1; and wherein Donor is an electron donating group containing at least two electron-donating nitrogens and Donors can be different when n>1.

In some more specific embodiments, Donor is selected from the group consisting of:

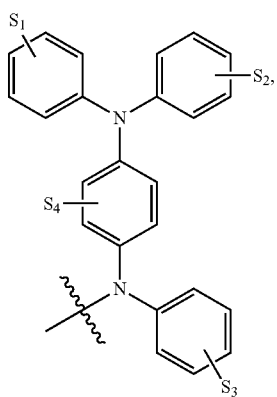

D1

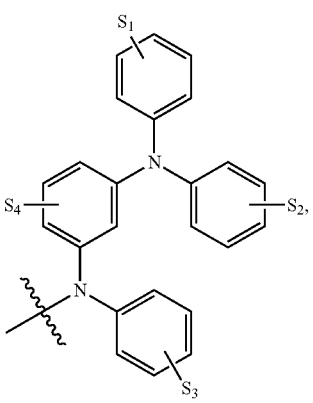

D2

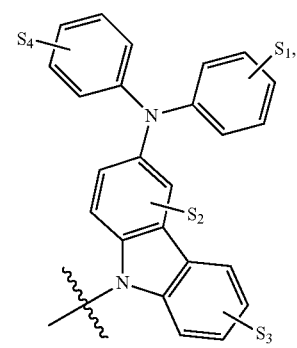

D3

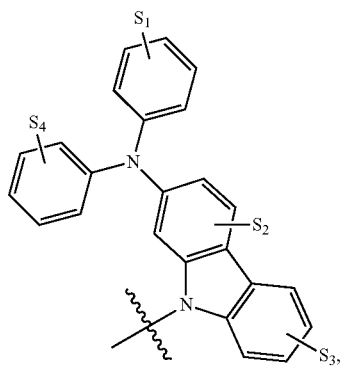

D4

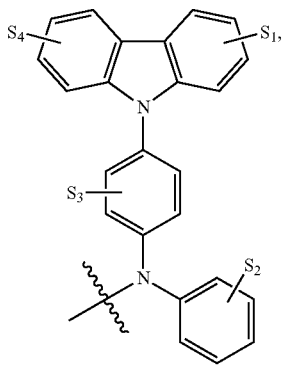

D5

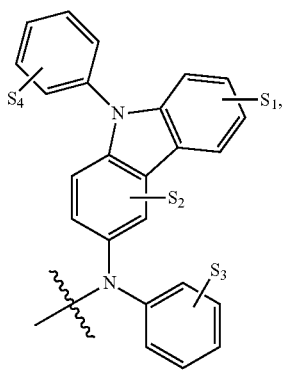

D6

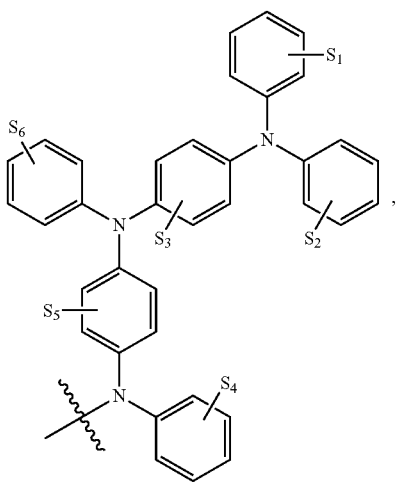

D7

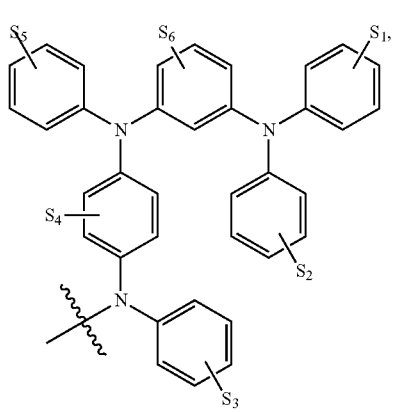
D8
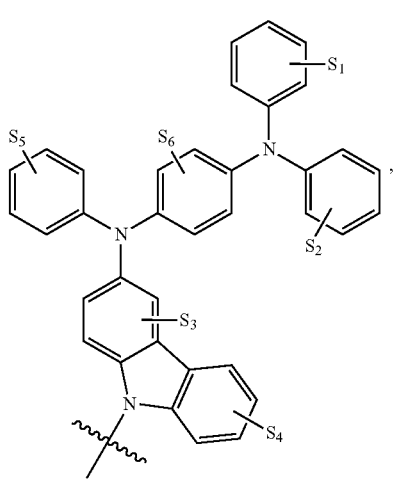
D11
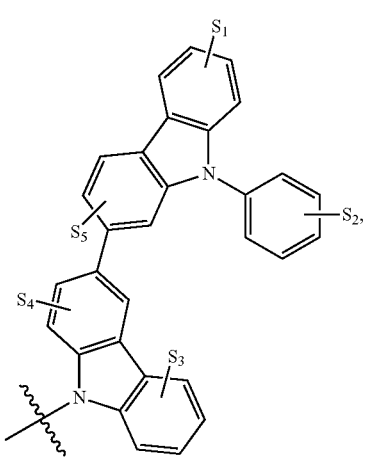
D9
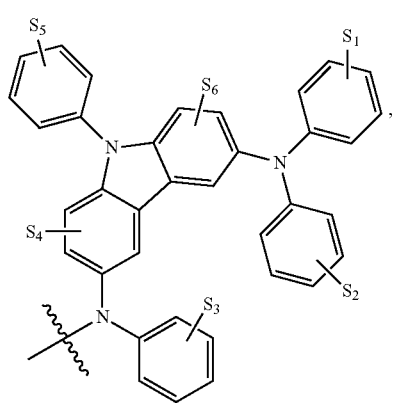
D12
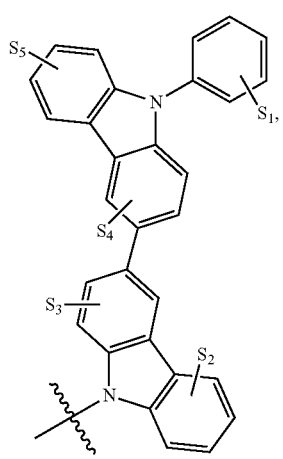
D10
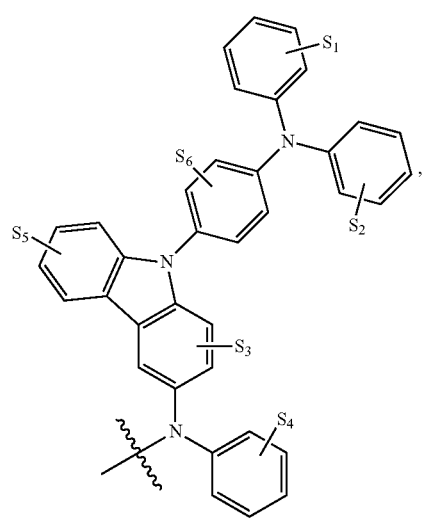
D13

-continued
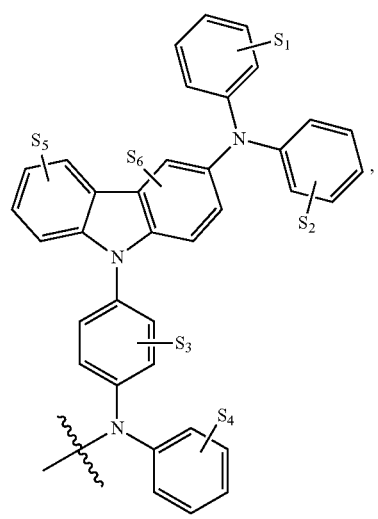
D14
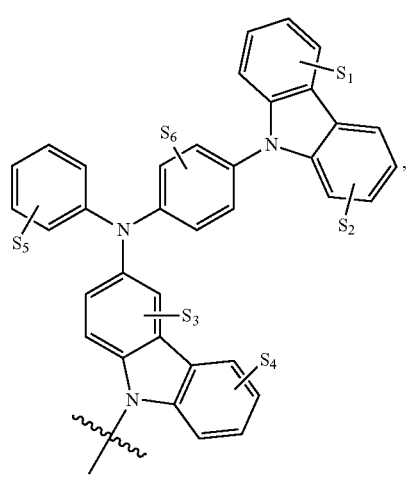
D17
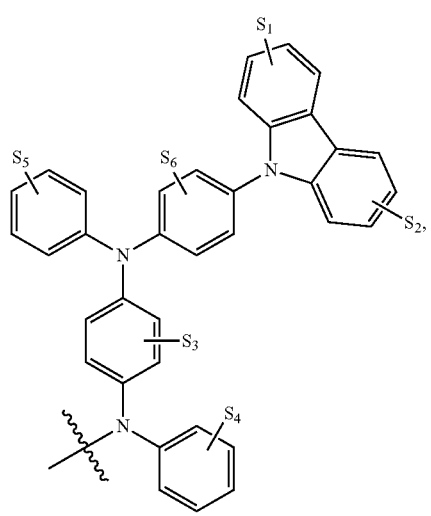
D15
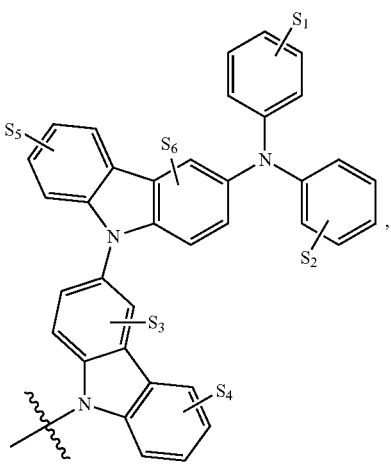
D18
D16
D19

-continued
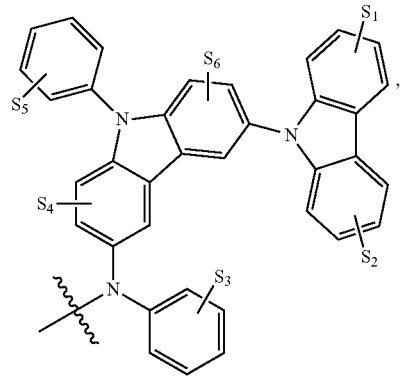
D20
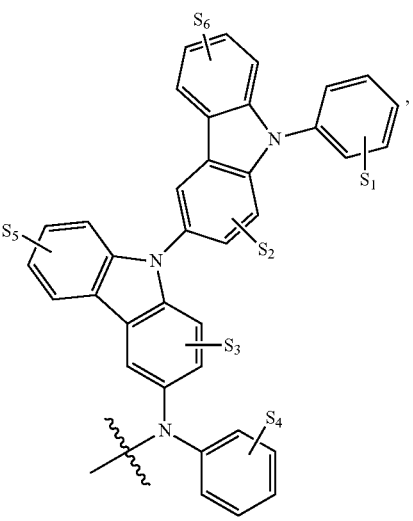
D21
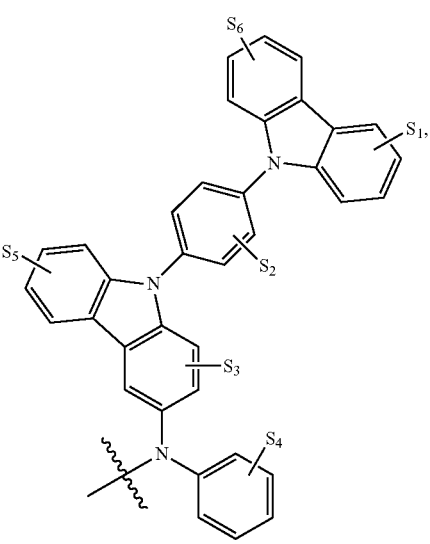
D22
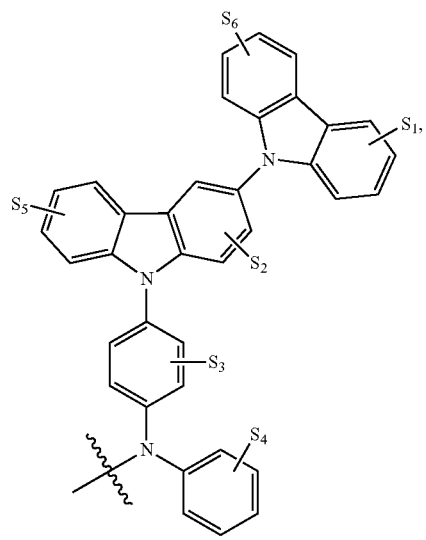
D23
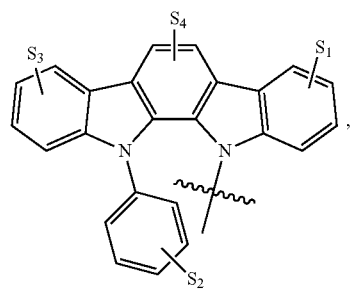
D24
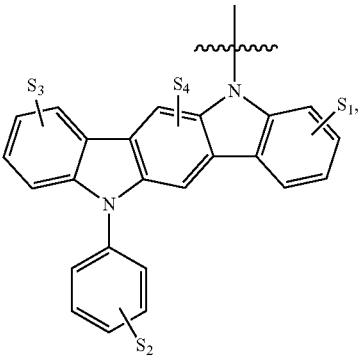
D25
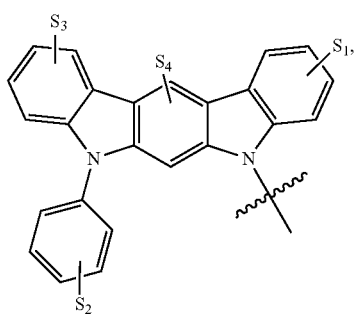
D26

D27
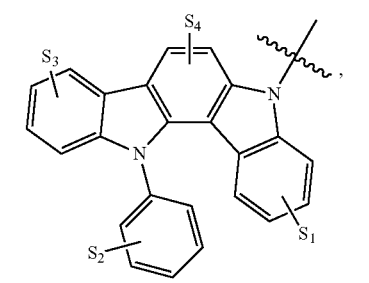
D28
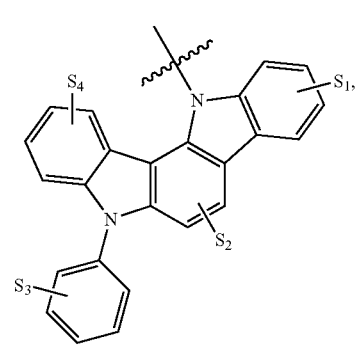
D29
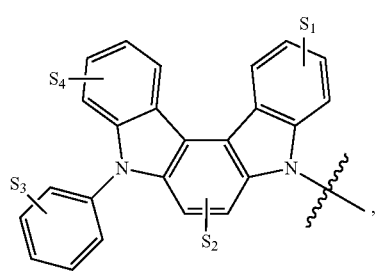
D33
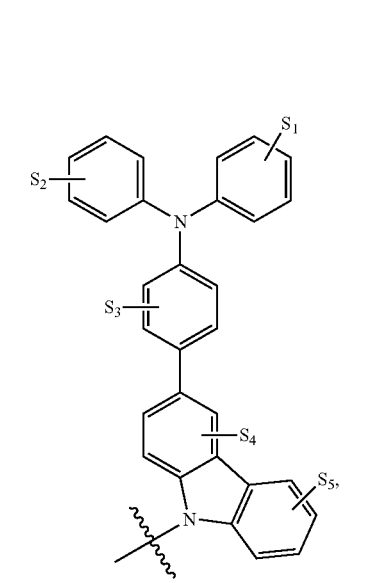
D34
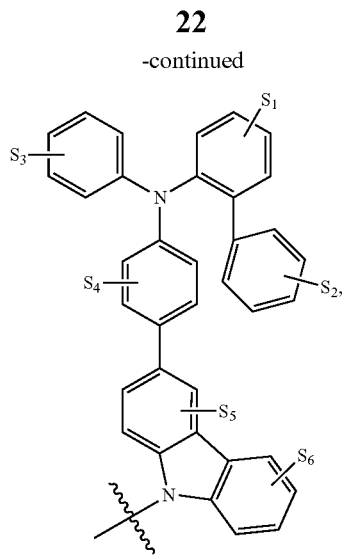
D35
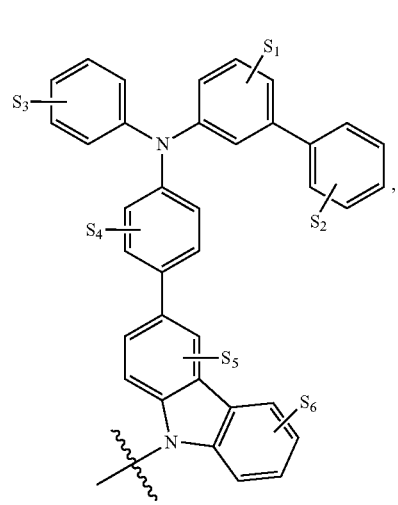
D36
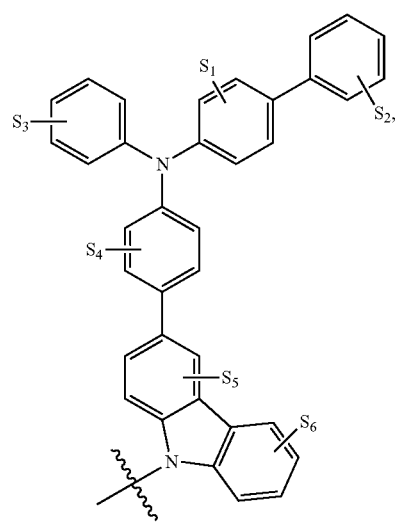

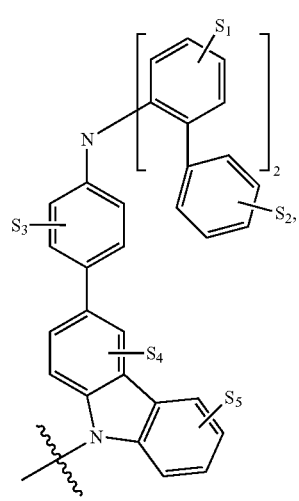
D37
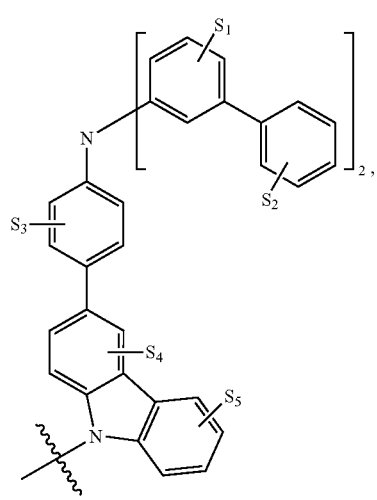
D38
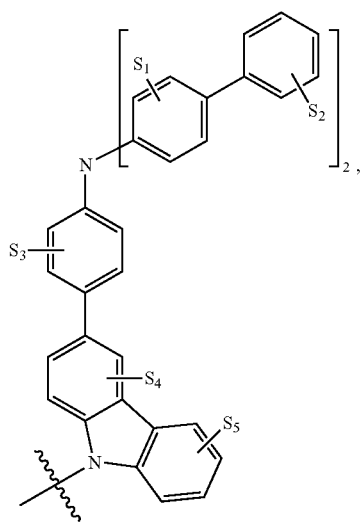
D39
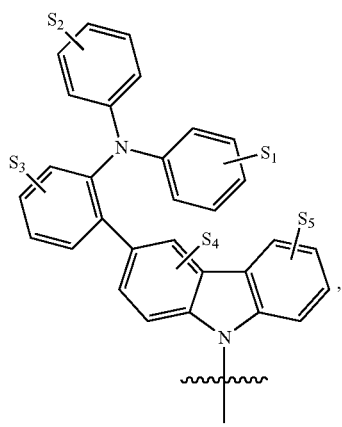
D40
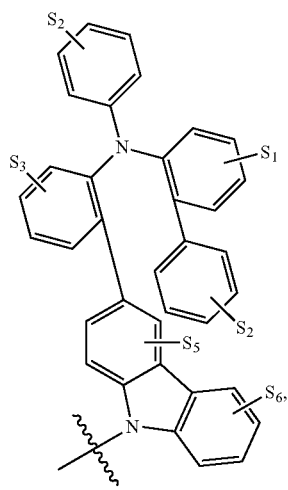
D41
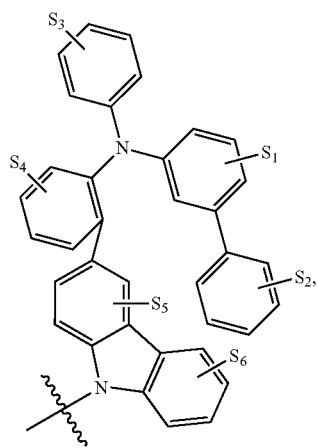
D42

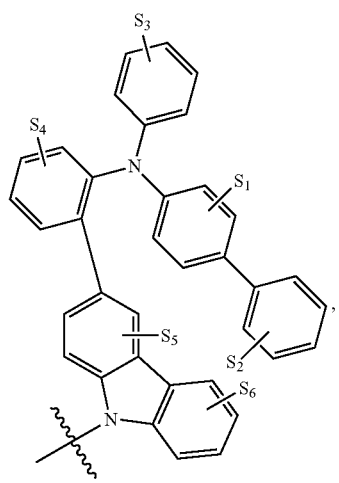 D43
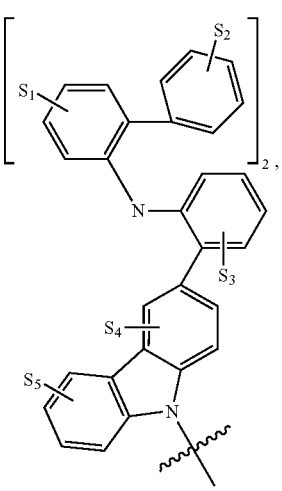 D44
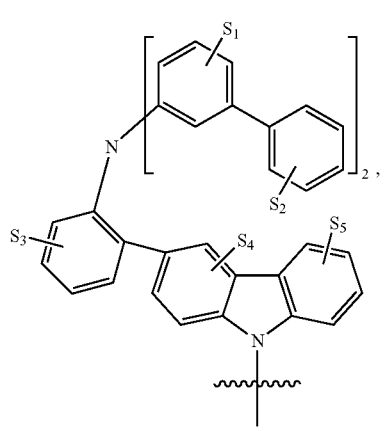 D45
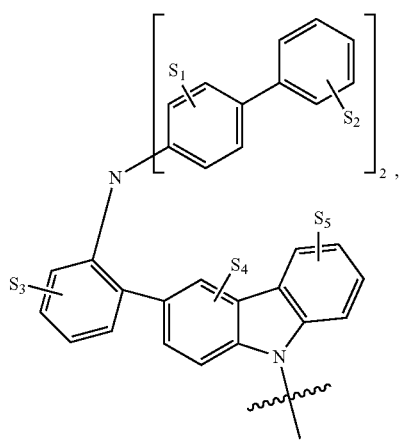 D46
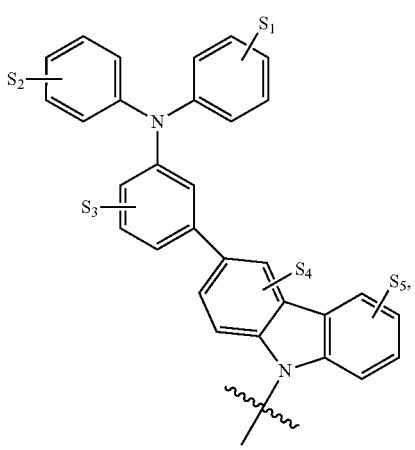 D47
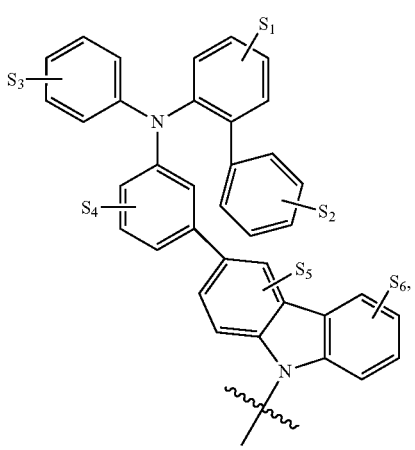 D48

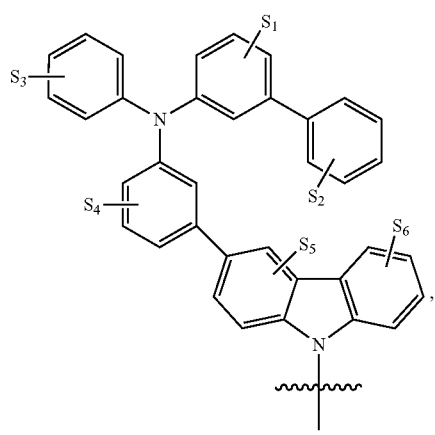
D49
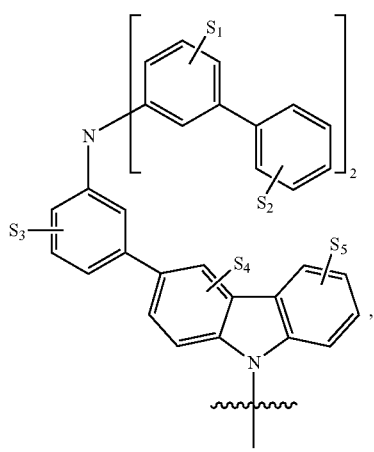
D52
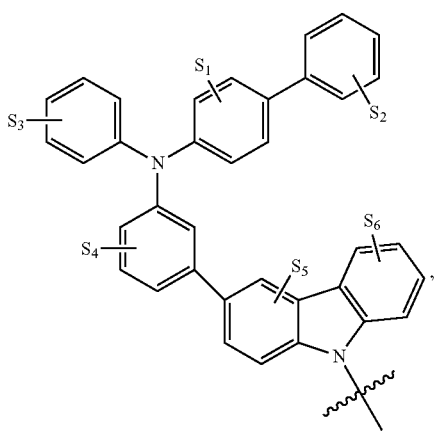
D50
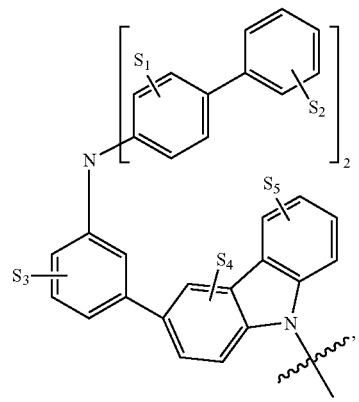
D53
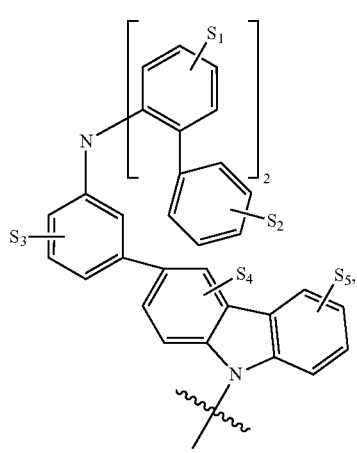
D51
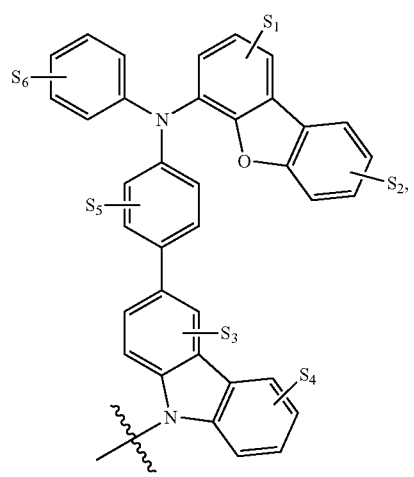
D54

D55
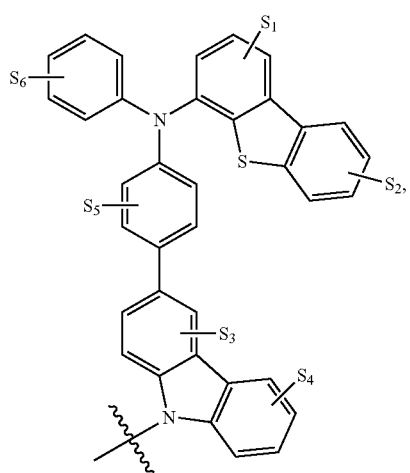
D56
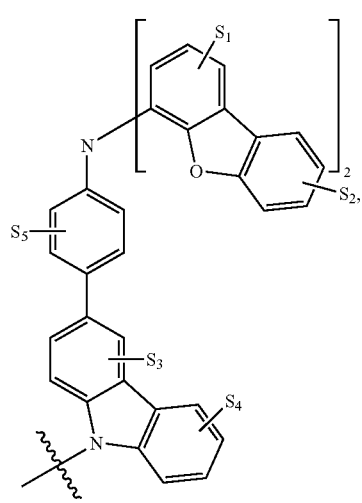
D57
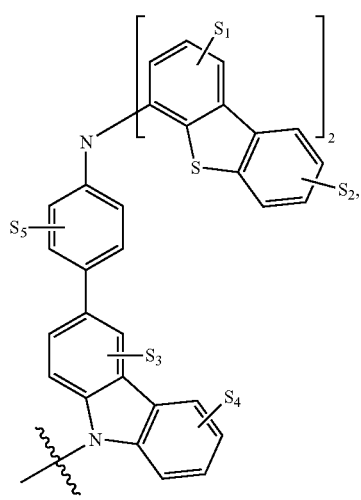
D58
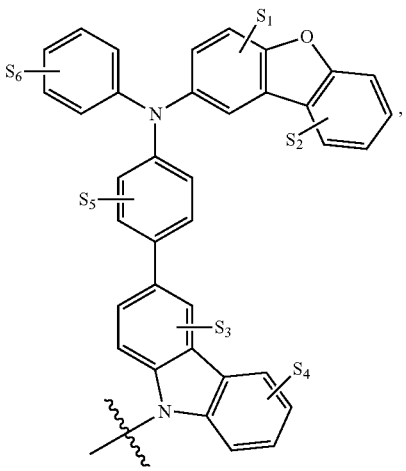
D59
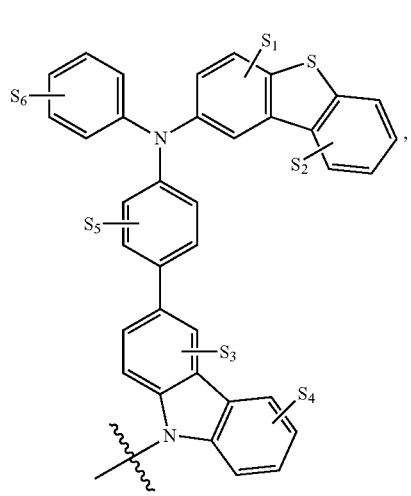
D60
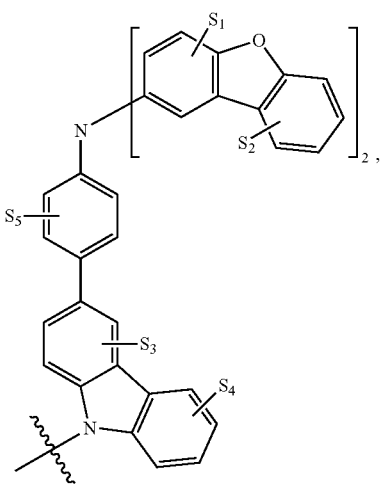

-continued
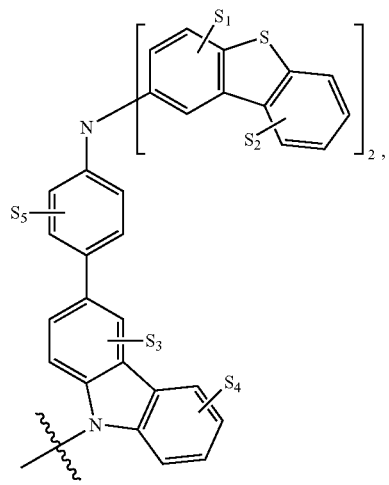
D61

D62
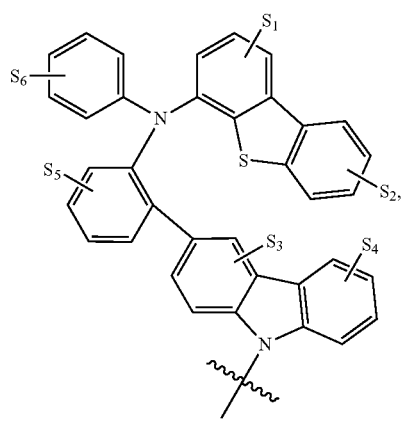
D63
-continued
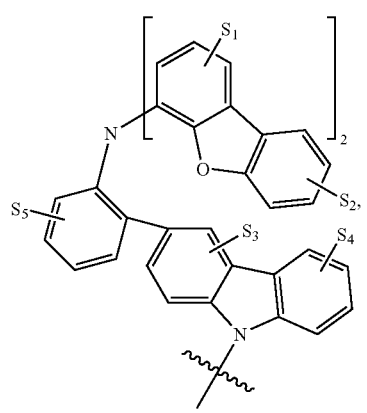
D64
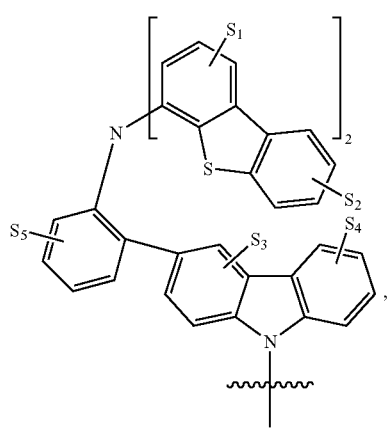
D65
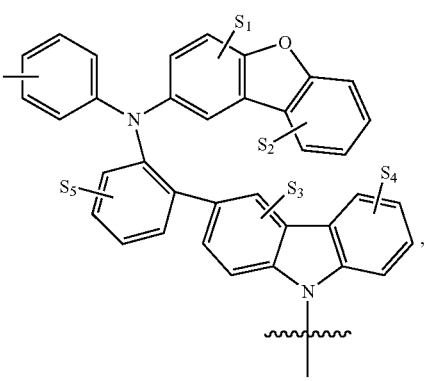
D66
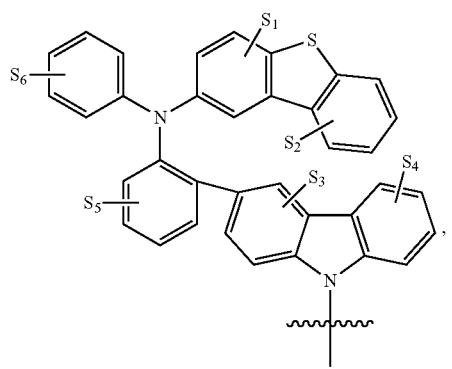
D67

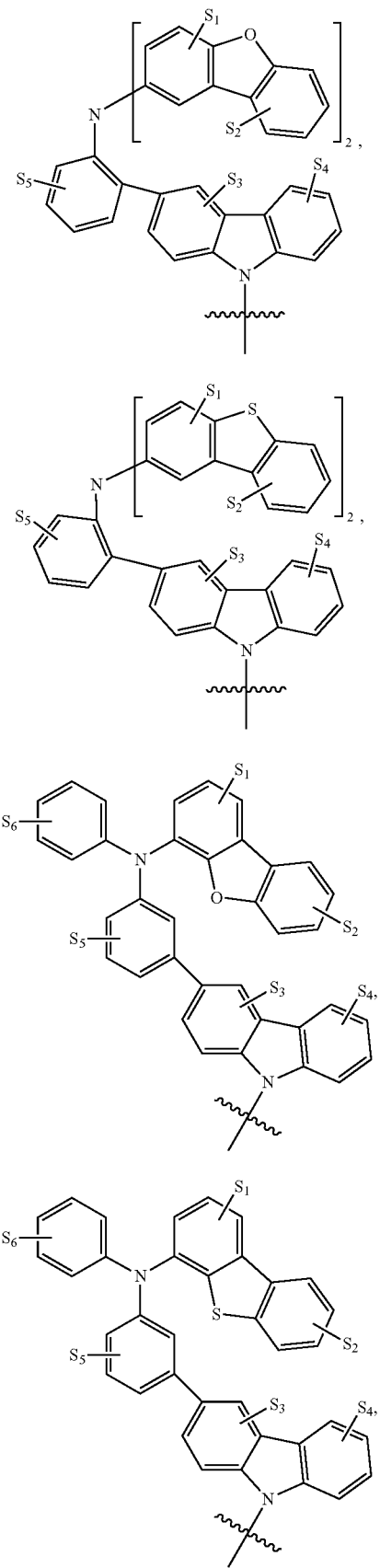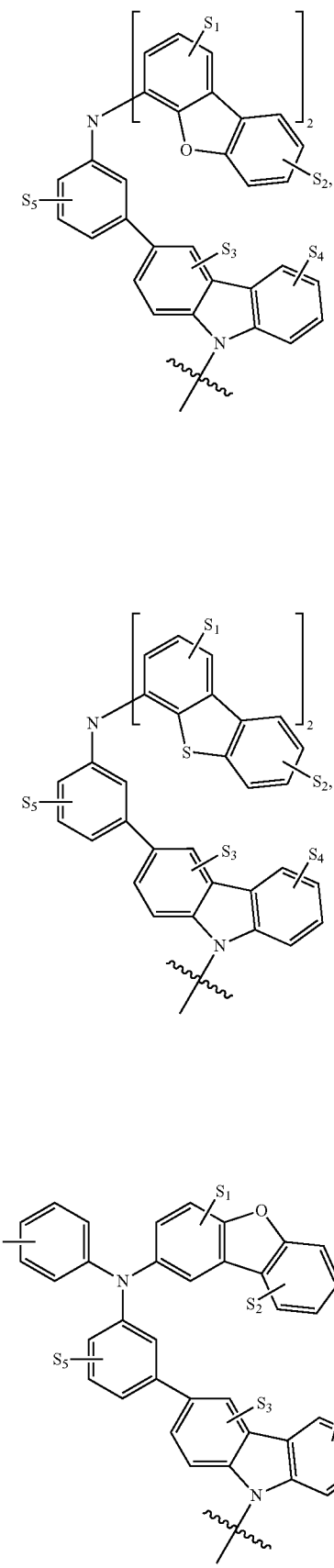

D75
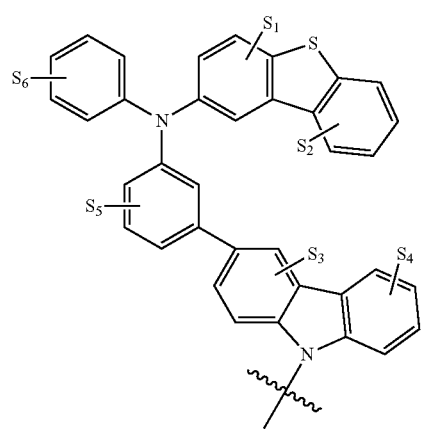
D76
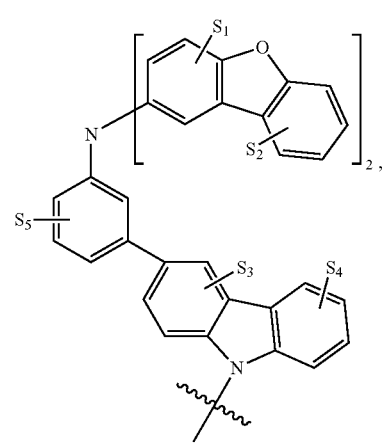
D77
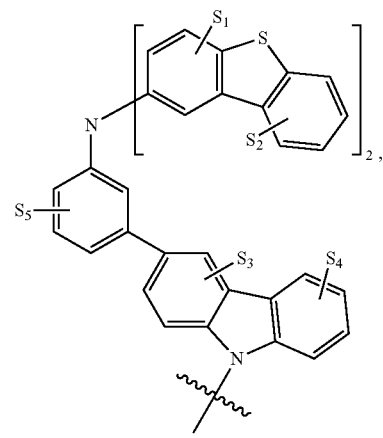
D78
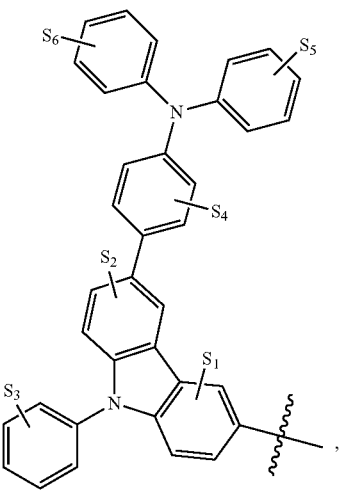
D79
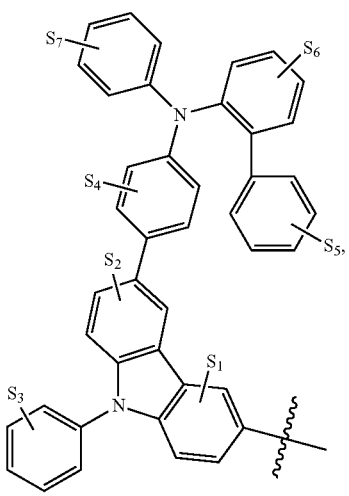
D80
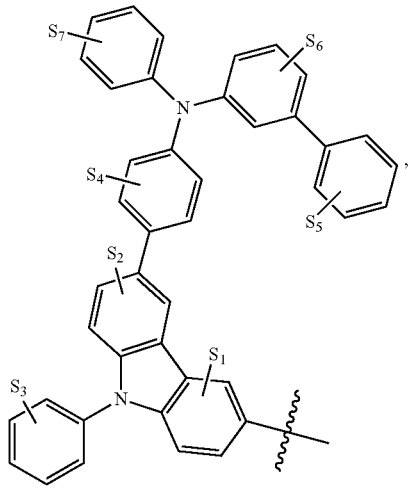

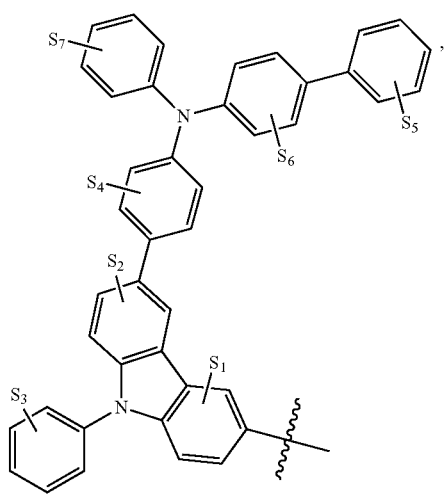
D81
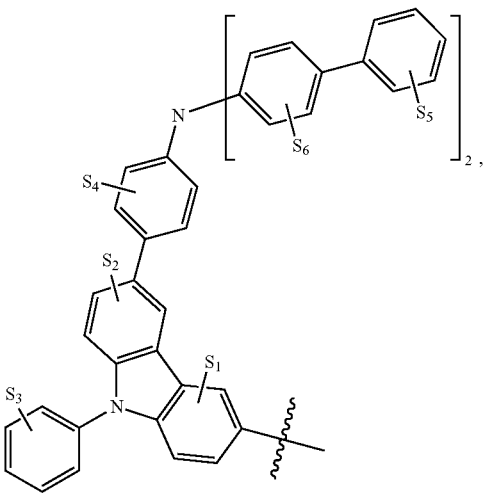
D84
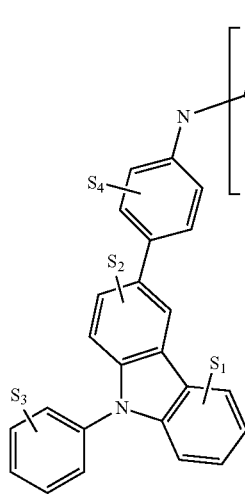
D82
D83
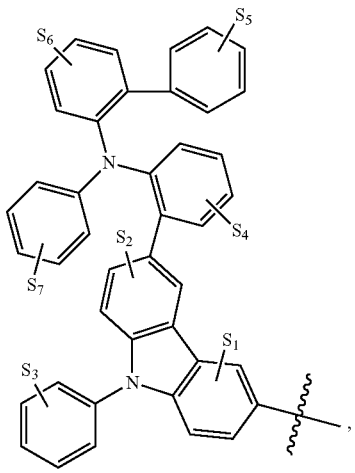
D85
D86

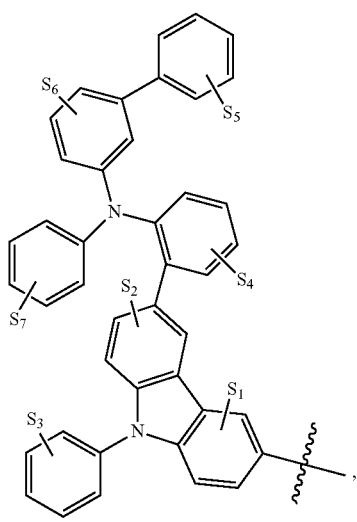
D87
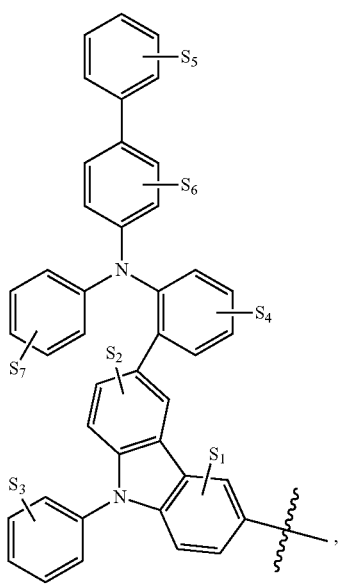
B88
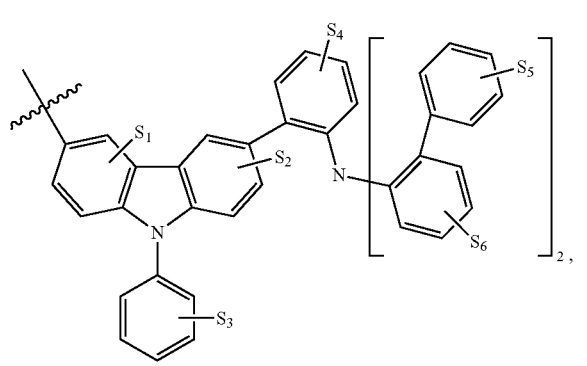
D89
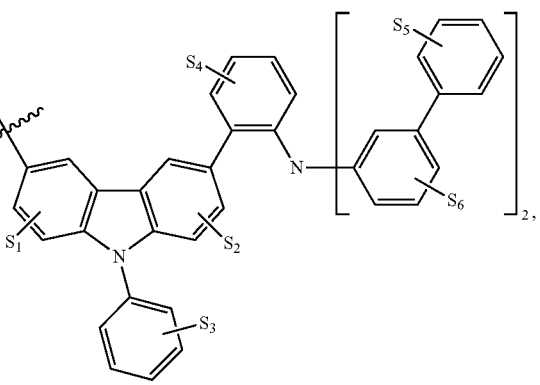
D90
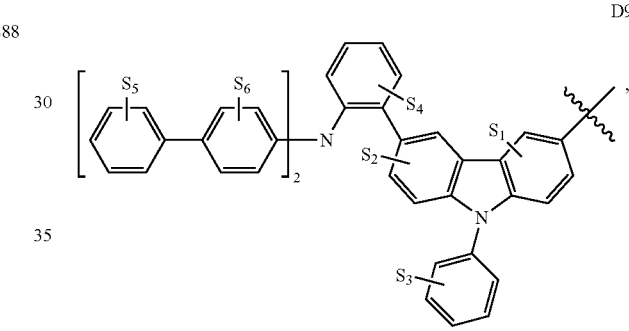
D91
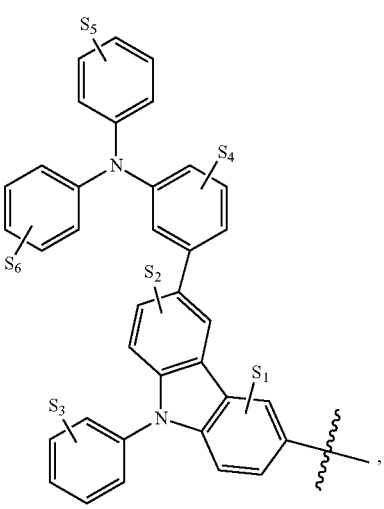
D92

D93
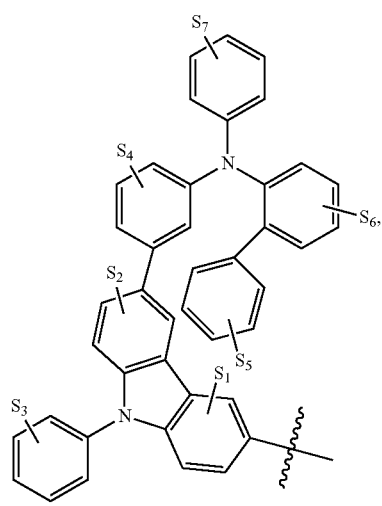
D94
D95
D96
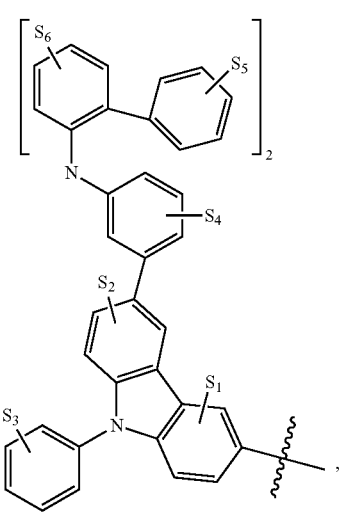
D97
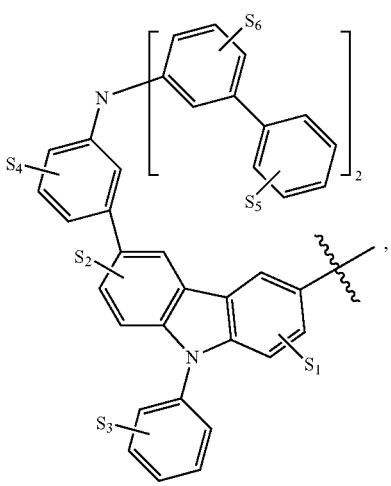
D98
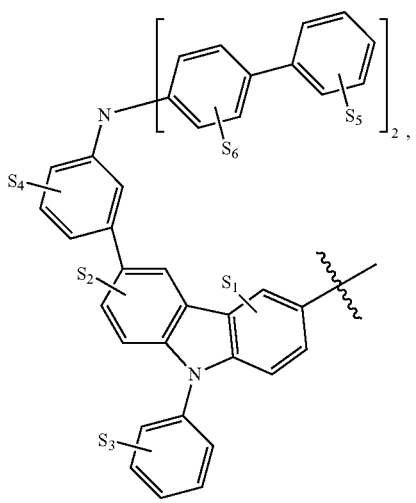

-continued
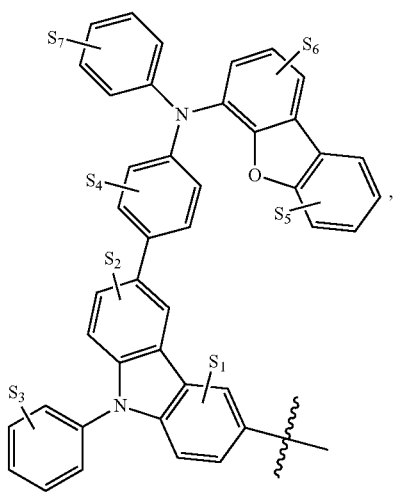
D99
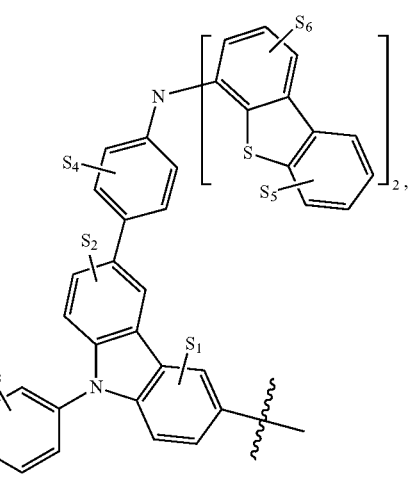
D102
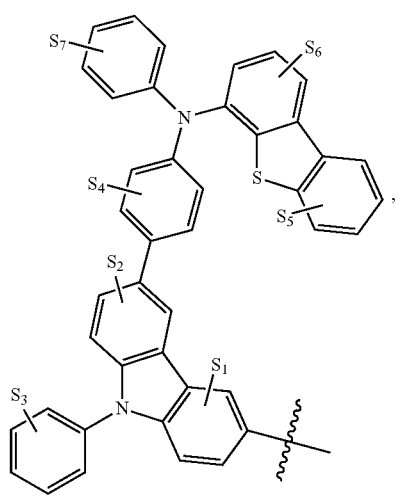
D100
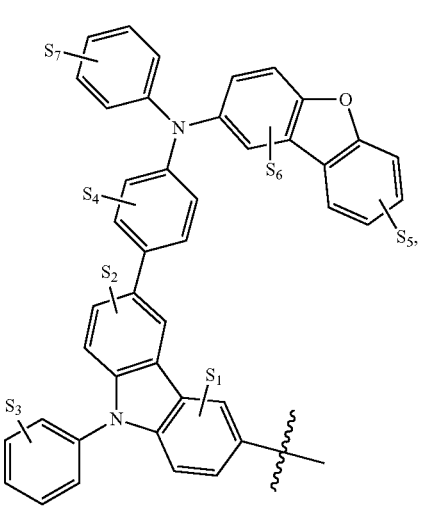
D103
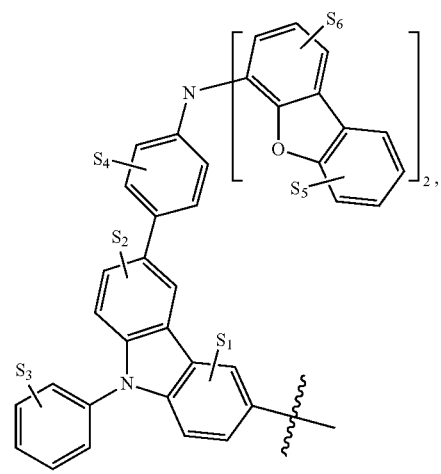
D101
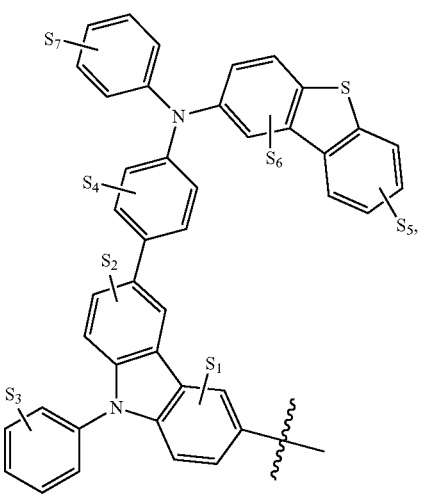
D104

-continued
D105
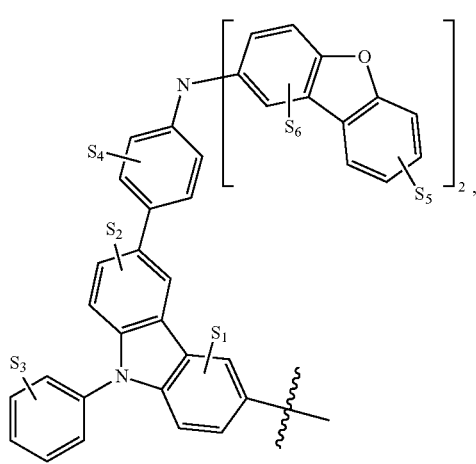
D106
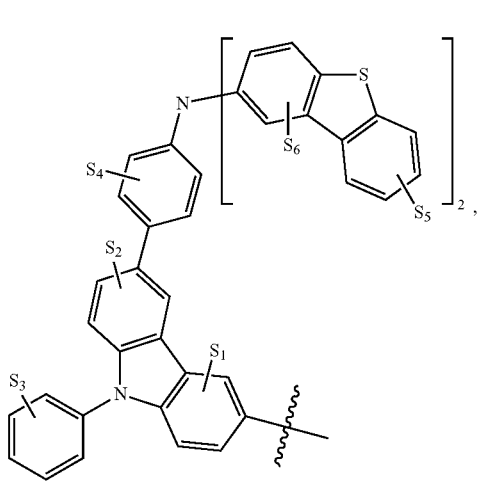
D107
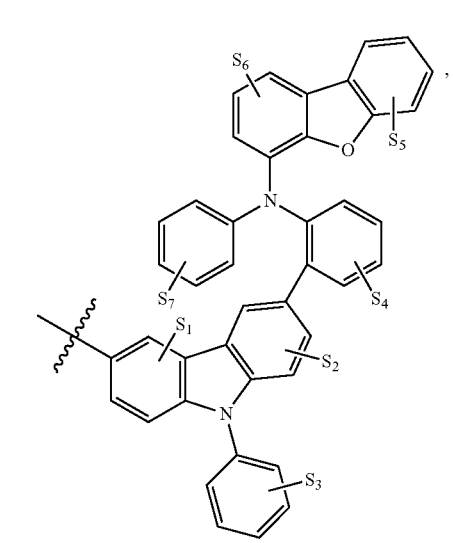
D108
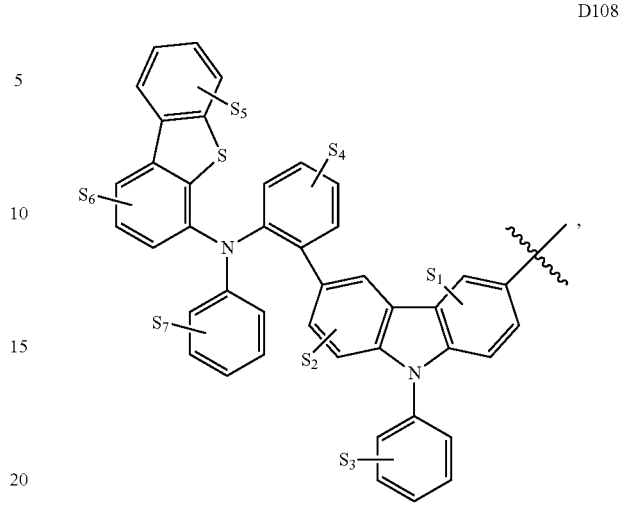
D109
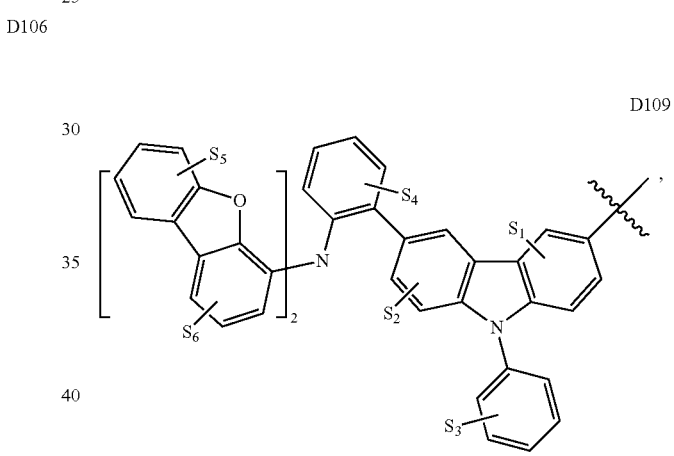
D110
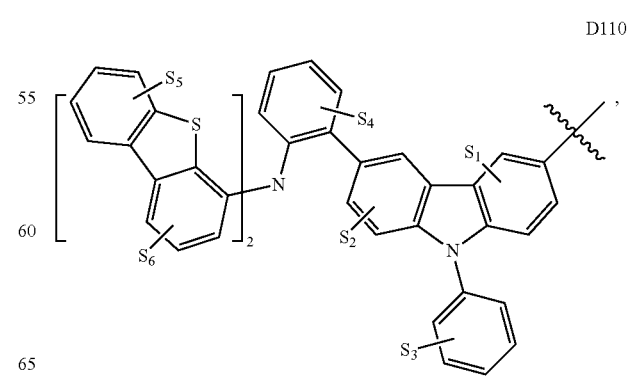

D111
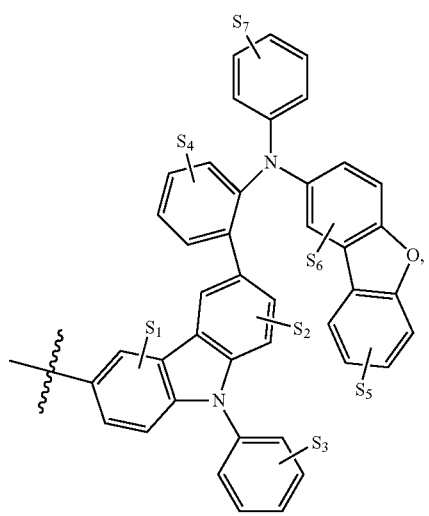
D112
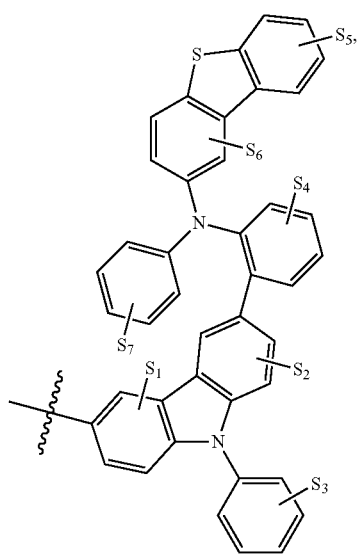
D113
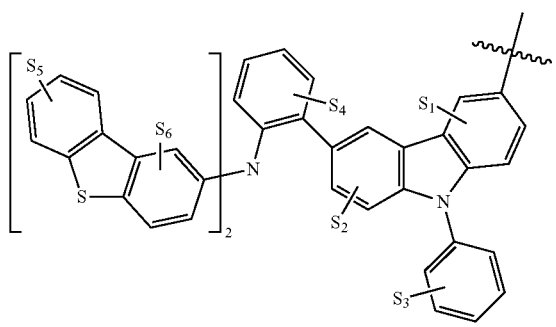
D114
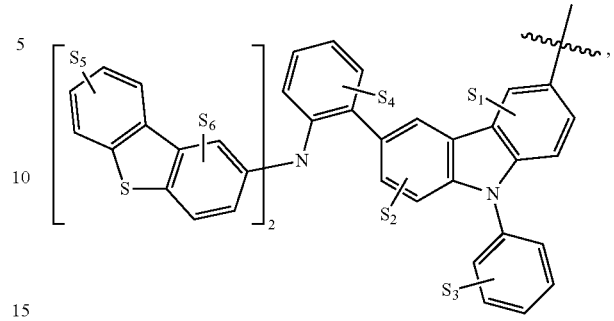
D115
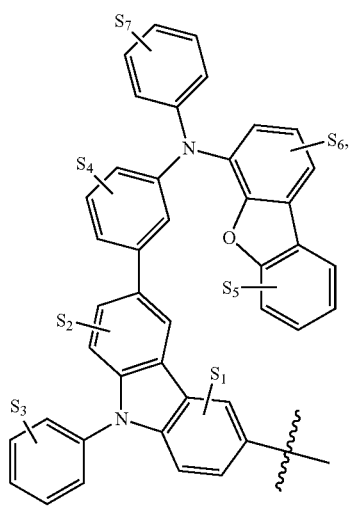
D116
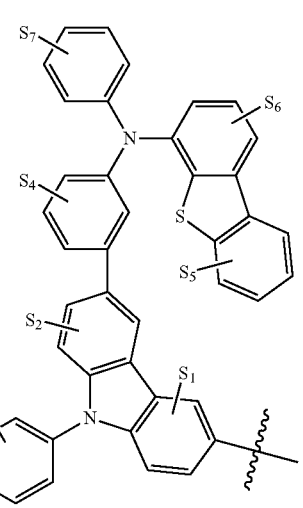

-continued
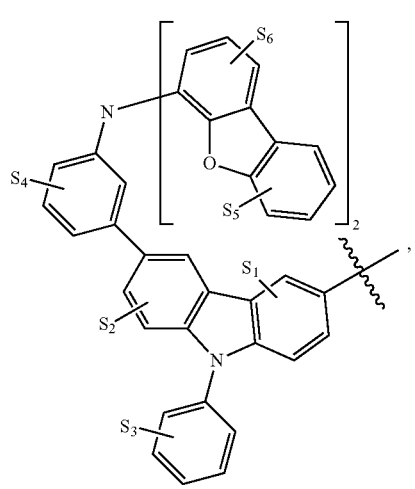
D117
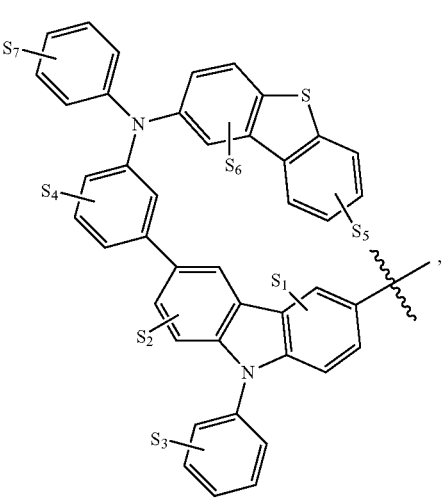
D120
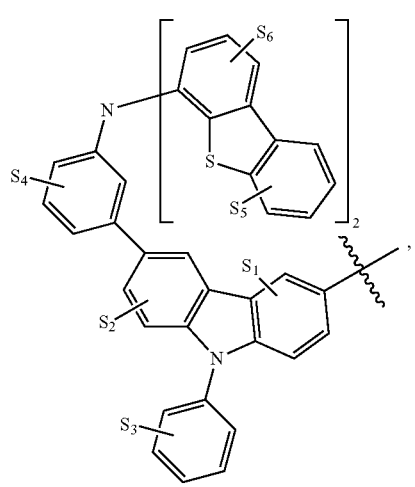
D118
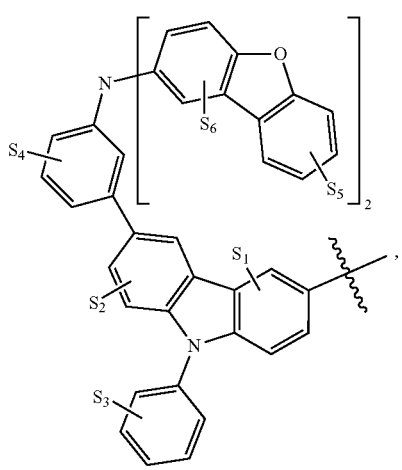
D121
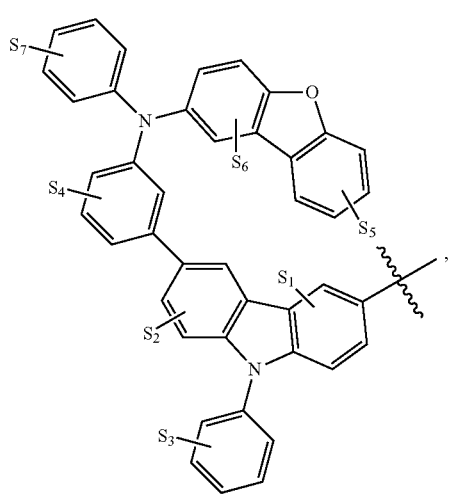
D119
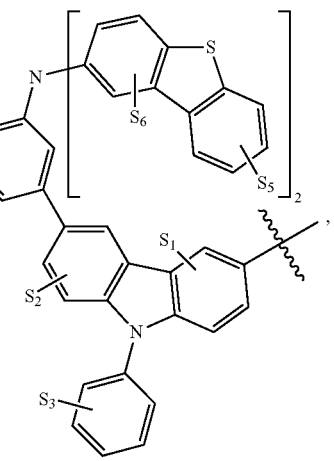
D122

D123
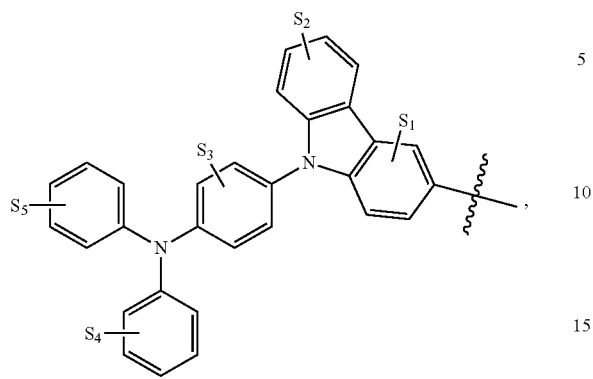
D124
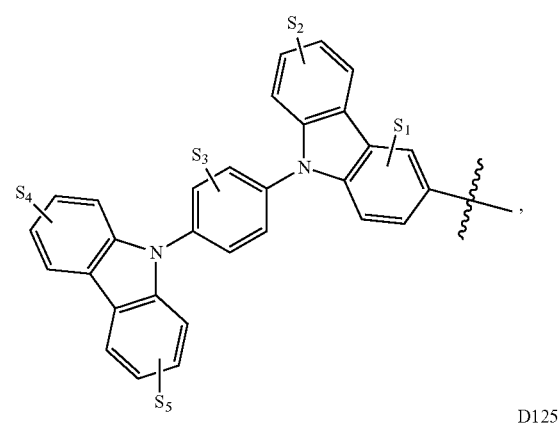
D125
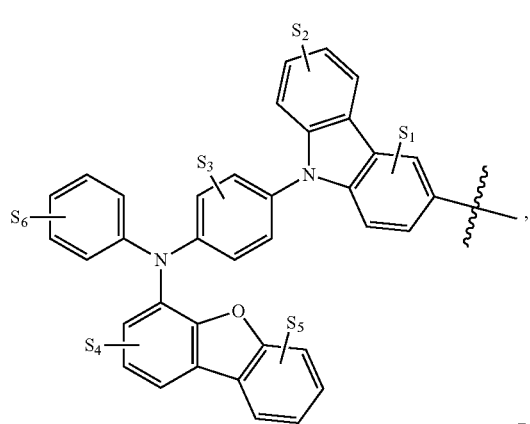
D126
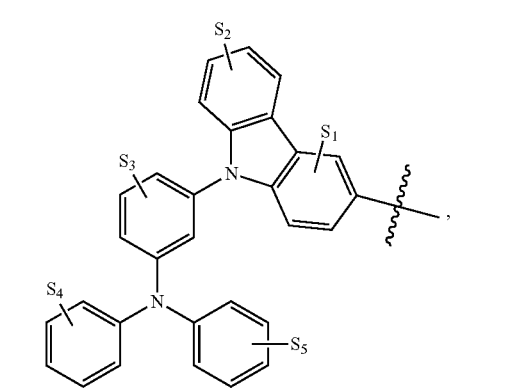
D127
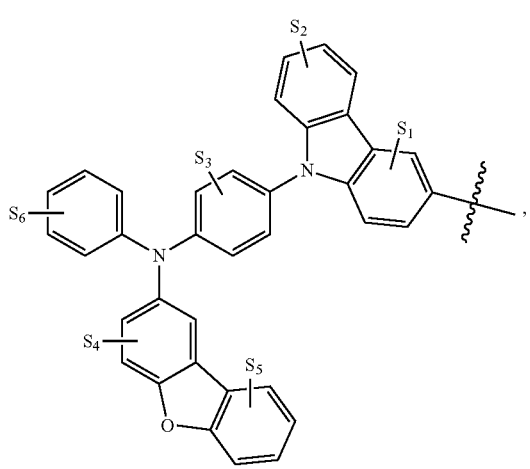
D128
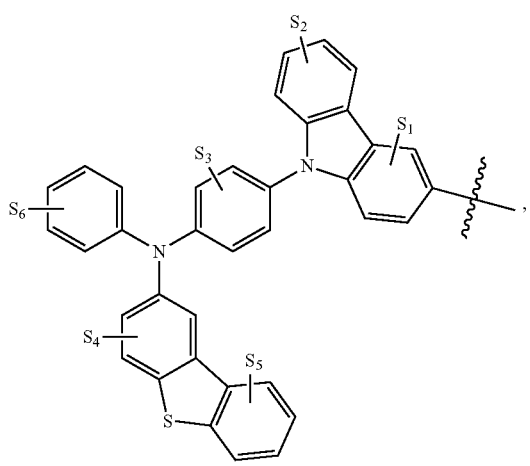
D129
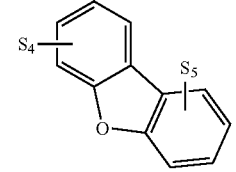

-continued
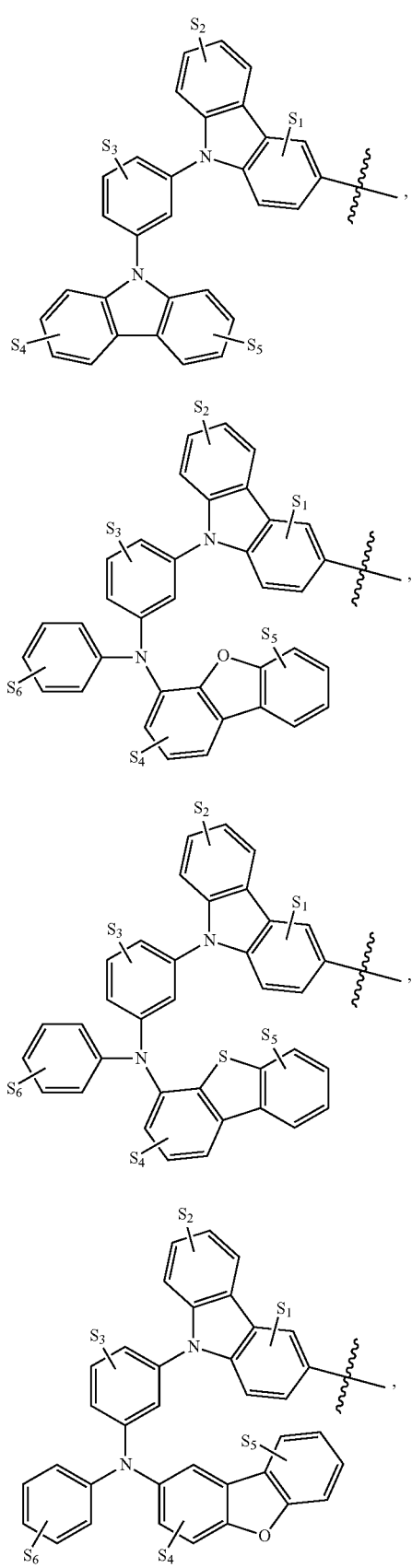
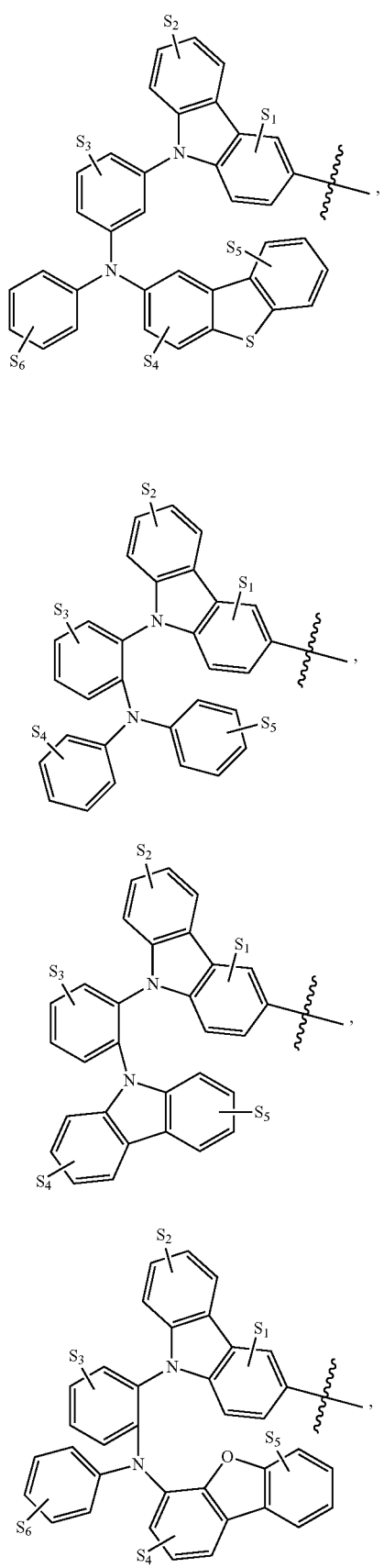

-continued

D138
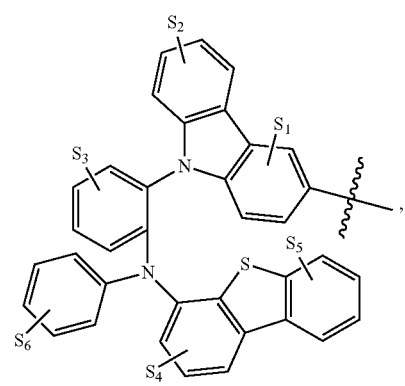

D139
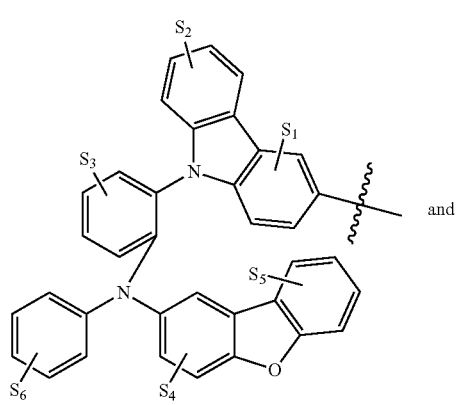
and

D140
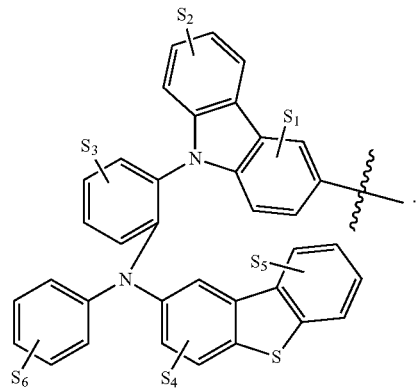

wherein $S_1$ to $S_7$ represent mono, di, tri, tetra or penta substitutions with hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

The linker L can be one of

L1
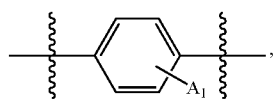

L2
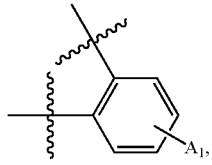

L3
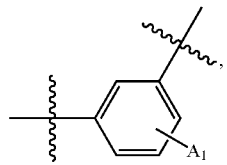

L4
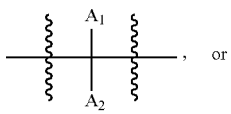
, or

L5
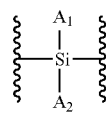

wherein $A_1$ to $A_2$ represent mono, di, tri or tetra substitutions with hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In some more specific embodiments, the donor-acceptor compound can be one of

Compound 1
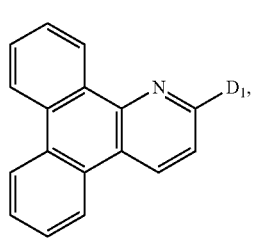

Compound 2
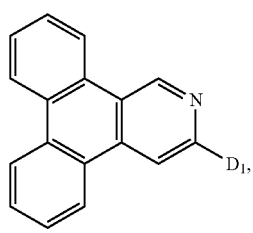

Compound 3
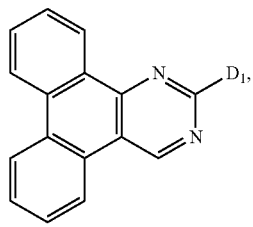

-continued
Compound 4
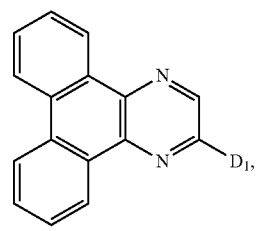
Compound 5

Compound 6

Compound 7
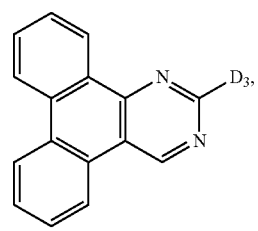
Compound 8
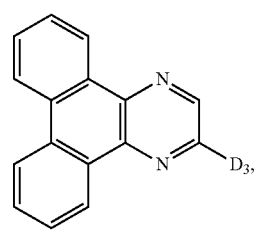
Compound 9
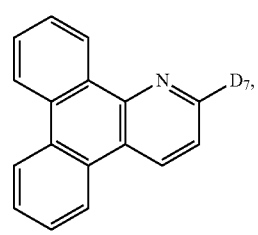
Compound 10
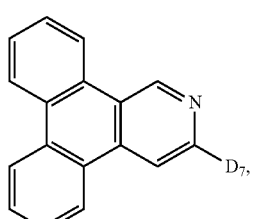
-continued
Compound 11
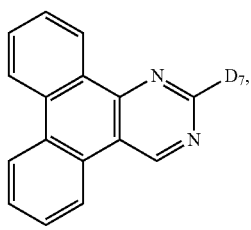
Compound 12
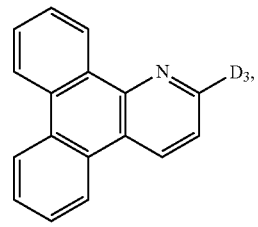
Compound 13
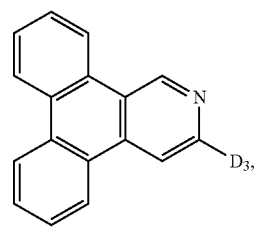
Compound 14
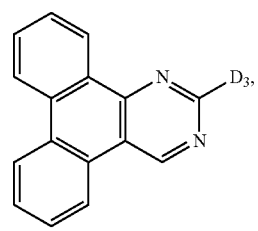
Compound 15
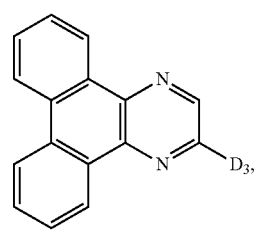
Compound 16
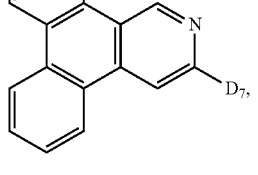

Compound 17
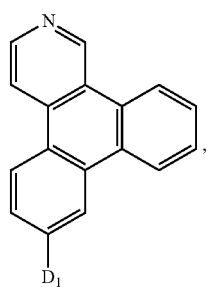
Compound 18
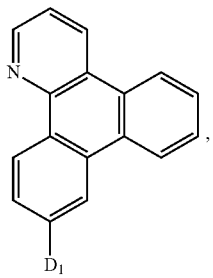
Compound 19
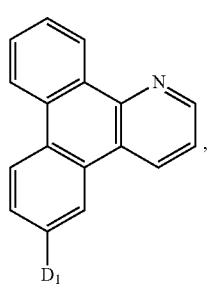
Compound 20
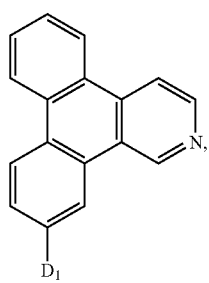
Compound 21
Compound 22
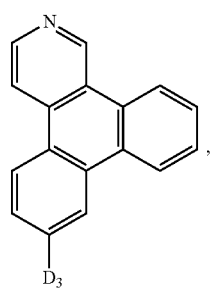
Compound 23
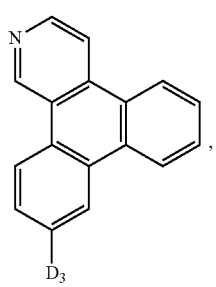
Compound 24
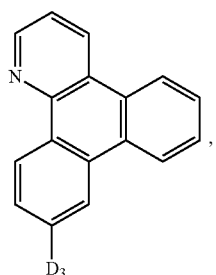
Compound 25
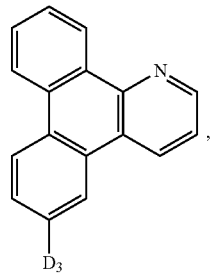
Compound 26
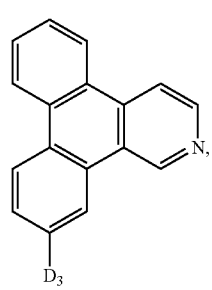

Compound 27
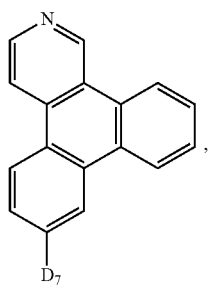
Compound 28
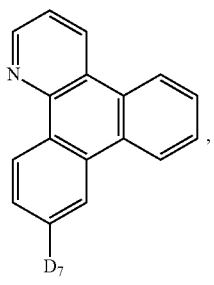
Compound 29

Compound 30
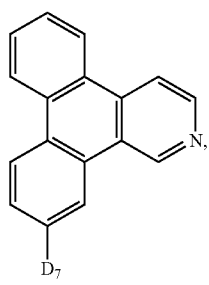
Compound 31
Compound 32
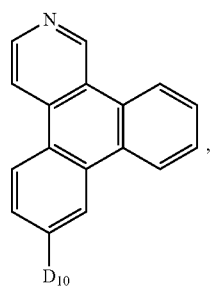
Compound 33
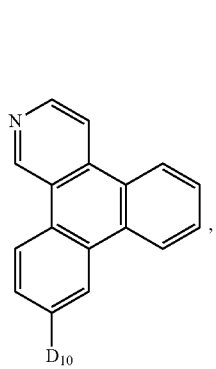
Compound 34
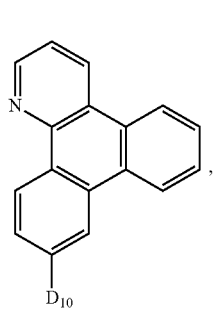
Compound 35
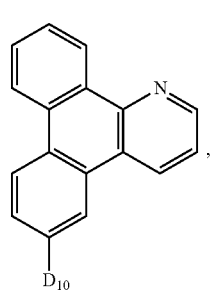
Compound 36
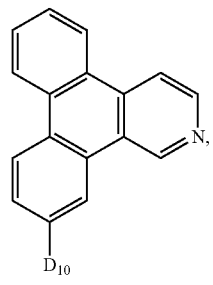

Compound 37
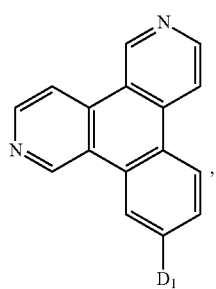
Compound 38
Compound 39
Compound 40
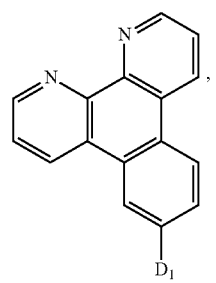
Compound 41
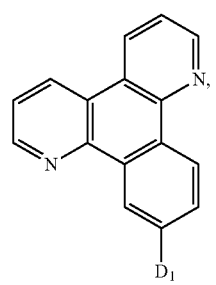
Compound 42
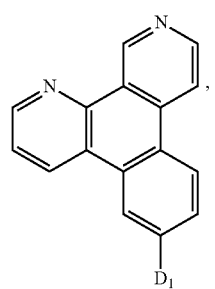
Compound 43
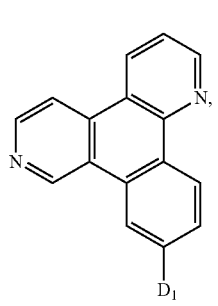
Compound 44
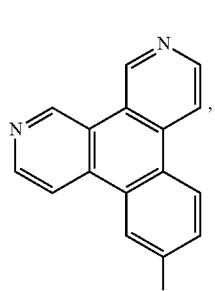
Compound 45
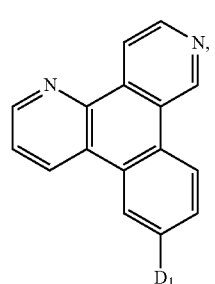
Compound 46
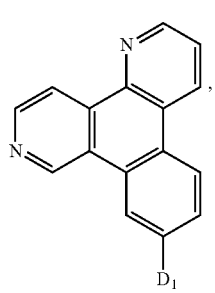

Compound 47
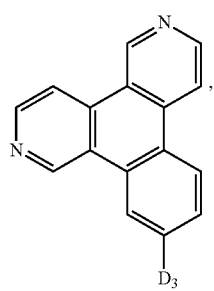
Compound 48
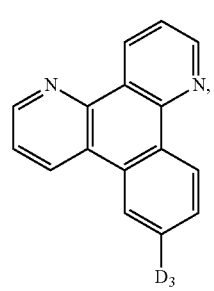
Compound 49
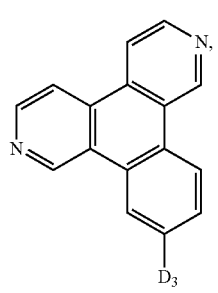
Compound 50
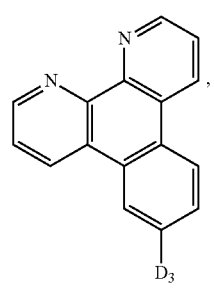
Compound 51
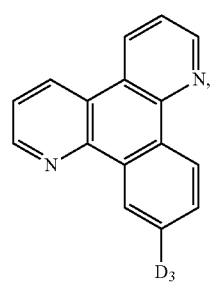
Compound 52
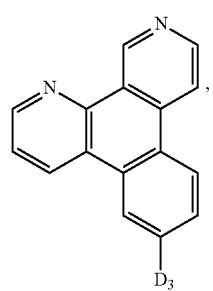
Compound 53
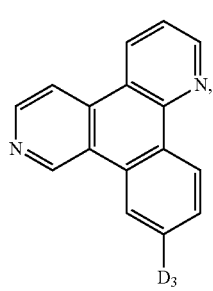
Compound 54
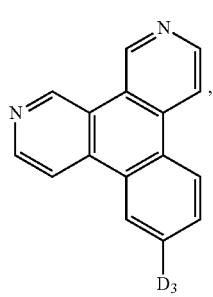
Compound 55
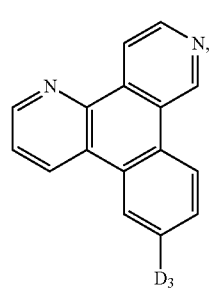
Compound 56
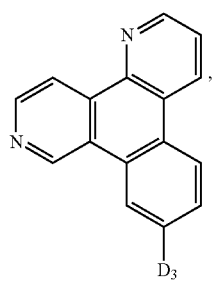

-continued
Compound 57
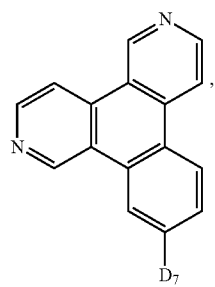
Compound 58

Compound 59
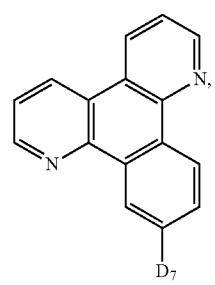
Compound 60
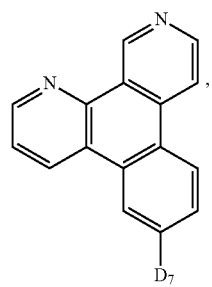
Compound 61
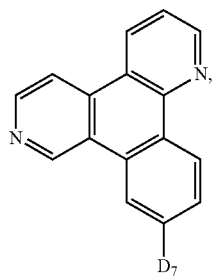
-continued
Compound 62
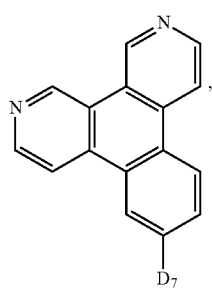
Compound 63
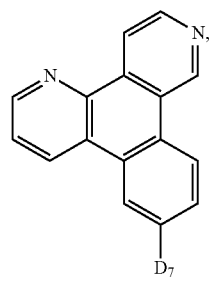
Compound 64
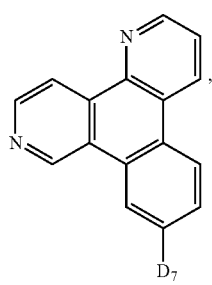
Compound 65
Compound 66

Compound 67
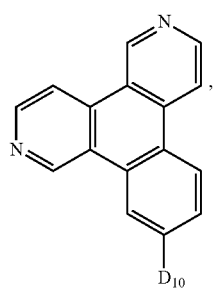
Compound 68
Compound 69
Compound 70
Compound 71
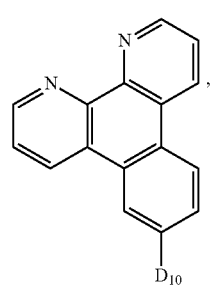
Compound 72
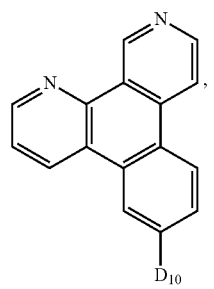
Compound 73
Compound 74
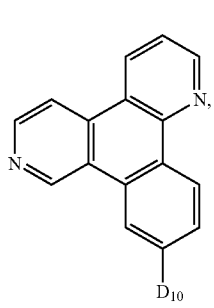
Compound 75
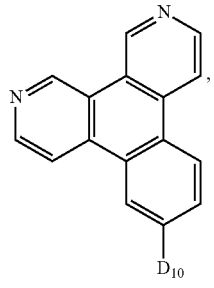
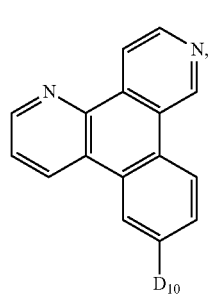
Compound 76
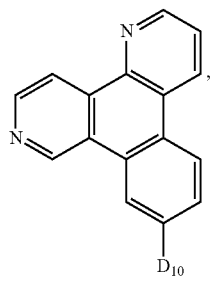

Compound 115
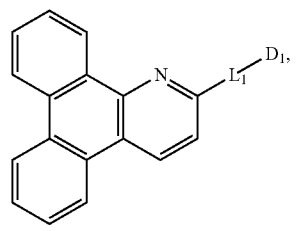
Compound 116
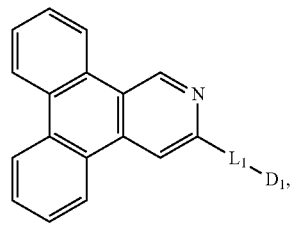
Compound 117
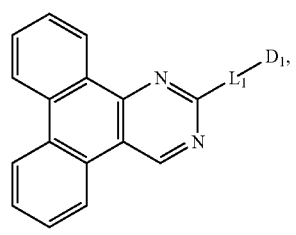
Compound 118
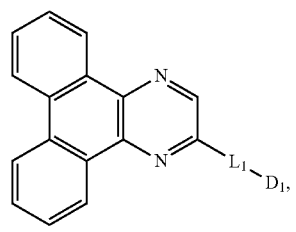
Compound 119
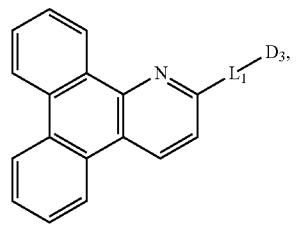
Compound 120
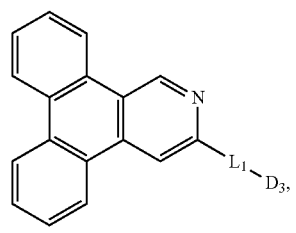
Compound 121

Compound 122
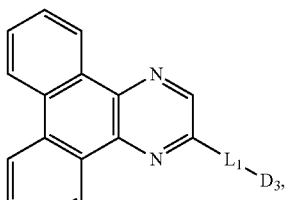
Compound 123
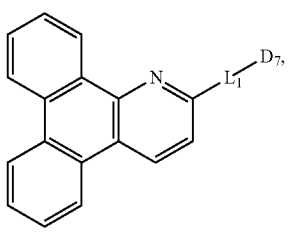
Compound 124
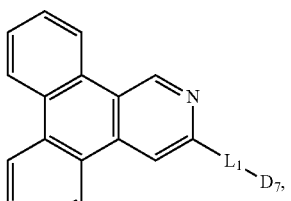
Compound 125
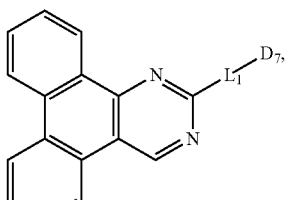
Compound 126
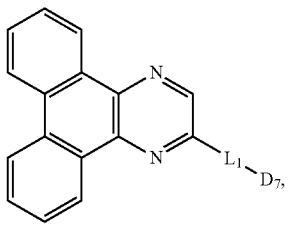
Compound 127
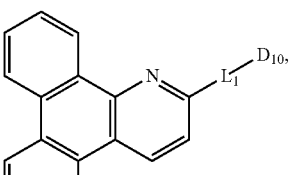
Compound 128
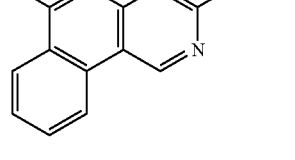

Compound 129
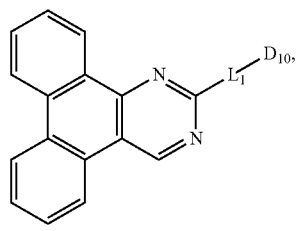
Compound 130
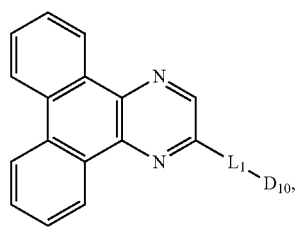
Compound 131
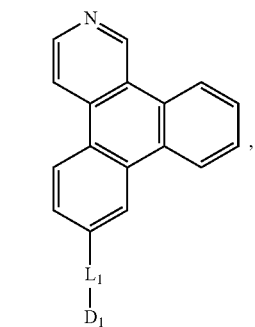
Compound 132
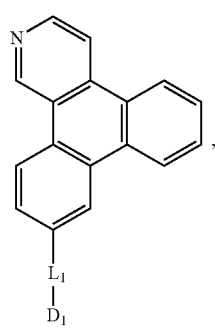
Compound 133
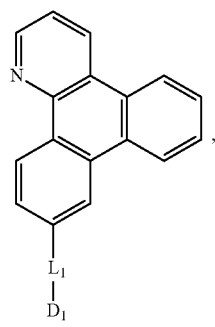
Compound 134
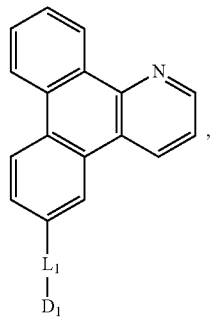
Compound 135
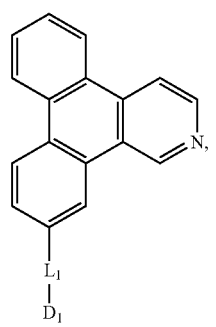
Compound 136
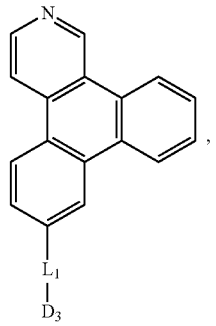
Compound 137
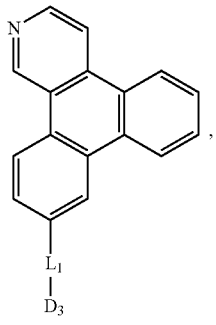
Compound 138
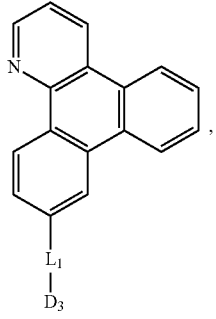

Compound 139
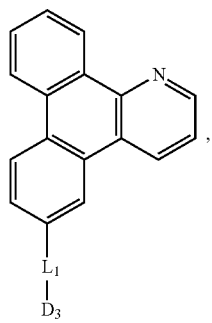
Compound 140
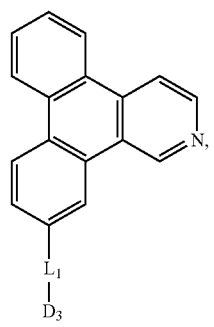
Compound 141
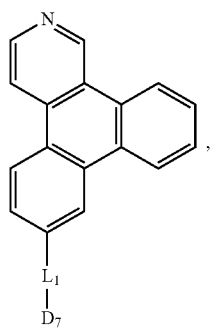
Compound 142
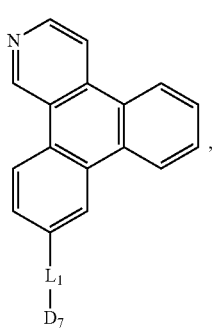
Compound 143
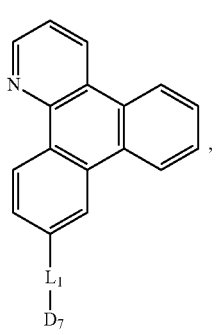
Compound 144
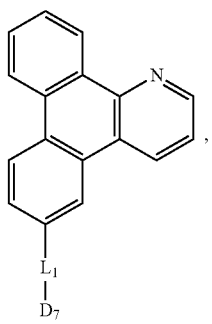
Compound 145
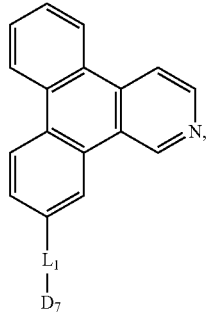
Compound 146
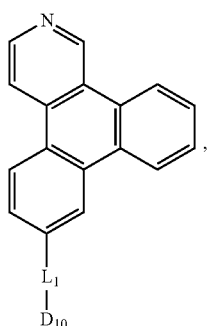
Compound 147
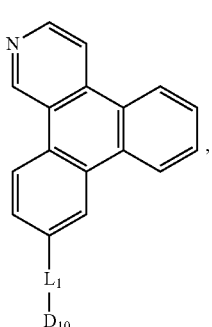
Compound 148
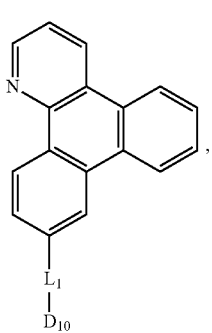

Compound 149
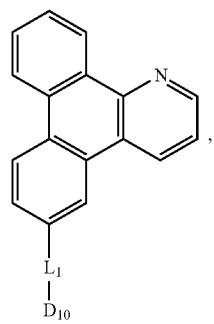
Compound 150
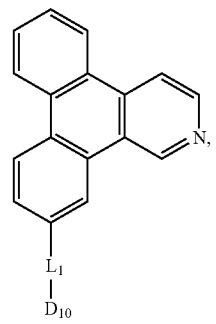
Compound 151
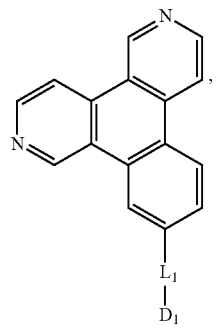
Compound 152
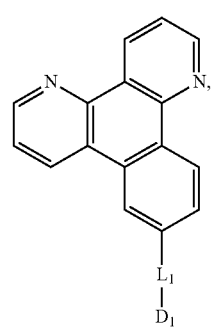
Compound 153
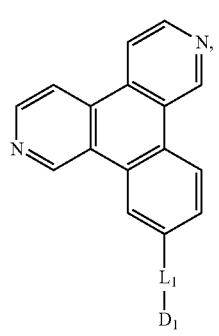
Compound 154
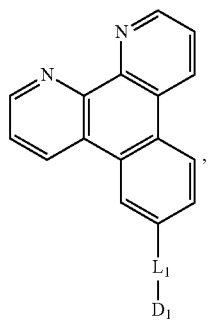
Compound 155
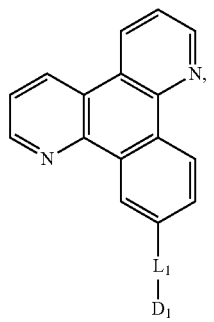
Compound 156
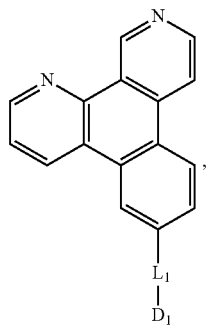
Compound 157
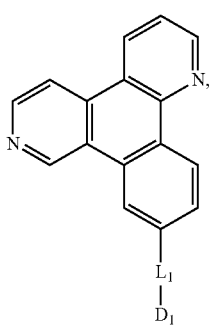
Compound 158
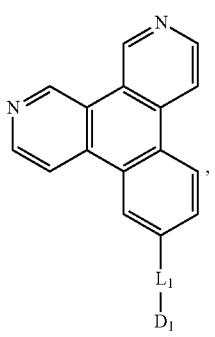

-continued
Compound 159
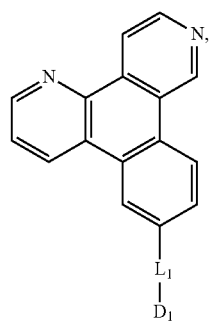
Compound 160
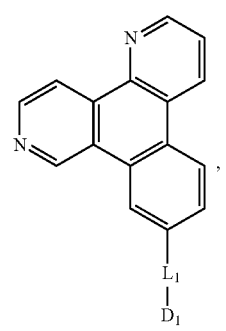
Compound 161
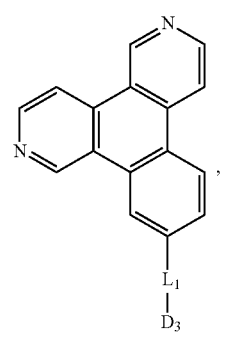
Compound 162
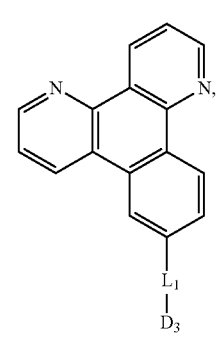
Compound 163
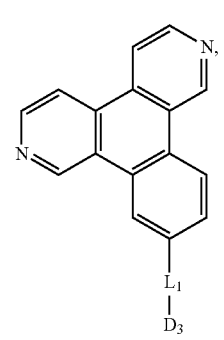
-continued
Compound 164
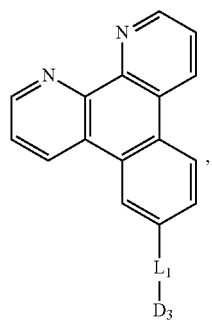
Compound 165
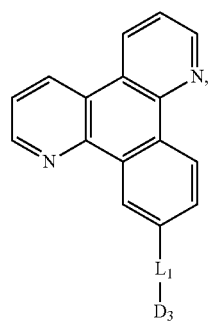
Compound 166
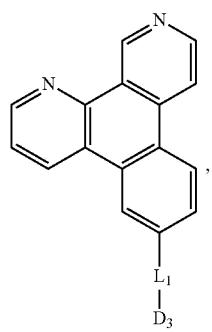
Compound 167
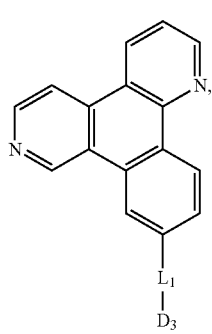
Compound 168
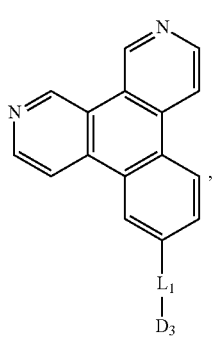

Compound 169
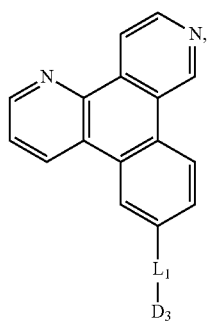
Compound 170
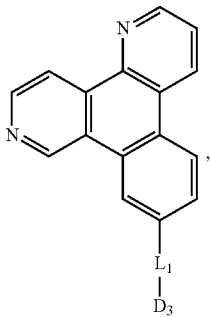
Compound 171
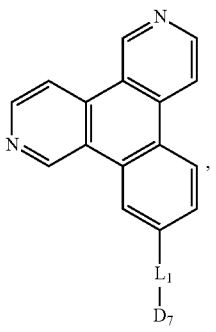
Compound 172
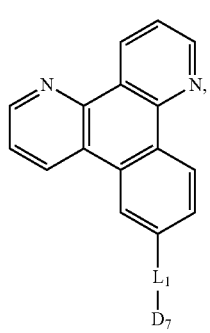
Compound 173
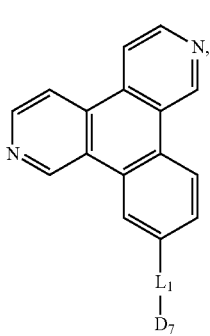
Compound 174
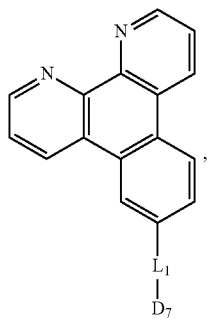
Compound 175
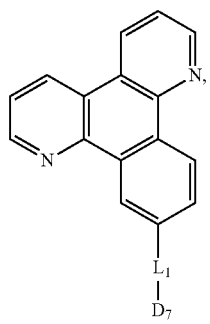
Compound 176
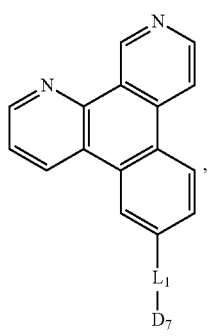
Compound 177
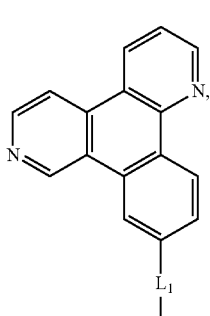
Compound 178
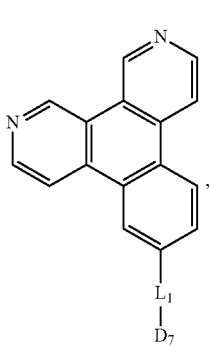

Compound 179
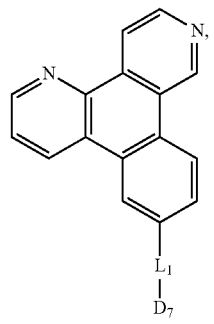
Compound 180
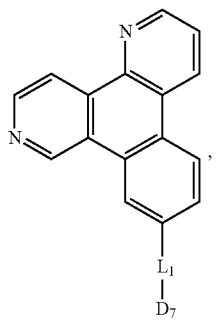
Compound 181
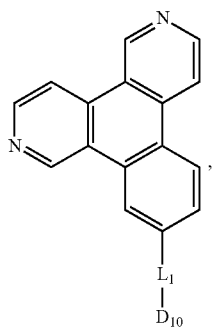
Compound 182
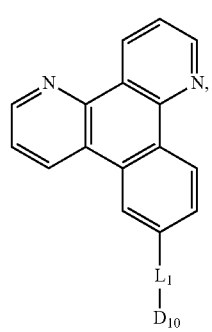
Compound 183
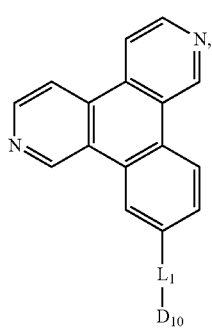
Compound 184
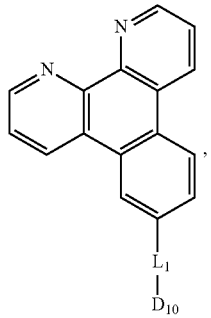
Compound 185
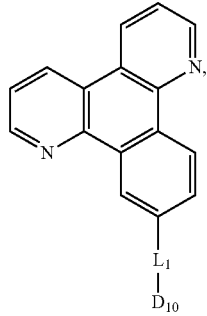
Compound 186
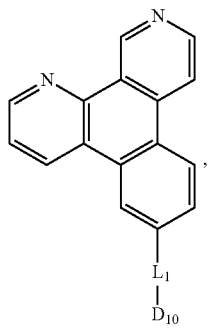
Compound 187
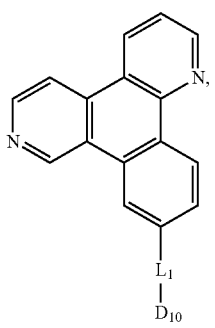
Compound 188
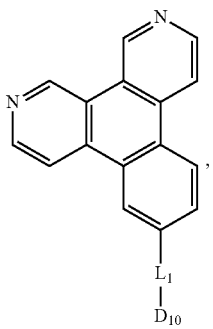

Compound 189
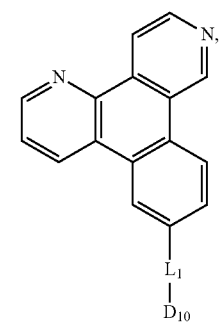
Compound 190
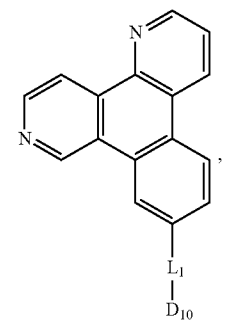
Compound 229
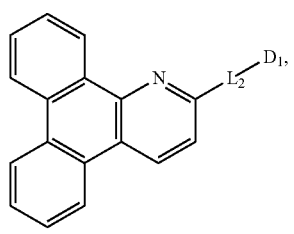
Compound 230
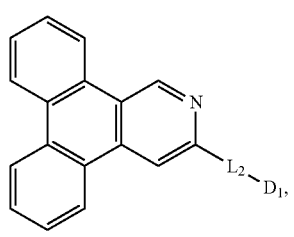
Compound 231
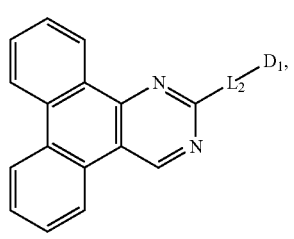
Compound 232
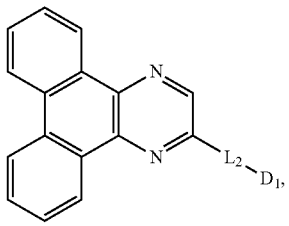
Compound 233
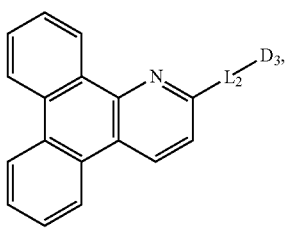
Compound 234
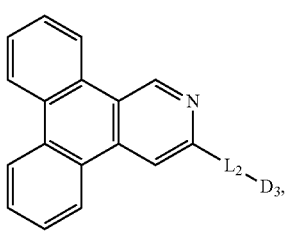
Compound 235
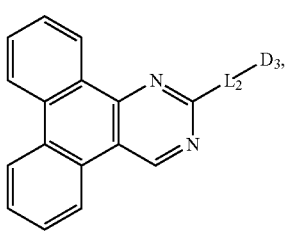
Compound 236
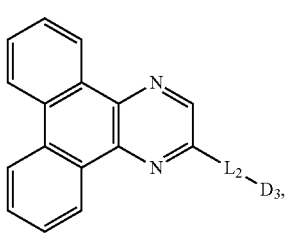
Compound 237

Compound 238
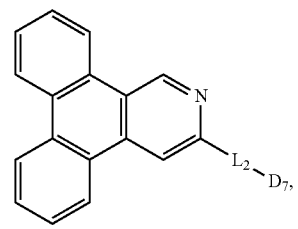
Compound 239
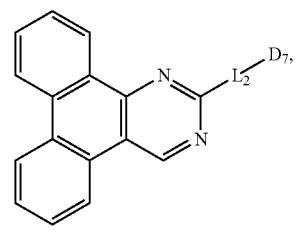
Compound 240
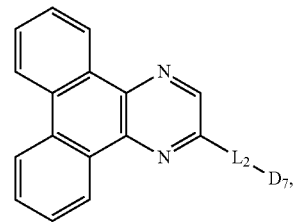
Compound 241
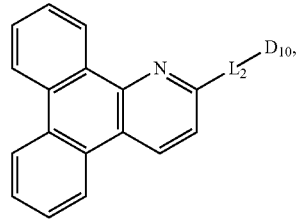
Compound 242
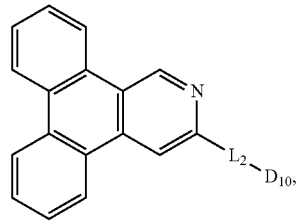
Compound 243
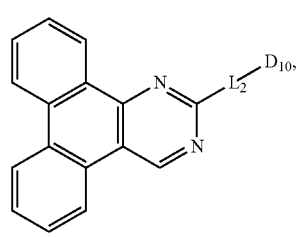
Compound 244
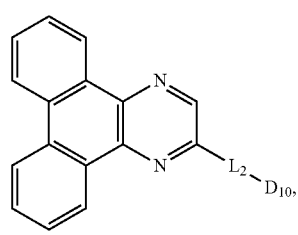
Compound 245
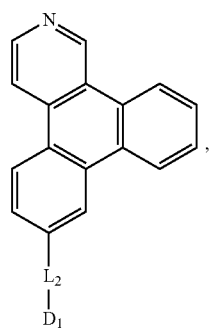
Compound 246
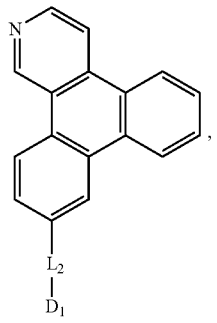
Compound 247
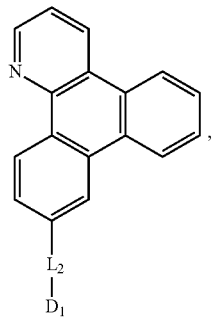
Compound 248
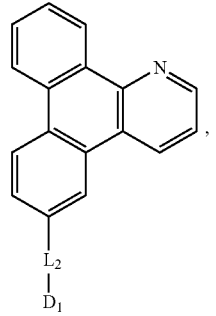
Compound 249

Compound 250
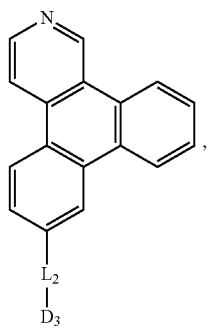
Compound 251
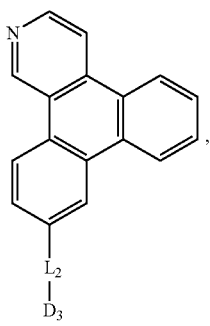
Compound 252
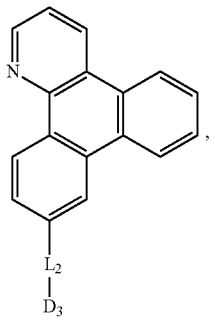
Compound 253
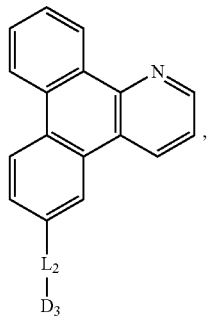
Compound 254
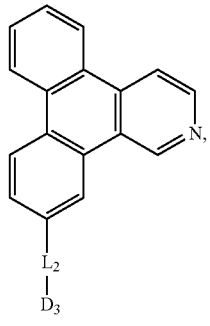
Compound 255
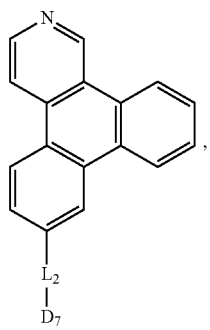
Compound 256
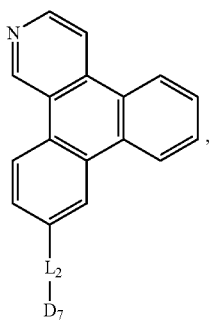
Compound 257
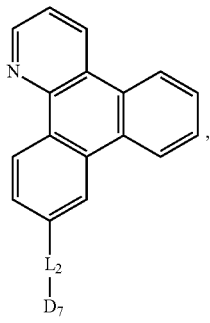
Compound 258
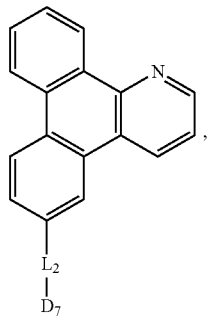
Compound 259
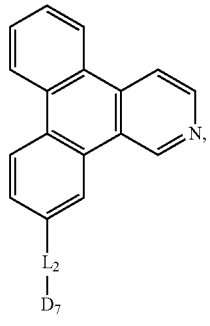

Compound 260
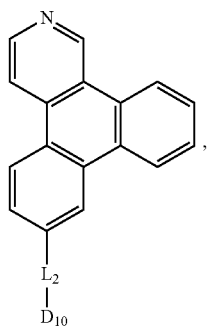
Compound 261
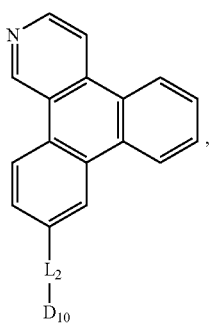
Compound 262
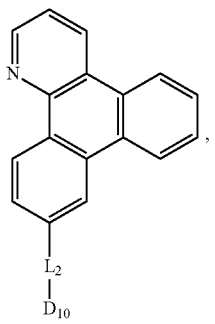
Compound 263
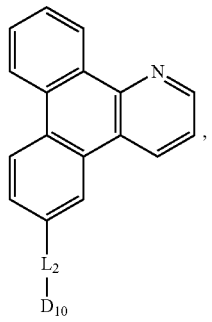
Compound 264
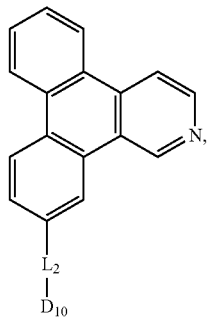
Compound 265
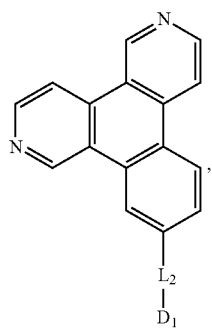
Compound 266
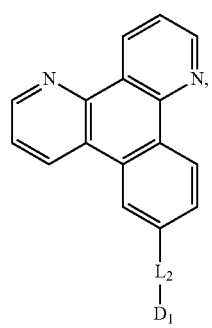
Compound 267
Compound 268
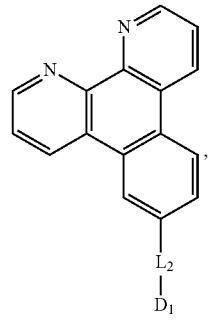
Compound 269

Compound 270
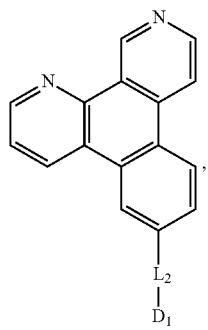
Compound 271
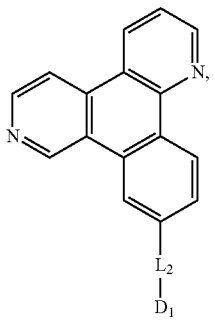
Compound 272
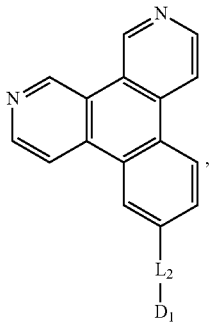
Compound 273
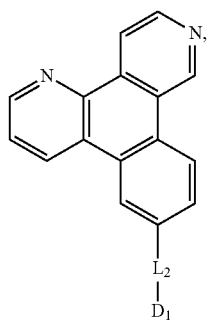
Compound 274
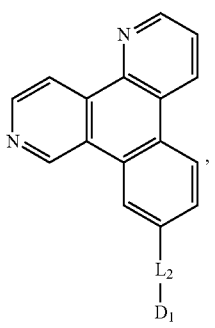
Compound 275
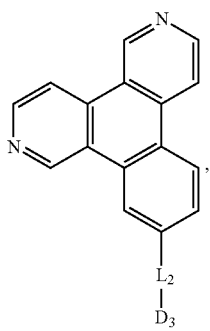
Compound 276
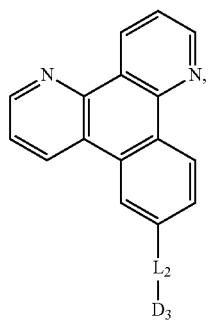
Compound 277
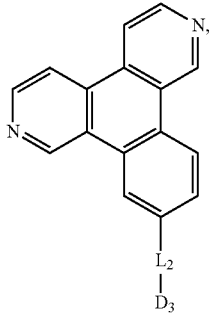
Compound 278
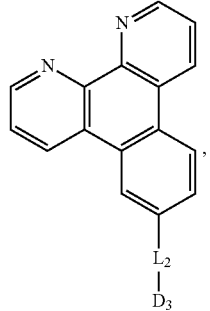
Compound 279
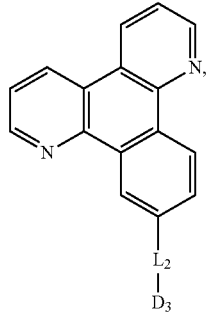

Compound 280
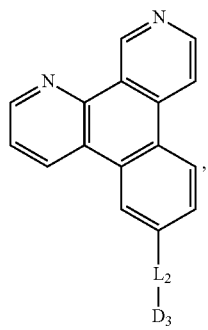
Compound 281
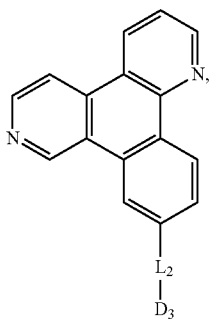
Compound 282
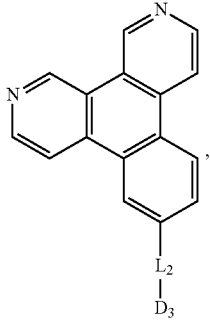
Compound 283
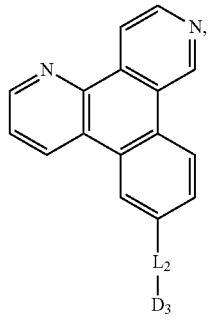
Compound 284
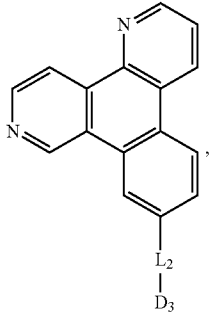
Compound 285
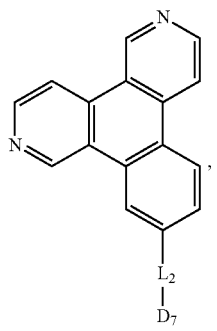
Compound 286
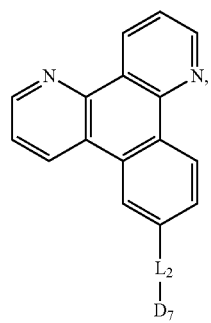
Compound 287
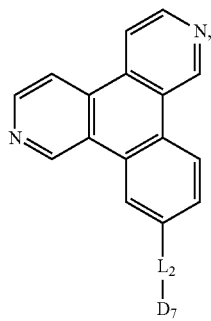
Compound 288
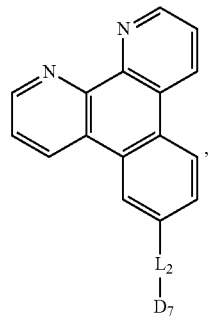
Compound 289
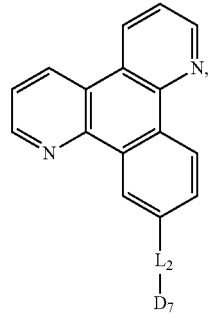

-continued
Compound 290
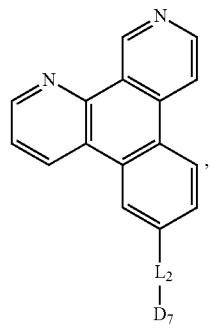
L₂—D₇
Compound 291
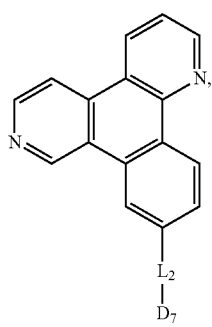
L₂—D₇
Compound 292
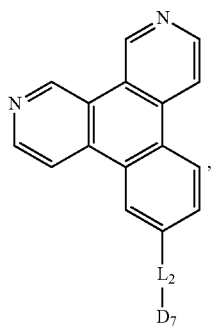
L₂—D₇
Compound 293
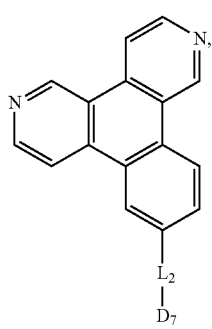
L₂—D₇
Compound 294
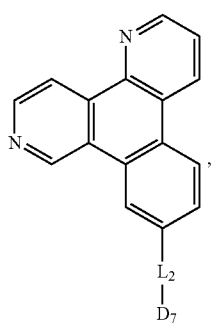
L₂—D₇
-continued
Compound 295
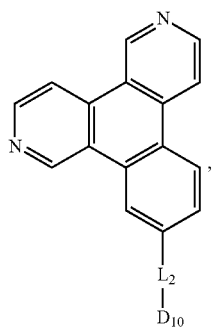
L₂—D₁₀
Compound 296
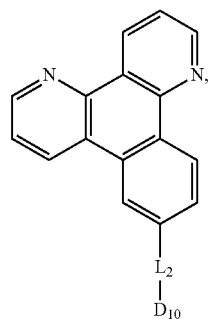
L₂—D₁₀
Compound 297
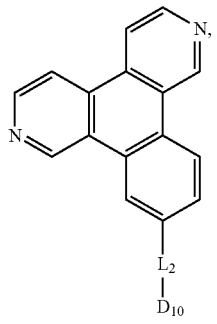
L₂—D₁₀
Compound 298

L₂—D₁₀
Compound 299

L₂—D₁₀

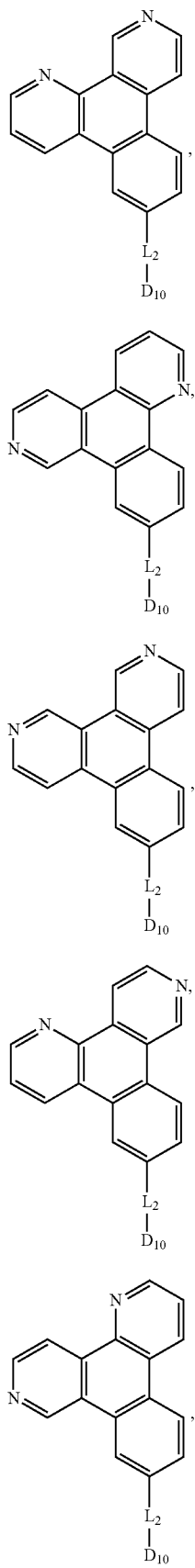
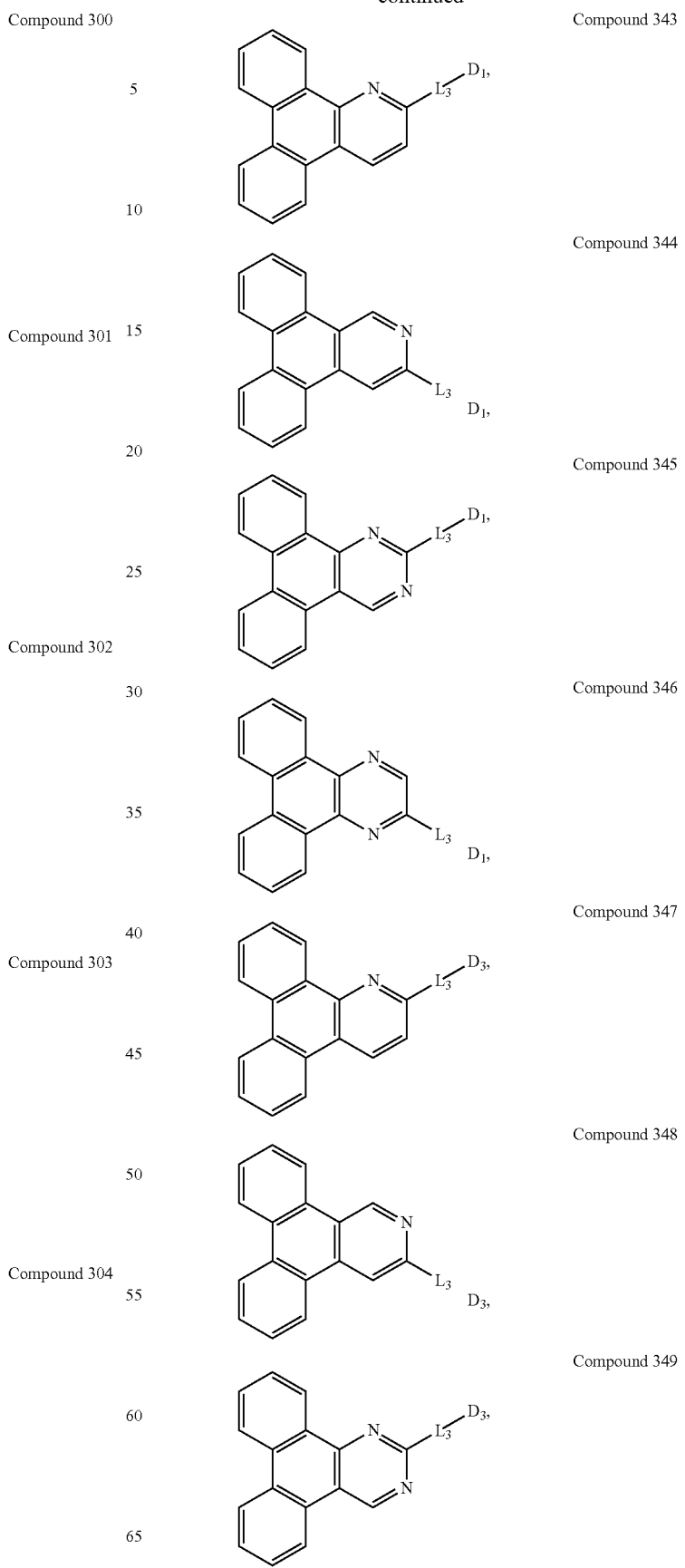

-continued
Compound 350
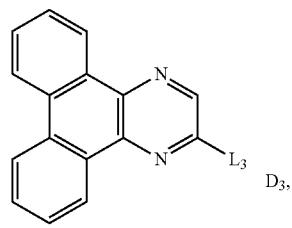
D₃,
Compound 351
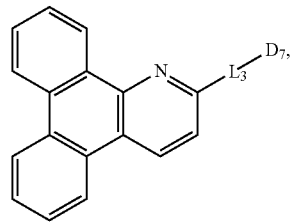
D₇,
Compound 352
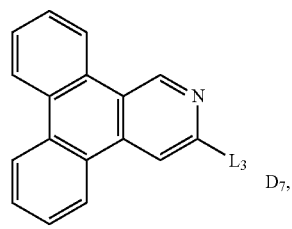
D₇,
Compound 353
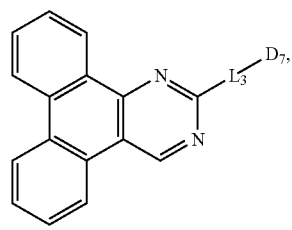
D₇,
Compound 354
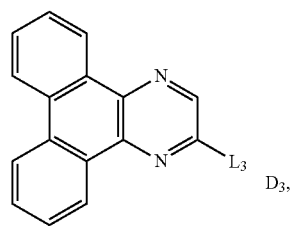
D₃,
Compound 355
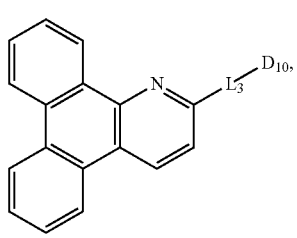
D₁₀,
Compound 356
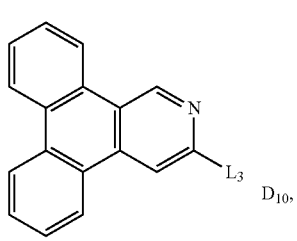
D₁₀,
-continued
Compound 357
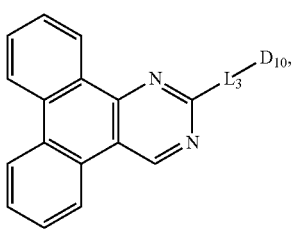
D₁₀,
Compound 358
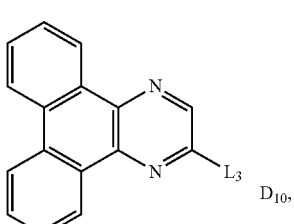
D₁₀,
Compound 359
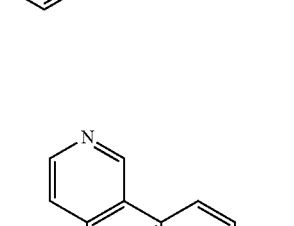
,
Compound 360
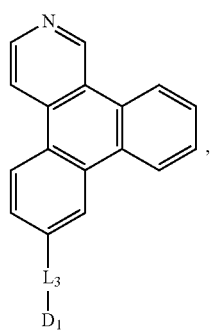
,
Compound 361
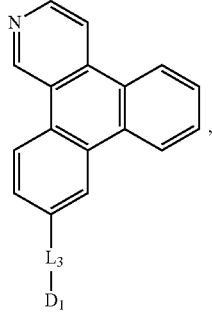
, Compound 362
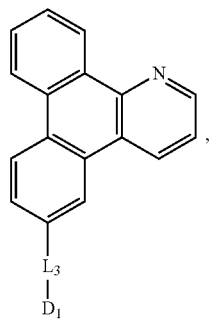
Compound 363
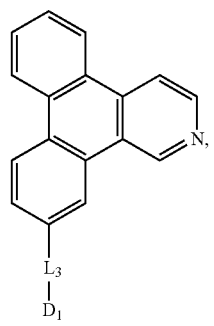
Compound 364
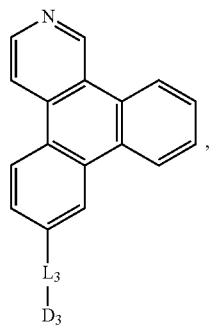
Compound 365
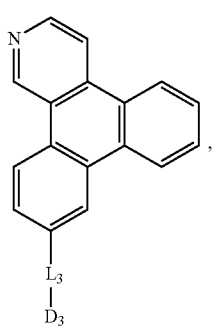
Compound 366
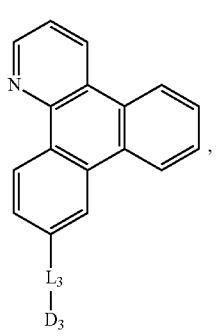
Compound 367
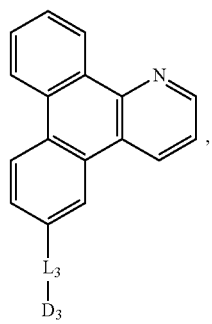
Compound 368
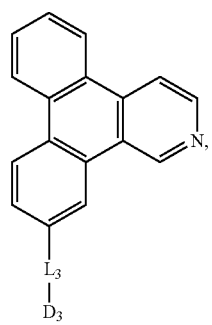
Compound 369
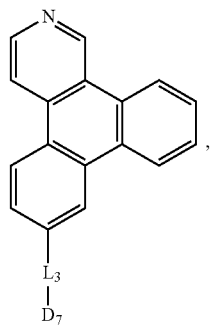
Compound 370
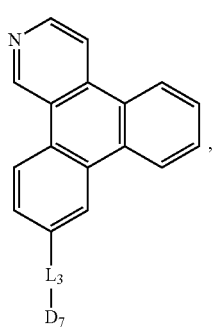
Compound 371
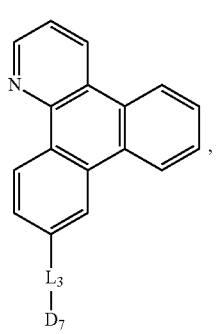

Compound 372
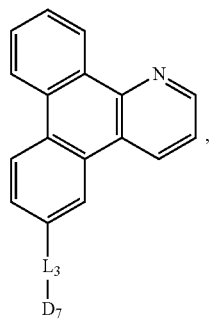
Compound 373
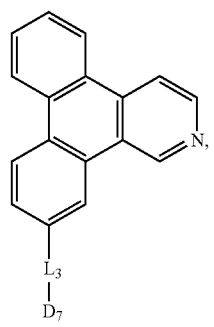
Compound 374
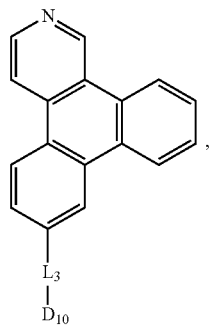
Compound 375
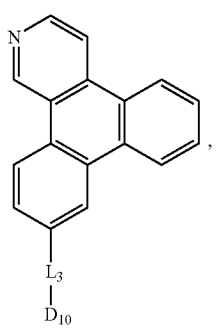
Compound 376
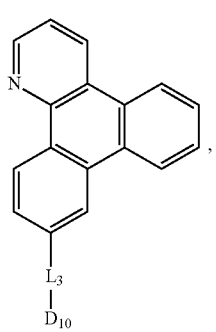
Compound 377
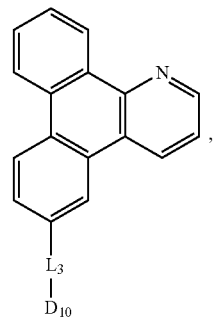
Compound 378
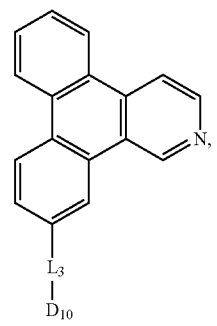
Compound 379
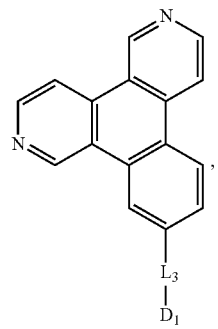
Compound 380
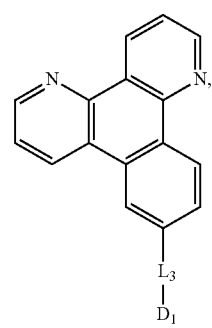
Compound 381
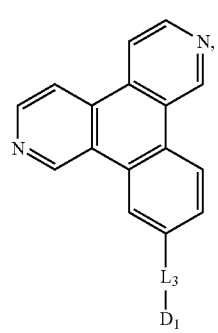

| Compound 382 | 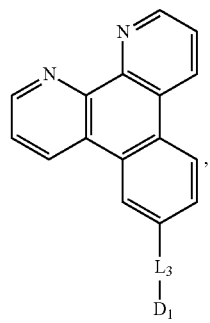 | Compound 387 | 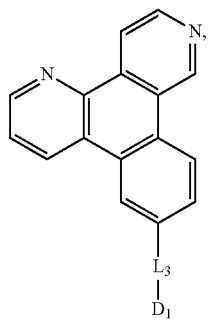 |
| Compound 383 | 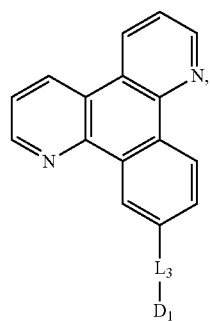 | Compound 388 | 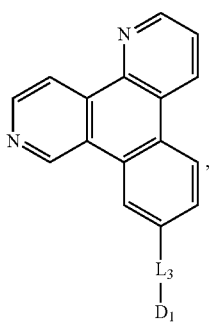 |
| Compound 384 | 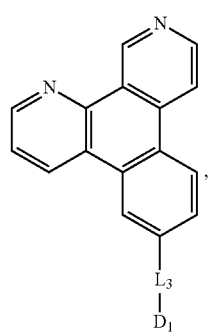 | Compound 389 | 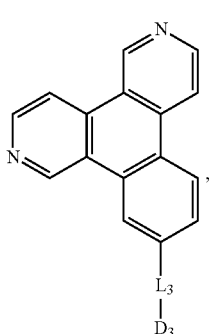 |
| Compound 385 | 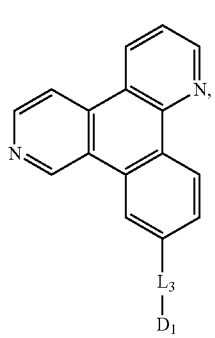 | Compound 390 | 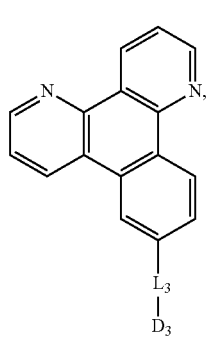 |
| Compound 386 | 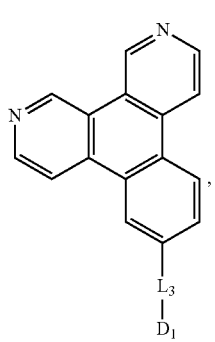 | Compound 391 | 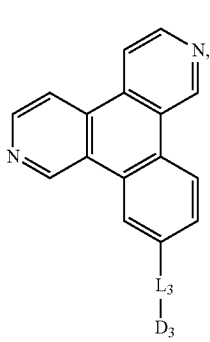 |

| | |
|---|---|
| Compound 392 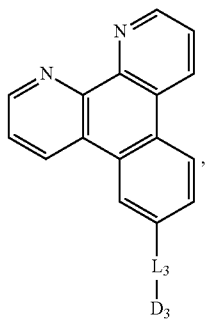 | Compound 397 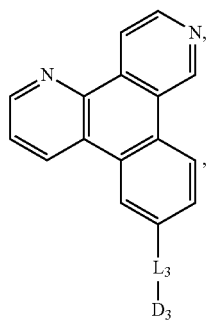 |
| Compound 393 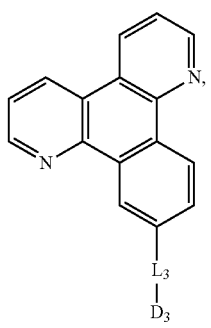 | Compound 398 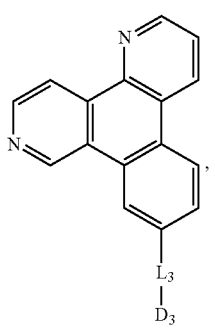 |
| Compound 394 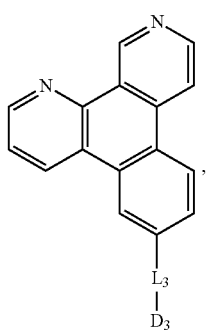 | Compound 399 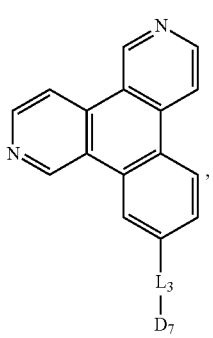 |
| Compound 395 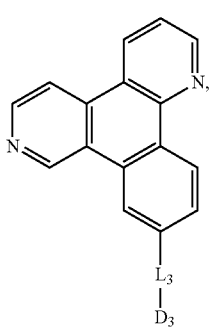 | Compound 400 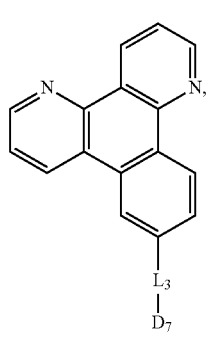 |
| Compound 396 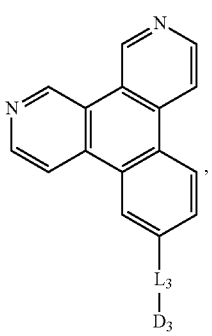 | Compound 401 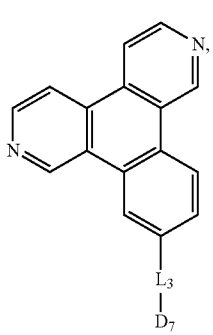 |

-continued
Compound 402
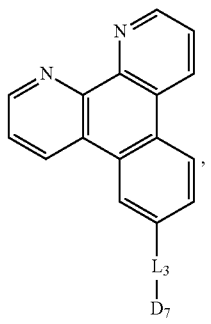
Compound 403
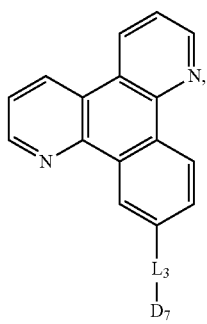
Compound 404
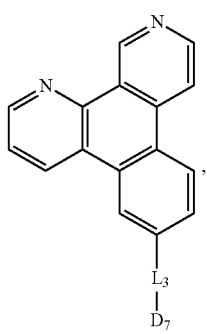
Compound 405
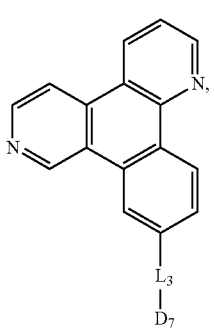
Compound 406
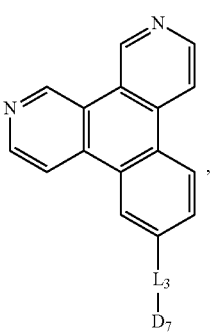
-continued
Compound 407
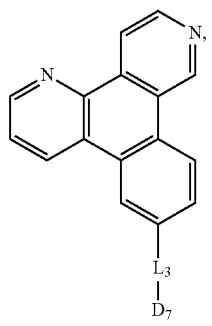
Compound 408
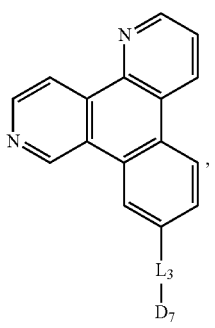
Compound 409
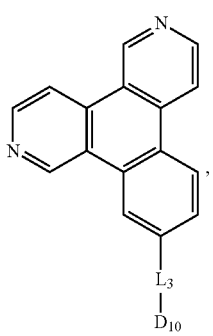
Compound 410

Compound 411
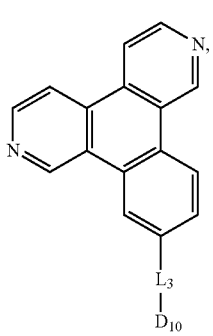

Compound 412
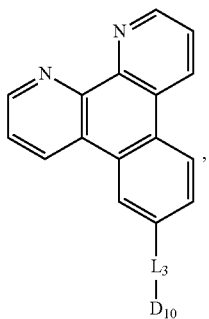
Compound 413
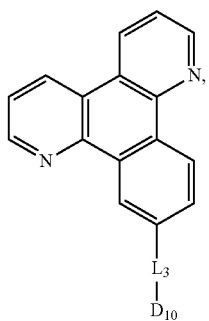
Compound 414
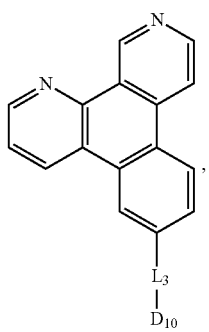
Compound 415
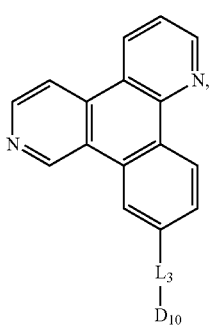
Compound 416
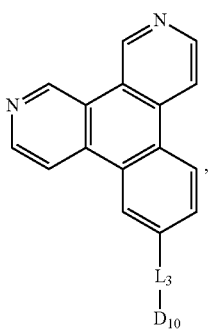
Compound 417
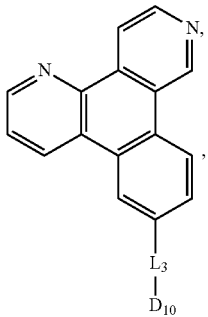
Compound 418
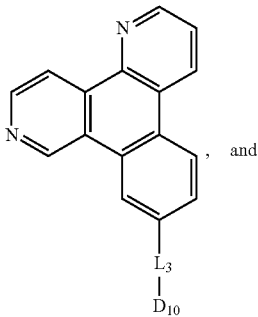
and
Compound 457
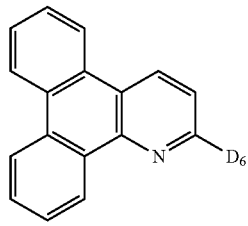
wherein D1, D3, D6, D7, and D10 are
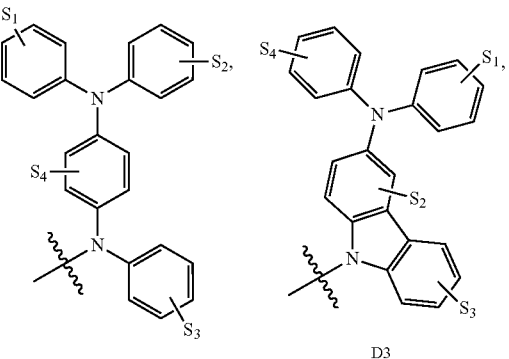
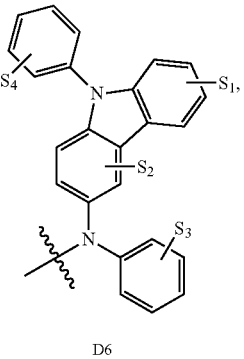
D6

-continued

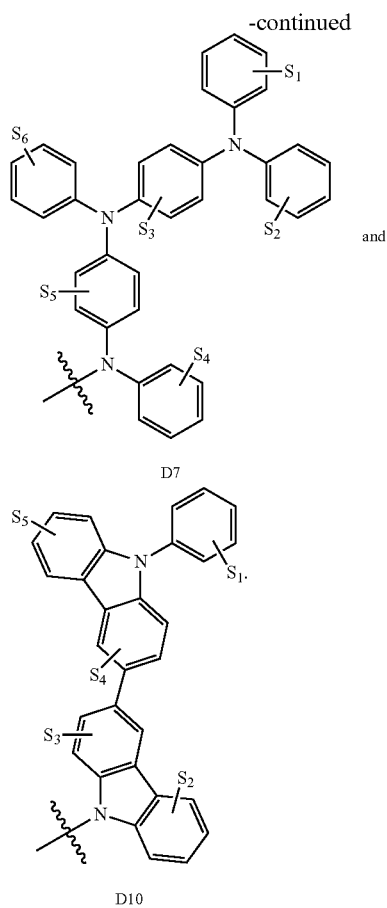

D7

D10

In other embodiments $S_1$ to $S_7$ and $A_1$-$A_2$ are H. The resulting compounds are denoted as Compound No.-H. For example, Compound 1-H is Compound 1-H

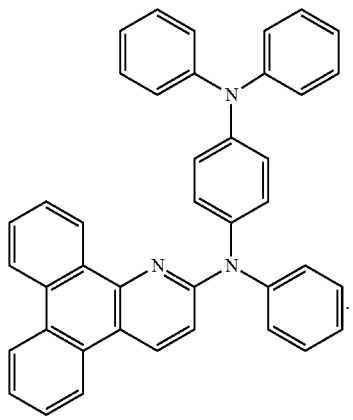

According to another embodiment, the donor-acceptor compound has the structure according to Formula 1 as defined above but at least one of the R comprises a donor group with at least one electron-donating nitrogen.

According to another aspect of the present disclosure, a first device that includes a first organic light emitting device is provided. The organic light emitting device includes an anode, a cathode, and an organic emissive layer disposed between the anode and the cathode. The organic emissive layer comprises a first emitting compound having the structure according to Formula 1, and its variations as described herein.

The first emitting compound has the structure according to the formula:

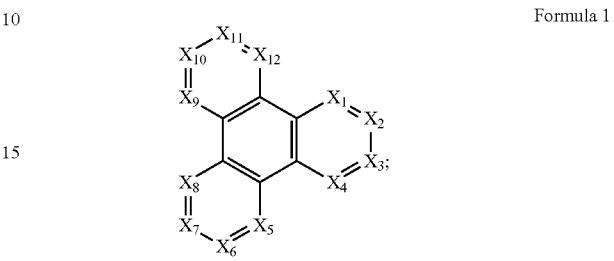

Formula 1 wherein $X_1$ to $X_{12}$ is independently selected from the group consisting of C—R and N;

at least one of $X_1$ to $X_{12}$ is N;

each R is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and wherein at least one of the R comprises a donor group with at least one electron-donating nitrogen.

In some specific embodiments, the first emitting compound is selected from the group consisting of Formula 2

Formula 3

Formula 4
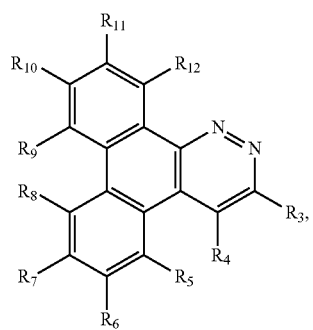
Formula 5
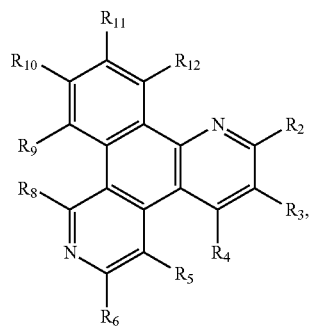
Formula 6
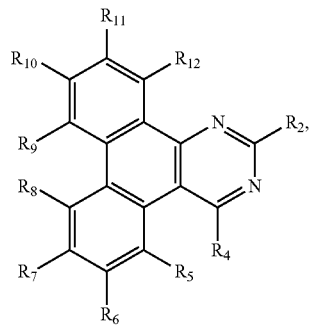
Formula 7
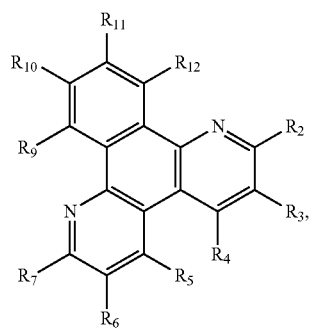
Formula 8
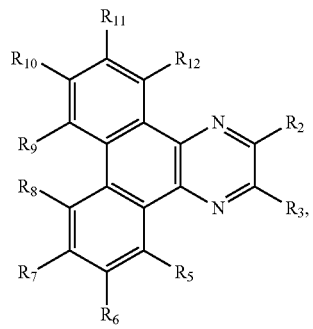
Formula 9
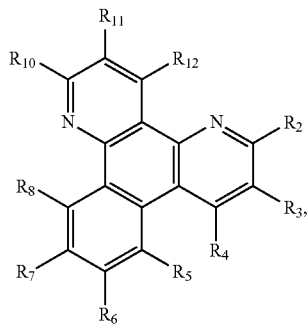
Formula 10
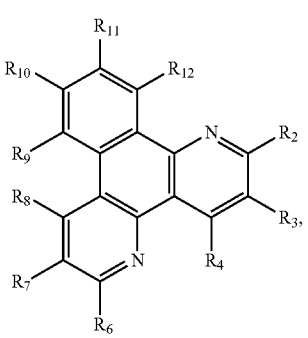
Formula 11
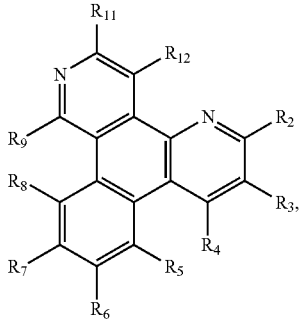
Formula 12
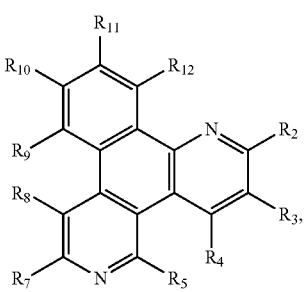
Formula 13
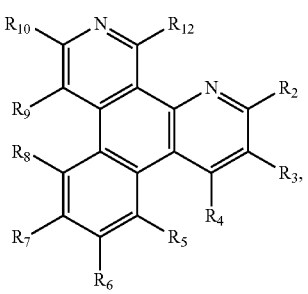

-continued

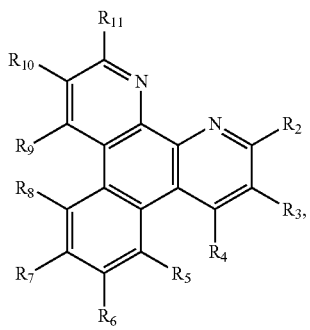
Formula 14

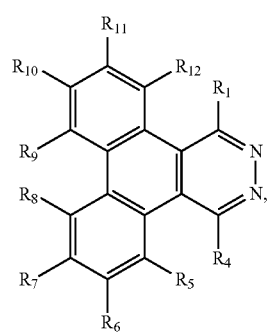
Formula 15

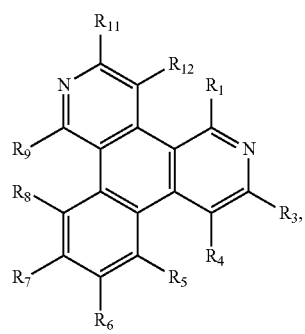
Formula 16

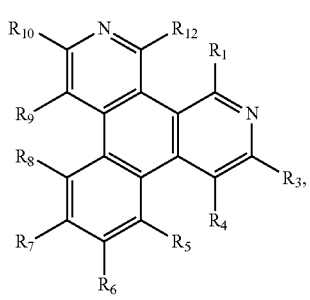
Formula 17

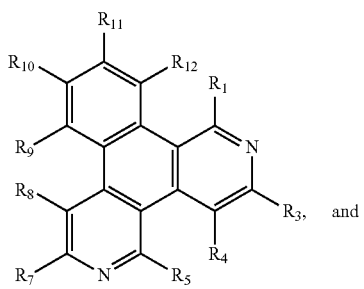
Formula 18 and

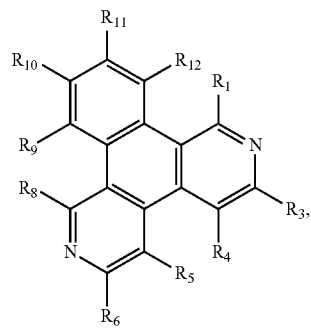
Formula 19 wherein $R_1$ to $R_{12}$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;

at least one of $R_1$ to $R_{12}$ is $$(L)_m\text{---}(Donor)_n;$$

wherein L is a linker,
m is 1 or 0,
$n \geq 1$; and
wherein Donor is an electron donating group containing at least one electron-donating nitrogen and Donors can be different when n>1.

In some embodiments, the Donor is selected from the group consisting of:

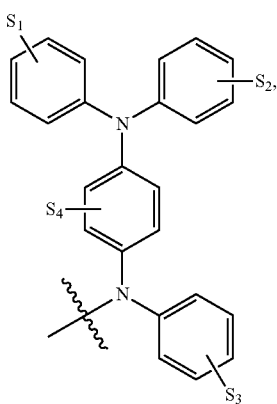
D1

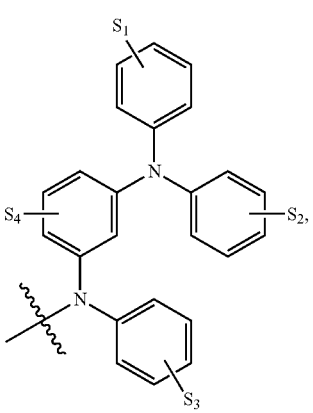
D2
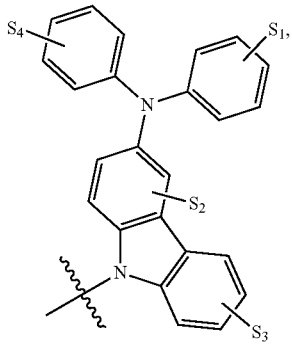
D3
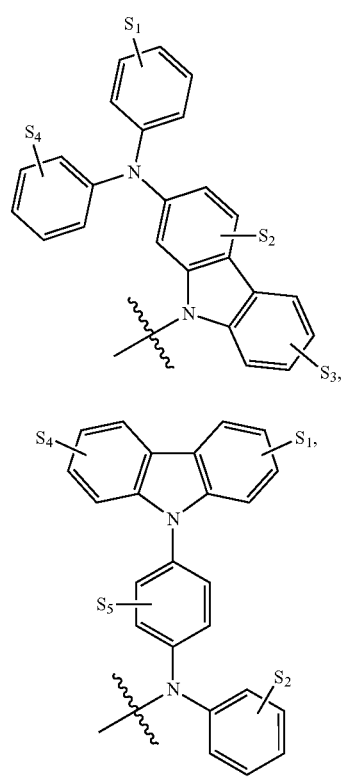
D4
D5
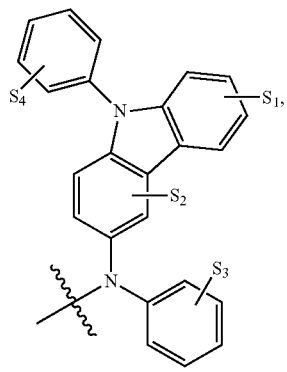
D6
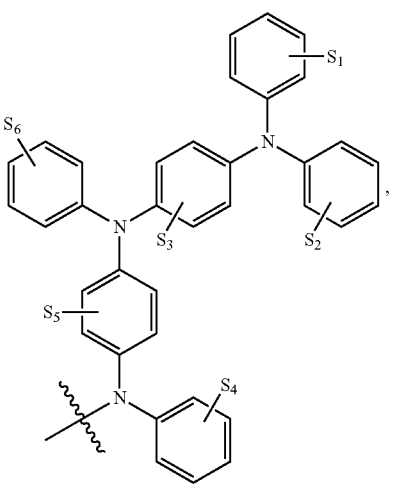
D7
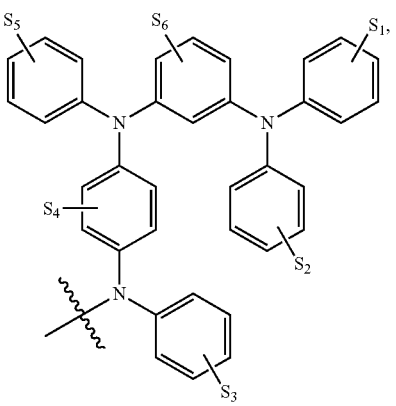
D8

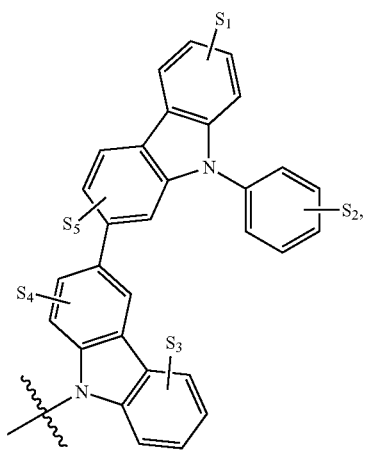
D9
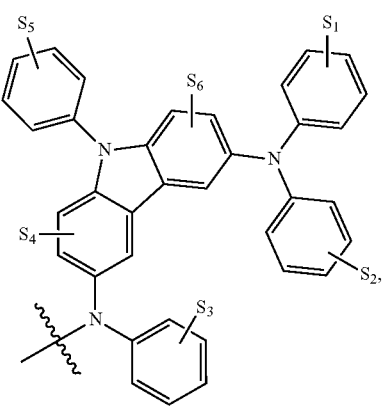
D12
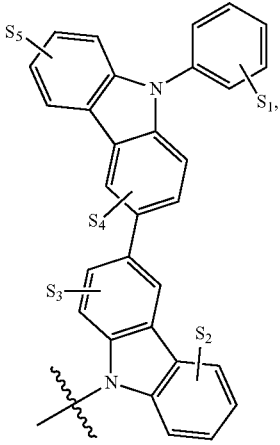
D10
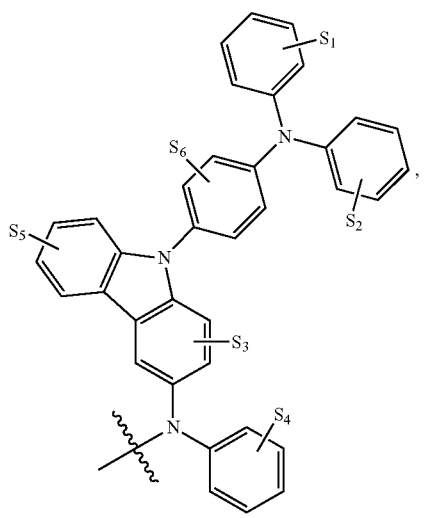
D13
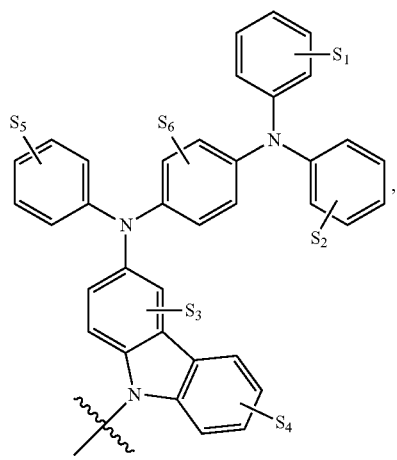
D11
D14

-continued
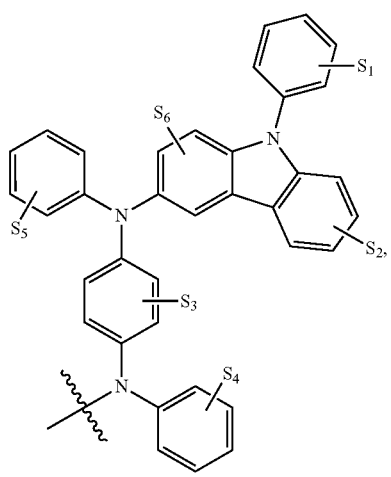
D15
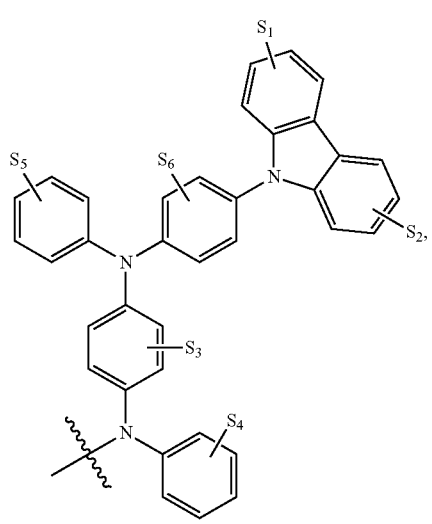
D16
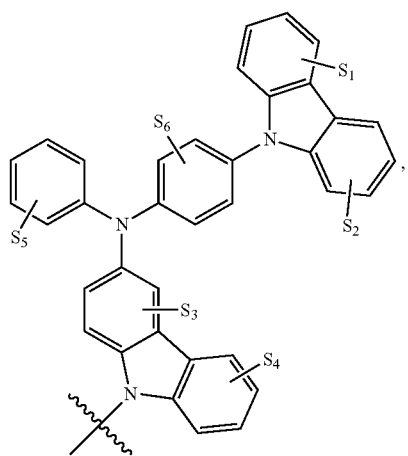
D17
-continued
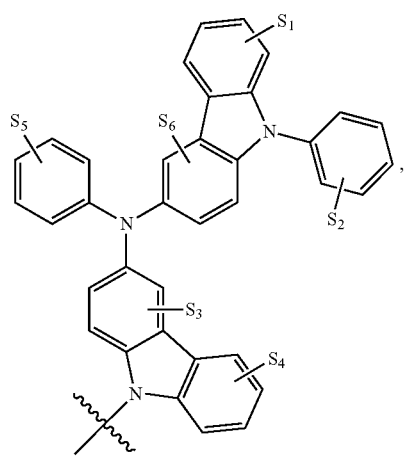
D18
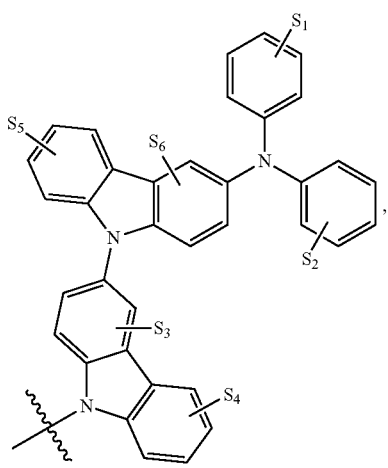
D19
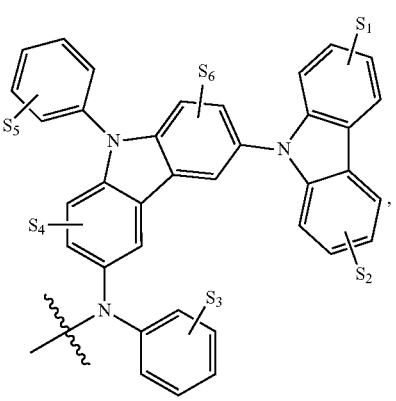
D20

-continued
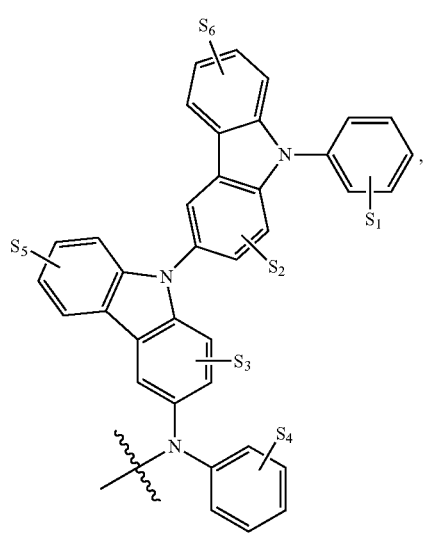 D21
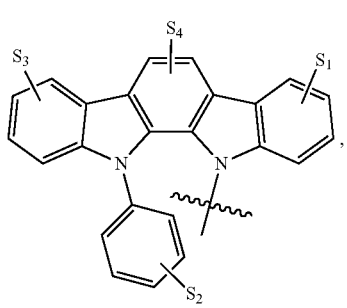 D24
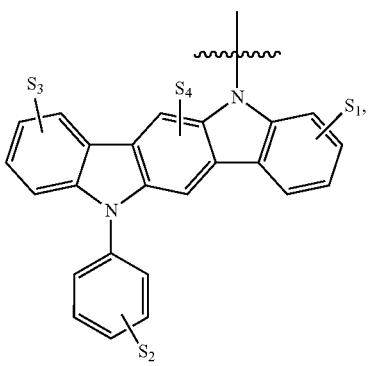 D25
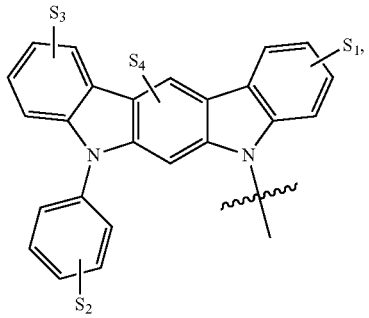 D22
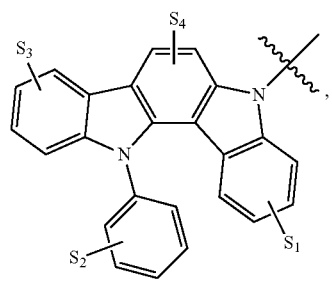 D26
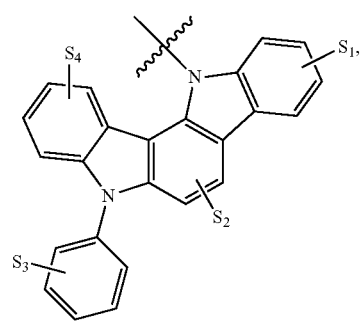 D23
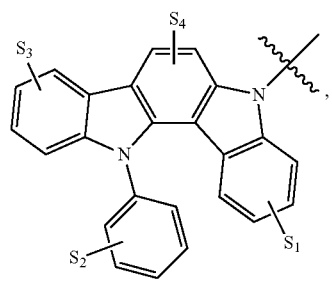 D27
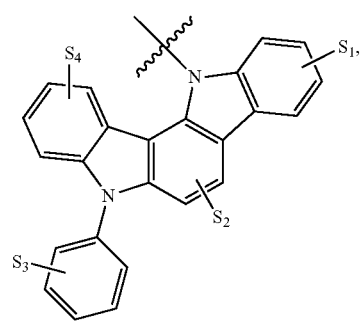 D28

D29 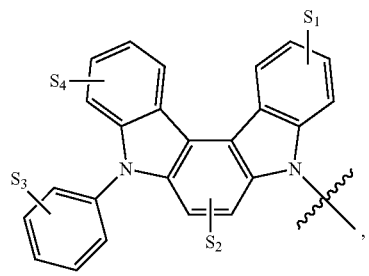
D30 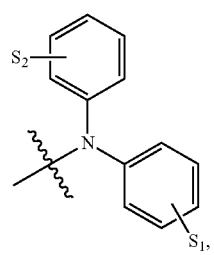
D31 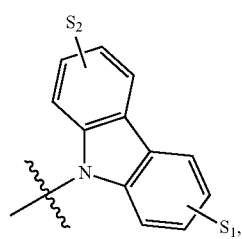
D32 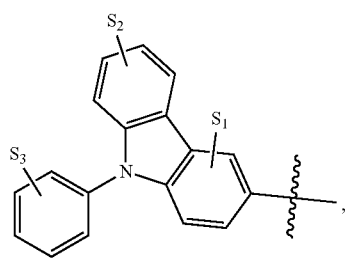
D33 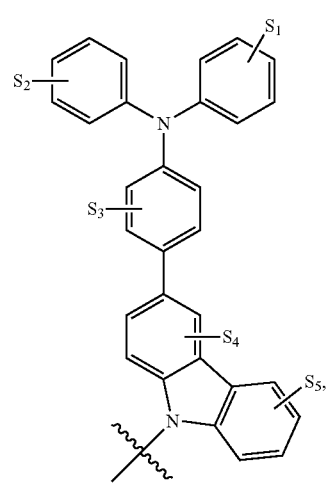
D34 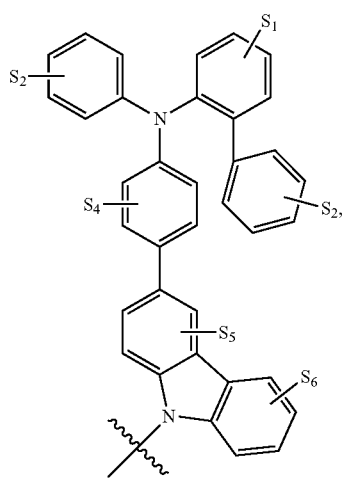
D35 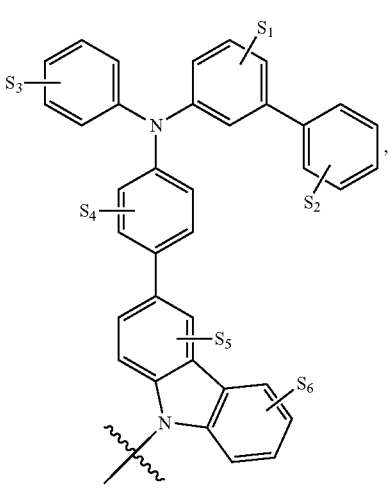
D36

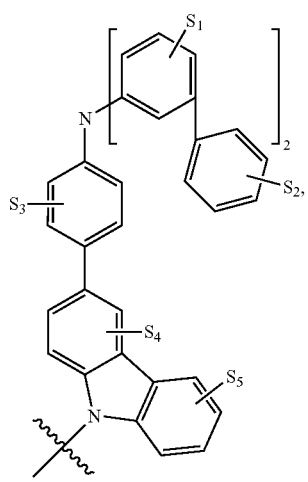
D37
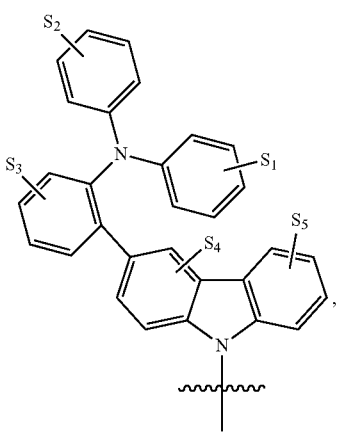
D40
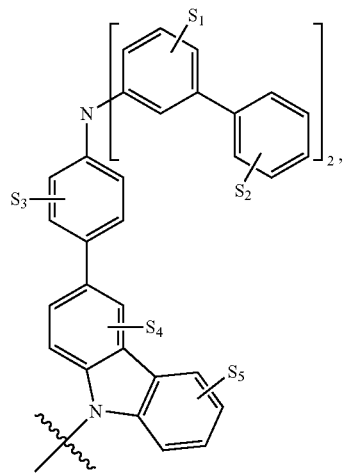
D38
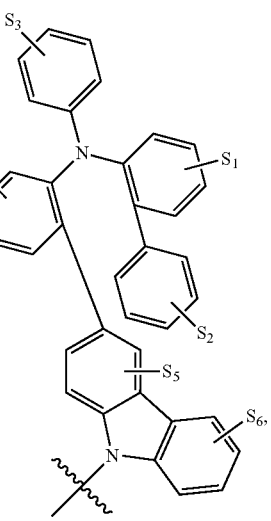
D41
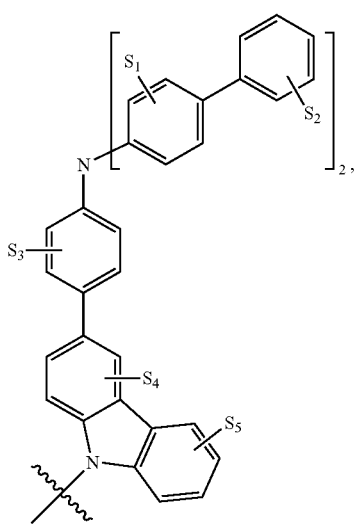
D39
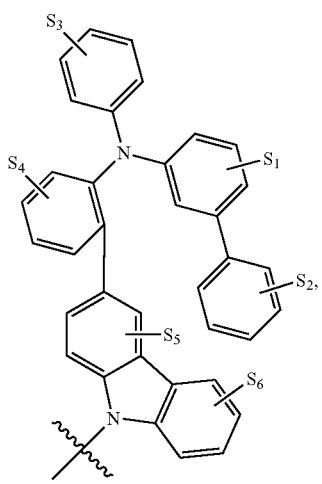
D42

D43
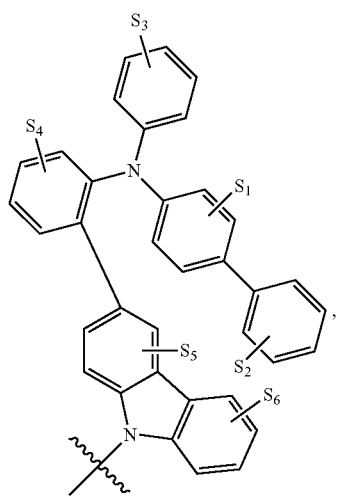
D44
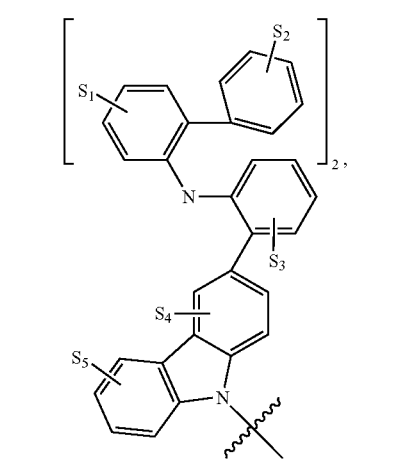
D45
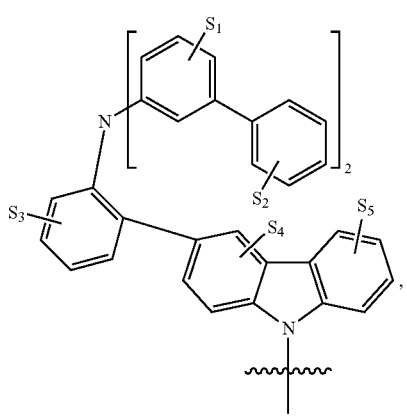
D46
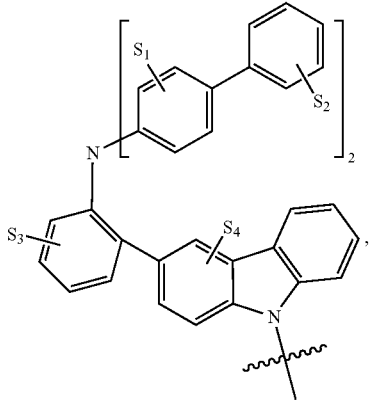
D47
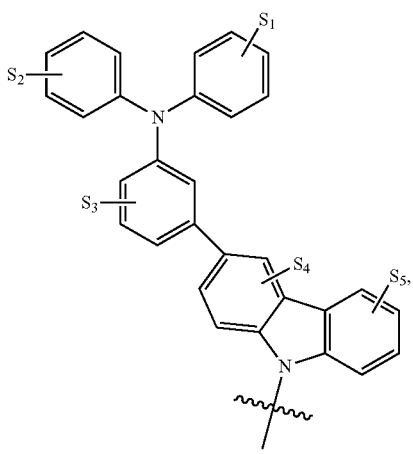
D48
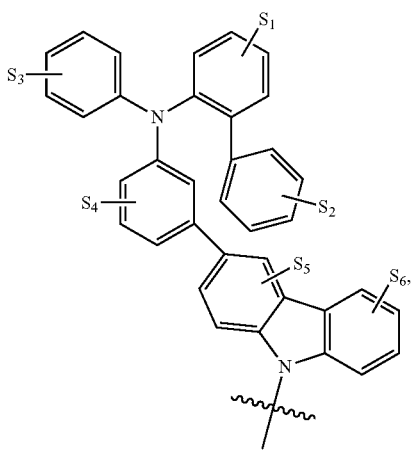

D49
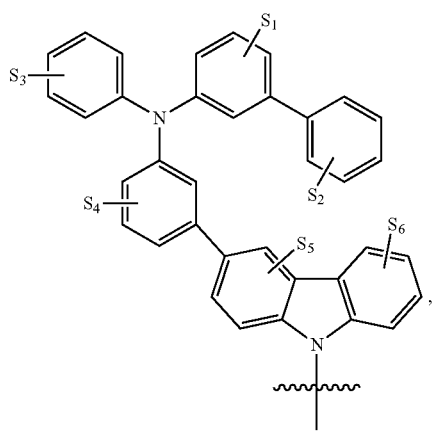
D50
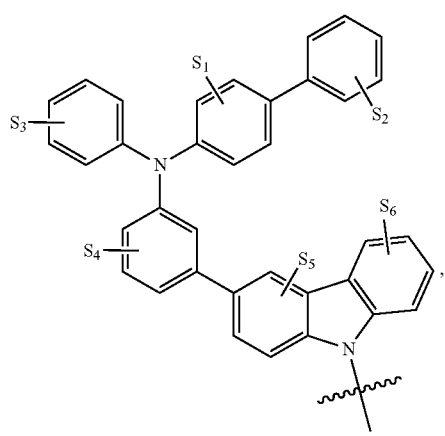
D51
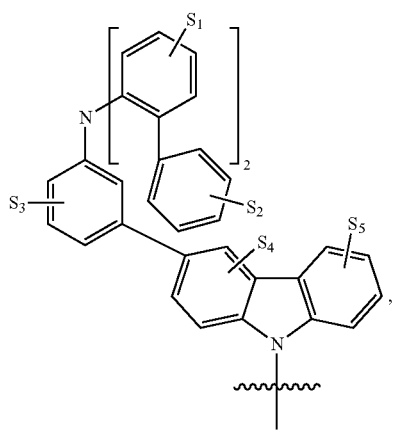
D52
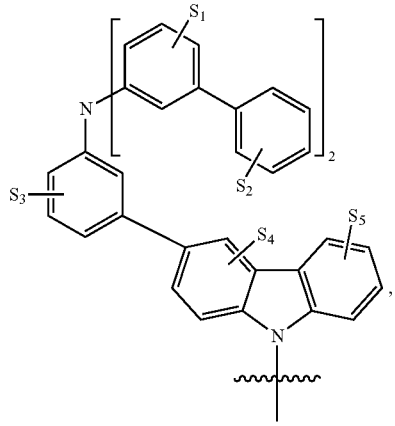
D53
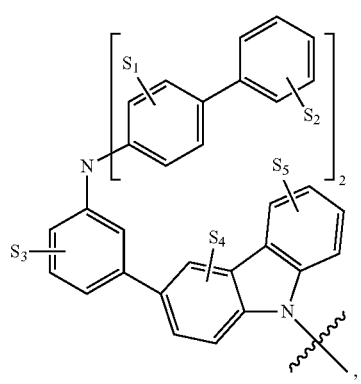
D54
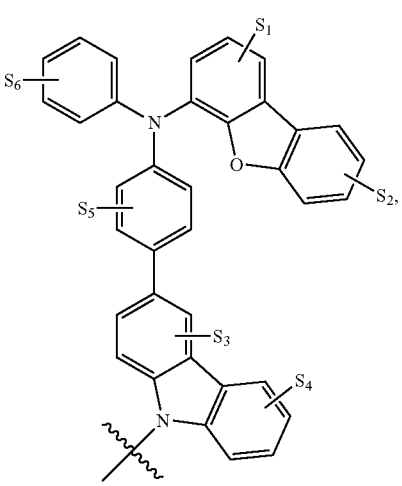

D55
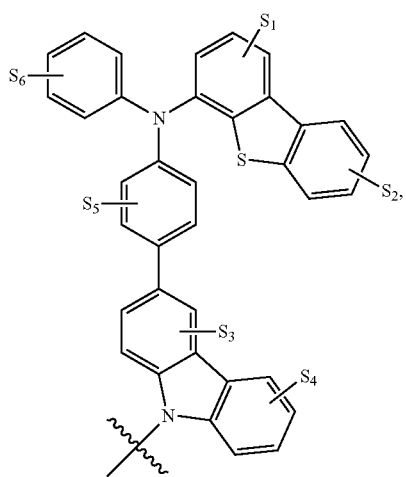
D56
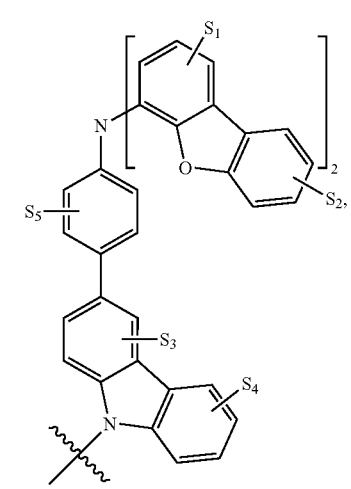
D57
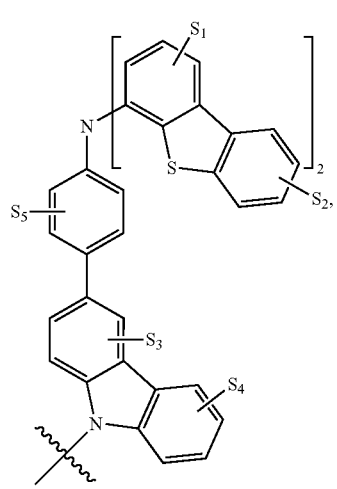
D58
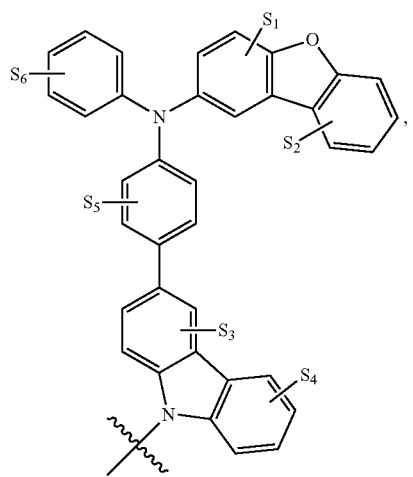
D59
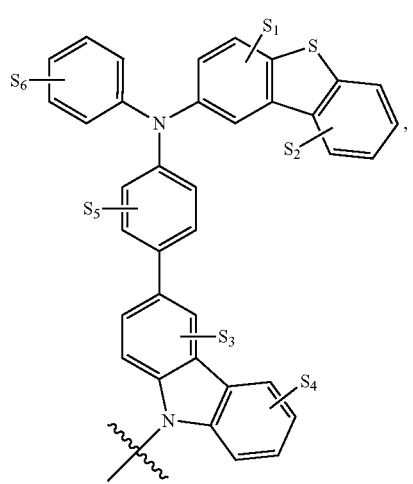
D60
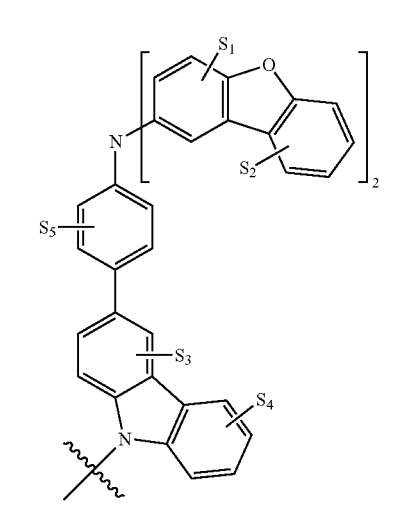

-continued
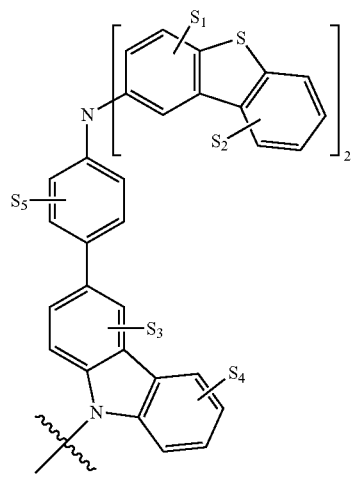
D61
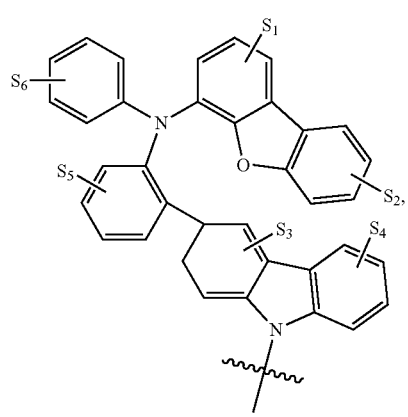
D62
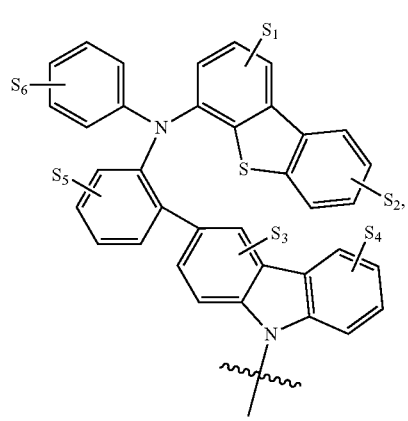
D63
-continued
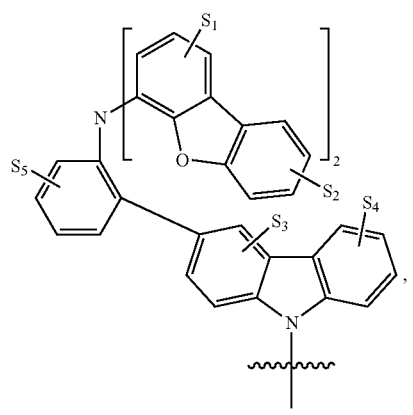
D64
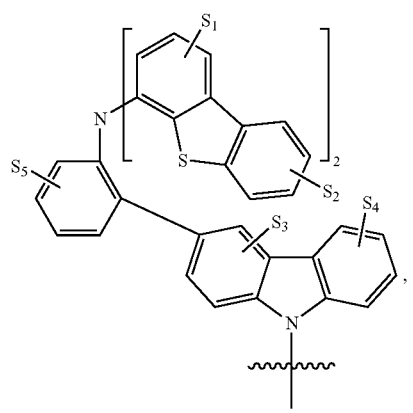
D65
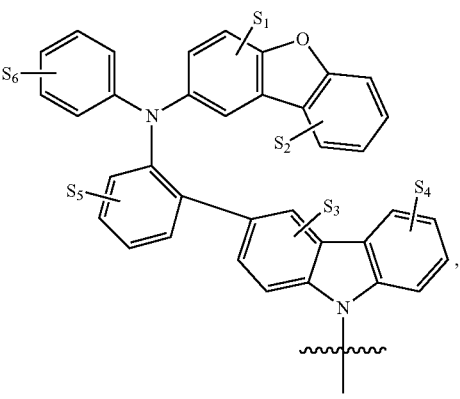
D66
D67

-continued
D68
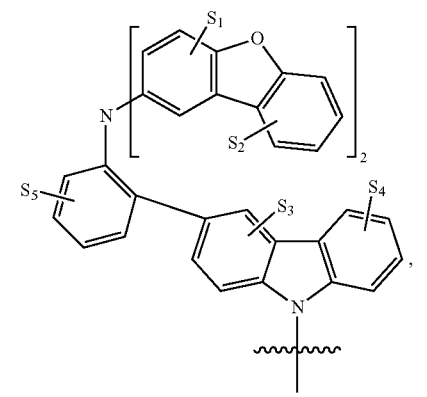
D69
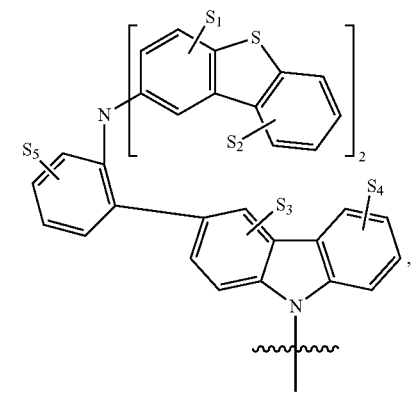
D70
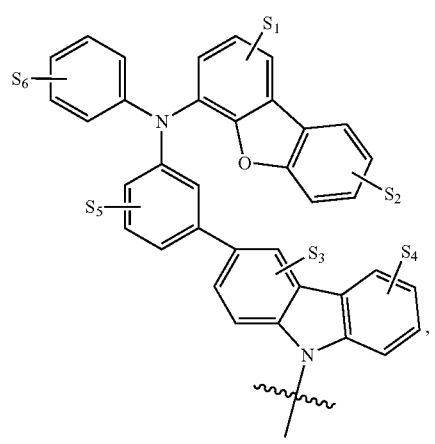
D71
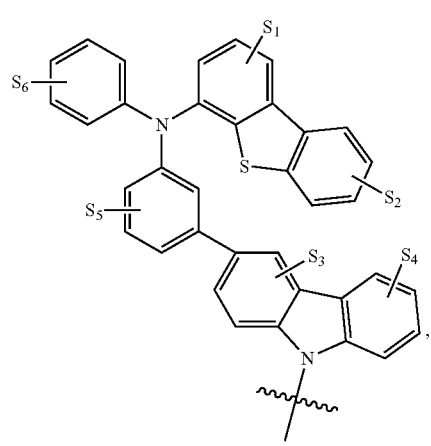
-continued
D72
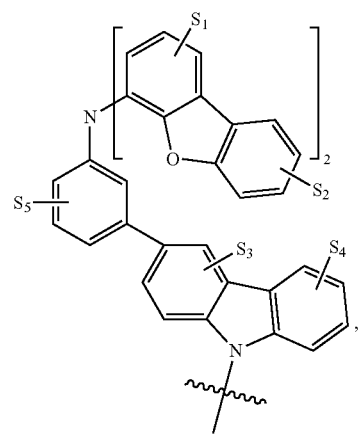
D73
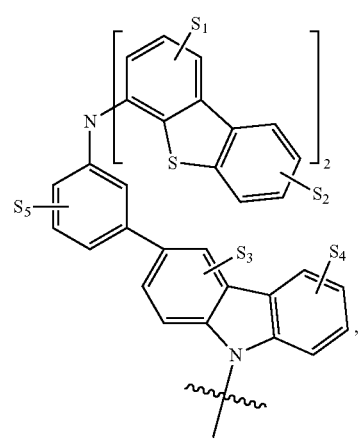
D74
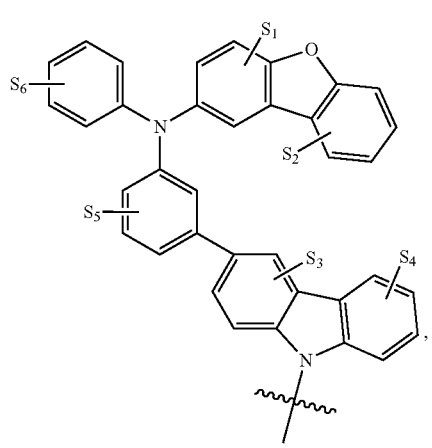

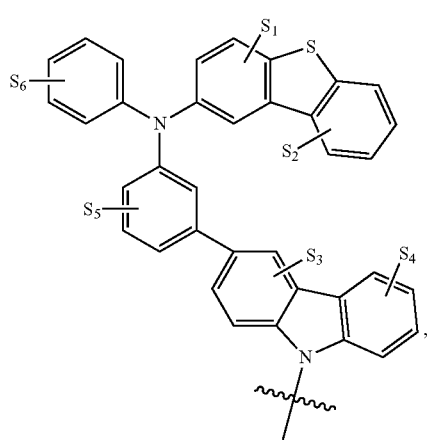 D75
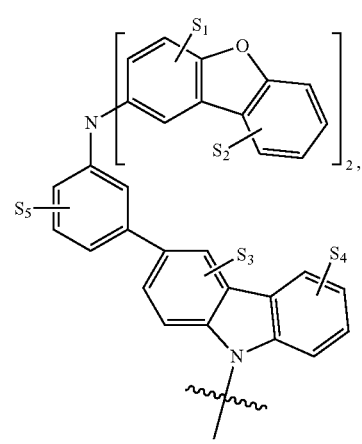 D76
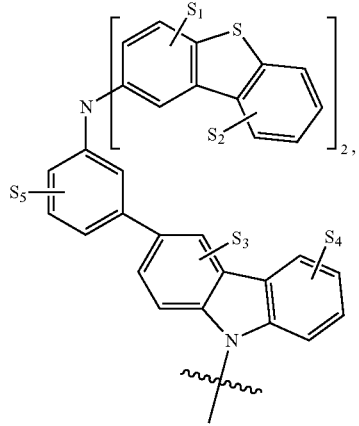 D77
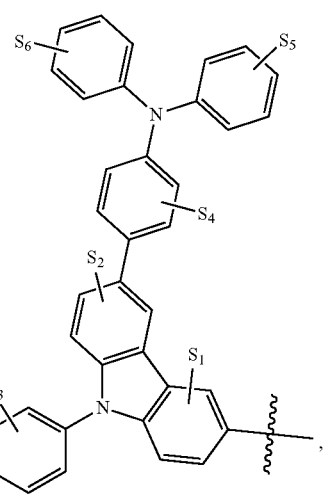 D78
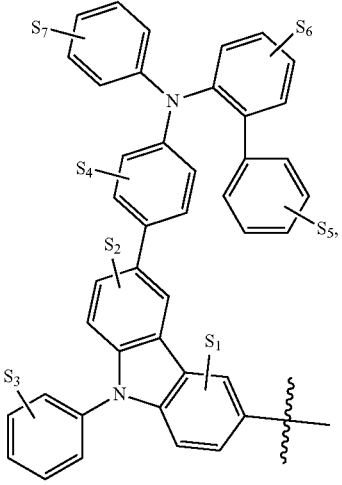 D79
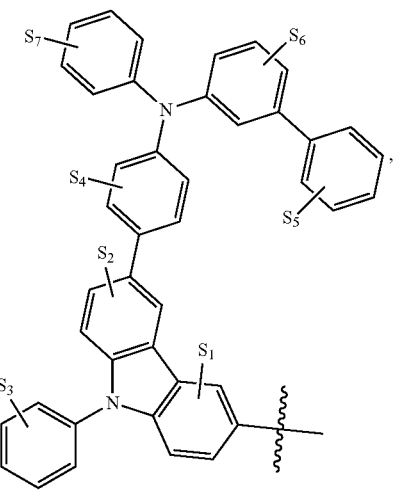 D80

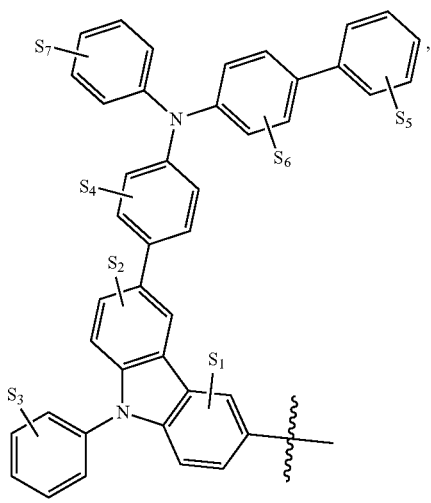
D81
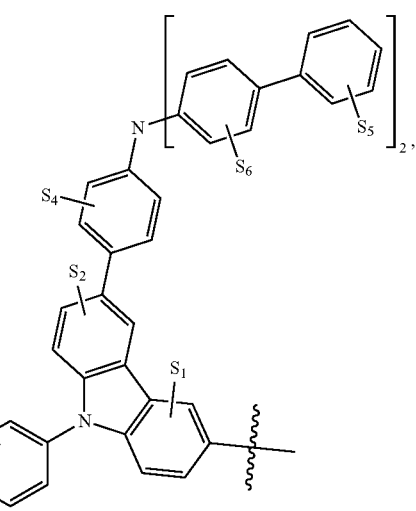
D84
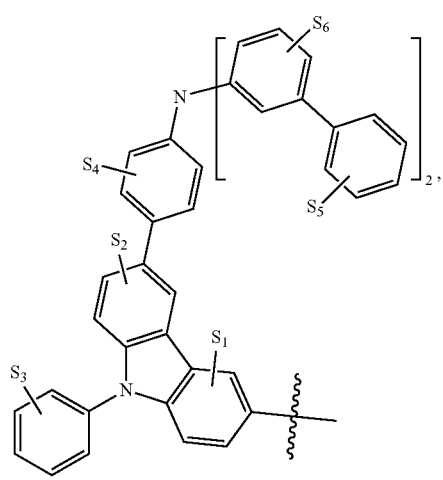
D82
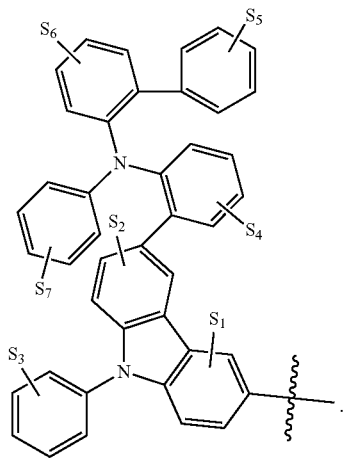
D85
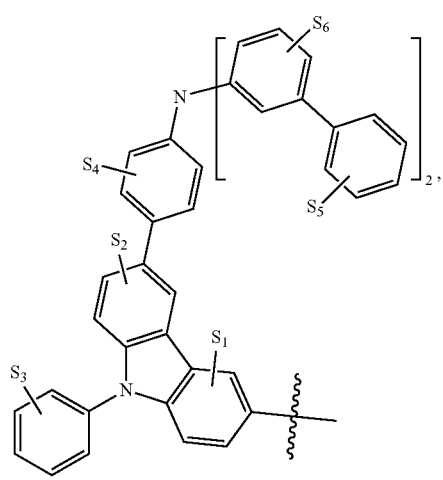
D83
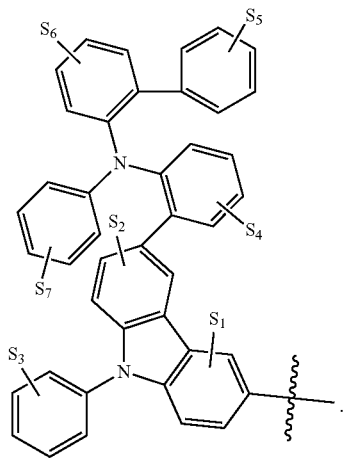
D86

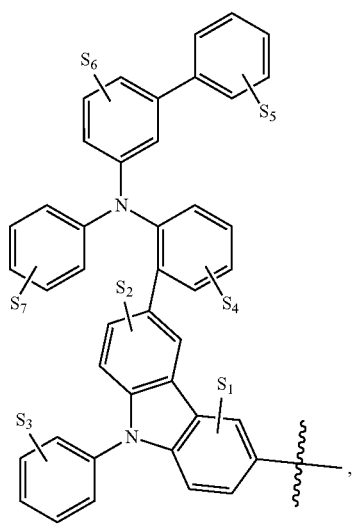
D87
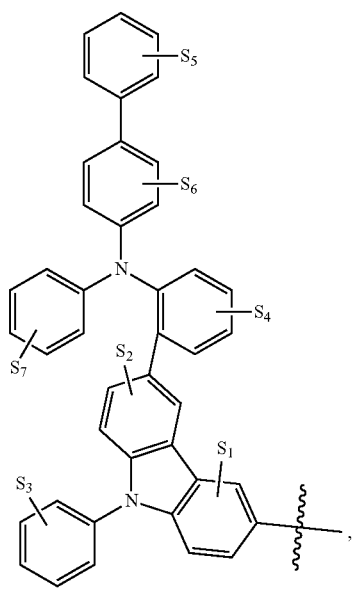
D88
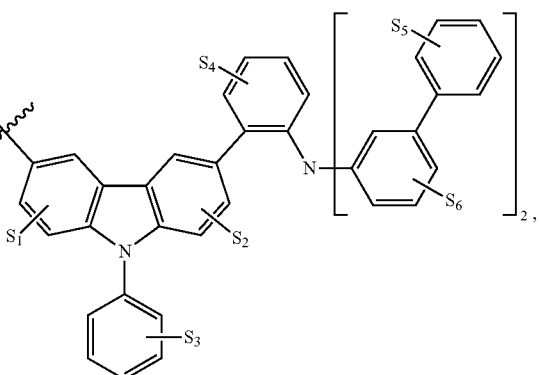
D89
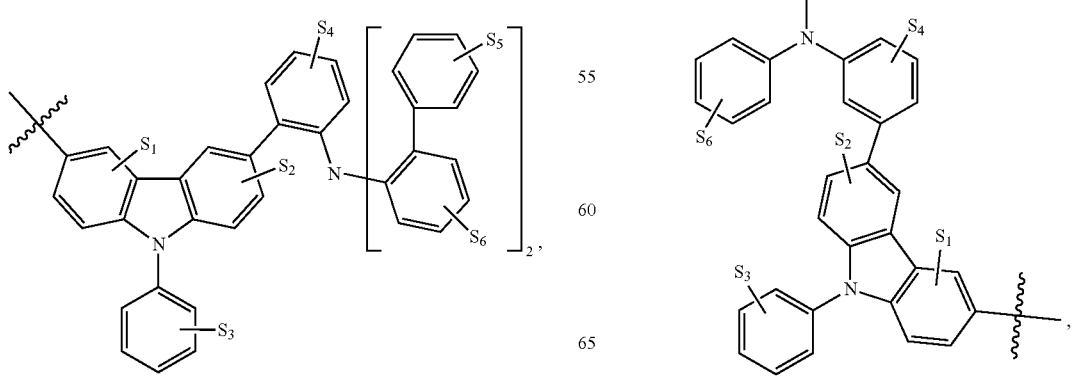

149
-continued
D93
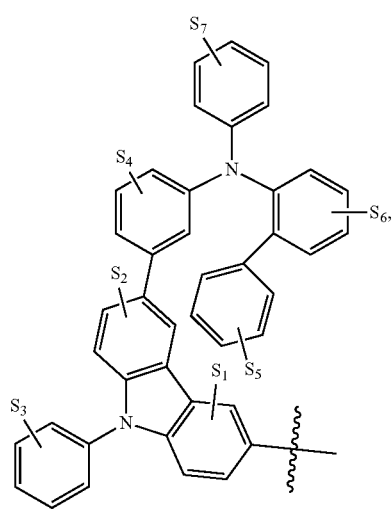
D94
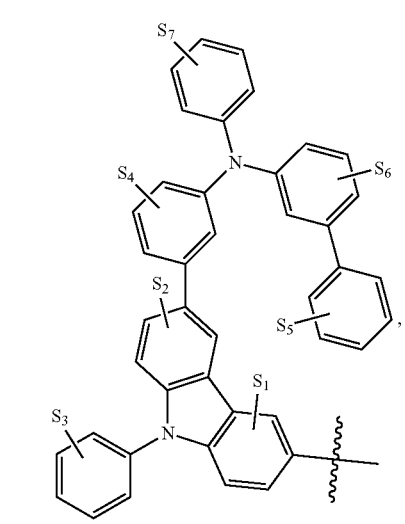
D95
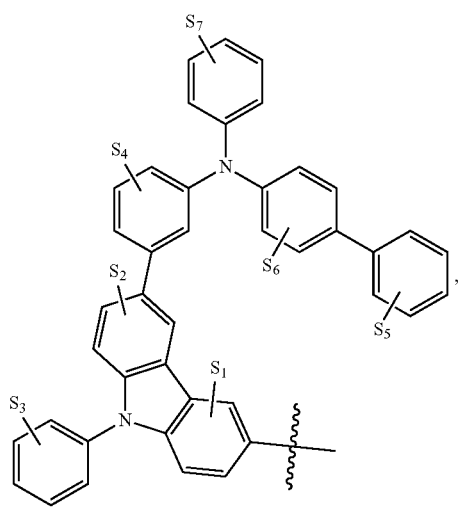
150
-continued
D96
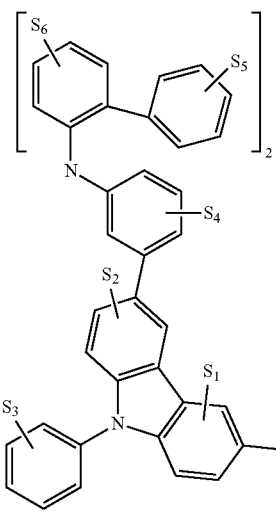
D97
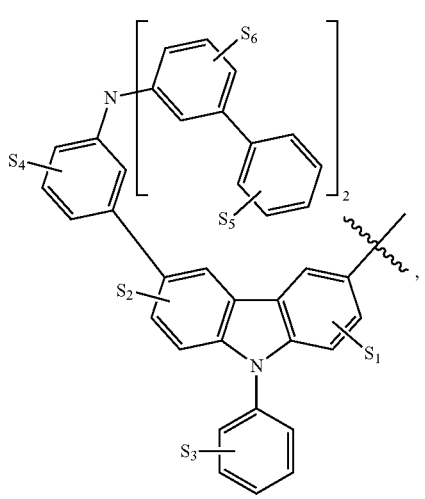
D98
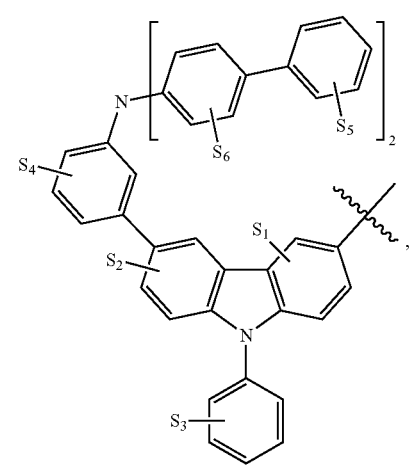

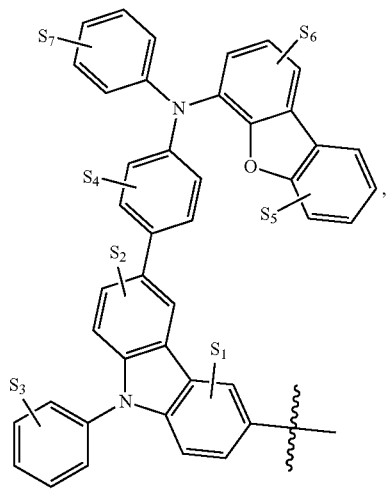
D99
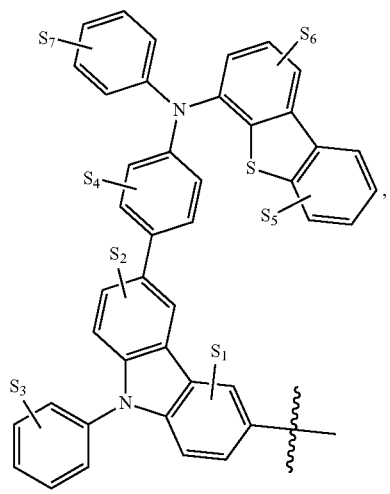
D100
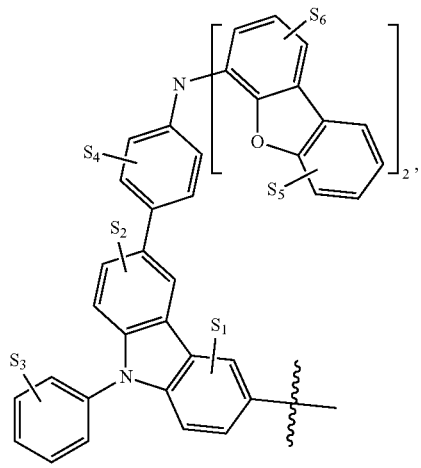
D101
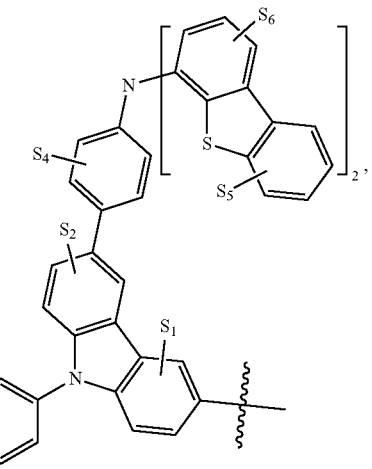
D102
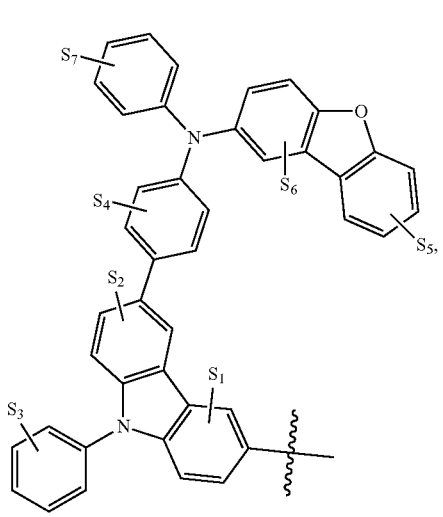
D103
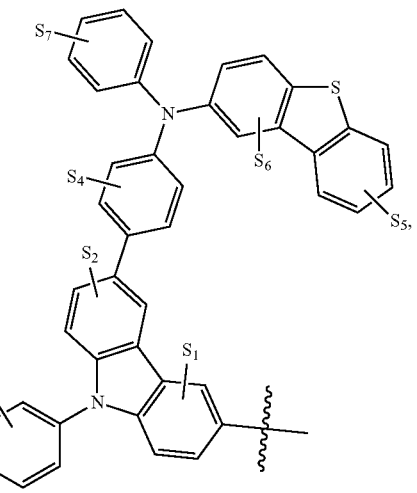
D104

-continued
D105
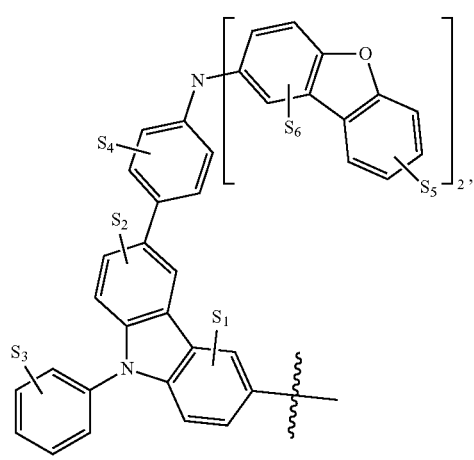
D106
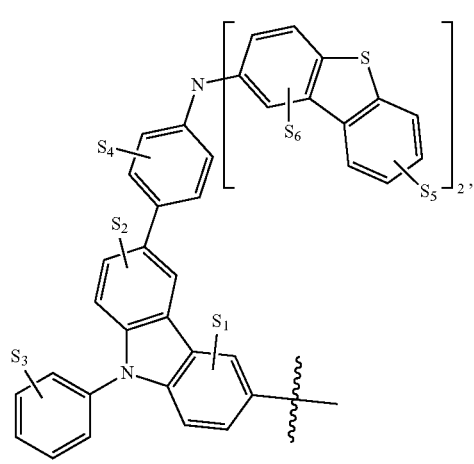
D107
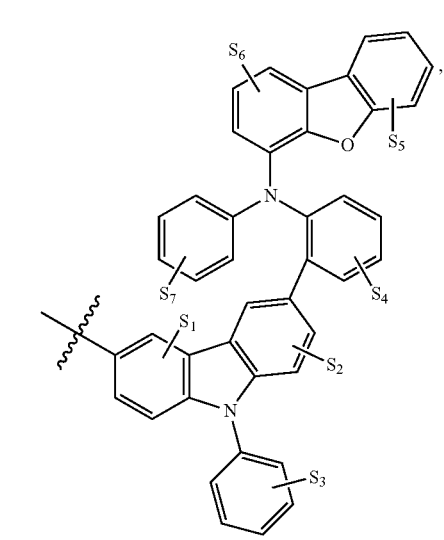
-continued
D108
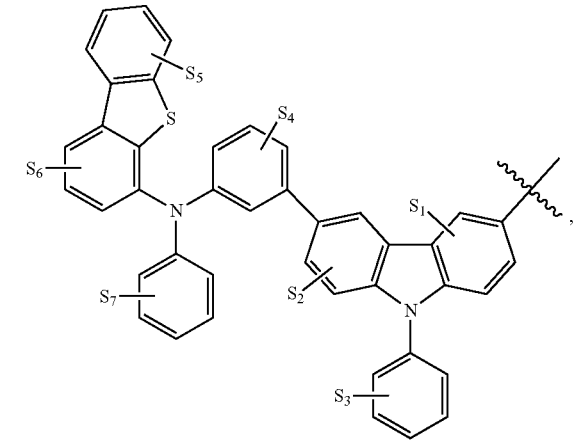
D109
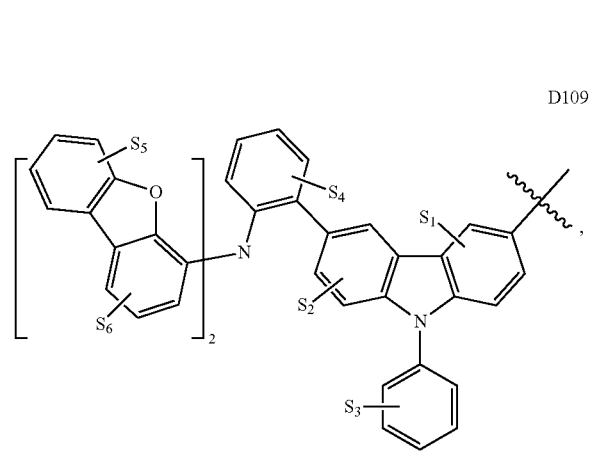
D110
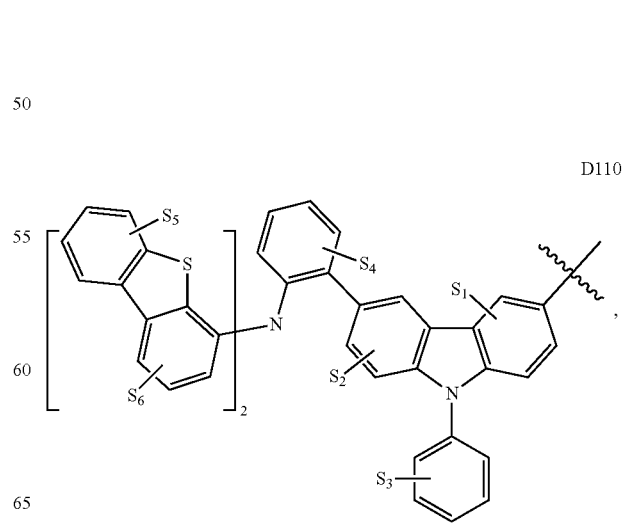

D111
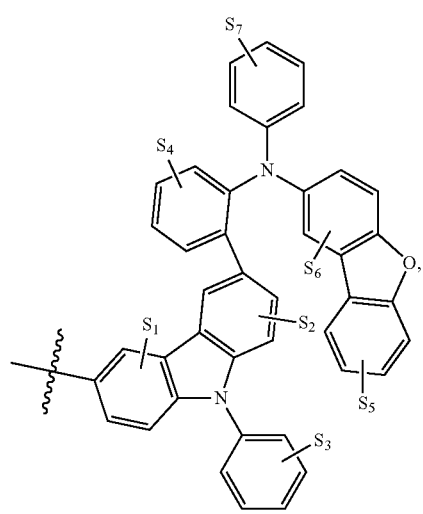
D112
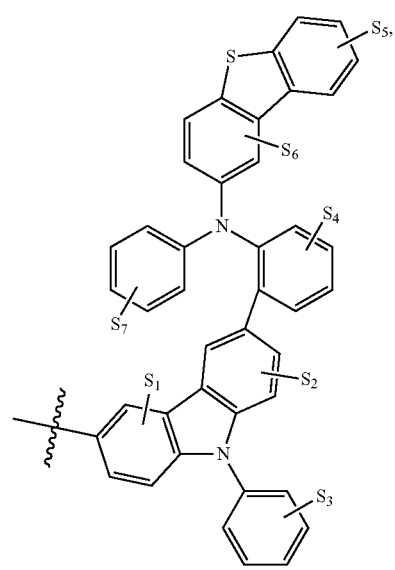
D113
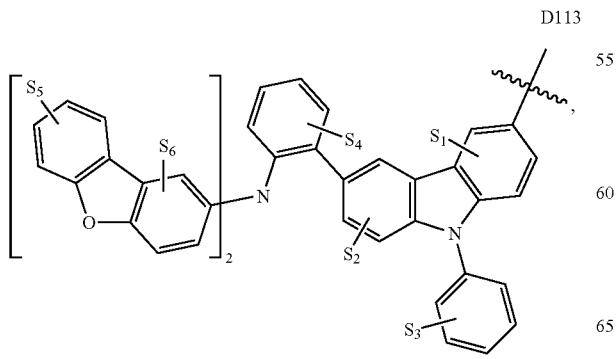
D114
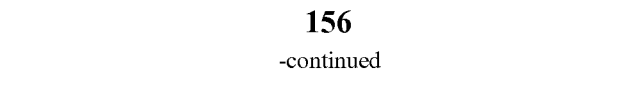
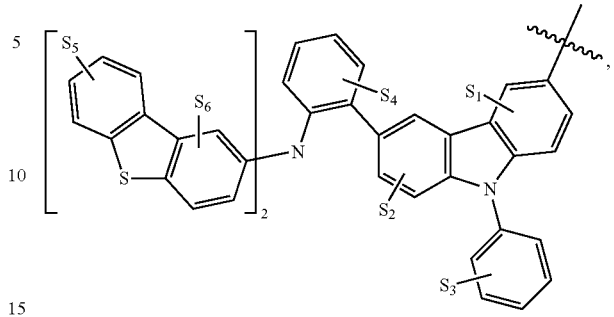
D115
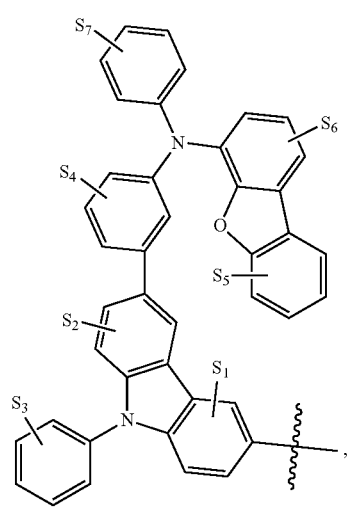
D116
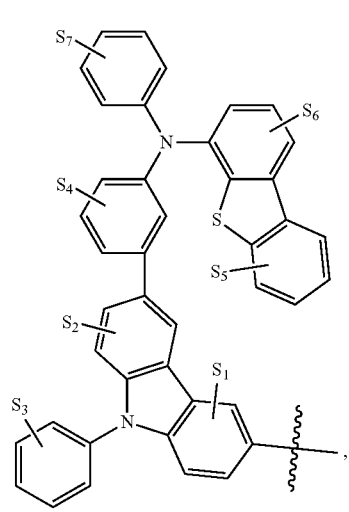

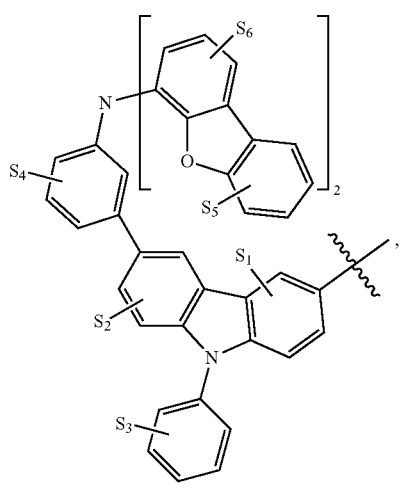
D117
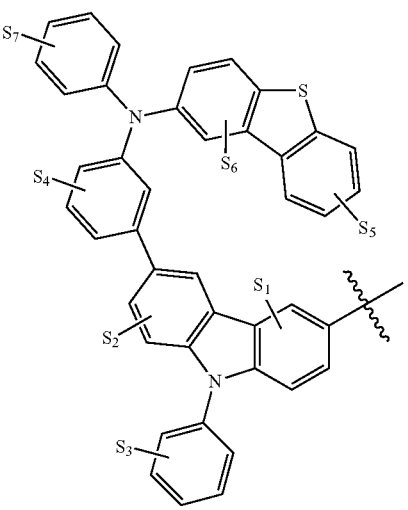
D120
D118
D121
D119

D122
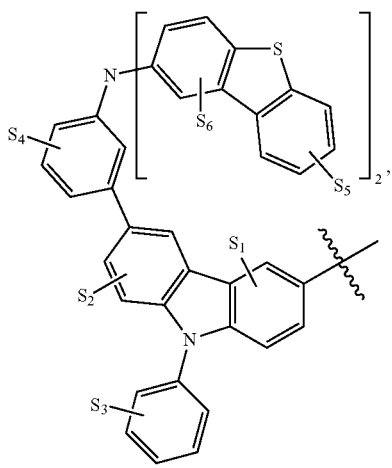

D123
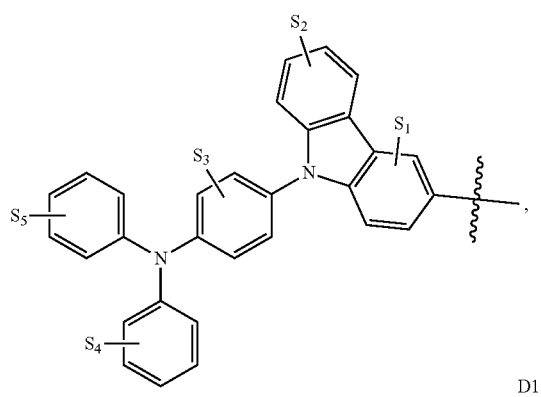
D124
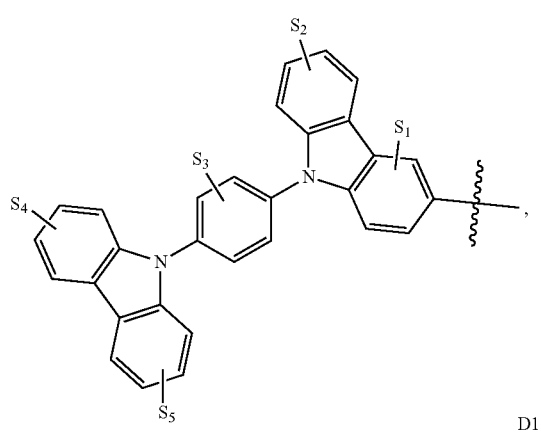
D125
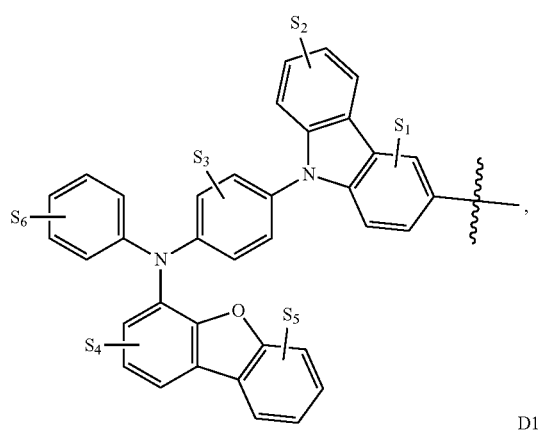
D126
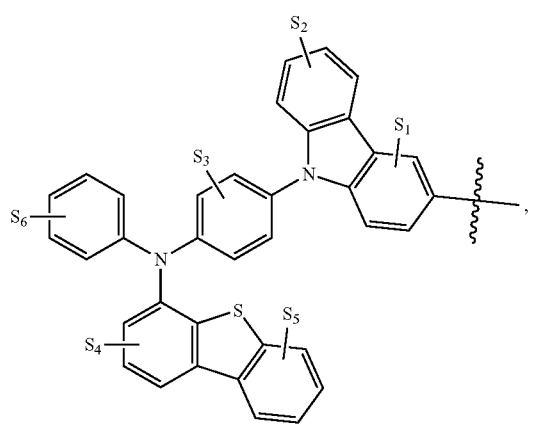
D127
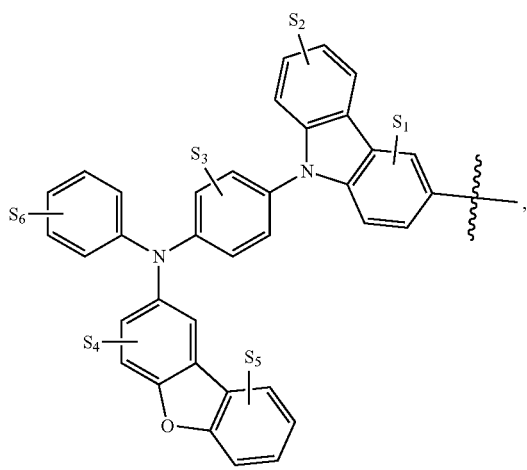
D128
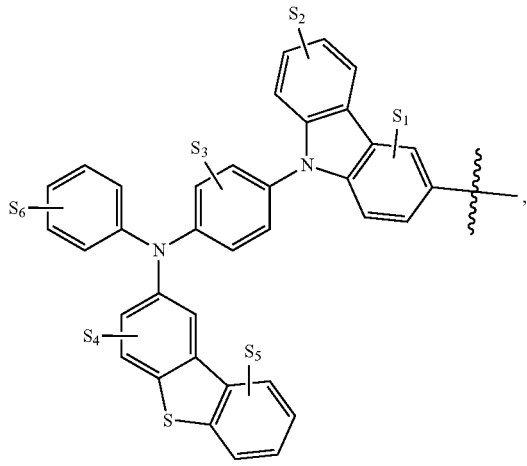
D129
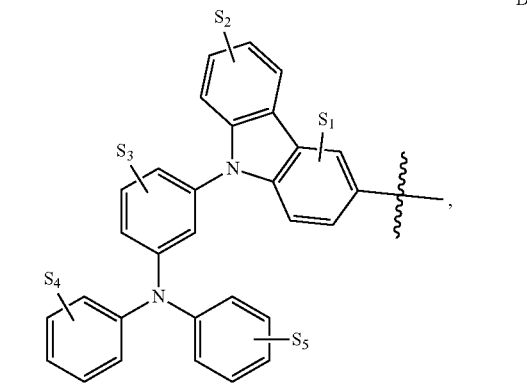

D130
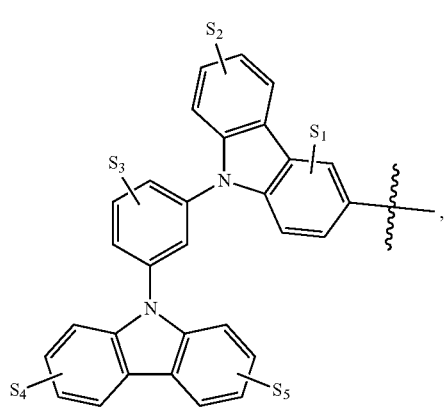
D131
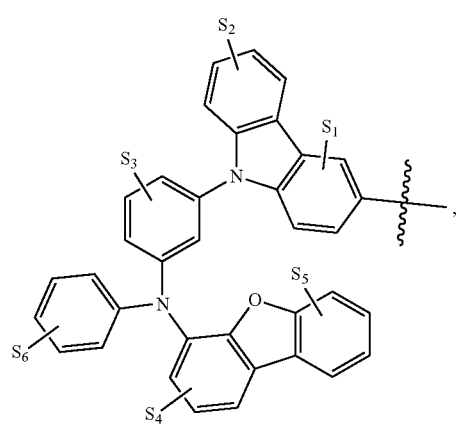
D132
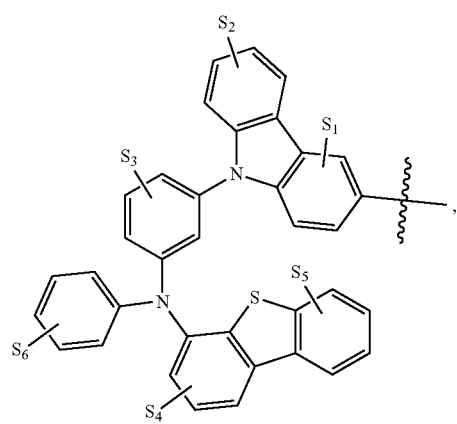
D133
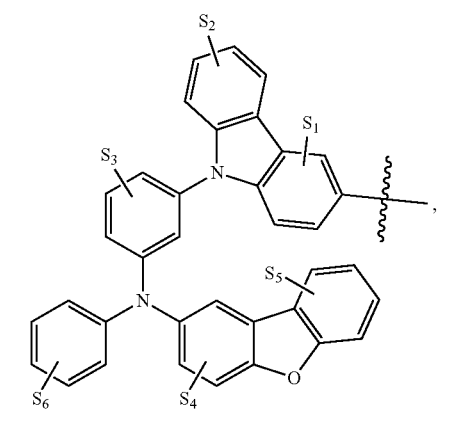
D134
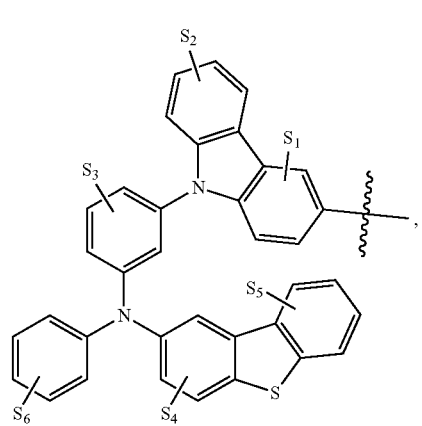
D135
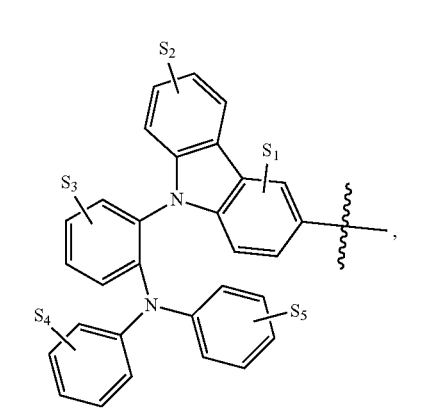
D136
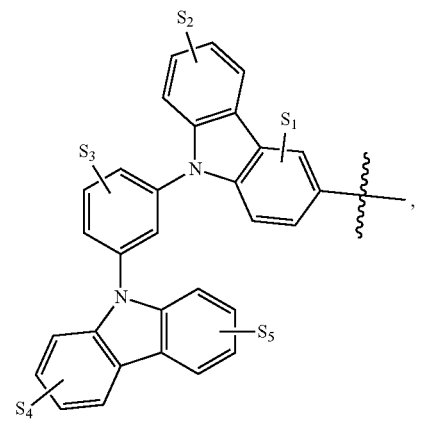
D137
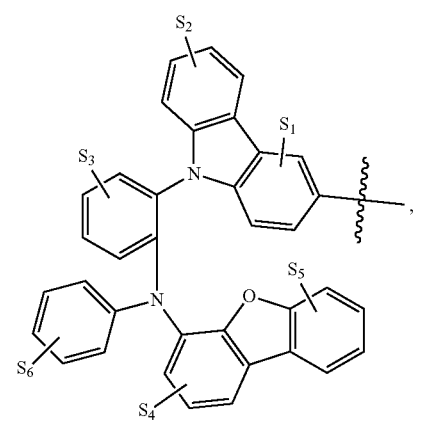

-continued

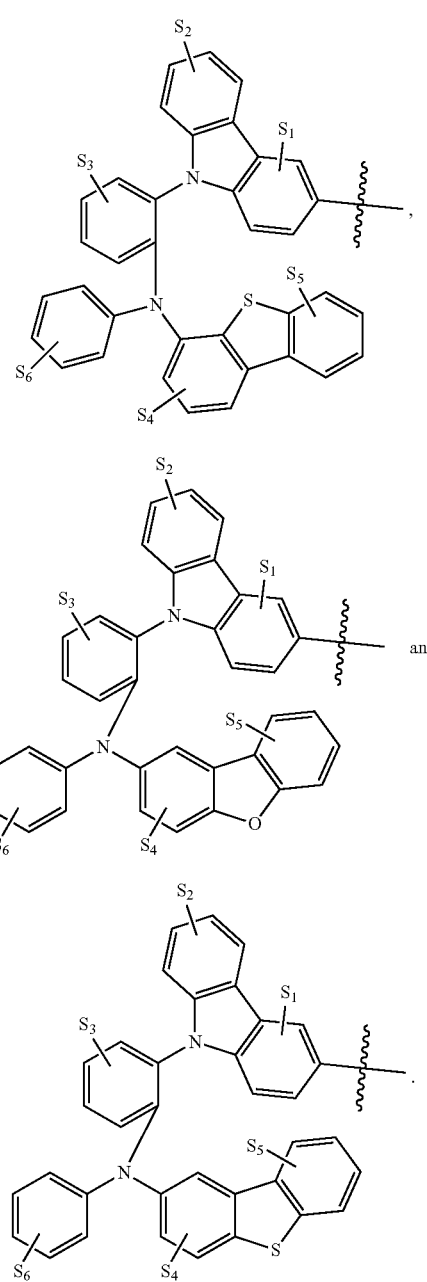

wherein S₁ to S₇ represent mono, di, tri, tetra or penta substitutions with hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In the first device according to some embodiments, L is one of

L1

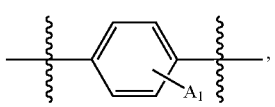

-continued

L2

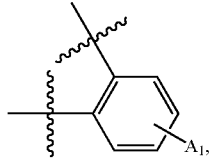

L3

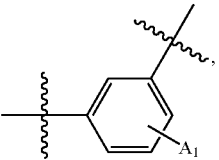

L4

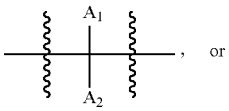

, or

L5

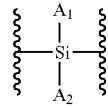

wherein A₁ to A₂ represent mono, di, tri or tetra substitutions with hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In the first device according to other embodiments, the first emitting compound is one of Compound 1

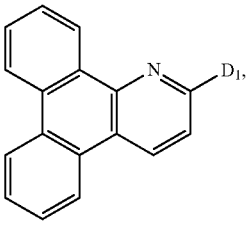

Compound 2

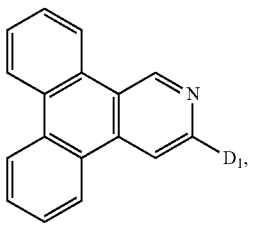

Compound 3

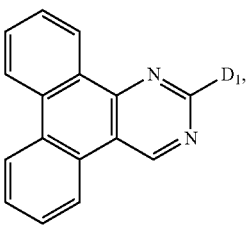

Compound 4
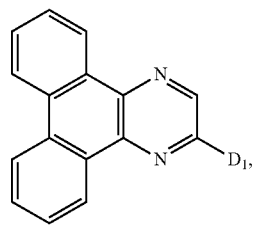
Compound 5
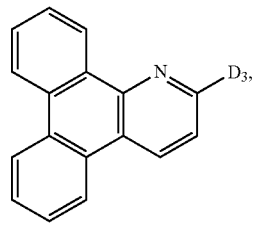
Compound 6
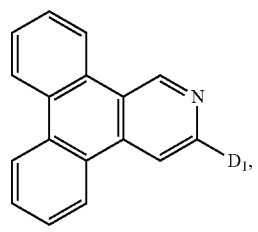
Compound 7
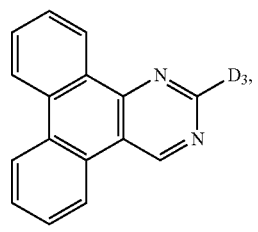
Compound 8
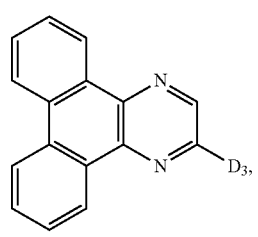
Compound 9
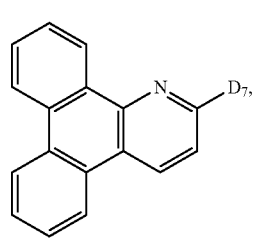
Compound 10
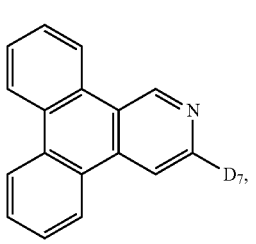
Compound 11
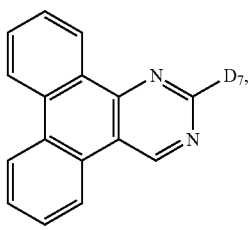
Compound 12
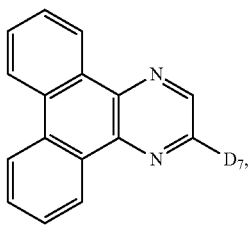
Compound 13
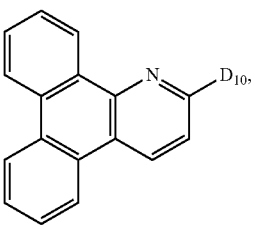
Compound 14
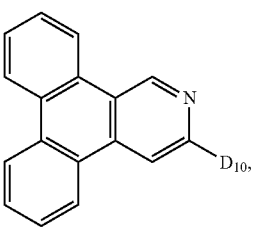
Compound 15
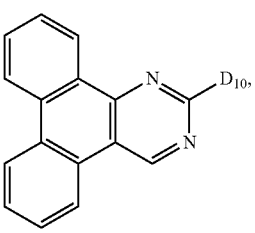
Compound 16
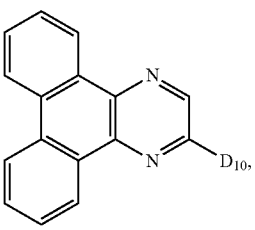

Compound 17
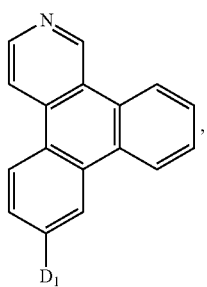
Compound 18
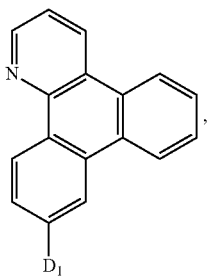
Compound 19
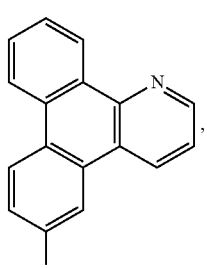
Compound 20
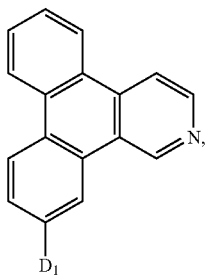
Compound 21
Compound 22
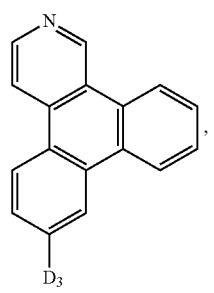
Compound 23

Compound 24
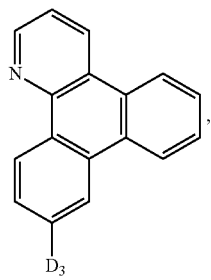
Compound 25
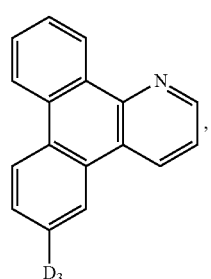
Compound 26
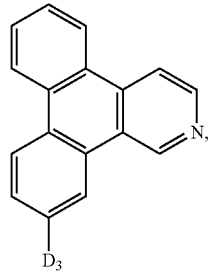

-continued
Compound 27
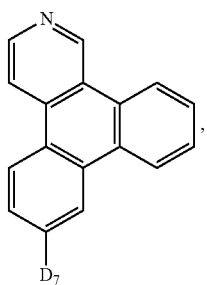
Compound 28
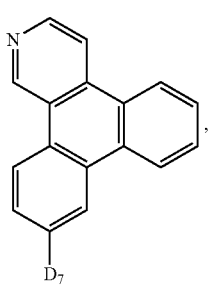
Compound 29
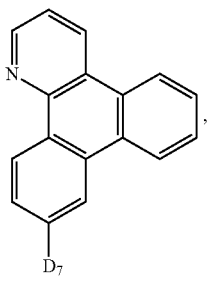
Compound 30
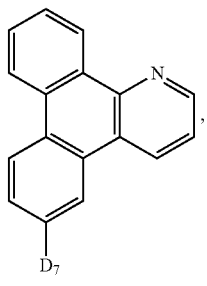
Compound 31
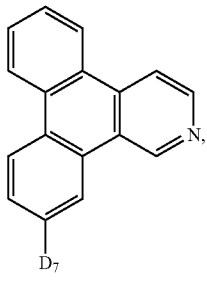
-continued
Compound 32
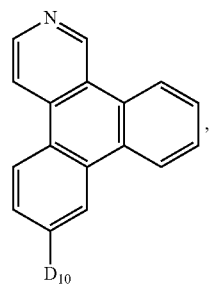
Compound 33
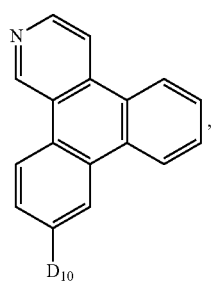
Compound 34
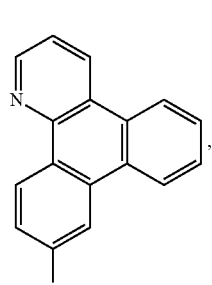
Compound 35
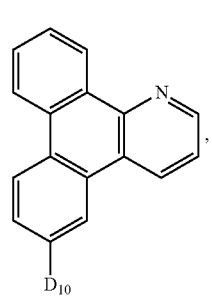
Compound 36
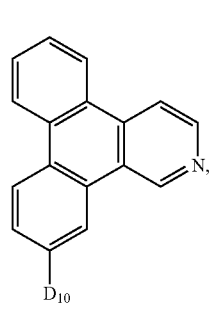

-continued
Compound 37
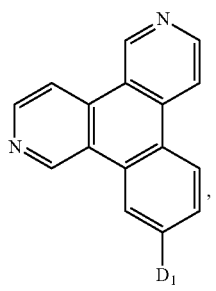
Compound 38
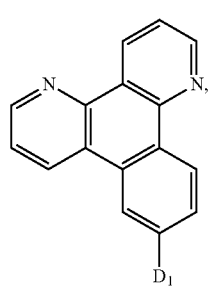
Compound 39
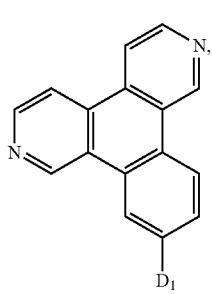
Compound 40
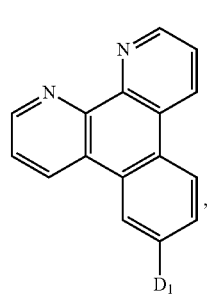
Compound 41
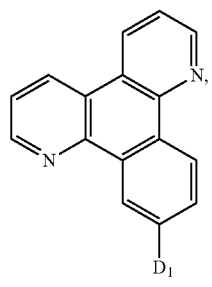
Compound 42
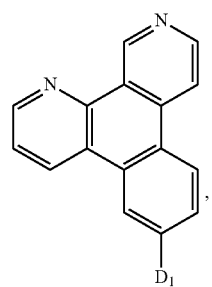
Compound 43
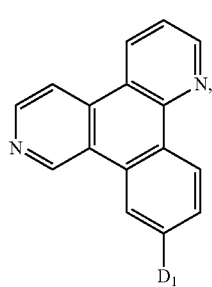
Compound 44
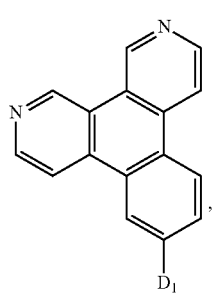
Compound 45
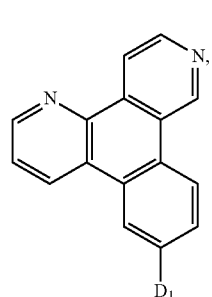
Compound 46
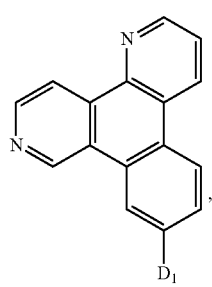

Compound 47
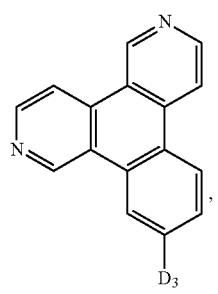
Compound 48
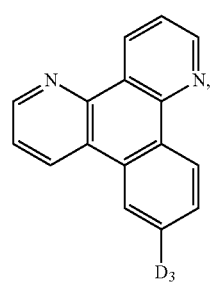
Compound 49
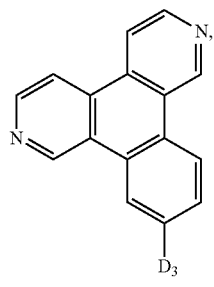
Compound 50
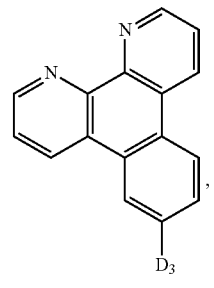
Compound 51
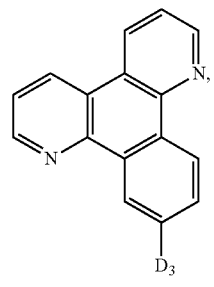
Compound 52
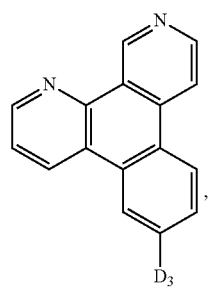
Compound 53
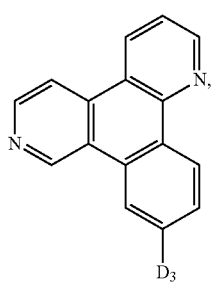
Compound 54
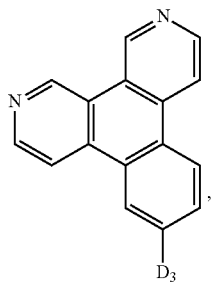
Compound 55
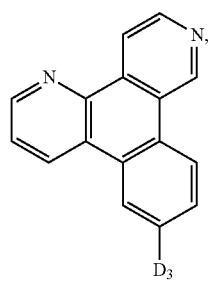
Compound 56
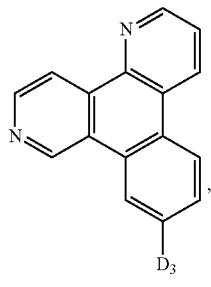

Compound 57
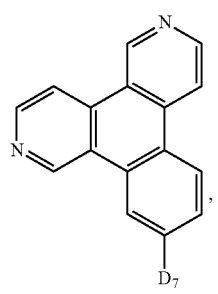
Compound 58
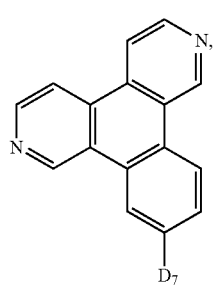
Compound 59
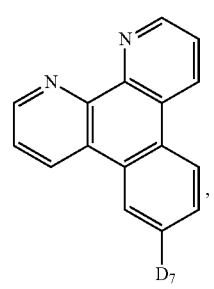
Compound 60
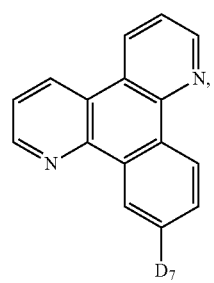
Compound 61
Compound 62
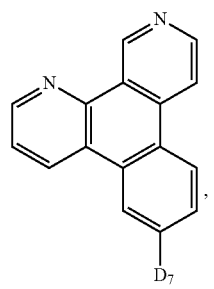
Compound 63
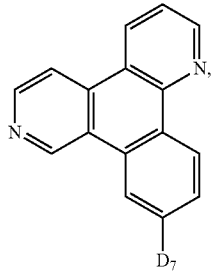
Compound 64
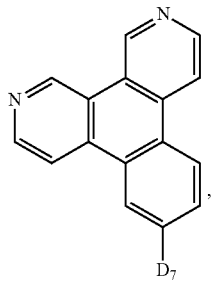
Compound 65
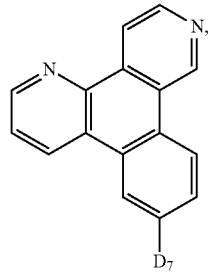
Compound 66
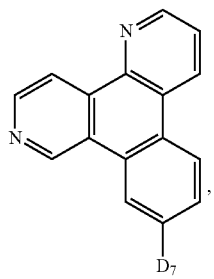

Compound 67
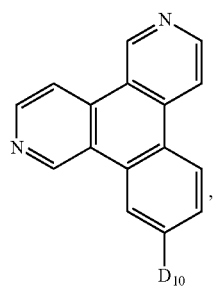
Compound 68
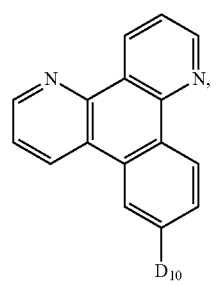
Compound 69
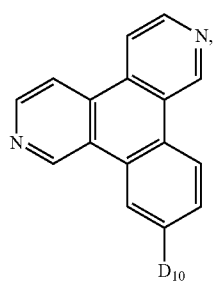
Compound 70
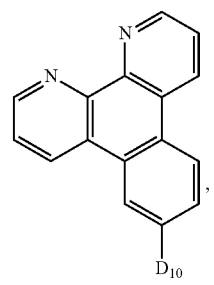
Compound 71
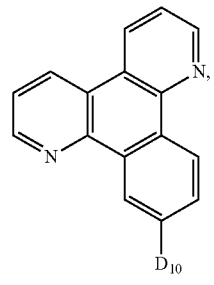
Compound 72
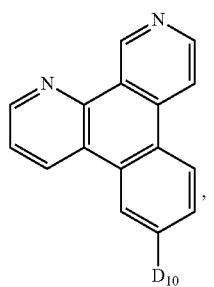
Compound 73
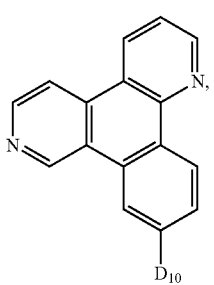
Compound 74
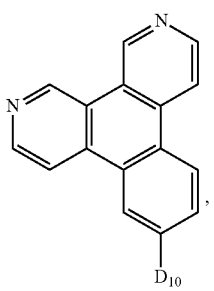
Compound 75
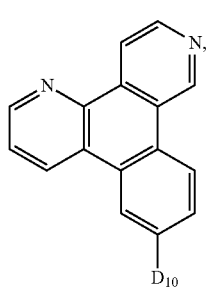
Compound 76
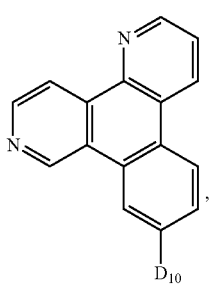

-continued
Compound 77
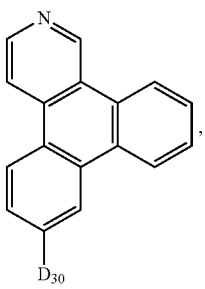
Compound 78
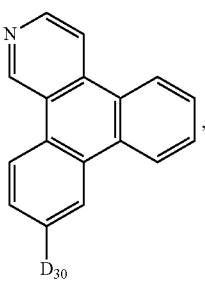
Compound 79
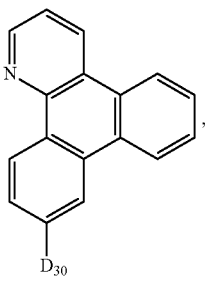
Compound 80
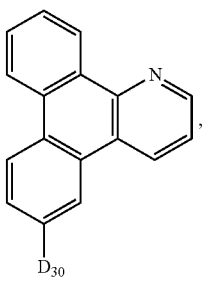
Compound 81
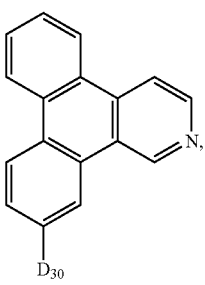
-continued
Compound 82
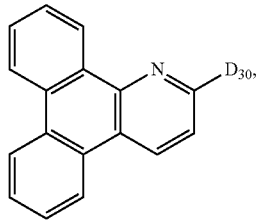
Compound 83
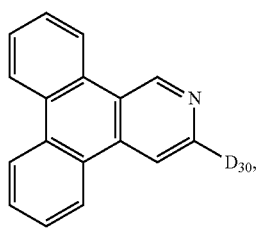
Compound 84
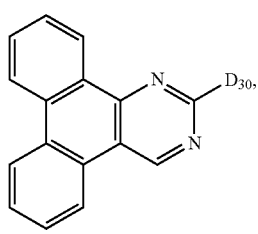
Compound 85
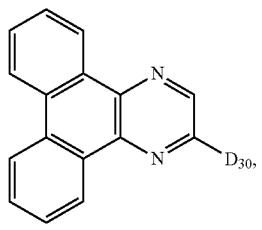
Compound 86
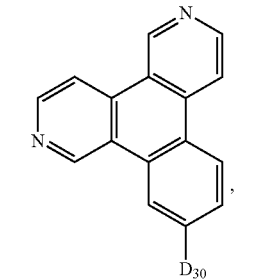
Compound 87

Compound 88
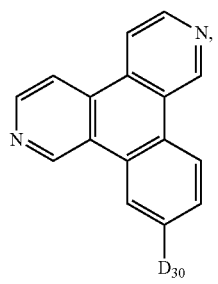
Compound 89
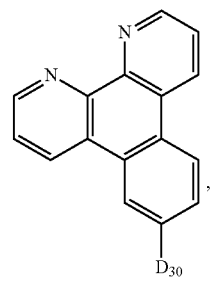
Compound 90
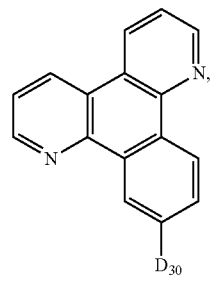
Compound 91
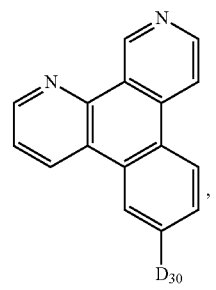
Compound 92
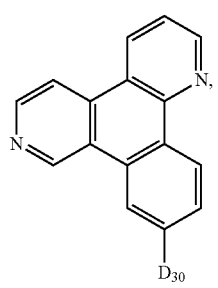
Compound 93
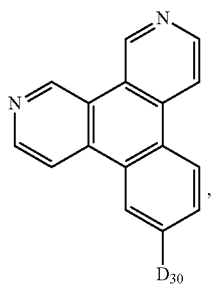
Compound 94
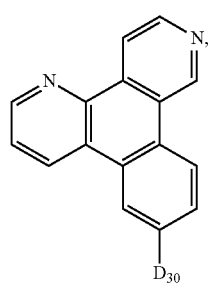
Compound 95
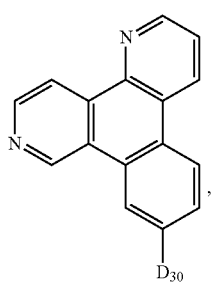
Compound 96
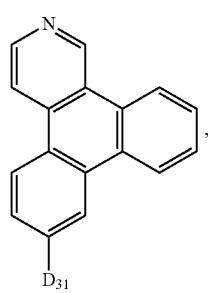
Compound 97
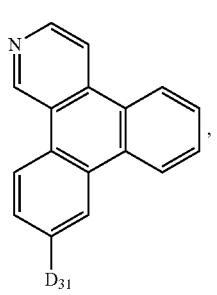

Compound 98
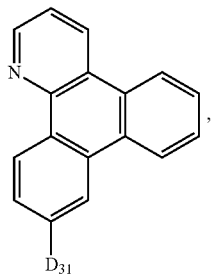
Compound 99
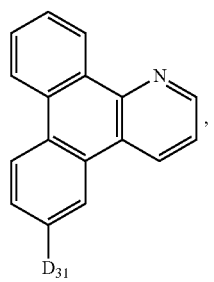
Compound 100
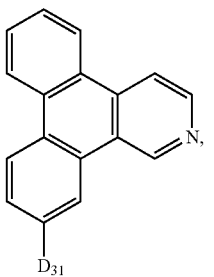
Compound 101
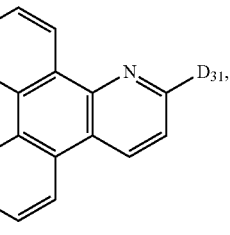
Compound 102
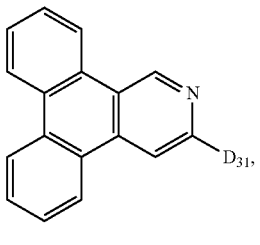
Compound 103
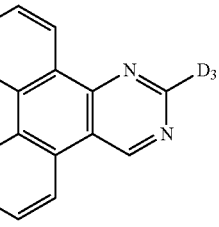
Compound 104
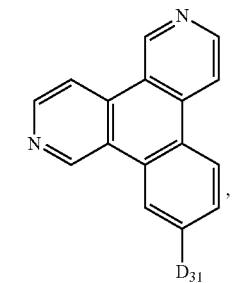
Compound 105

Compound 106

Compound 107

Compound 108
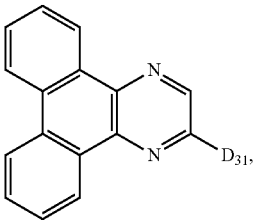

Compound 109
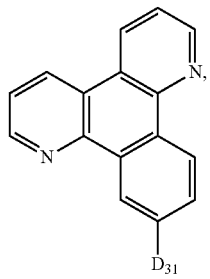
Compound 110
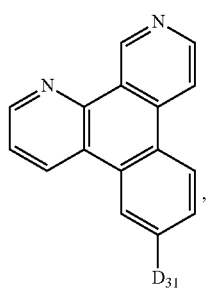
Compound 111
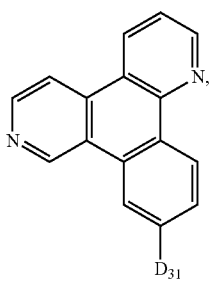
Compound 112
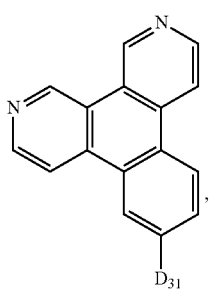
Compound 113
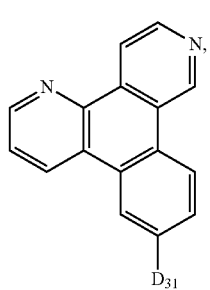
Compound 114
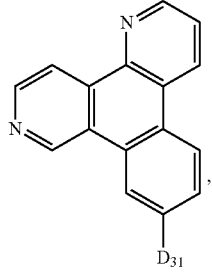
Compound 115
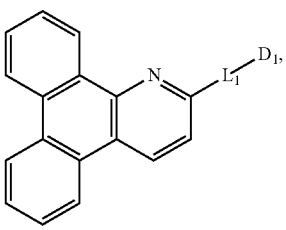
Compound 116
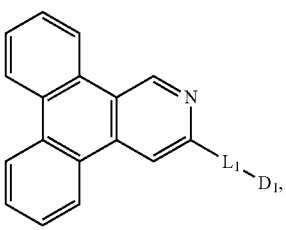
Compound 117
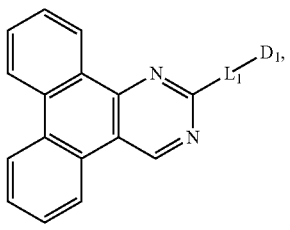
Compound 118
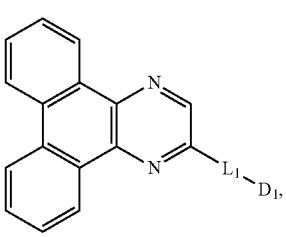
Compound 119
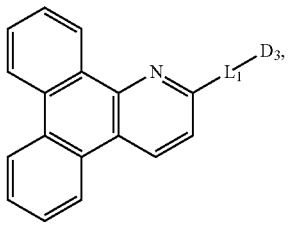

Compound 120
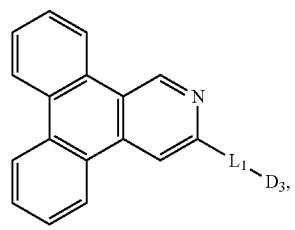
Compound 121
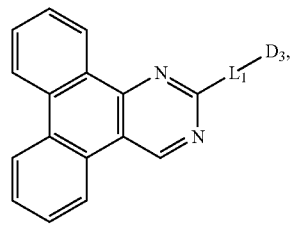
Compound 122
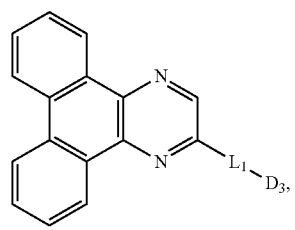
Compound 123
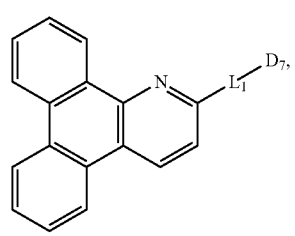
Compound 124
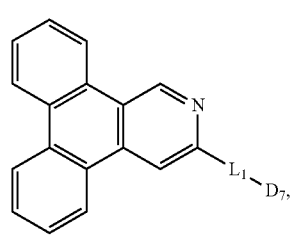
Compound 125
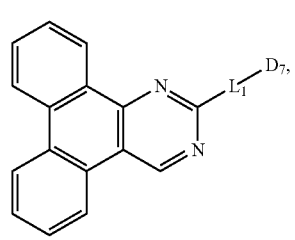
Compound 126
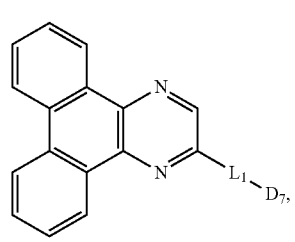
Compound 127
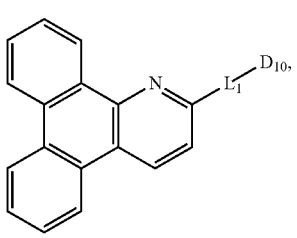
Compound 128
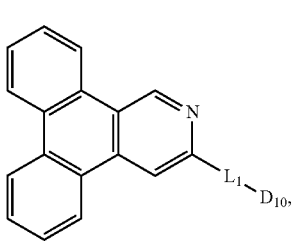
Compound 129
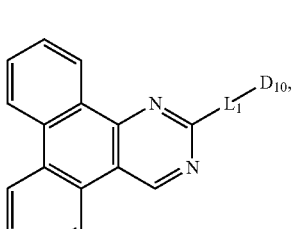
Compound 130
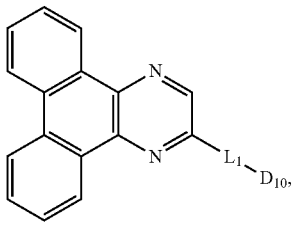
Compound 131
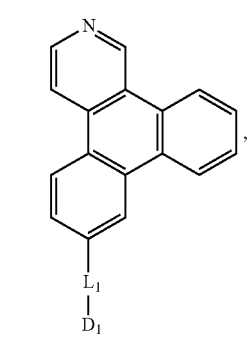
Compound 132
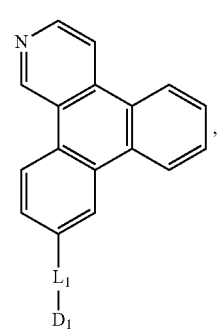

Compound 133
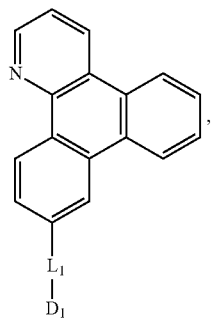
Compound 134
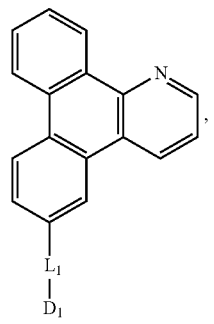
Compound 135
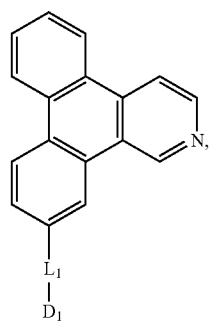
Compound 136
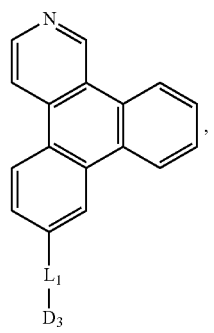
Compound 137
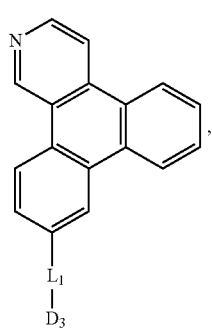
Compound 138

Compound 139
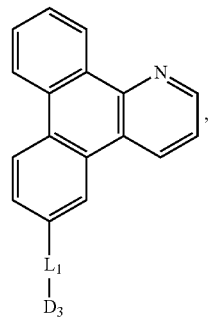
Compound 140
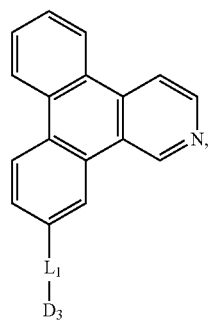
Compound 141
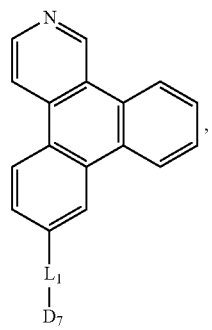
Compound 142
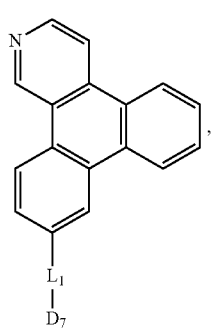

Compound 143
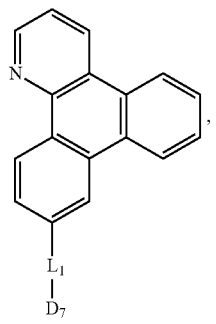
Compound 144
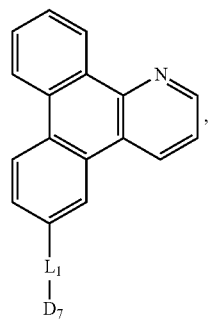
Compound 145
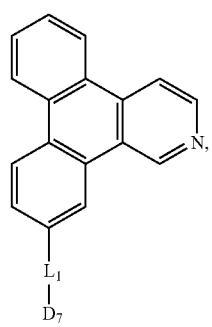
Compound 146
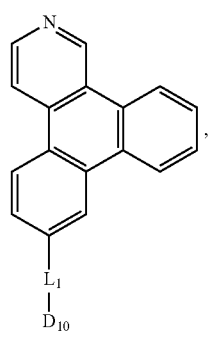
Compound 147
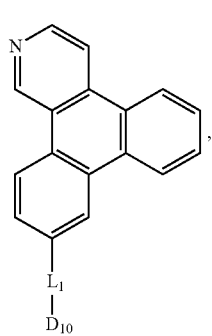
Compound 148
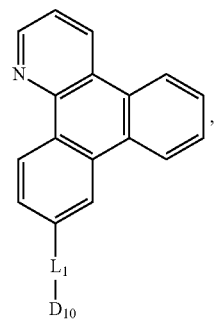
Compound 149
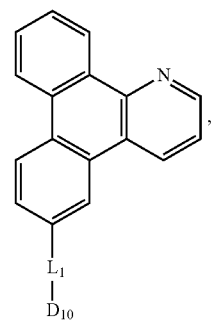
Compound 150
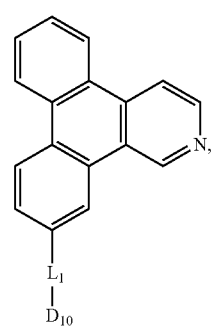
Compound 151
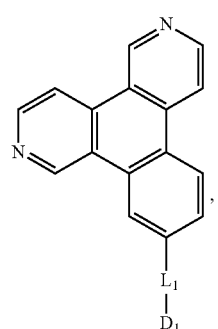
Compound 152
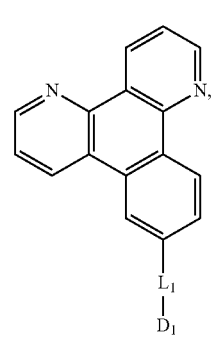

-continued
Compound 153
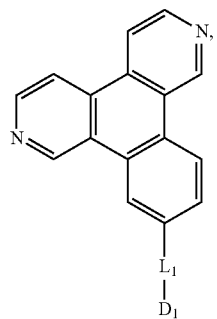
Compound 154
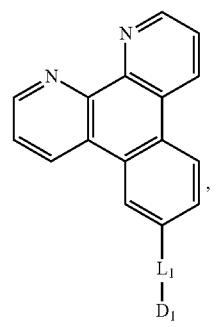
Compound 155
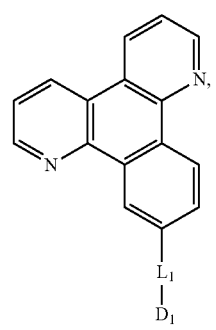
Compound 156
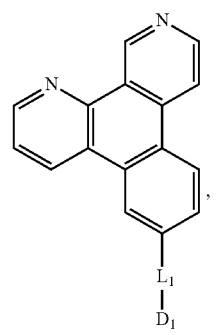
Compound 157
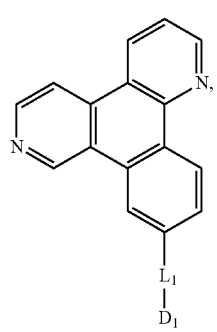
-continued
Compound 158
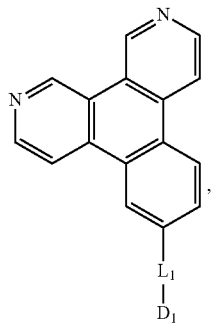
Compound 159
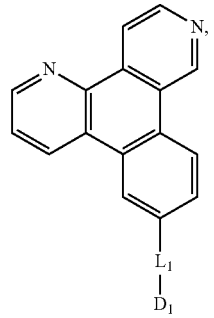
Compound 160
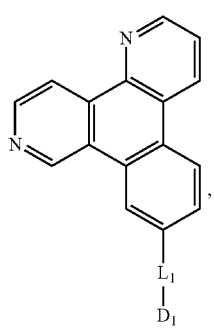
Compound 161
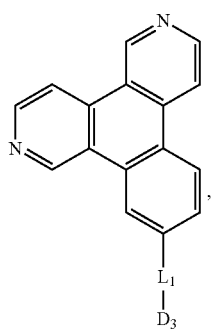
Compound 162
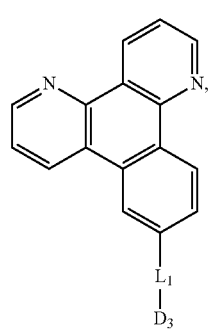

Compound 163
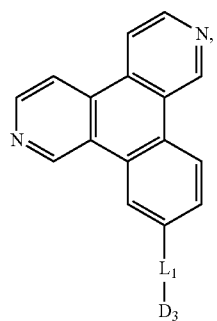
Compound 164
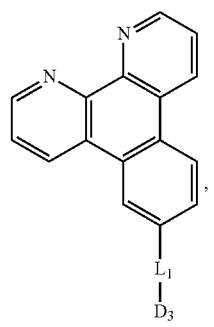
Compound 165
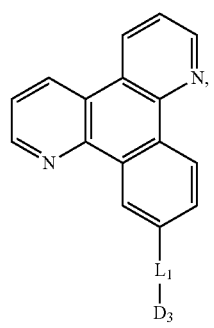
Compound 166
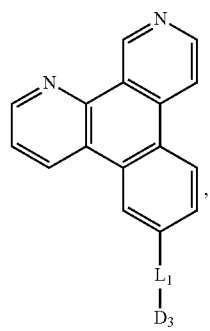
Compound 167
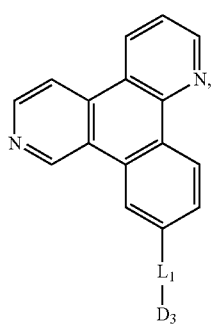
Compound 168
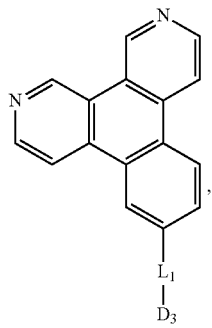
Compound 169
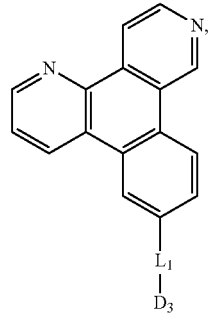
Compound 170
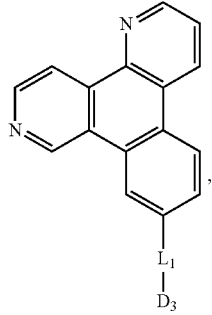
Compound 171
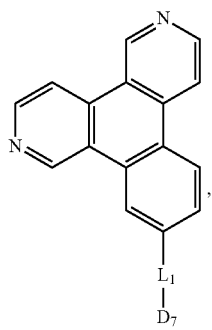
Compound 172
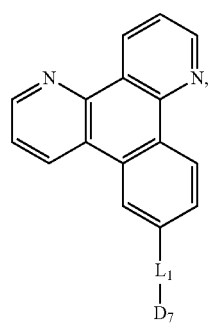

-continued
Compound 173
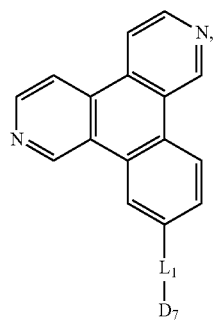
Compound 174
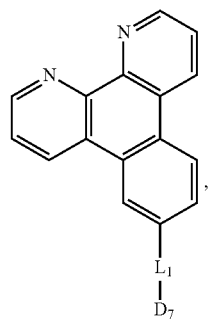
Compound 175
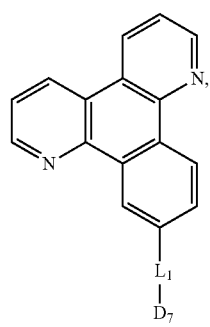
Compound 176
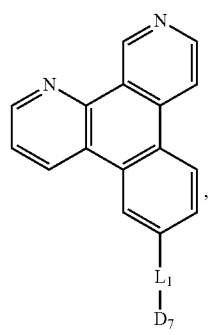
Compound 177
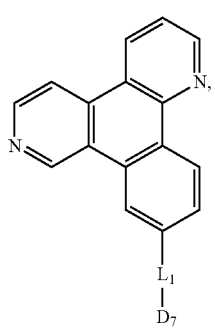
-continued
Compound 178
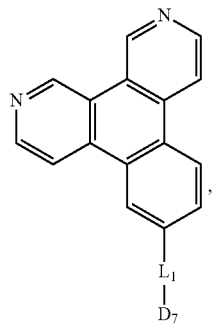
Compound 179
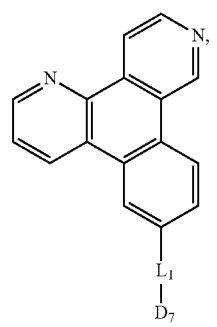
Compound 180
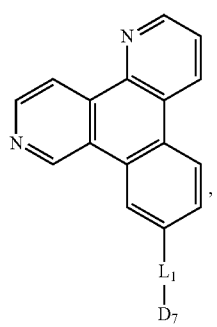
Compound 181
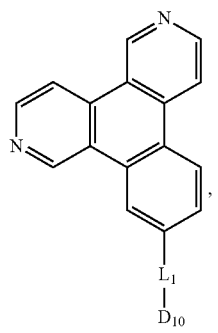
Compound 182
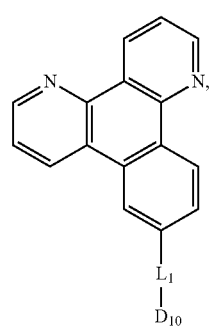

Compound 183
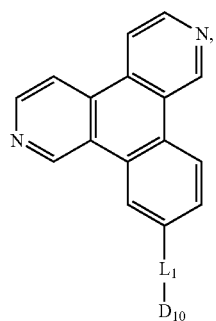
Compound 184
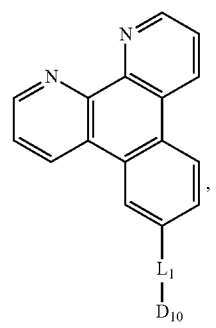
Compound 185
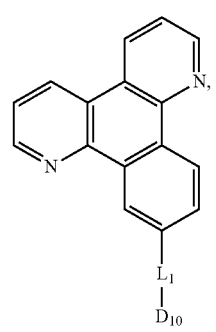
Compound 186
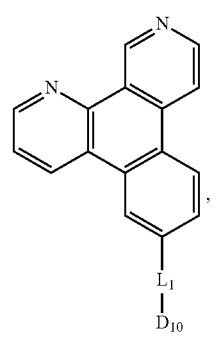
Compound 187
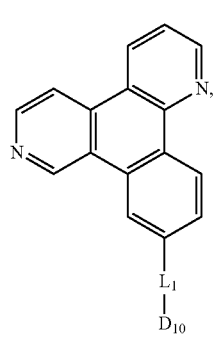
Compound 188
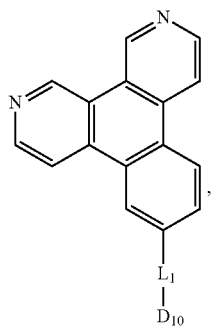
Compound 189
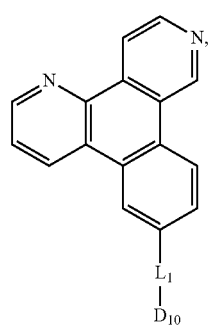
Compound 190
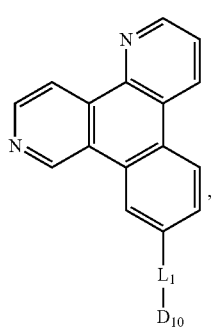
Compound 191
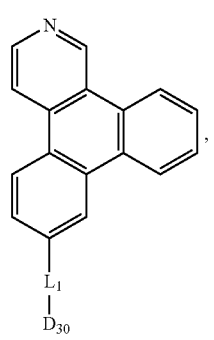
Compound 192
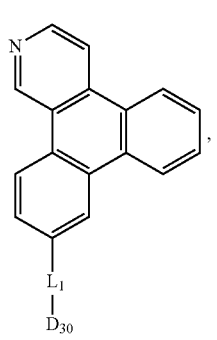

Compound 193
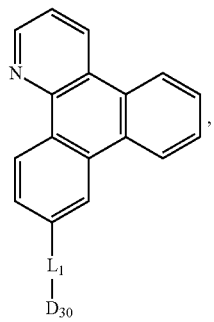
Compound 194
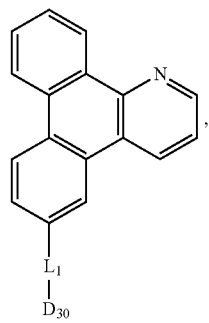
Compound 195
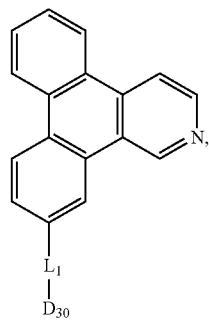
Compound 196
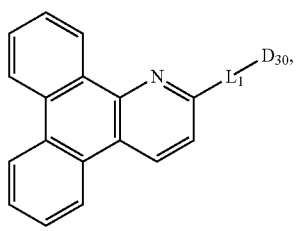
Compound 197
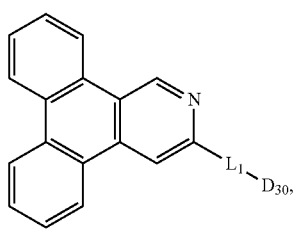
Compound 198
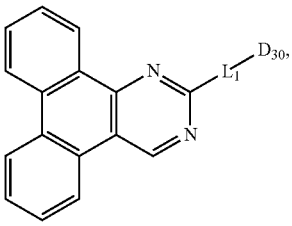
Compound 199
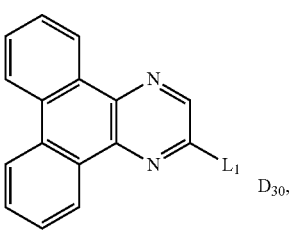
Compound 200
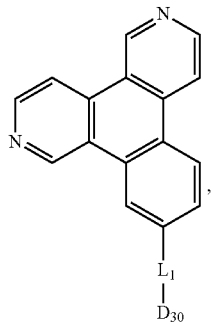
Compound 201
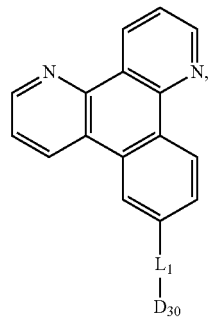
Compound 202
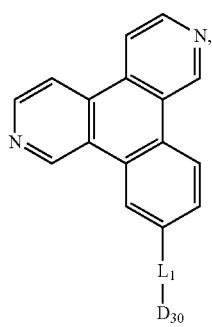

Compound 203
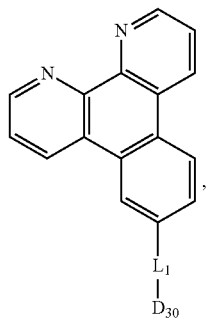
Compound 204
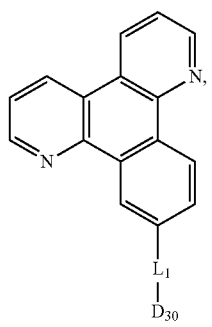
Compound 205
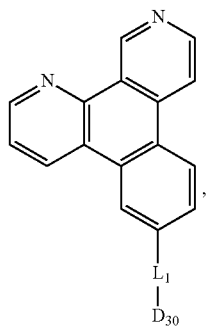
Compound 206
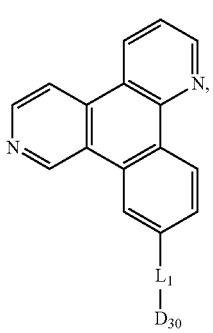
Compound 207
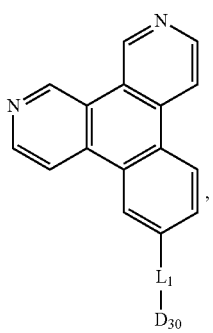
Compound 208
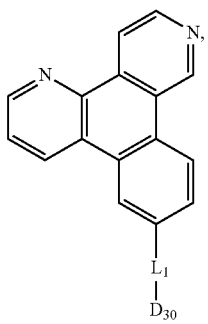
Compound 209
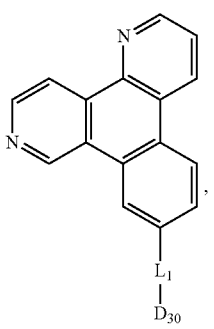
Compound 210
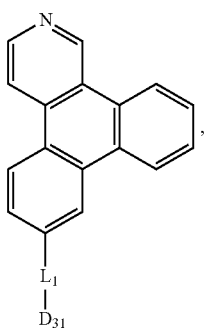
Compound 211
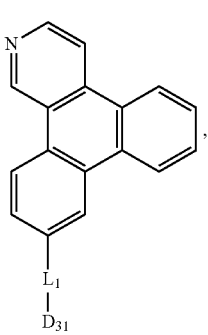
Compound 212
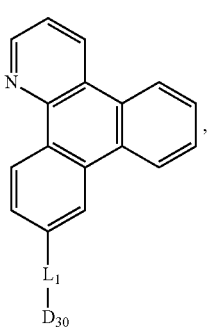

Compound 213
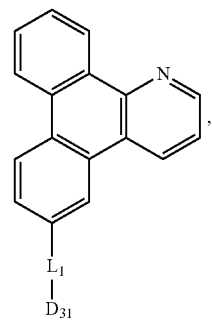
Compound 214
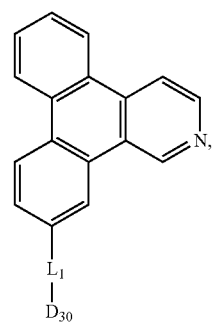
Compound 215
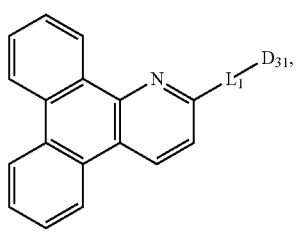
Compound 216
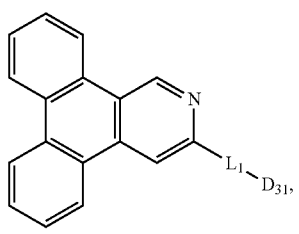
Compound 217
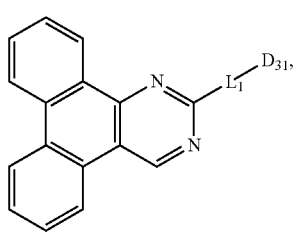
Compuond 218
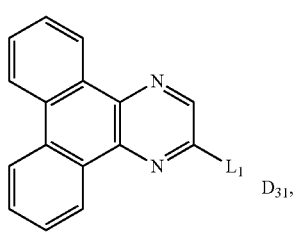
Compound 219
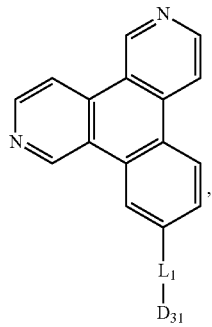
Compound 220
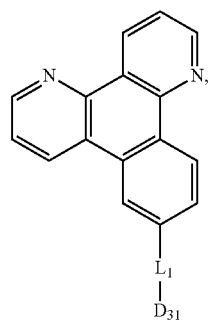
Compound 221
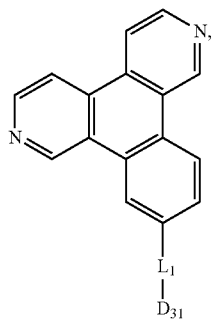
Compound 222
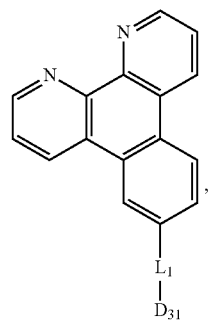
Compound 223
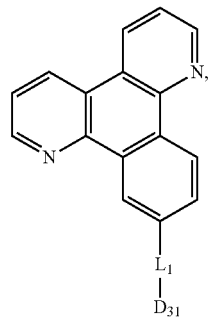

Compound 224
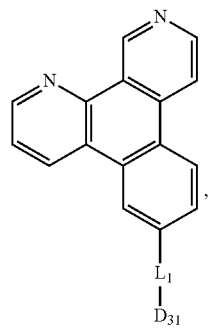
Compound 225
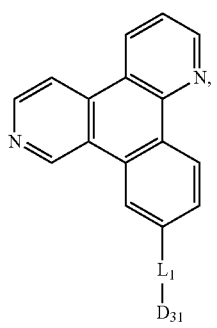
Compound 226
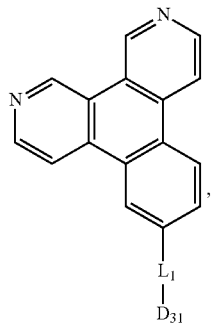
Compound 227
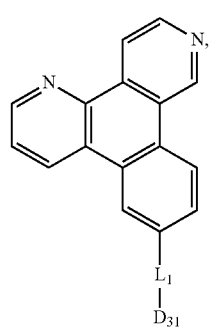
Compound 228
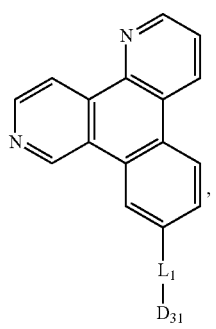
Compound 229
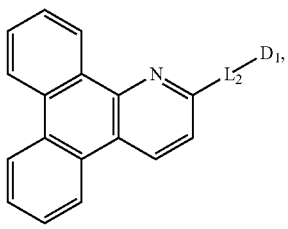
Compound 230
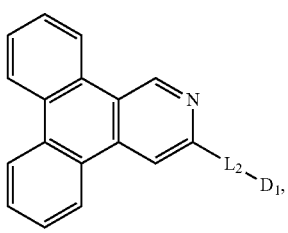
Compound 231
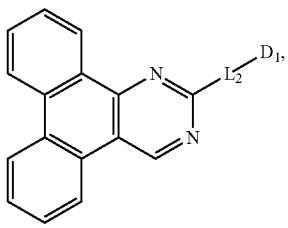
Compound 232
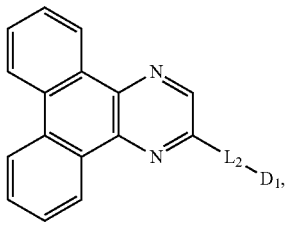
Compound 233
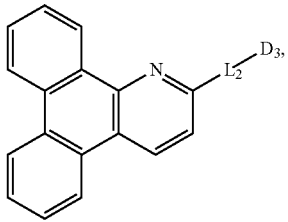
Compound 234
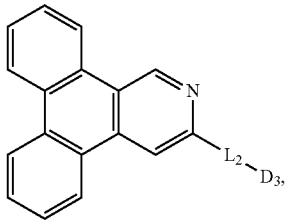
Compound 235
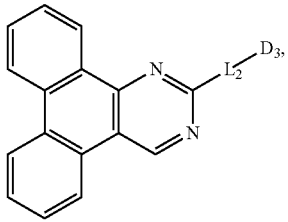

Compound 236
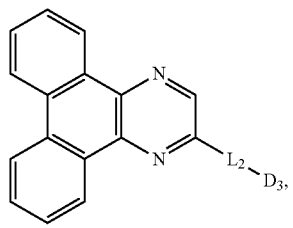
Compound 237
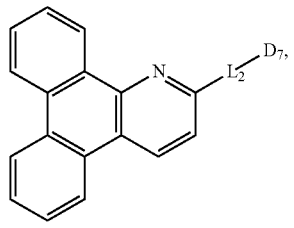
Compound 238
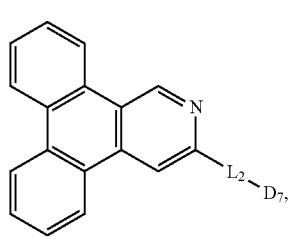
Compound 239
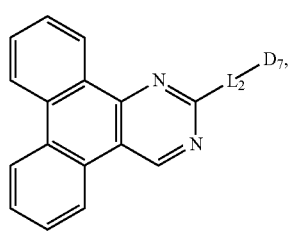
Compound 240
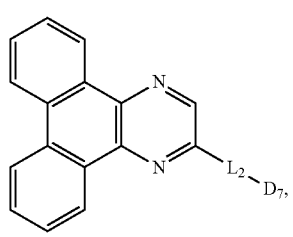
Compound 241
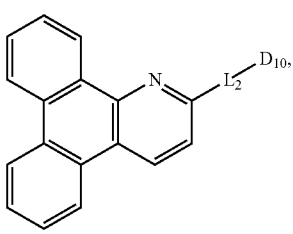
Compound 242
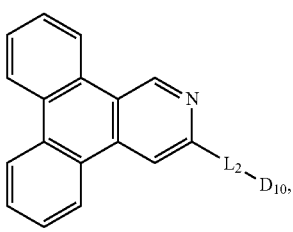
Compound 243
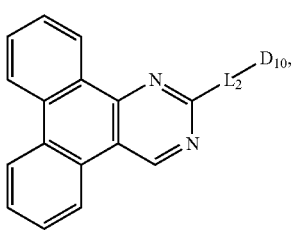
Compound 244
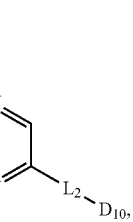
Compound 245
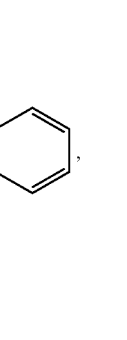
Compound 246
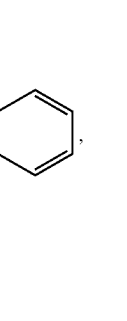
Compound 247
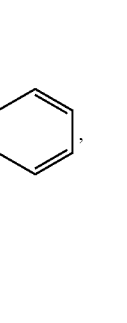

211
-continued
Compound 248
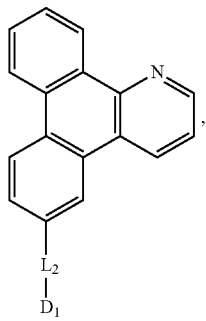
Compound 249
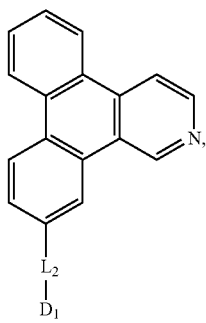
Compound 250
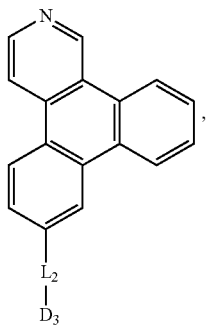
Compound 251
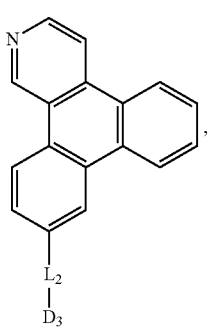
Compound 252
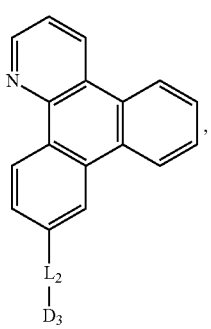
212
-continued
Compound 253
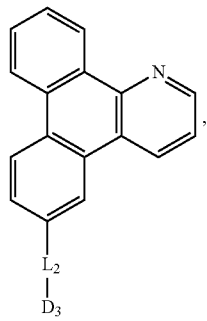
Compound 254

Compound 255
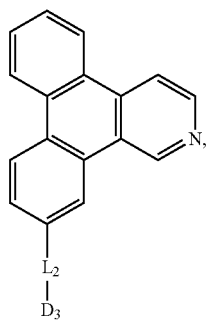
Compound 256
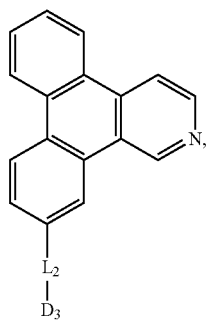
Compound 257
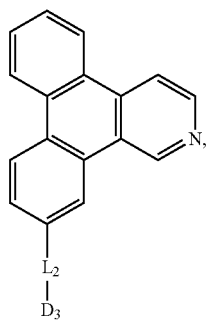

213
-continued
Compound 258
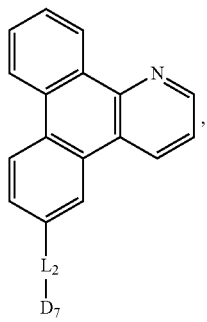
Compound 259
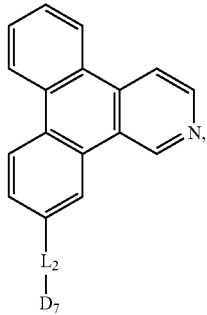
Compound 260
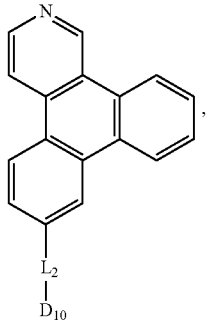
Compound 261
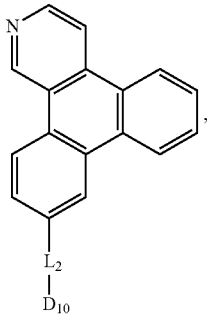
Compound 262
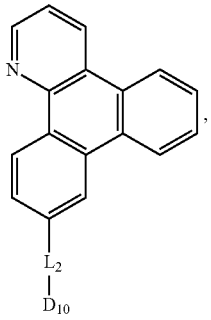
214
-continued
Compound 263
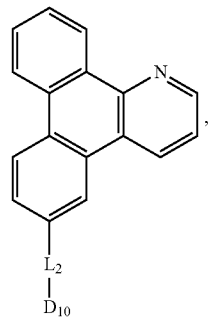
Compound 264
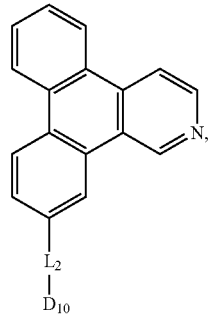
Compound 265
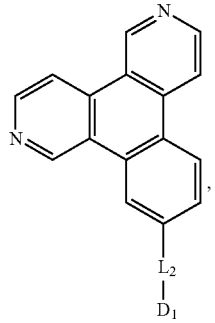
Compound 266
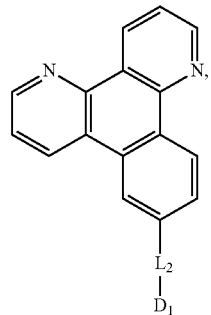
Compound 267
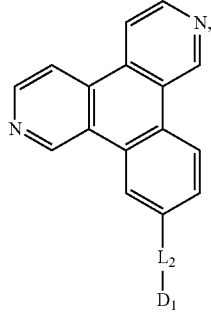

-continued
Compound 268
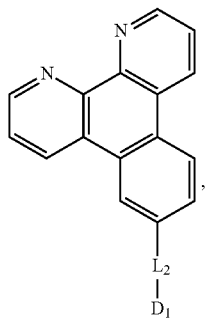
Compound 269
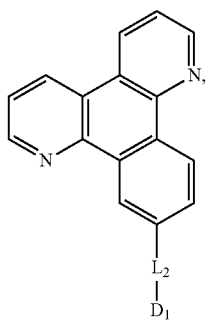
Compound 270
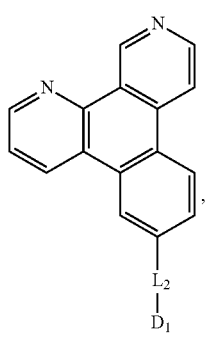
Compound 271
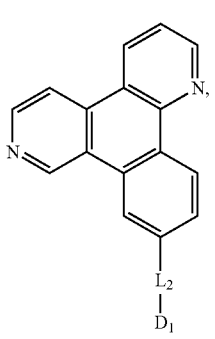
Compound 272
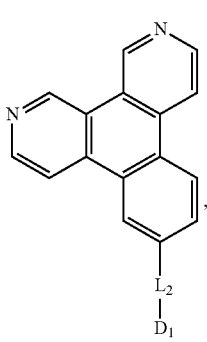
-continued
Compound 273
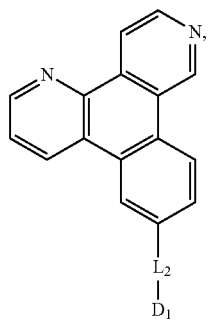
Compound 274
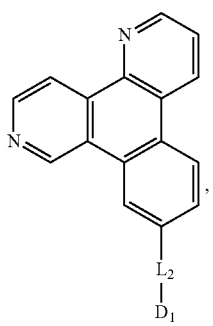
Compound 275
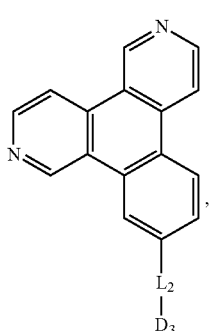
Compound 276
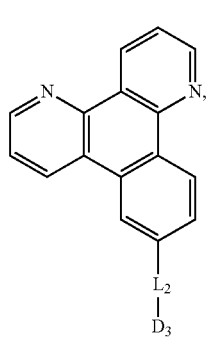
Compound 277
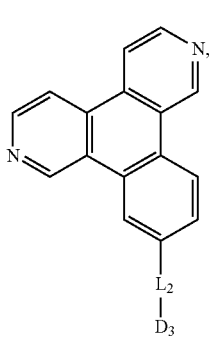

-continued
Compound 278
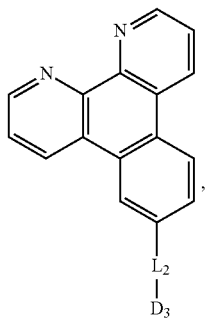
Compound 279
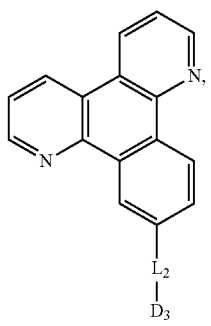
Compound 280
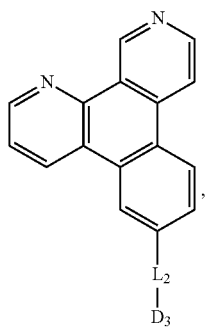
Compound 281
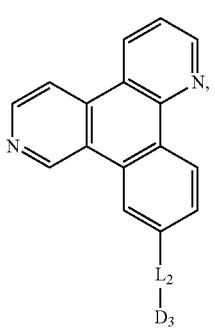
Compound 282
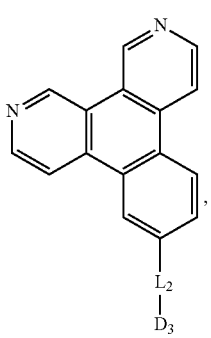
-continued
Compound 283
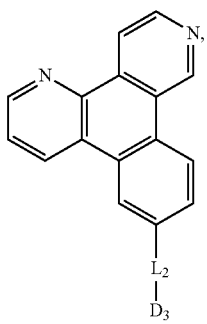
Compound 284
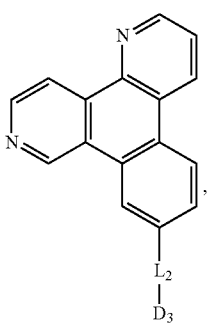
Compound 285
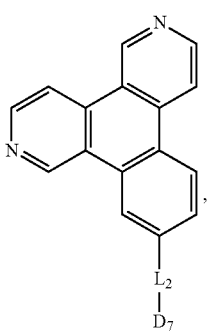
Compound 286
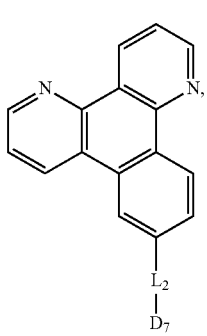
Compound 287
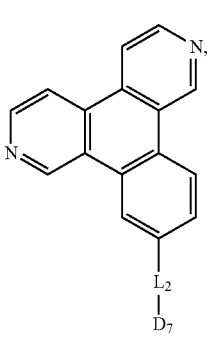

-continued
Compound 288
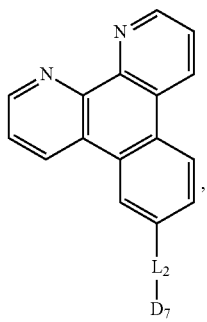
Compound 289
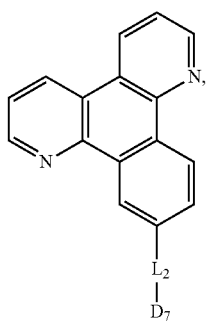
Compound 290
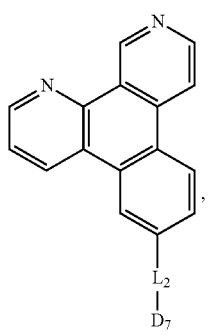
Compound 291
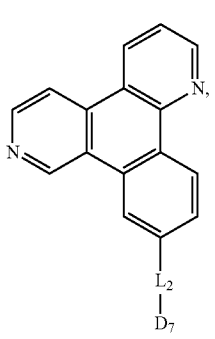
Compound 292
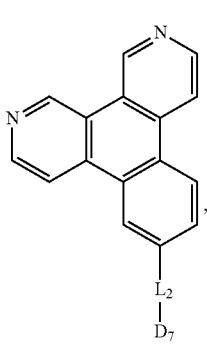
-continued
Compound 293
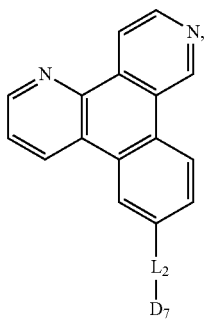
Compound 294
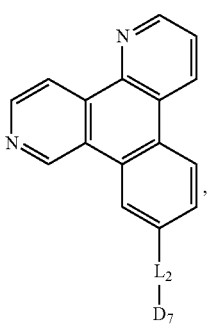
Compound 295
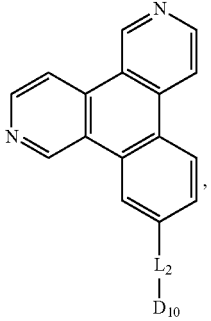
Compound 296
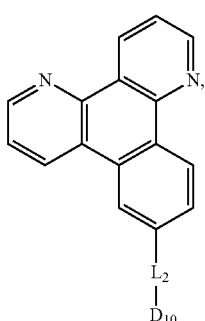
Compound 297
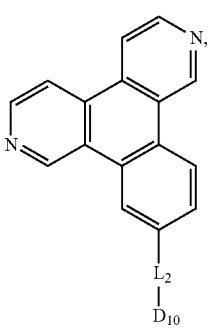

221
-continued
Compound 298
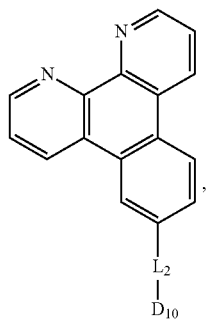
Compound 299
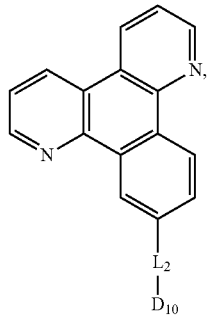
Compound 300
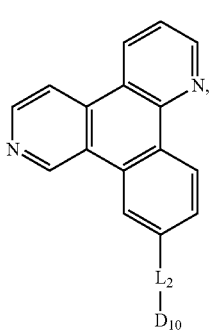
Compound 301
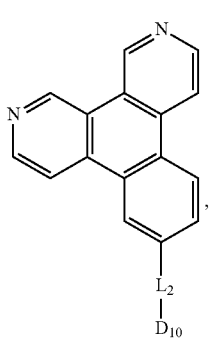
Compound 302
222
-continued
Compound 303
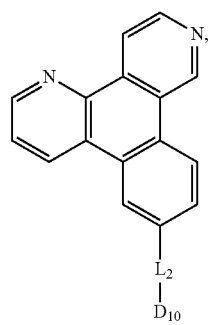
Compound 304
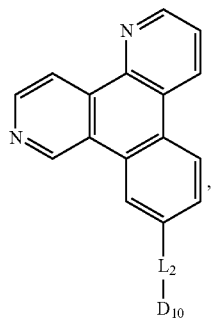
Compound 305
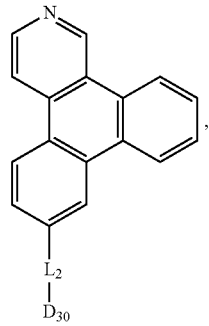
Compound 306
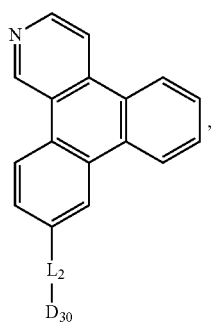
Compound 307
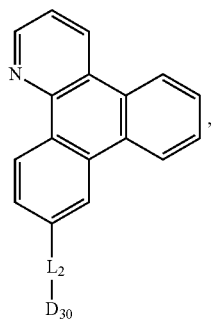

Compound 308
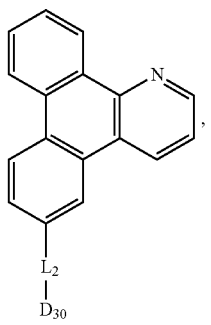
Compound 309
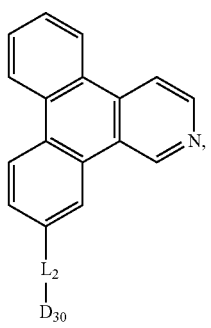
Compound 310
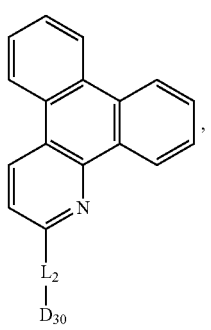
Compound 311
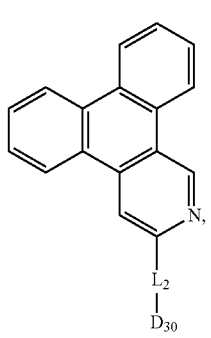
Compound 312
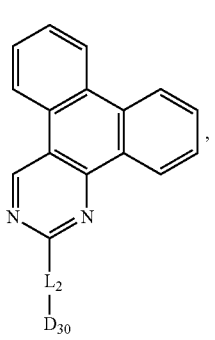
Compound 313
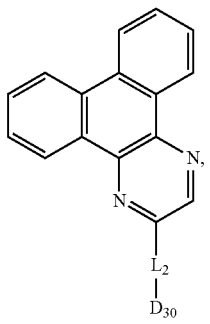
Compound 314
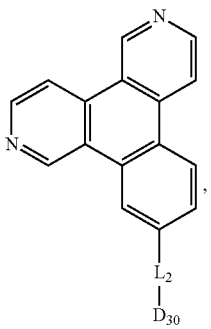
Compound 315
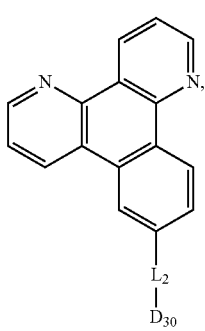
Compound 316
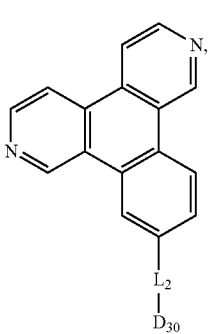
Compound 317
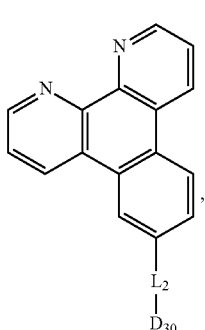

Compound 318
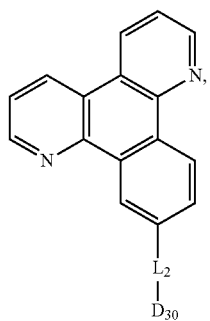
Compound 319
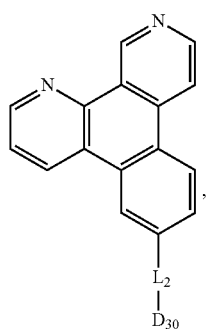
Compound 320
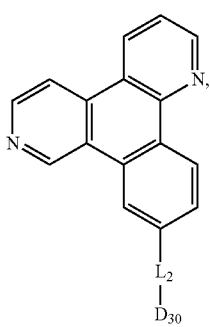
Compound 321
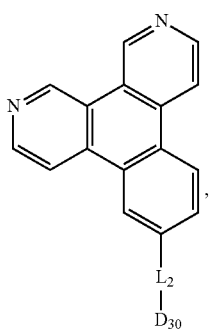
Compound 322
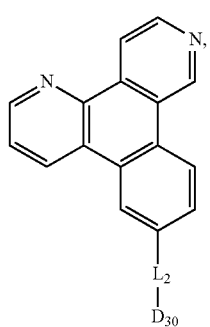
Compound 323
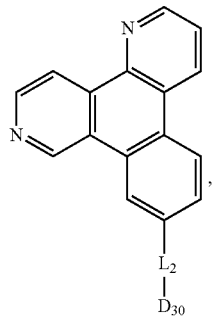
Compound 324
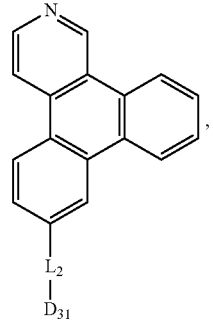
Compound 325
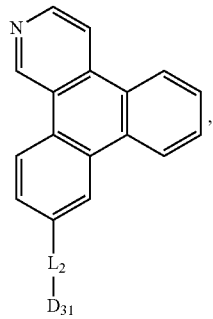
Compound 326
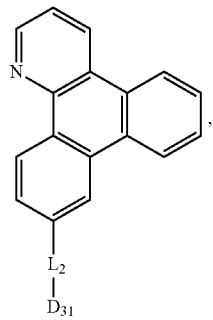
Compound 327
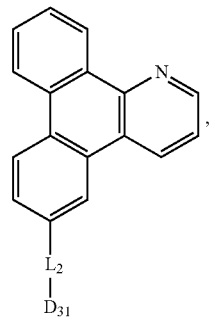

Compound 328
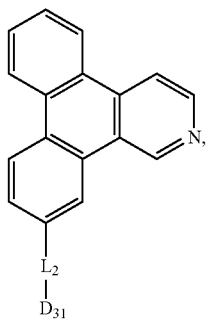
Compound 329
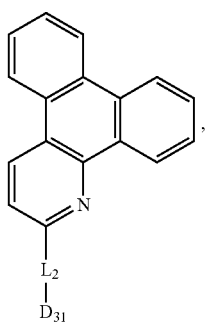
Compound 330

Compound 331
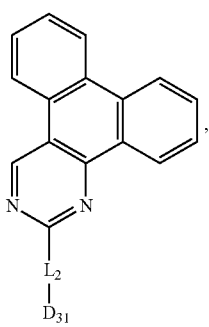
Compound 332

Compound 333
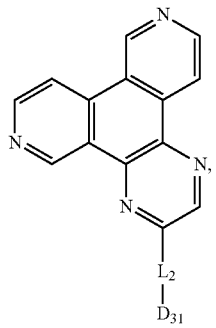
Compound 334
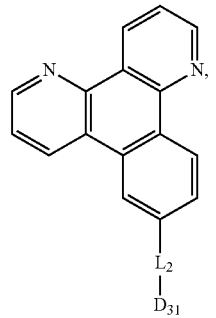
Compound 335
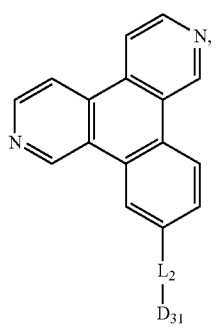
Compound 336
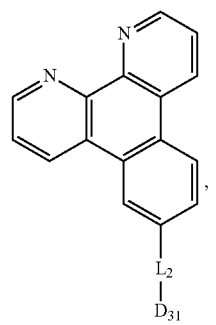
Compound 337
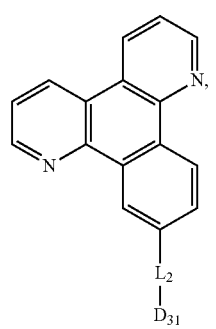

Compound 338
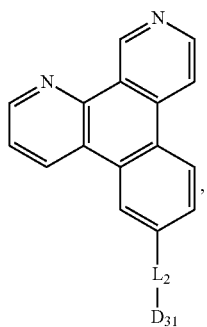
Compound 339
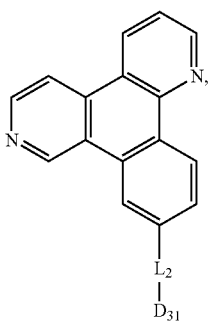
Compound 340
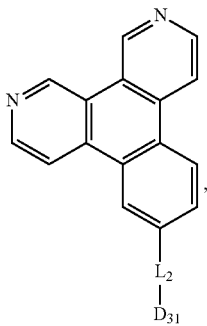
Compound 341
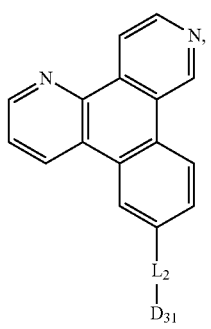
Compound 342
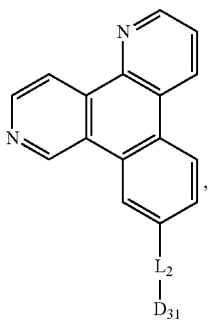
Compound 343
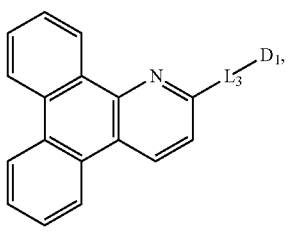
Compound 344
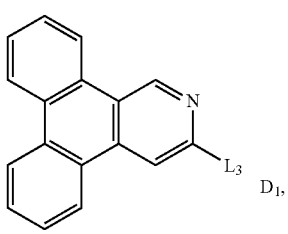
Compound 345
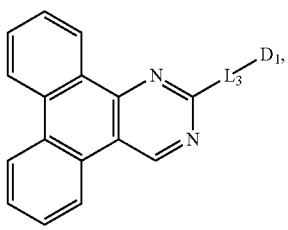
Compound 346
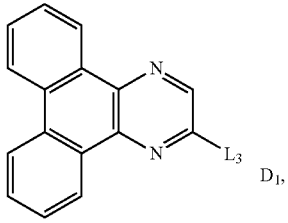
Compound 347
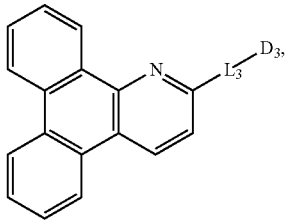
Compound 348
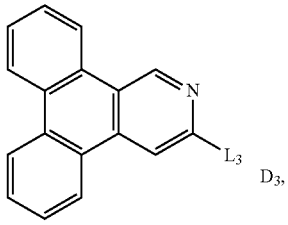
Compound 349
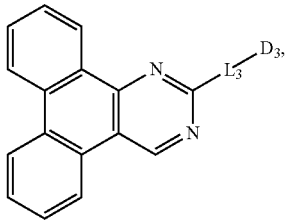

-continued
Compound 350
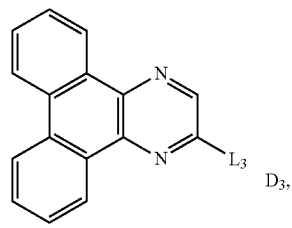
Compound 351
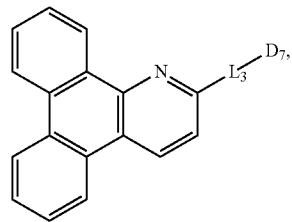
Compound 352
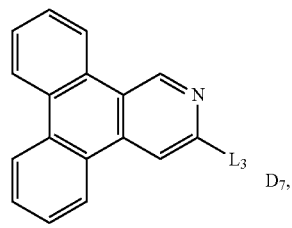
Compound 353
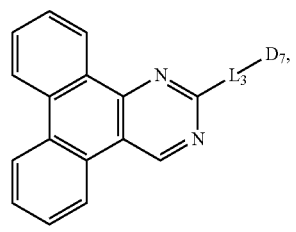
Compound 354
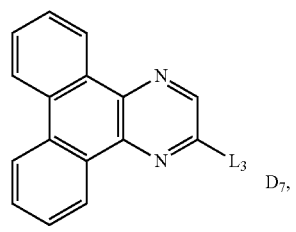
Compound 355
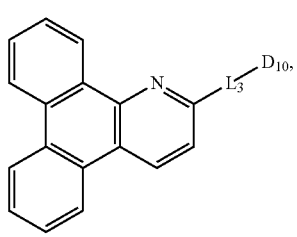
Compound 356
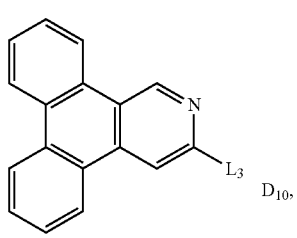
-continued
Compound 357
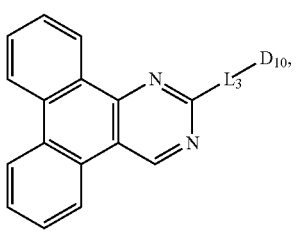
Compound 358
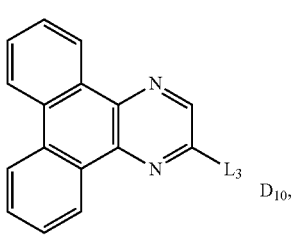
Compound 359
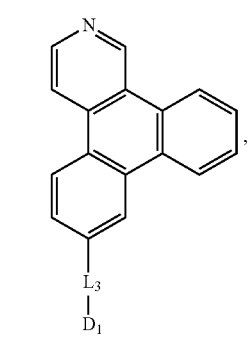
Compound 360
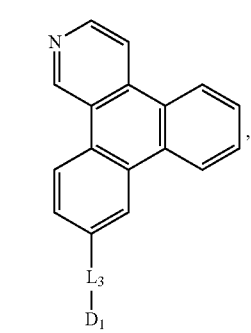
Compound 361
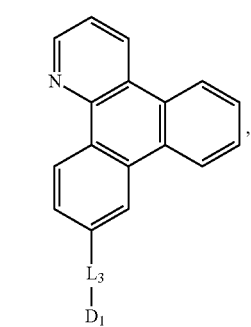

Compound 362
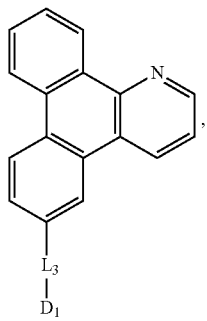
Compound 363
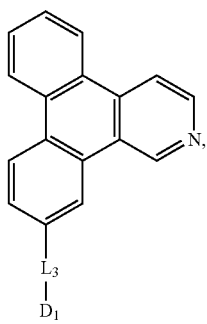
Compound 364
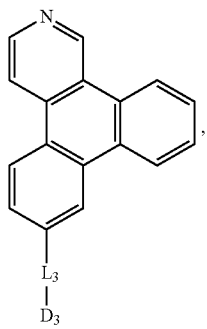
Compound 365
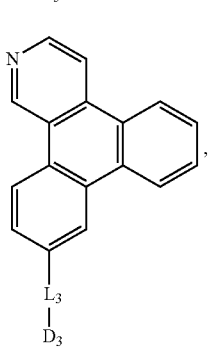
Compound 366
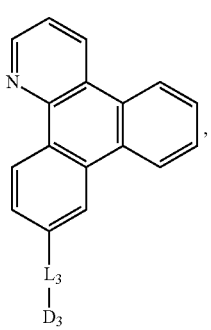
Compound 367
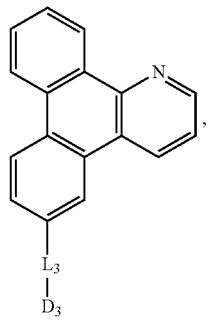
Compound 368
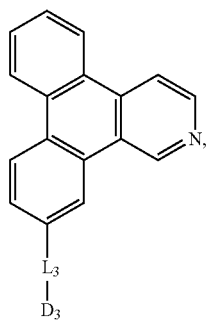
Compound 369
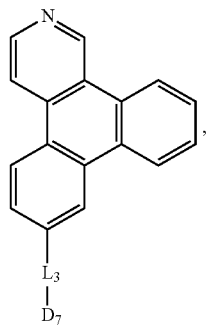
Compound 370
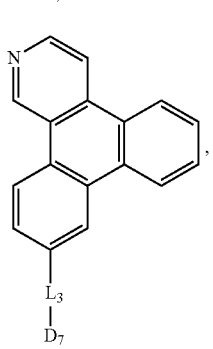
Compound 371
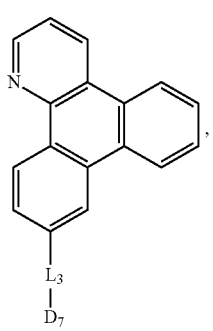

235
-continued
Compound 372
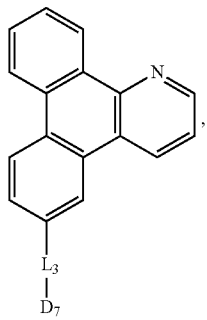
Compound 373
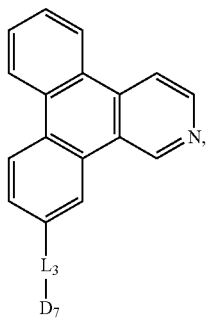
Compound 374
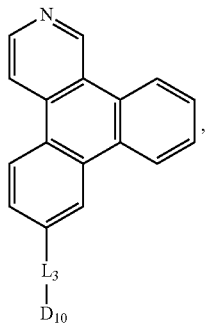
Compound 375
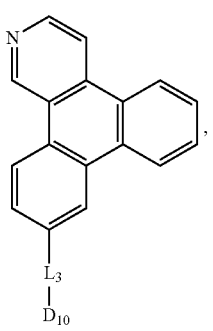
Compound 376
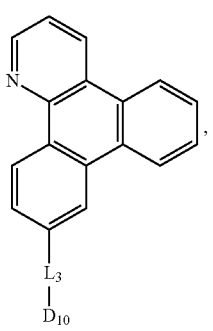
236
-continued
Compound 377
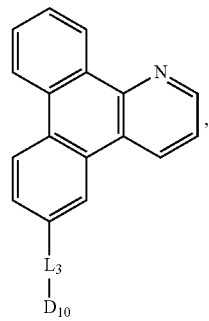
Compound 378
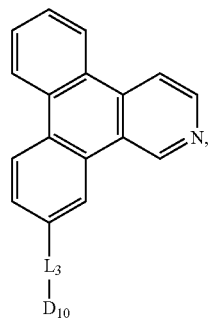
Compound 379
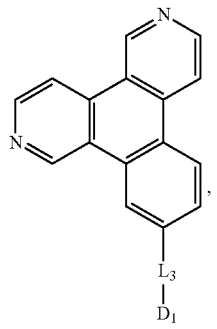
Compound 380
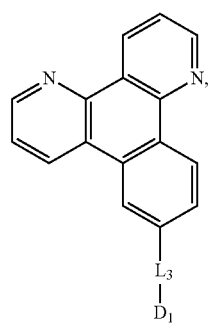
Compound 381
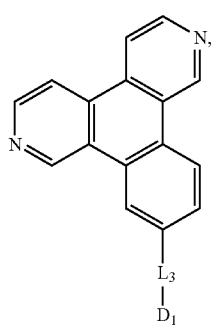

Compound 382
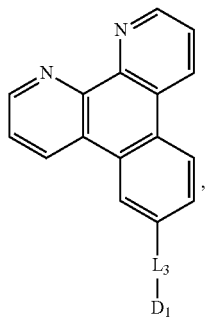
Compound 383
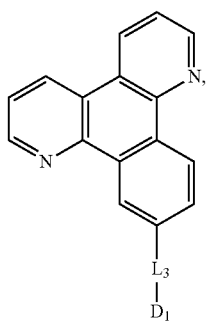
Compound 384

Compound 385

Compound 386
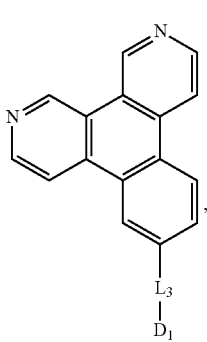
Compound 387
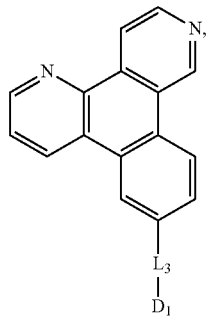
Compound 388
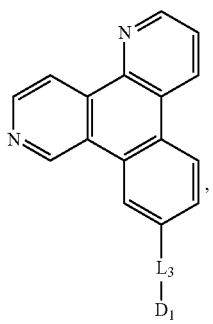
Compound 389
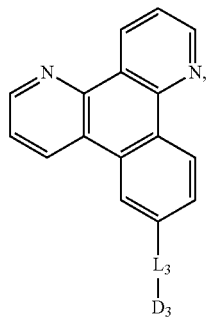
Compound 390
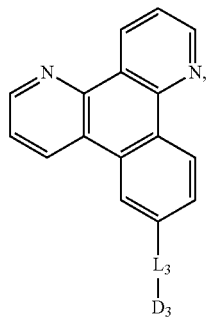
Compound 391
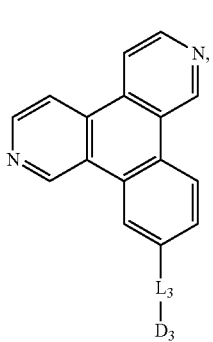

-continued
Compound 392
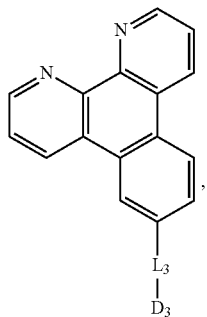
Compound 393
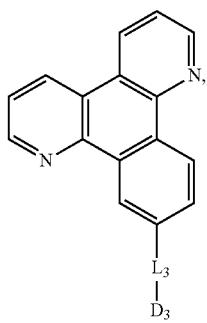
Compound 394
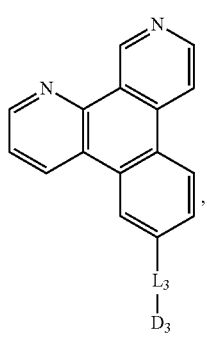
Compound 395
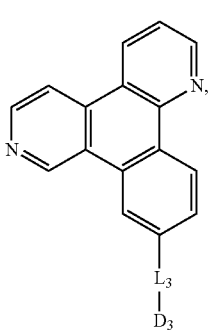
Compound 396
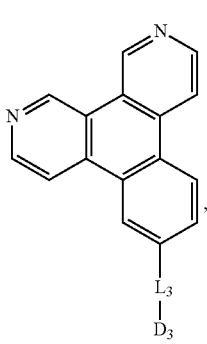
-continued
Compound 397
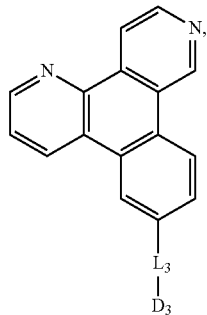
Compound 398
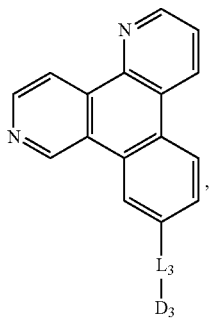
Compound 399
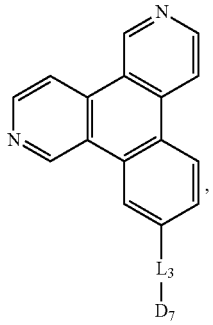
Compound 400
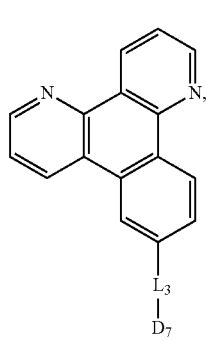
Compound 401
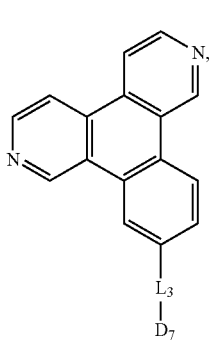

-continued
Compound 402
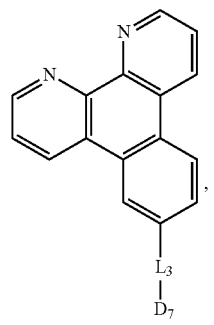
Compound 403
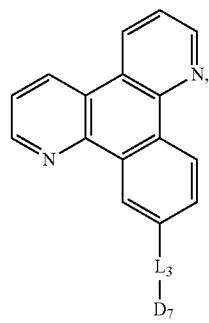
Compound 404
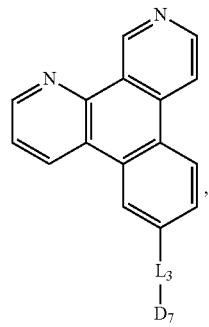
Compound 405
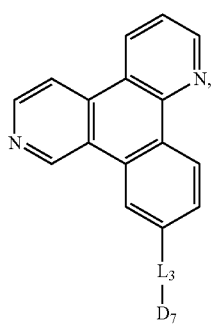
Compound 406
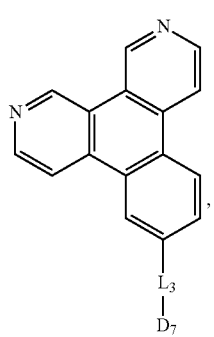
-continued
Compound 407
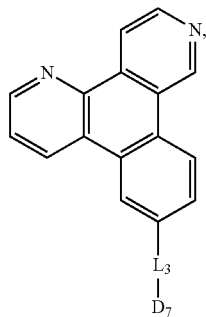
Compound 408
Compound 409
Compound 410
Compound 411

Compound 412
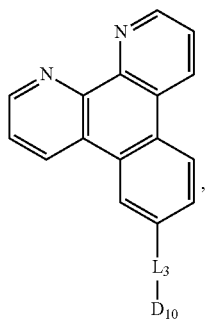
Compound 413
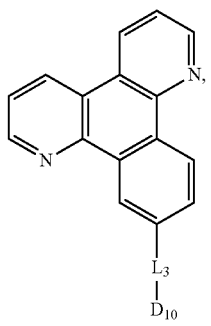
Compound 414
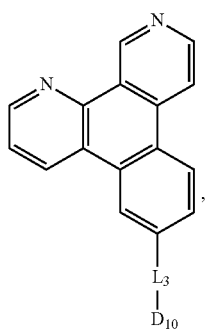
Compound 415
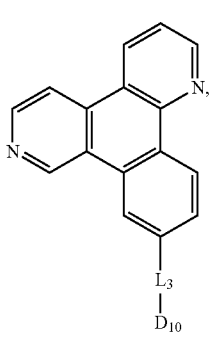
Compound 416
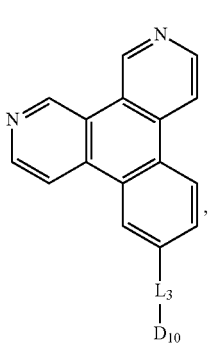
Compound 417
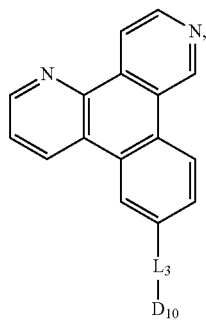
Compound 418
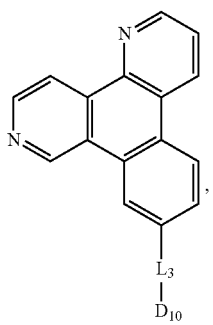
Compound 419
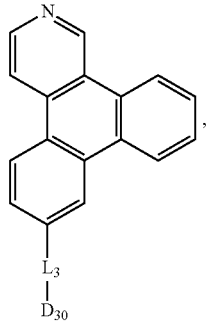
Compound 420
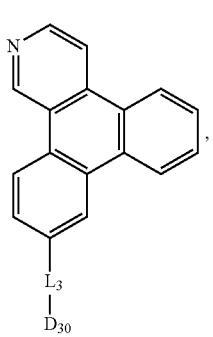
Compound 421
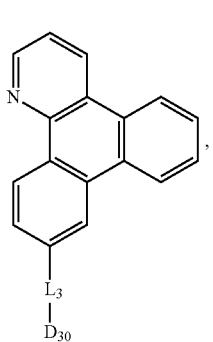

Compound 422
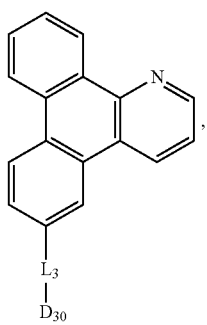
Compound 423
Compound 424
Compound 425
Compound 426
Compound 427
Compound 428
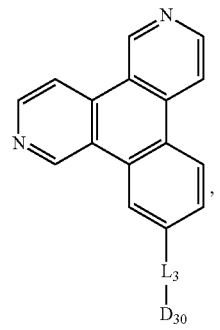
Compound 429
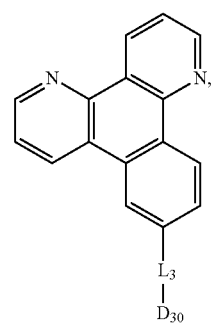
Compound 430
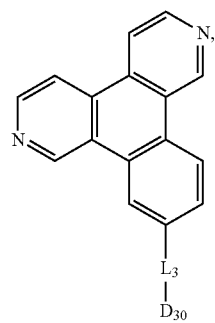
Compound 431
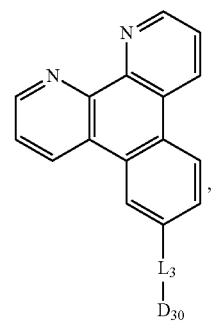
Compound 432
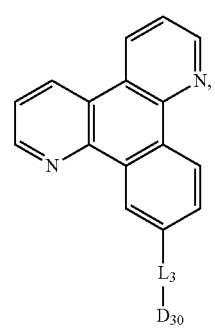

Compound 433
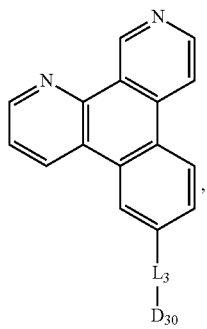
Compound 434
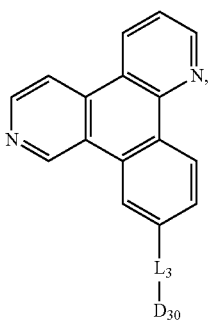
Compound 435
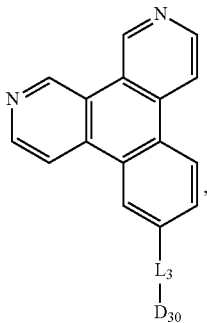
Compound 436
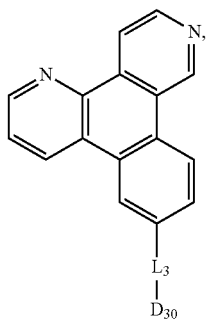
Compound 437
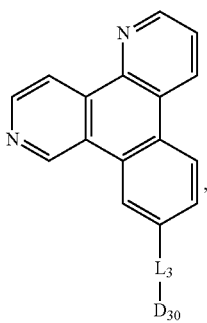
Compound 438
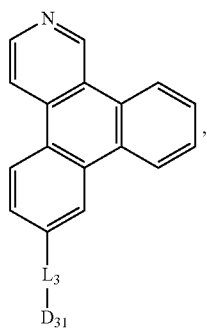
Compound 439
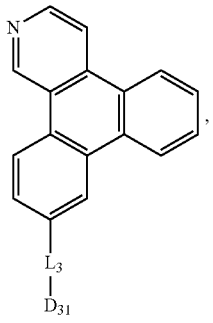
Compound 440
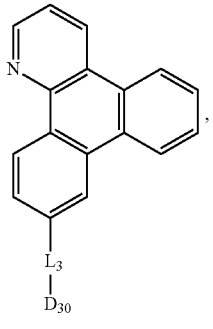
Compound 441
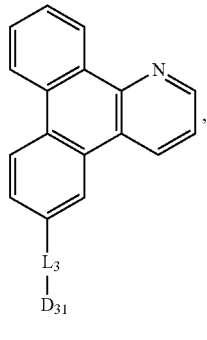
Compound 442
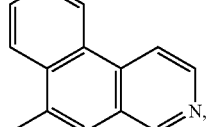
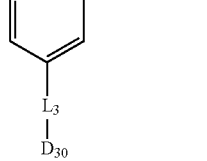

Compound 443
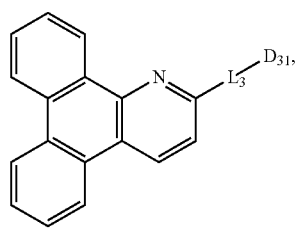
Compound 444
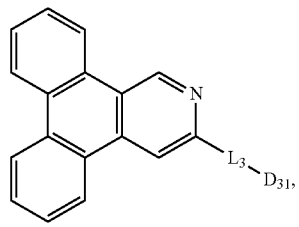
Compound 445
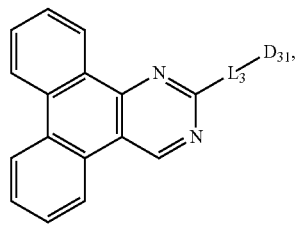
Compound 446
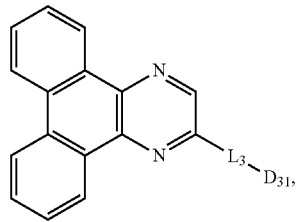
Compound 447
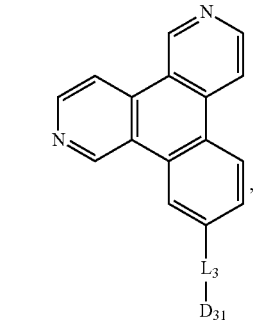
Compound 448
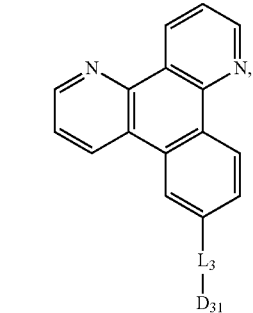
Compound 449
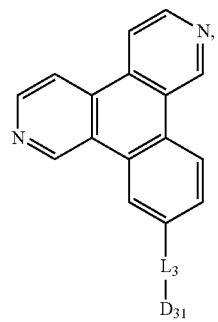
Compound 450
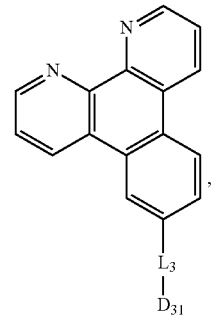
Compound 451
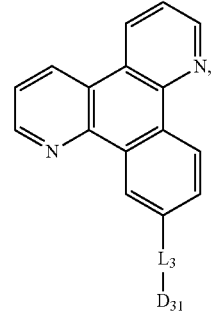
Compound 452
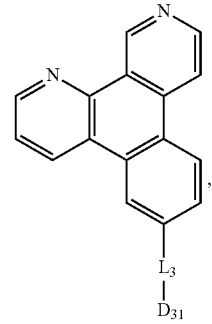
Compound 453
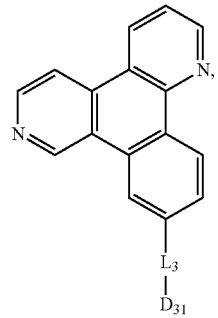

-continued
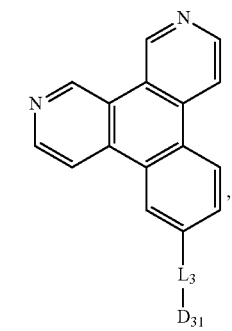
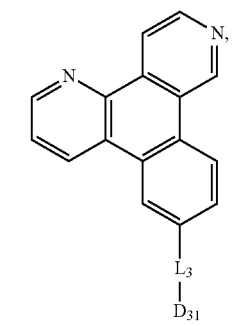
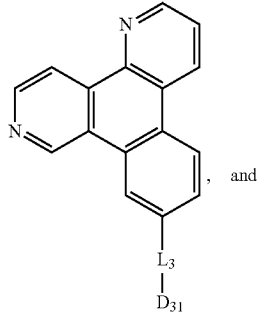, and
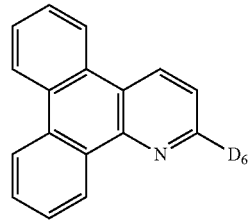
wherein D1, D3, D6, D7, D10, D30 and D31 are
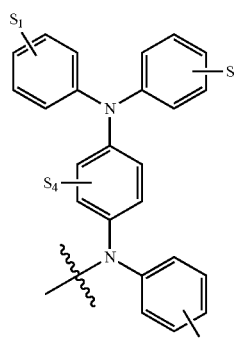
D1
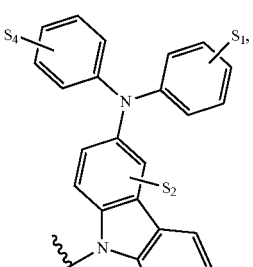
D3
Compound 454
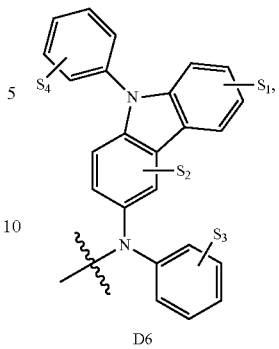
D6
Compound 455
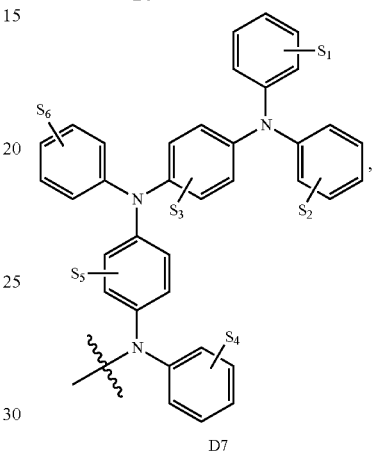
D7
Compound 456
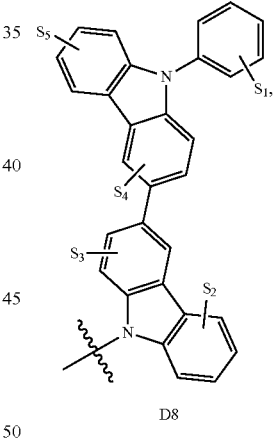
D8
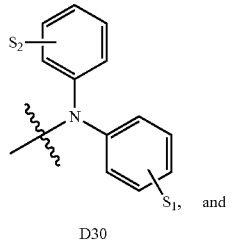
D30, and
Compound 457
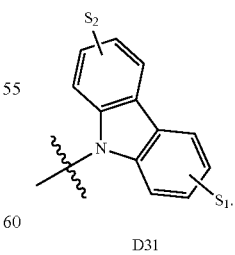
D31
In some other embodiments of the first device, $S_1$ to $S_7$ and $A_1$-$A_2$ are H. The resulting compounds are denoted as Compound No.-H. For example, Compound 1-H is

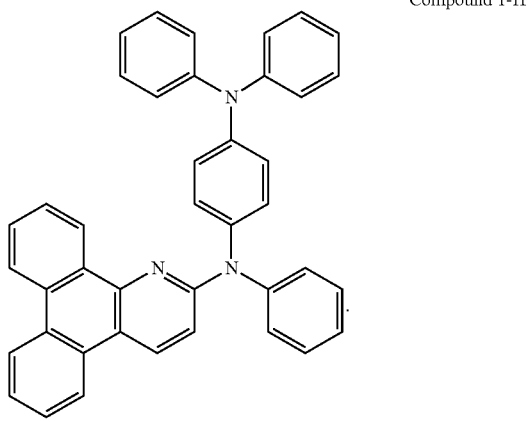

Compound 1-H

The first device emits a luminescent radiation at room temperature when a voltage is applied across the organic light emitting device, wherein the luminescent radiation comprises a delayed fluorescence process. In the first device, the emissive layer can further comprises a first phosphorescent emitting material. In other embodiments, the emissive layer further comprises a second phosphorescent emitting material. The emissive layer further comprises a host material, In some embodiments, the first device emits a white light at room temperature when a voltage is applied across the organic light emitting device by using, for example, Compound 9-H and Compound 4-H as the emitters. In some embodiments, the first emitting compound emits a blue light with a peak wavelength of about 400 nm to about 500 nm, for example Compound 9-H, Compound 15-H, Compound 129-H and Compound 457-H. In some embodiments, the first emitting compound emits a yellow light with a peak wavelength of about 530 nm to about 580 nm, for example Compound 4-H and Compound 12-H.

According to another aspect of the present disclosure, the first device comprises a second organic light emitting device, wherein the second organic light emitting device is stacked on the first organic light emitting device. The first device can be a consumer product. The first device can be an organic light-emitting device. The first device can be a lighting panel.

According to another embodiment of the first device, at least one of the R comprises a donor group with at least two electron-donating nitrogens.

In yet another aspect of the present disclosure, a formulation that includes a compound according to Formula 1 is described. The formulation can include one or more components selected from the group consisting of a solvent, a host, a hole injection material, hole transport material, an electron transport layer material (see below).

Combination with Other Materials

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

HIL/HTL:

A hole injecting/transporting material to be used in the present invention is not particularly limited, and any compound may be used as long as the compound is typically used as a hole injecting/transporting material. Examples of the material include, but not limit to: a phthalocyanine or porphryin derivative; an aromatic amine derivative; an indolocarbazole derivative; a polymer containing fluorohydrocarbon; a polymer with conductivity dopants; a conducting polymer, such as PEDOT/PSS; a self-assembly monomer derived from compounds such as phosphonic acid and sliane derivatives; a metal oxide derivative, such as $MoO_x$; a p-type semiconducting organic compound, such as 1,4,5,8,9,12-Hexaazatriphenylenehexacarbonitrile; a metal complex, and a cross-linkable compounds.

Examples of aromatic amine derivatives used in HIL or HTL include, but not limit to, the following general structures:

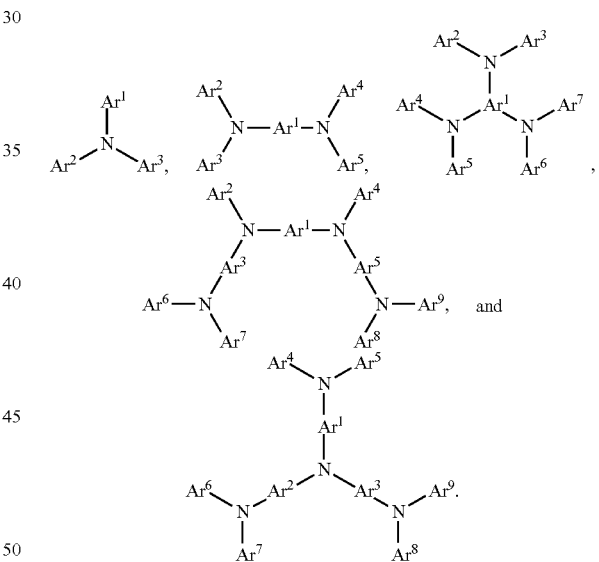

Each of $Ar^1$ to $Ar^9$ is selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each Ar is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, $Ar^1$ to $Ar^9$ is independently selected from the group consisting of:

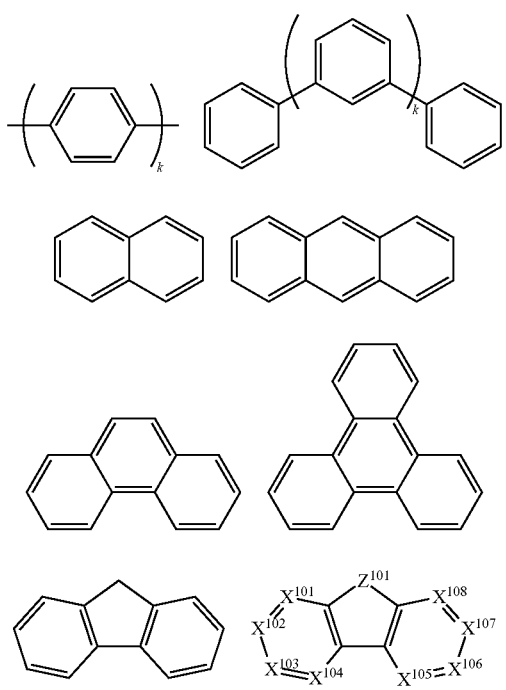

k is an integer from 1 to 20; $X^{101}$ to $X^{108}$ is C (including CH) or N; $Z^{101}$ is $NAr^1$, O, or S; $Ar^1$ has the same group defined above.

Examples of metal complexes used in HIL or HTL include, but not limit to the following general formula:

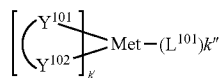

Met is a metal, which can have an atomic weight greater than 40; $(Y^{101}\text{-}Y^{102})$ is a bidentate ligand, $Y^{101}$ and $Y^{102}$ are independently selected from C, N, O, P, and S; $L^{101}$ is an ancillary ligand; k' is an integer value from 1 to the maximum number of ligands that may be attached to the metal; and k'+k" is the maximum number of ligands that may be attached to the metal.

In one aspect, $(Y^{101}\text{-}Y^{102})$ is a 2-phenylpyridine derivative. In another aspect, $(Y^{101}\text{-}Y^{102})$ is a carbene ligand. In another aspect, Met is selected from Ir, Pt, Os, and Zn. In a further aspect, the metal complex has a smallest oxidation potential in solution vs. $Fc^+/Fc$ couple less than about 0.6 V.

Host:

The light emitting layer of the organic EL device of the present invention preferably contains at least a metal complex as light emitting material, and may contain a host material using the metal complex as a dopant material. Examples of the host material are not particularly limited, and any metal complexes or organic compounds may be used as long as the triplet energy of the host is larger than that of the dopant. While the Table below categorizes host materials as preferred for devices that emit various colors, any host material may be used with any dopant so long as the triplet criteria is satisfied.

Examples of metal complexes used as host are preferred to have the following general formula:

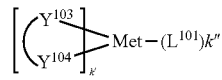

wherein Met is a metal; $(Y^{103}\text{-}Y^{104})$ is a bidentate ligand, $Y^{103}$ and $Y^{104}$ are independently selected from C, N, O, P, and S; $L^{101}$ is an another ligand; k' is an integer value from 1 to the maximum number of ligands that may be attached to the metal; and k'+k" is the maximum number of ligands that may be attached to the metal.

In one aspect, the metal complexes are:

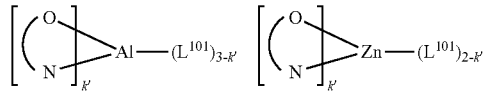

wherein (O—N) is a bidentate ligand, having metal coordinated to atoms O and N. In another aspect, Met is selected from Ir and Pt. In a further aspect, $(Y^{103}\text{-}Y^{104})$ is a carbene ligand.

Examples of organic compounds used as host are selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atome, sulfur atom, silicon atom, phosphorus atom, boron atom, chain structural unit and the aliphatic cyclic group. Wherein each group is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, host compound contains at least one of the following groups in the molecule:

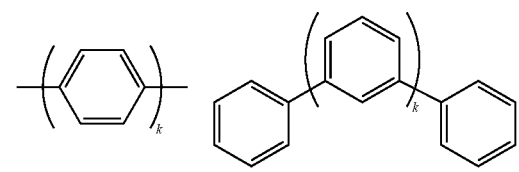

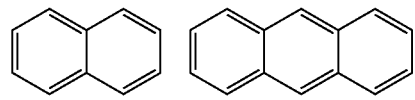

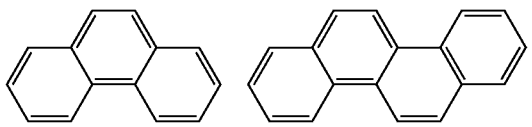

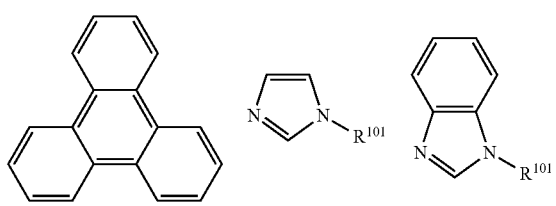

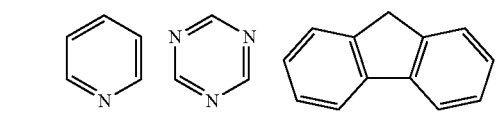

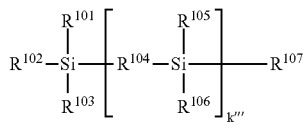

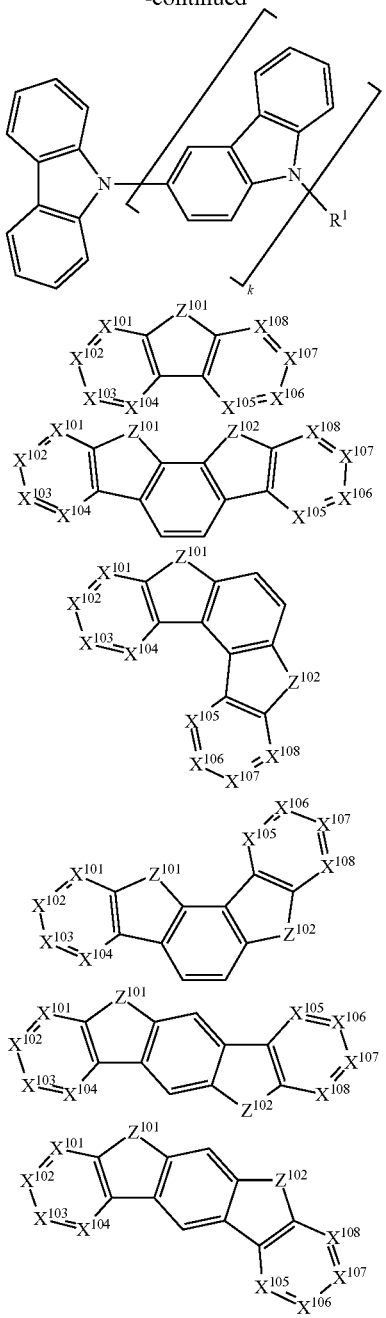

wherein $R^{101}$ to $R^{107}$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above. k is an integer from 0 to 20 or 1 to 20; k''' is an integer from 0 to 20. $X^{101}$ to $X^{108}$ is selected from C (including CH) or N; and $Z^{101}$ and $Z^{102}$ is selected from $NR^{101}$, O, or S.

HBL:

A hole blocking layer (HBL) may be used to reduce the number of holes and/or excitons that leave the emissive layer. The presence of such a blocking layer in a device may result in substantially higher efficiencies as compared to a similar device lacking a blocking layer. Also, a blocking layer may be used to confine emission to a desired region of an OLED.

In one aspect, compound used in HBL contains the same molecule or the same functional groups used as host described above.

In another aspect, compound used in HBL contains at least one of the following groups in the molecule:

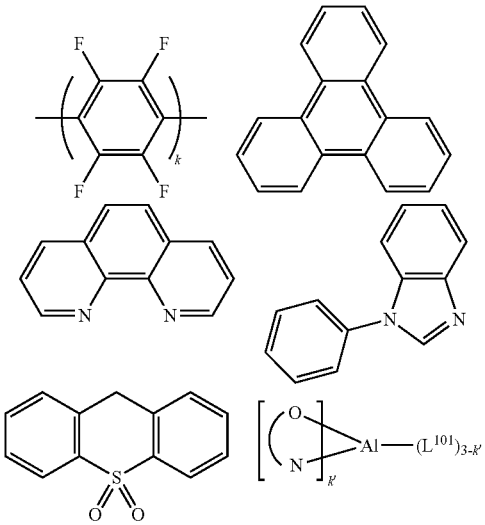

wherein k is an integer from 1 to 20; $L^{101}$ is an another ligand, k' is an integer from 1 to 3.

ETL:

Electron transport layer (ETL) may include a material capable of transporting electrons. Electron transport layer may be intrinsic (undoped), or doped. Doping may be used to enhance conductivity. Examples of the ETL material are not particularly limited, and any metal complexes or organic compounds may be used as long as they are typically used to transport electrons.

In one aspect, compound used in ETL contains at least one of the following groups in the molecule:

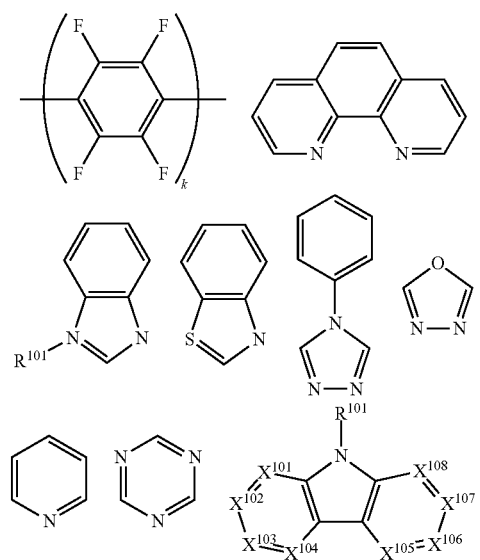

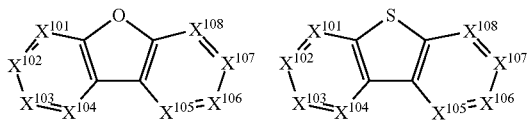

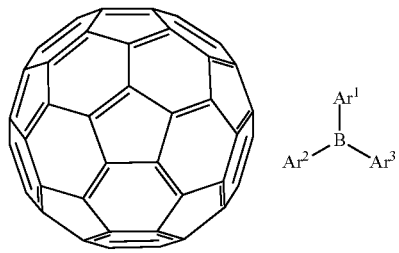

wherein $R^{101}$ is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above. $Ar^1$ to $Ar^3$ has the similar definition as Ar's mentioned above. k is an integer from 1 to 20. $X^{101}$ to $X^{108}$ is selected from C (including CH) or N.

In another aspect, the metal complexes used in ETL contains, but not limit to the following general formula:

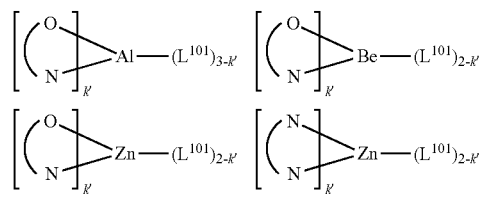

wherein (O—N) or (N—N) is a bidentate ligand, having metal coordinated to atoms O, N or N, N; $L^{101}$ is another ligand; k' is an integer value from 1 to the maximum number of ligands that may be attached to the metal.

In any above-mentioned compounds used in each layer of the OLED device, the hydrogen atoms can be partially or fully deuterated. Thus, any specifically listed substituent, such as, without limitation, methyl, phenyl, pyridyl, etc. encompasses undeuterated, partially deuterated, and fully deuterated versions thereof. Similarly, classes of substituents such as, without limitation, alkyl, aryl, cycloalkyl, heteroaryl, etc. also encompass undeuterated, partially deuterated, and fully deuterated versions thereof.

In addition to and/or in combination with the materials disclosed herein, many hole injection materials, hole transporting materials, host materials, dopant materials, exiton/hole blocking layer materials, electron transporting and electron injecting materials may be used in an OLED. Non-limiting examples of the materials that may be used in an OLED in combination with materials disclosed herein are listed in Table 1 below. Table 1 lists non-limiting classes of materials, non-limiting examples of compounds for each class, and references that disclose the materials.

TABLE 1

| MATERIAL | EXAMPLES OF MATERIAL | PUBLICATIONS |
|---|---|---|
| *Hole injection materials* | | |
| Phthalocyanine and porphryin compounds | 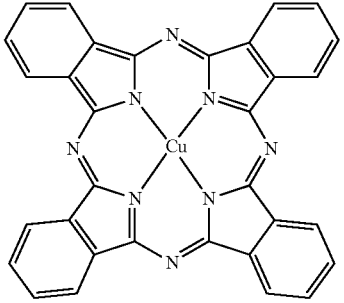 | Appl. Phys. Lett. 69, 2160 (1996) |
| Starburst triarylamines | 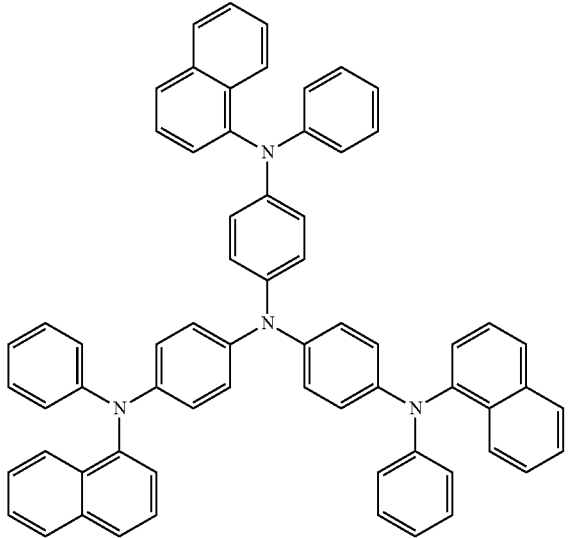 [SMILES: c1ccc(N(c2ccc(N(c3ccc(N(c4ccccc4)c4cccc5ccccc45)cc3)c3ccc(N(c4ccccc4)c4cccc5ccccc45)cc3)cc2)c2cccc3ccccc23)cc1] | J. Lumin. 72-74, 985 (1997) |
| $CF_x$ Fluorohydrocarbon polymer | $-\!\!\left[\!-CH_xF_y-\!\right]_n\!\!-$ | Appl. Phys. Lett. 78, 673 (2001) |
| Conducting polymers (e.g., PEDOT:PSS, polyaniline, polypthiophene) | 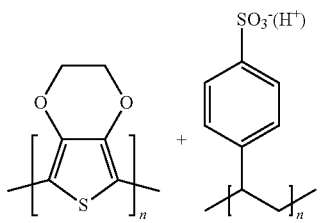 | Synth. Met. 87, 171 (1997) WO2007002683 |
| Phosphonic acid and sliane SAMs | 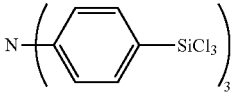 | US20030162053 |
| Triarylamine or polythiophene polymers with conductivity dopants | 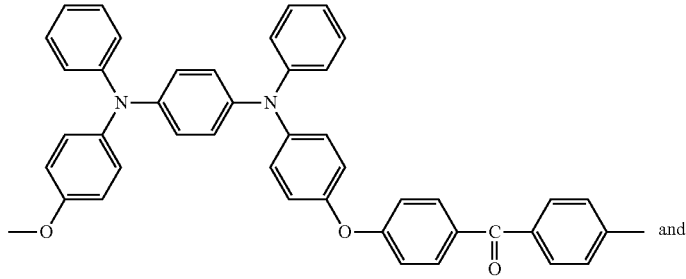 and | EP1725079A1 |

TABLE 1-continued
| MATERIAL | EXAMPLES OF MATERIAL | PUBLICATIONS |
|---|---|---|
| | 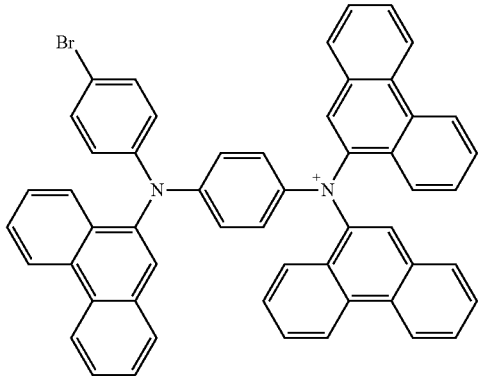 [SMILES: Brc1ccc(N(c2ccc(N(c3cc4ccccc4c4ccccc34)c3cc4ccccc4c4ccccc34)cc2)c2cc3ccccc3c3ccccc23)cc1] | |
| Organic compounds with conductive inorganic compounds, such as molybdenum and tungsten oxides | 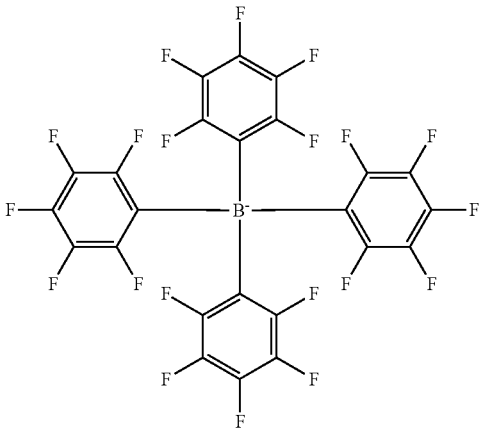 [SMILES: Fc1c(F)c(F)c([B-](c2c(F)c(F)c(F)c(F)c2F)(c2c(F)c(F)c(F)c(F)c2F)c2c(F)c(F)c(F)c(F)c2F)c(F)c1F] + MoO$_x$ | US20050123751 SID Symposium Digest, 37, 923 (2006) WO2009018009 |
| n-type semiconducting organic complexes | 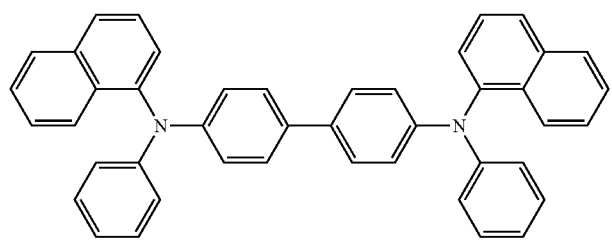 | US20020158242 |
| Metal organometallic complexes | 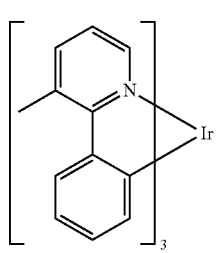 | US20060240279 |

TABLE 1-continued

| MATERIAL | EXAMPLES OF MATERIAL | PUBLICATIONS |
| --- | --- | --- |
| Cross-linkable compounds | | US20080220265 |
| Polythiophene based polymers and copolymers | | WO 2011075644<br>EP2350216 |
| Hole transporting materials | | |
| Triarylamines<br>(e.g., TPD, α-NPD) | | Appl. Phys. Lett.<br>51, 913 (1987)<br>U.S. Pat. No.<br>5,061,569<br>EP650955<br>J. Mater. Chem.<br>3, 319 (1993)<br>Appl. Phys. Lett.<br>90, 183503<br>(2007)<br><br>Appl. Phys. Lett.<br>90, 183503<br>(2007) |

TABLE 1-continued

| MATERIAL | EXAMPLES OF MATERIAL | PUBLICATIONS |
| --- | --- | --- |
| Triaylamine on spirofluorene core | | Synth. Met. 91, 209 (1997) |
| Arylamine carbazole compounds | | Adv. Mater. 6, 677 (1994), US20080124572 |
| Triarylamine with (di)benzothiophene/ (di)benzofuran | | US20070278938, US20080106190 US20110163302 |
| Indolocarbazoles | | Synth. Met. 111, 421 (2000) |

TABLE 1-continued

| MATERIAL | EXAMPLES OF MATERIAL | PUBLICATIONS |
|---|---|---|
| Isoindole compounds | | Chem. Mater. 15, 3148 (2003) |
| Metal carbene complexes | | US20080018221 |

Phosphorescent PLED host materials
Red hosts

| | | |
|---|---|---|
| Arylcarbazoles | | Appl. Phys. Lett. 78, 1622 (2001) |
| Metal 8-hydroxyquinolates (e.g., Alq$_3$, BAlq) | | Nature 395, 151 (1998) |
| | | US20060202194 |

TABLE 1-continued
| MATERIAL | EXAMPLES OF MATERIAL | PUBLICATIONS |
|---|---|---|
| | 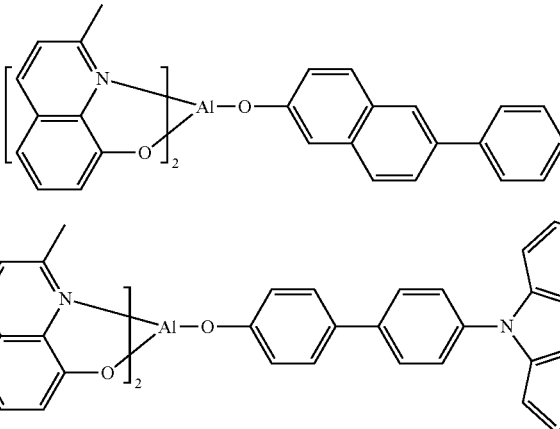 | WO2005014551 |
| | 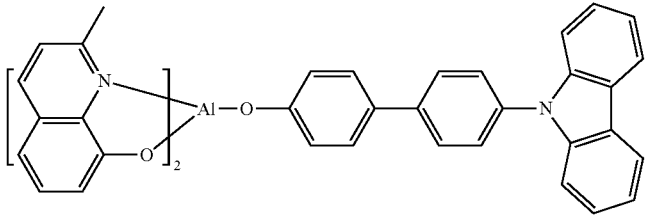 | WO2006072002 |
| Metal phenoxybenzothiazole compounds | 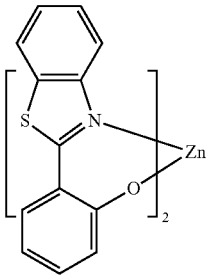 | Appl. Phys. Lett. 90, 123509 (2007) |
| Conjugated oligomers and polymers (e.g., polyfluorene) | 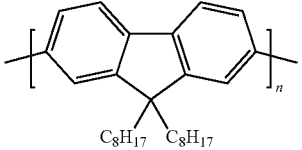 | Org. Electron. 1, 15 (2000) |
| Aromatic fused rings | 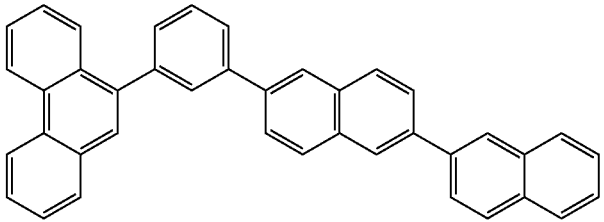 [SMILES: c1cc(-c2ccc3cc(-c4ccc5ccccc5c4)ccc3c2)cc(-c2cc3ccccc3c3ccccc23)c1] | WO2009066779, WO2009066778, WO2009063833, US20090045731, US20090045730, WO2009008311, US20090008605, US20090009065 |
| Zinc complexes | 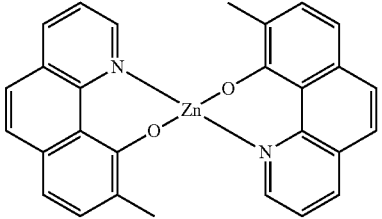 | WO2010056066 |
| Chrysene based compounds | 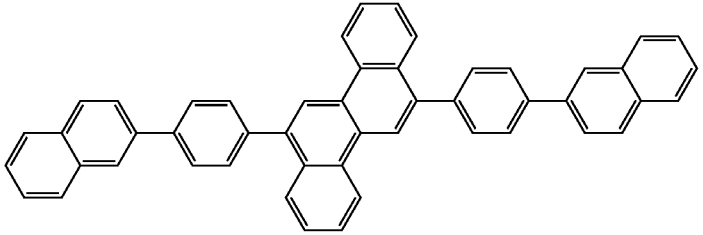 [SMILES: c1ccc2cc(-c3ccc(-c4cc5c6ccccc6c(-c6ccc(-c7ccc8ccccc8c7)cc6)cc5c5ccccc45)cc3)ccc2c1] | WO2011086863 |

TABLE 1-continued
| MATERIAL | EXAMPLES OF MATERIAL | PUBLICATIONS |
|---|---|---|
| | Green hosts | |
| Arylcarbazoles | 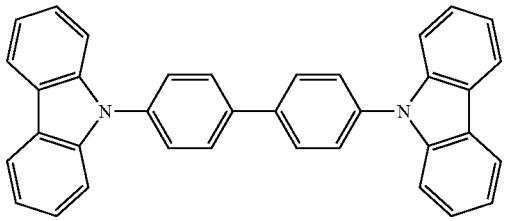 [SMILES: c1ccc2c(c1)c1ccccc1n2-c1ccc(-c2ccc(-n3c4ccccc4c4ccccc43)cc2)cc1] | Appl. Phys. Lett. 78, 1622 (2001) |
| | 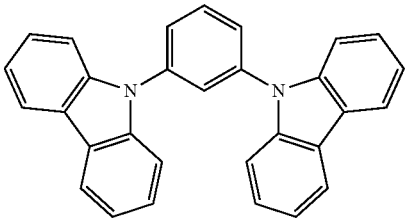 [SMILES: c1cc(-n2c3ccccc3c3ccccc32)cc(-n2c3ccccc3c3ccccc32)c1] | US20030175553 |
| | 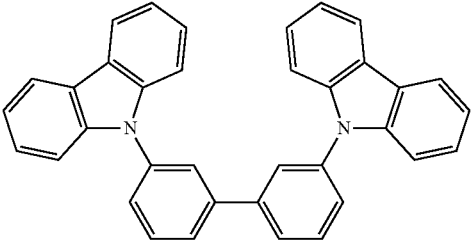 [SMILES: c1cc(-c2cccc(-n3c4ccccc4c4ccccc43)c2)cc(-n2c3ccccc3c3ccccc32)c1] | WO2001039234 |
| Aryltriphenylene compounds | 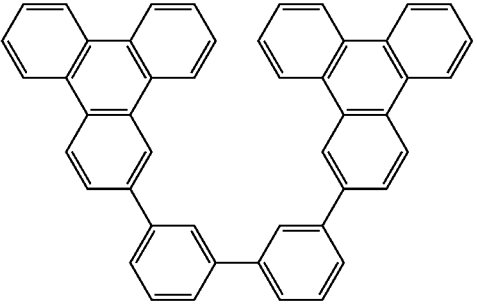 [SMILES: c1cc(-c2cccc(-c3ccc4c5ccccc5c5ccccc5c4c3)c2)cc(-c2ccc3c4ccccc4c4ccccc4c3c2)c1] | US20060280965 |
| | 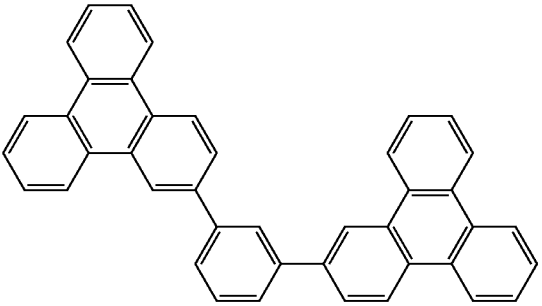 [SMILES: c1cc(-c2ccc3c4ccccc4c4ccccc4c3c2)cc(-c2ccc3c4ccccc4c4ccccc4c3c2)c1] | US20060280965 |
| | 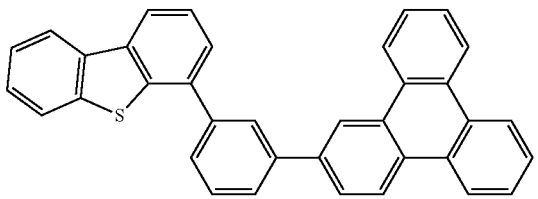 [SMILES: c1cc(-c2ccc3c4ccccc4c4ccccc4c3c2)cc(-c2cccc3c2sc2ccccc23)c1] | WO2009021126 |

TABLE 1-continued
| MATERIAL | EXAMPLES OF MATERIAL | PUBLICATIONS |
|---|---|---|
| Poly-fused heteroaryl compounds | 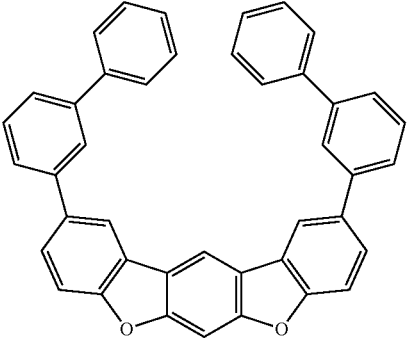 [SMILES: c1ccc(-c2cccc(-c3ccc4oc5cc6oc7ccc(-c8cccc(-c9ccccc9)c8)cc7c6cc5c4c3)c2)cc1] | US20090309488<br>US20090302743<br>US20100012931 |
| Donor acceptor type molecules | 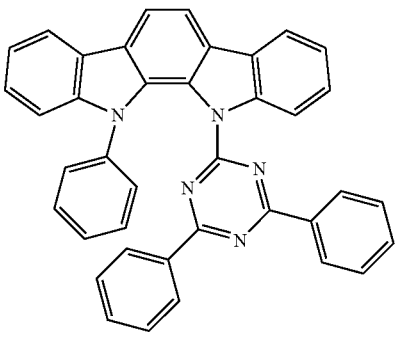 [SMILES: c1ccc(-c2nc(-c3ccccc3)nc(-n3c4ccccc4c4ccc5c6ccccc6n(-c6ccccc6)c5c43)n2)cc1] | WO2008056746 |
|  | 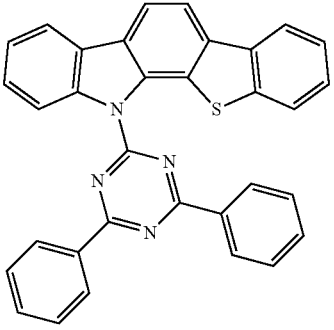 [SMILES: c1ccc(-c2nc(-c3ccccc3)nc(-n3c4ccccc4c4ccc5c6ccccc6sc5c43)n2)cc1] | WO2010107244 |
| Aza-carbazole/DBT/DBF | 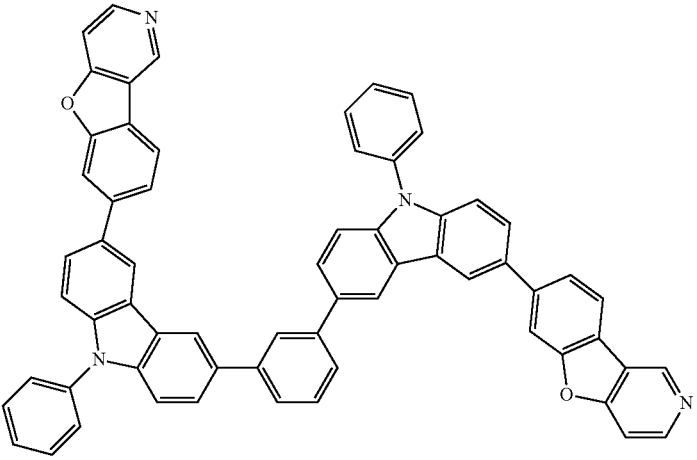 [SMILES: c1ccc(-n2c3ccc(-c4cccc(-c5ccc6c(c5)c5cc(-c7ccc8c(c7)oc7ccncc78)ccc5n6-c5ccccc5)c4)cc3c3cc(-c4ccc5c(c4)oc4ccncc45)ccc32)cc1] | JP2008074939 |

| MATERIAL | EXAMPLES OF MATERIAL | PUBLICATIONS |
|---|---|---|
|  | 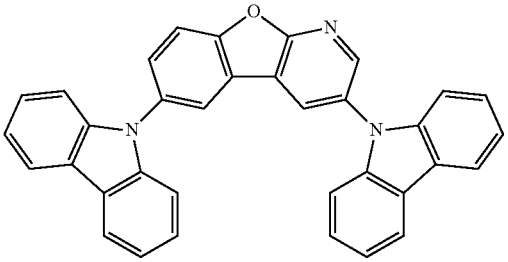 [SMILES: c1ccc2c(c1)c1ccccc1n2-c1ccc2oc3ncc(-n4c5ccccc5c5ccccc54)cc3c2c1] | US20100187984 |
| Polymers (e.g., PVK) | 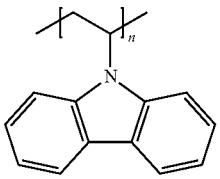 | Appl. Phys. Lett. 77, 2280 (2000) |
| Spirofluorene compound | 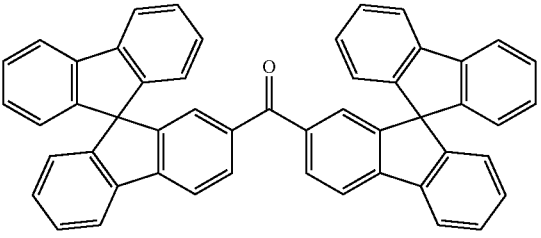 [SMILES: O=C(c1ccc2c(c1)C1(c3ccccc3-c3ccccc31)c1ccccc1-2)c1ccc2c(c1)C1(c3ccccc3-c3ccccc31)c1ccccc1-2] | WO2004093207 |
| Metal phenoxybenzooxazole compounds | 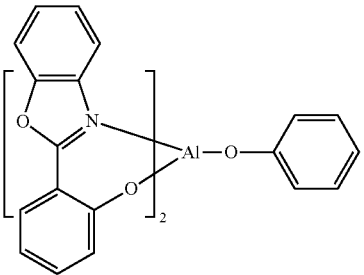 | WO2005089025 |
|  | 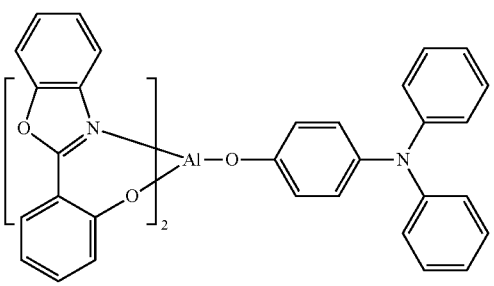 | WO2006132173 |
|  | 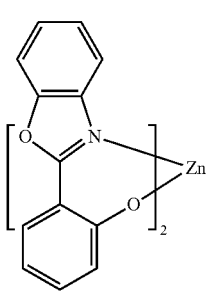 | JP200511610 |

TABLE 1-continued

| MATERIAL | EXAMPLES OF MATERIAL | PUBLICATIONS |
|---|---|---|
| Spirofluorene-carbazole compounds | | JP2007254297 |
| | | JP2007254297 |
| Indolocabazoles | | WO2007063796 |
| | | WO2007063754 |
| 5-member ring electron deficient heterocycles (e.g., triazole, oxadiazole) | | J. Appl. Phys. 90, 5048 (2001) |

TABLE 1-continued

| MATERIAL | EXAMPLES OF MATERIAL | PUBLICATIONS |
| --- | --- | --- |
| | | WO2004107822 |
| Tetraphenylene complexes | | US20050112407 |
| Metal phenoxypyridine compounds | | WO2005030900 |
| Metal coordination complexes (e.g., Zn, Al with N^N ligands) | | US20040137268, US20040137267 |

Blue hosts

| Arylcarbazoles | | Appl. Phys. Lett, 82, 2422 (2003) |
| --- | --- | --- |

| MATERIAL | EXAMPLES OF MATERIAL | PUBLICATIONS |
|---|---|---|
| | 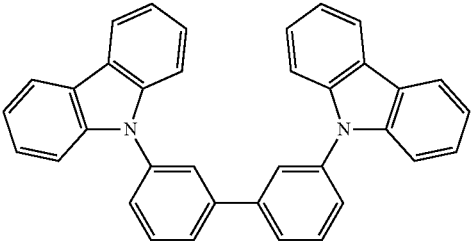 [SMILES: c1cc(-c2cccc(-n3c4ccccc4c4ccccc43)c2)cc(-n2c3ccccc3c3ccccc32)c1] | US20070190359 |
| Dibenzothiophene/ Dibenzofuran-carbazole compounds | 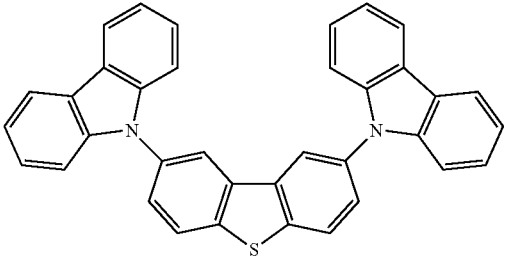 [SMILES: c1ccc2c(c1)c1ccccc1n2-c1ccc2sc3ccc(-n4c5ccccc5c5ccccc54)cc3c2c1] | WO2006114966, US20090167162 |
| | 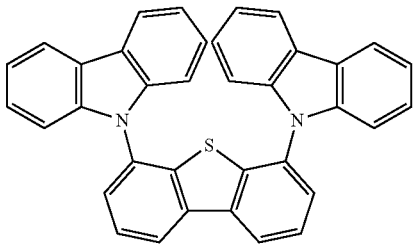 [SMILES: c1cc(-n2c3ccccc3c3ccccc32)c2sc3c(-n4c5ccccc5c5ccccc54)cccc3c2c1] | US20090167162 |
| | 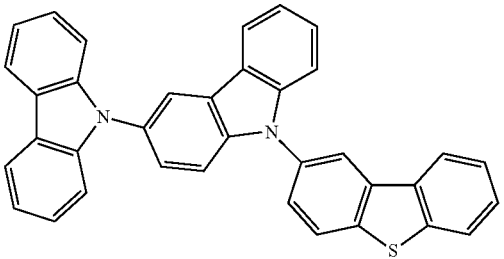 [SMILES: c1ccc2c(c1)sc1ccc(-n3c4ccccc4c4cc(-n5c6ccccc6c6ccccc65)ccc43)cc12] | WO2009086028 |
| | 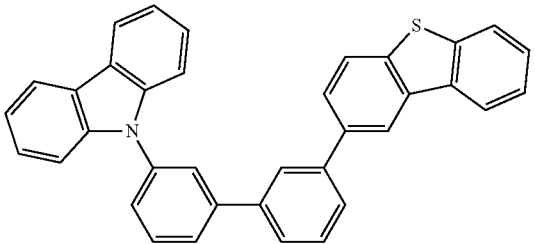 [SMILES: c1cc(-c2cccc(-n3c4ccccc4c4ccccc43)c2)cc(-c2ccc3sc4ccccc4c3c2)c1] | US20090030202, US20090017330 |
| | 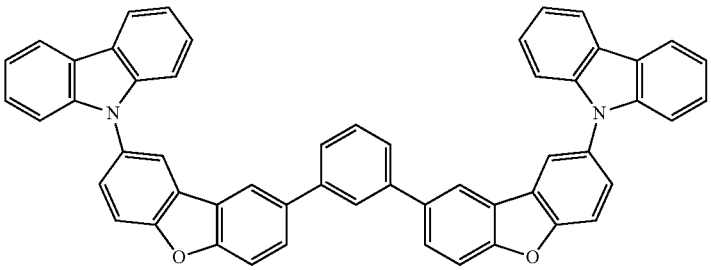 [SMILES: c1cc(-c2ccc3oc4ccc(-n5c6ccccc6c6ccccc65)cc4c3c2)cc(-c2ccc3oc4ccc(-n5c6ccccc6c6ccccc65)cc4c3c2)c1] | US20100084966 |

TABLE 1-continued
| MATERIAL | EXAMPLES OF MATERIAL | PUBLICATIONS |
|---|---|---|
| Silicon aryl compounds | 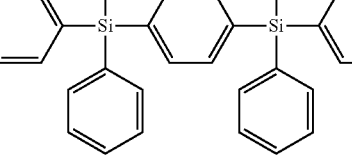 | US20050238919 |
| | 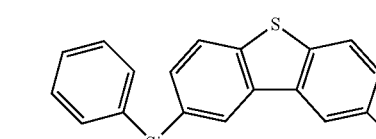 | WO2009003898 |
| Silicon/Germanium aryl compounds | 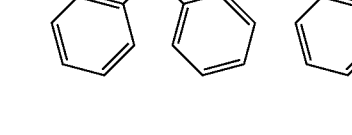 | EP2034538A |
| Aryl benzoyl ester | 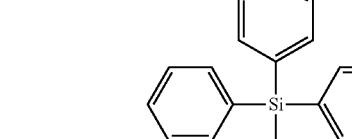 | WO2006100298 |
| Carbazole linked by non-conjugated groups | 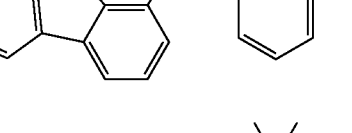 | US20040115476 |
| Aza-carbazoles | 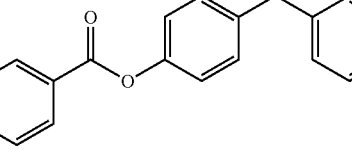 | US20060121308 |

TABLE 1-continued

| MATERIAL | EXAMPLES OF MATERIAL | PUBLICATIONS |
| --- | --- | --- |
| High triplet metal organometallic complex | | U.S. Pat. No. 7,154,114 |

Phosphorescent dopants
Red dopants

| | | |
| --- | --- | --- |
| Heavy metal porphyrins (e.g., PtOEP) | | Nature 395, 151 (1998) |
| Iridium(III) organometallic complexes | | Appl. Phys. Lett. 78, 1622 (2001) |
| | | US2006835469 |
| | | US2006835469 |

TABLE 1-continued

| MATERIAL | EXAMPLES OF MATERIAL | PUBLICATIONS |
|---|---|---|
| | | US20060202194 |
| | | US20060202194 |
| | | US20070087321 |
| | | US20080261076<br>US20100090591 |
| | | US20070087321 |

TABLE 1-continued

| MATERIAL | EXAMPLES OF MATERIAL | PUBLICATIONS |
|---|---|---|
| | | Adv. Mater. 19, 739 (2007) |
| | | WO2009100991 |
| | | WO2008101842 |
| | | U.S. Pat. No. 7,232,618 |
| Platinum(II) organometallic complexes | | WO2003040257 |

TABLE 1-continued
| MATERIAL | EXAMPLES OF MATERIAL | PUBLICATIONS |
|---|---|---|
| | 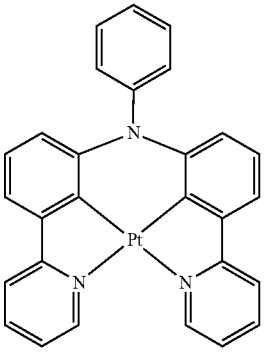 | US20070103060 |
| Osminum(III) complexes | 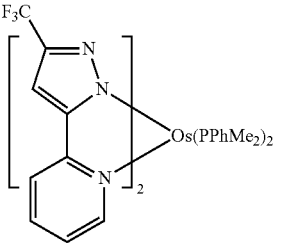 | Chem. Mater. 17, 3532 (2005) |
| Ruthenium(II) complexes | 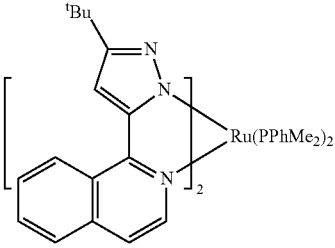 | Adv. Mater. 17, 1059 (2005) |
| Rhenium (I), (II), and (III) complexes | 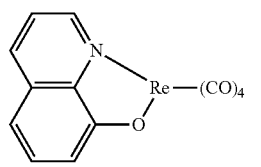 | US20050244673 |
Green dopants
| | | |
|---|---|---|
| Iridium(III) organometallic complexes | 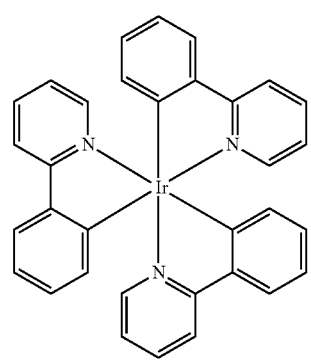
and its derivatives | Inorg. Chem. 40, 1704 (2001) |

TABLE 1-continued
| MATERIAL | EXAMPLES OF MATERIAL | PUBLICATIONS |
|---|---|---|
| | 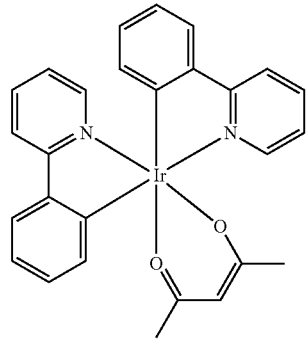 | US20020034656 |
| | 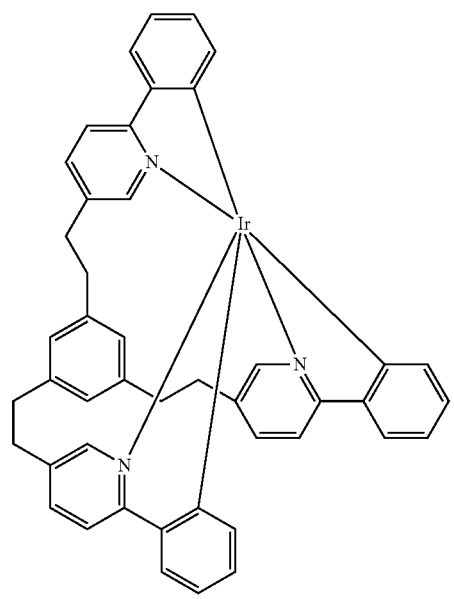 | U.S. Pat. No. 7,332,232 |
| | 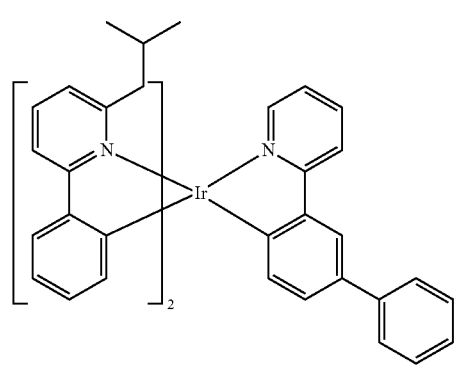 | US20090108737 |

TABLE 1-continued

| MATERIAL | EXAMPLES OF MATERIAL | PUBLICATIONS |
|---|---|---|
| | | WO2010028151 |
| | | EP1841834B |
| | | US20060127696 |
| | | US20090039776 |
| | | U.S. Pat. No. 6,921,915 |

TABLE 1-continued
| MATERIAL | EXAMPLES OF MATERIAL | PUBLICATIONS |
|---|---|---|
| | 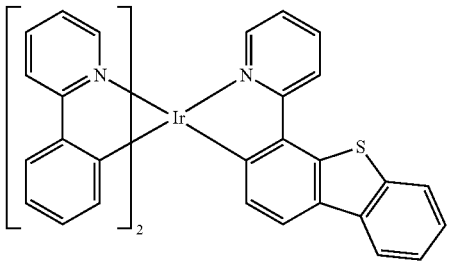 | US20100244004 |
| | 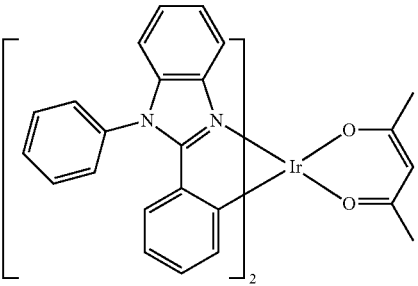 | U.S. Pat. No. 6,687,266 |
| | 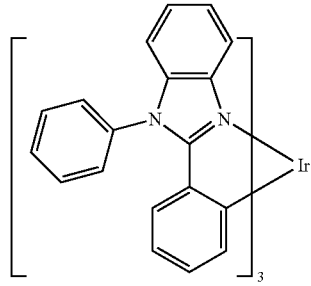 | Chem. Mater. 16, 2480 (2004) |
| | 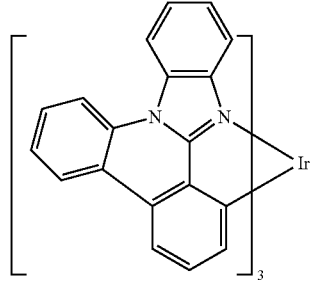 | US20070190359 |
| | 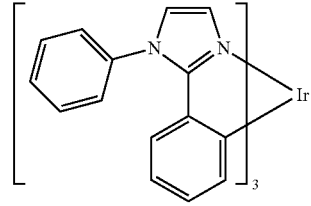 | US 20060008670 JP2007123392 |
| | 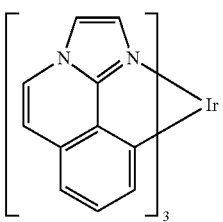 | WO2010086089, WO2011044988 |

TABLE 1-continued

| MATERIAL | EXAMPLES OF MATERIAL | PUBLICATIONS |
|---|---|---|
| | | Adv. Mater. 16, 2003 (2004) |
| | | Angew. Chem. Int. Ed. 2006, 45, 7800 |
| | | WO2009050290 |
| | | US20090165846 |
| | | US20080015355 |
| | | US20010015432 |

TABLE 1-continued

| MATERIAL | EXAMPLES OF MATERIAL | PUBLICATIONS |
| --- | --- | --- |
| | | US20100295032 |
| Monomer for polymeric metal organometallic compounds | | U.S. Pat. No. 7,250,226, U.S. Pat. No. 7,396,598 |
| Pt(II) organometallic complexes, including polydentated ligands | | Appl. Phys. Lett. 86, 153505 (2005) |
| | | Appl. Phys. Lett. 86, 153505 (2005) |
| | | Chem. Lett. 34, 592 (2005) |

TABLE 1-continued

| MATERIAL | EXAMPLES OF MATERIAL | PUBLICATIONS |
|---|---|---|
| | (structure) | WO2002015645 |
| | (structure) | US20060263635 |
| | (structure) | US20060182992<br>US20070103060 |
| Cu complexes | (structure) | WO2009000673 |

TABLE 1-continued

| MATERIAL | EXAMPLES OF MATERIAL | PUBLICATIONS |
|---|---|---|
| | | US20070111026 |
| Gold complexes | | Chem. Commun. 2906 (2005) |
| Rhenium(III) complexes | | Inorg. Chem. 42, 1248 (2003) |
| Osmium(II) complexes | | U.S. Pat. No. 7,279,704 |

TABLE 1-continued

| MATERIAL | EXAMPLES OF MATERIAL | PUBLICATIONS |
|---|---|---|
| Deuterated organometallic complexes | | US20030138657 |
| Organometallic complexes with two or more metal centers | | US20030152802 |
| | | U.S. Pat. No. 7,090,928 |
| Blue dopants | | |
| Iridium(III) organometallic complexes | | WO2002002714 |

TABLE 1-continued

| MATERIAL | EXAMPLES OF MATERIAL | PUBLICATIONS |
|---|---|---|
| | | WO2006009024 |
| | | US20060251923<br>US20110057559<br>US20110204333 |
| | | U.S. Pat. No.<br>7,393,599,<br>WO2006056418,<br>US20050260441,<br>WO2005019373 |
| | | U.S. Pat. No.<br>7,534,505 |
| | | WO2011051404 |
| | | U.S. Pat. No.<br>7,445,855 |

TABLE 1-continued

| MATERIAL | EXAMPLES OF MATERIAL | PUBLICATIONS |
|---|---|---|
| | | US20070190359, US20080297033 US20100148663 |
| | | U.S. Pat. No. 7,338,722 |
| | | US20020134984 |
| | | Angew. Chem. Int. Ed. 47, 4542 (2008) |
| | | Chem. Mater. 18, 5119 (2006) |

TABLE 1-continued

| MATERIAL | EXAMPLES OF MATERIAL | PUBLICATIONS |
|---|---|---|
| | | Inorg. Chem. 46, 4308 (2007) |
| | | WO2005123873 |
| | | WO2005123873 |
| | | WO2007004380 |
| | | WO2006082742 |

US 9,537,106 B2
317                                                                                                        318
TABLE 1-continued
| MATERIAL | EXAMPLES OF MATERIAL | PUBLICATIONS |
|---|---|---|
| Osmium(II) complexes | 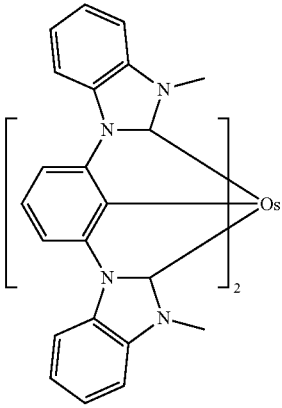 | U.S. Pat. No. 7,279,704 |
|  | 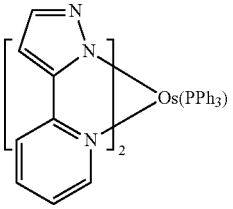 | Organometallics 23, 3745 (2004) |
| Gold complexes | 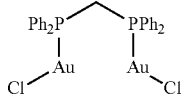 | Appl. Phys. Lett. 74, 1361 (1999) |
| Platinum(II) complexes | 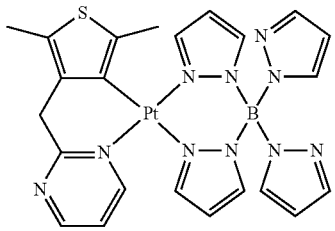 | WO2006098120, WO2006103874 |
| Pt tetradentate complexes with at least one metal-carbene bond | 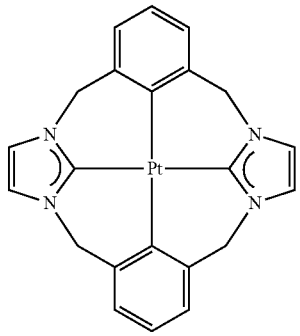 | U.S. Pat. No. 7,655,323 |
| Exciton/hole blocking layer materials | | |
| Bathocuprine compounds (e.g., BCP, BPhen) | 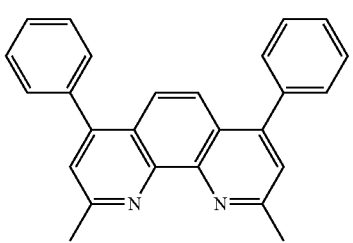 [SMILES: Cc1cc(-c2ccccc2)c2ccc3c(-c4ccccc4)cc(C)nc3c2n1] | Appl. Phys. Lett. 75, 4 (1999) |

TABLE 1-continued

| MATERIAL | EXAMPLES OF MATERIAL | PUBLICATIONS |
|---|---|---|
| | | Appl. Phys. Lett. 79, 449 (2001) |
| Metal 8-hydroxyquinolates (e.g., BAlq) | | Appl. Phys. Lett. 81, 162 (2002) |
| 5-member ring electron deficient heterocycles such as triazole, oxadiazole, imidazole, benzoimidazole | | Appl. Phys. Lett. 81, 162 (2002) |
| Triphenylene compounds | | US20050025993 |

TABLE 1-continued
| MATERIAL | EXAMPLES OF MATERIAL | PUBLICATIONS |
|---|---|---|
| Fluorinated aromatic compounds | 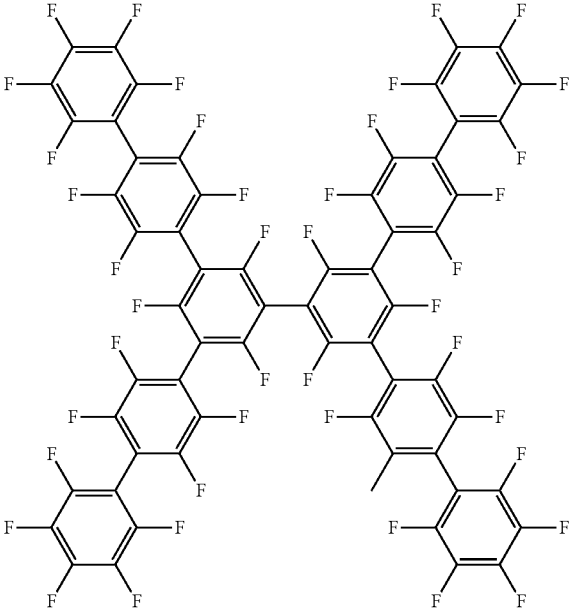 [SMILES: Cc1c(F)c(-c2c(F)c(-c3c(F)c(F)c(-c4c(F)c(F)c(F)c(F)c4F)c(F)c3F)c(F)c(-c3c(F)c(-c4c(F)c(F)c(-c5c(F)c(F)c(F)c(F)c5F)c(F)c4F)c(F)c(-c4c(F)c(F)c(-c5c(F)c(F)c(F)c(F)c5F)c(F)c4F)c3F)c2F)c(F)c(F)c1-c1c(F)c(F)c(F)c(F)c1F] | Appl. Phys. Lett. 79, 156 (2001) |
| Phenothiazine-S-oxide | 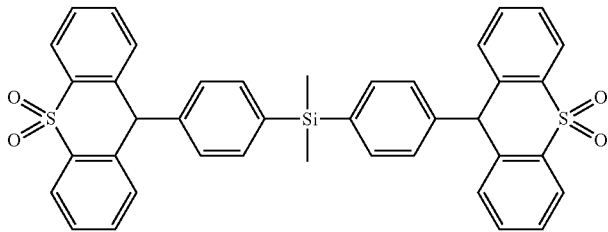 [SMILES: C[Si](C)(c1ccc(C2c3ccccc3S(=O)(=O)c3ccccc32)cc1)c1ccc(C2c3ccccc3S(=O)(=O)c3ccccc32)cc1] | WO2008132085 |
| Silylated five-membered nitrogen, oxygen, sulfur or phosphorus dibenzoheterocycles | 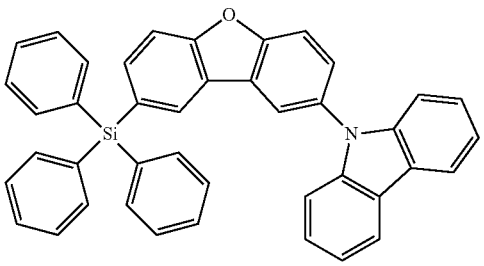 [SMILES: c1ccc([Si](c2ccccc2)(c2ccccc2)c2ccc3oc4ccc(-n5c6ccccc6c6ccccc65)cc4c3c2)cc1] | WO2010079051 |
| Aza-carbazoles | 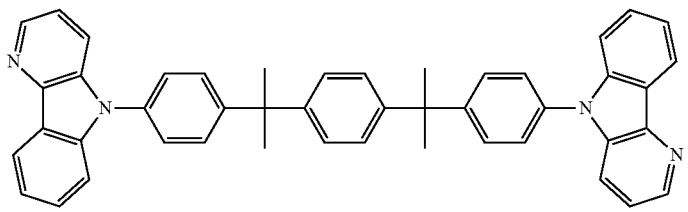 [SMILES: CC(C)(c1ccc(-n2c3ccccc3c3ncccc32)cc1)c1ccc(C(C)(C)c2ccc(-n3c4ccccc4c4ncccc43)cc2)cc1] | US20060121308 |

TABLE 1-continued

| MATERIAL | EXAMPLES OF MATERIAL | PUBLICATIONS |
|---|---|---|
| Electron transporting materials | | |
| Anthracene-benzoimidazole compounds | | WO2003060956 |
| | | US20090179554 |
| Aza triphenylene derivatives | | US20090115316 |
| Anthracene-benzothiazole compounds | | Appl. Phys. Lett. 89, 063504 (2006) |
| Metal 8-hydroxyquinolates (e.g., $Alq_3$, $Zrq_4$) | | Appl. Phys. Lett. 51, 913 (1987) U.S. Pat. No. 7,230,107 |

TABLE 1-continued

| MATERIAL | EXAMPLES OF MATERIAL | PUBLICATIONS |
| --- | --- | --- |
| Metal hydroxybenoquinolates | | Chem. Lett. 5, 905 (1993) |
| Bathocuprine compounds such as BCP, BPhen, etc | | Appl. Phys. Lett. 91, 263503 (2007) |
| | | Appl. Phys. Lett. 79, 449 (2001) |
| 5-member ring electron deficient heterocycles (e.g., triazole, oxadiazole, imidazole, benzoimidazole) | | Appl. Phys. Lett. 74, 865 (1999) |
| | | Appl. Phys. Lett. 55, 1489 (1989) |
| | | Jpn. J. Apply. Phys. 32, L917 (1993) |

TABLE 1-continued
| MATERIAL | EXAMPLES OF MATERIAL | PUBLICATIONS |
|---|---|---|
| Silole compounds | 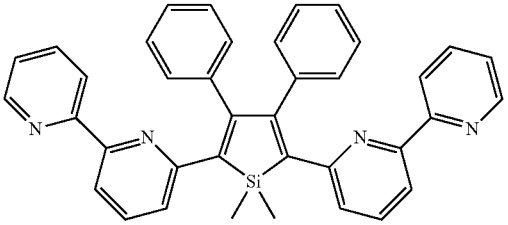 [SMILES: C[Si]1(C)C(c2cccc(-c3ccccn3)n2)=C(c2ccccc2)C(c2ccccc2)=C1c1cccc(-c2ccccn2)n1] | Org. Electron. 4, 113 (2003) |
| Arylborane compounds | 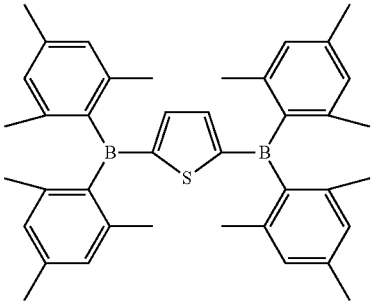 | J. Am. Chem. Soc. 120, 9714 (1998) |
| Fluorinated aromatic compounds | 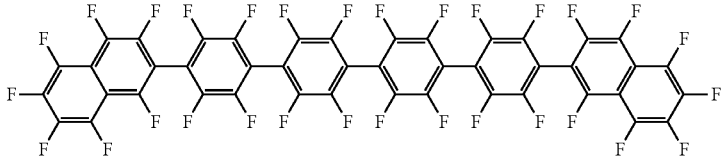 [SMILES: Fc1c(F)c(-c2c(F)c(F)c(-c3c(F)c(F)c4c(F)c(F)c(F)c(F)c4c3F)c(F)c2F)c(F)c(F)c1-c1c(F)c(F)c(-c2c(F)c(F)c(-c3c(F)c(F)c4c(F)c(F)c(F)c(F)c4c3F)c(F)c2F)c(F)c1F] | J. Am. Chem. Soc. 122, 1832 (2000) |
| Fullerene (e.g., C60) | 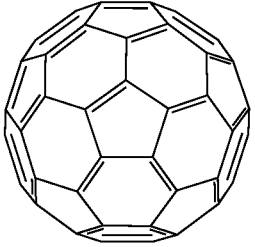 [SMILES: c1cc2c3ccc4c5ccc6c7ccc8c9ccc%10c1c1c2c2c3c4c3c5c6c4c7c8c5c9c%10c1c1c2c3c4c51] | US20090101870 |
| Triazine complexes | 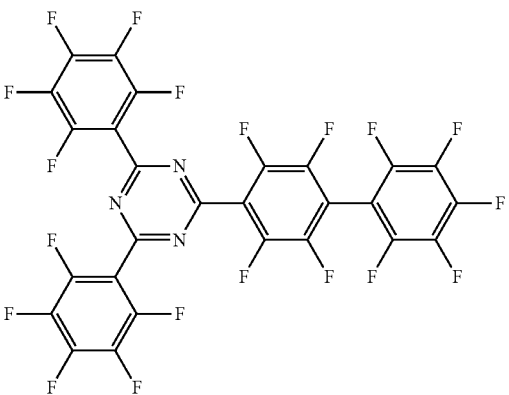 [SMILES: Fc1c(F)c(F)c(-c2nc(-c3c(F)c(F)c(F)c(F)c3F)nc(-c3c(F)c(F)c(-c4c(F)c(F)c(F)c(F)c4F)c(F)c3F)n2)c(F)c1F] | US20040036077 |

TABLE 1-continued

| MATERIAL | EXAMPLES OF MATERIAL | PUBLICATIONS |
|---|---|---|
| Zn (N^N) complexes | 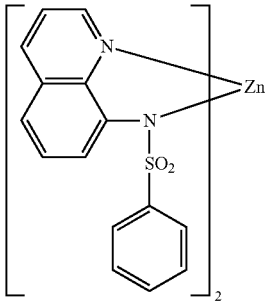 | U.S. Pat. No. 6,528,187 |

EXPERIMENTAL

Compound Examples

A. Synthesis of Compound 13-H

A.1. Synthesis of 2-([1,1'-biphenyl]-2-yl)-6-methoxypyridine

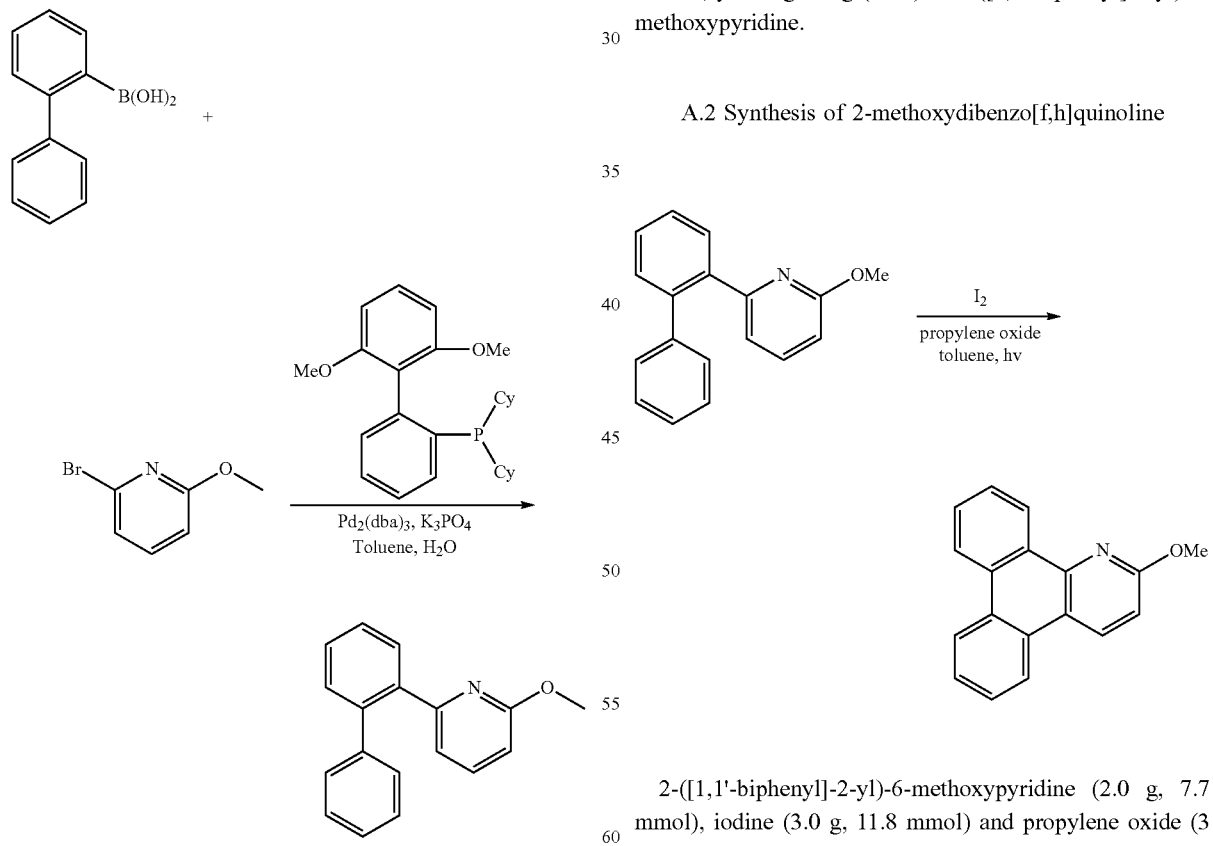

2-biphenylboronic acid (4 g, 20 mmol), and 2-bromo-6-methoxypyridine (2.4 g, 20 mmol) were mixed in 250 mL of toluene and 30 mL of deionized water. The resulting solution was bubbled with nitrogen for 15 min. $Pd_2(dba)_3$ (0.3 g, 0.3 mmol), 2-dicyclohexylphosphino-2',6'-dimethoxybiphenyl (0.6 g, 1.5 mmol) and $K_3PO_4$ (13.6 g, 64 mmol) were added. The mixture was refluxed overnight under nitrogen. After cooling, the aqueous layer was removed from the reaction mixture. The organic layer was dried over magnesium sulfate, filtered and concentrated. The residue was then purified by column chromatography using DCM:hexane (1:4, v/v) as the eluent. White solid was recrystallized from hexane, yielding 4.2 g (80%) of 2-([1,1'-biphenyl]-2-yl)-6-methoxypyridine.

A.2 Synthesis of 2-methoxydibenzo[f,h]quinoline 2-([1,1'-biphenyl]-2-yl)-6-methoxypyridine (2.0 g, 7.7 mmol), iodine (3.0 g, 11.8 mmol) and propylene oxide (3 mL) and 250 mL of toluene were charged into a double-walled quartz photochemical reactor equipped with a medium pressure mercury lamp. The solution was bubbled with nitrogen for 15 min. It was then irradiated for 24 h. After cooling, the reaction mixture was quenched by sodium sulfite and the organic layer was dried over magnesium sulfate and filtered. The solvent was then evaporated and the residue was then purified by column chromatography using DCM:hexane (1:4, v/v) as the eluent. White solid was recrystallized from methanol, yielding 1.5 g (75%) of 2-methoxydibenzo[f,h]quinoline.

A.3. Synthesis of 2-hydroxydibenzo[f,h]quinoline

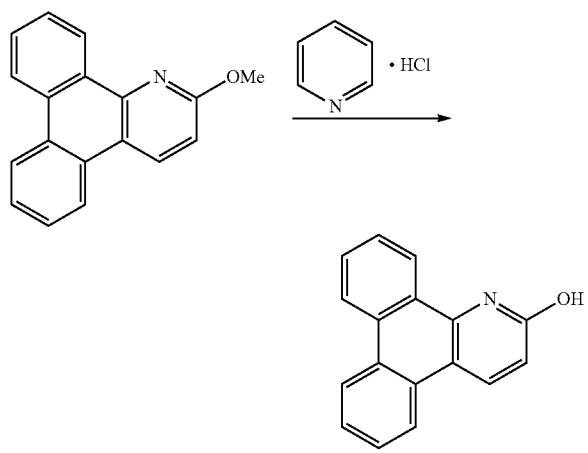

A mixture of 2-methoxydibenzo[f,h]quinoline (1 g, 3.8 mmol) and pyridine hydrochloride (4.5 g, 38 mmol) was heated at 220° C. for 2 hours under nitrogen. The solution was cooled and water was added, resulting in the formation of a white precipitate, which was collected by vacuum filtration, washed with water, and dried in vacuo, yielding 0.9 g (96%) of 2-hydroxydibenzo[f,h]quinoline.

A.4. Synthesis of dibenzo[f,h]quinolin-2-yl trifluoromethanesulfonate

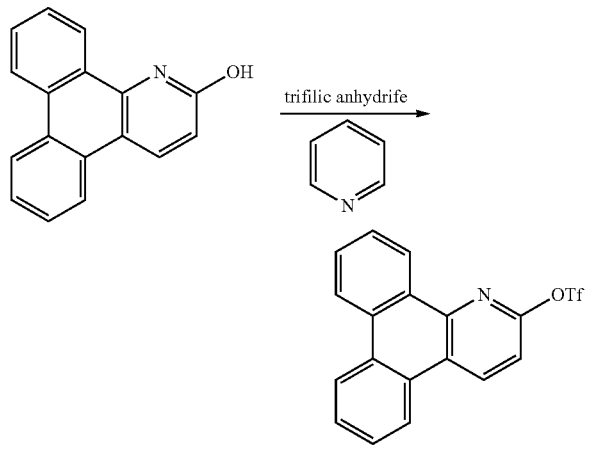

To a cooled solution (0° C.) of 2-hydroxydibenzo[f,h]quinoline (0.9 g, 3.6 mmol), pyridine (1.2 mL) and 200 mL of dichloromethane was added dropwise trifluoromethanesulfonyl anhydride (3.5 mL) under nitrogen. The reaction mixture was allowed to stir overnight at room temperature. The reaction mixture was cooled to 0° C. and quenched by water, the organic layer was dried over magnesium sulfate and filtered through filter paper. The solvent was then evaporated and the residue was then purified by column chromatography using DCM:hexane (1:4, v/v) as the eluent. The white solid was recrystallized from methanol, yielding 1.2 g (88%) of precursor dibenzo[f,h]quinolin-2-yl trifluoromethanesulfonate.

A.A. Example of Synthesis of Compound 13-H Using Precursor dibenzo[f,h]quinolin-2-Yl trifluoromethanesulfonate

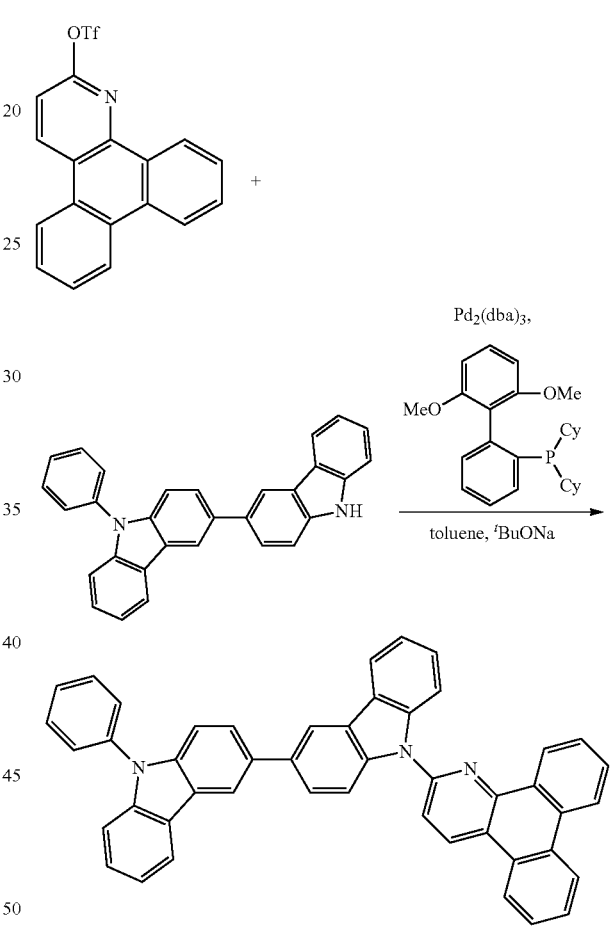

9-phenyl-9H,9'H-3,3'-bicarbazole (0.2 g, 0.48 mmol) and dibenzo[f,h]quinolin-2-yl trifluoromethanesulfonate (0.2 g, 0.49 mmol) were mixed in 70 mL of dry toluene. The resulting solution was bubbled with nitrogen for 15 min. $Pd_2(dba)_3$ (0.02 g, 0.02 mmol), 2-dicyclohexylphosphino-2',6'-dimethoxybiphenyl (0.04 g, 0.08 mmol) and $^tBuONa$ (0.15 g, 1.5 mmol) were added in sequence. The mixture was refluxed overnight under nitrogen. After cooling, the reaction mixture was filtered through celite/silica pad and the solvent was evaporated. The residue was then purified by column chromatography using DCM:hexane (1:4, v/v) as the eluent. The solid was recrystallized from methanol to yield 0.14 g (45%) of Compound 13-H.

A.B. Example of Synthesis of Compound 9-H Using Precursor dibenzo[f,h]quinolin-2-Yl trifluoromethanesulfonate

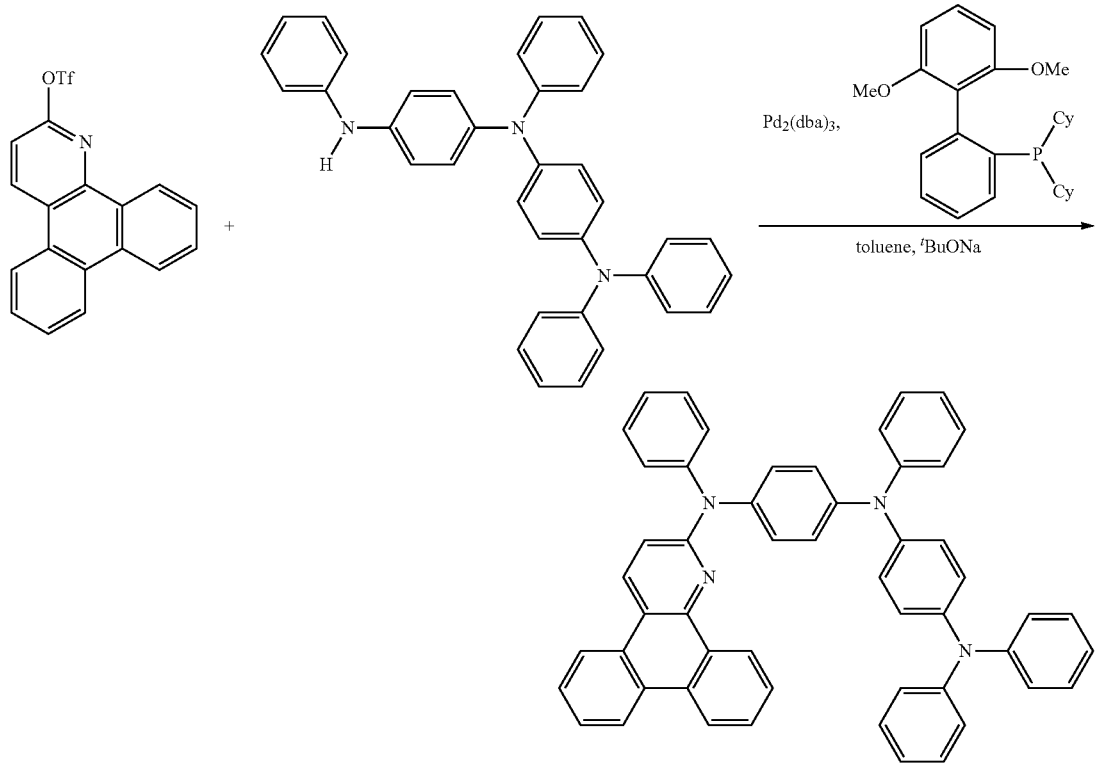

$N^1,N^1,N^4$-triphenyl-$N^4$-(4-(phenylamino)phenyl)benzene-1,4-diamine (0.25 g, 0.48 mmol) and dibenzo[f,h]quinolin-2-yl trifluoromethanesulfonate (0.2 g, 0.49 mmol) were mixed in 70 mL of dry toluene. The resulting solution was bubbled with nitrogen for 15 min. Pd$_2$(dba)$_3$ (0.02 g, 0.02 mmol), 2-dicyclohexylphosphino-2',6'-dimethoxybiphenyl (0.04 g, 0.08 mmol) and $^t$BuONa (0.15 g, 1.5 mmol) were added. The mixture was refluxed overnight under nitrogen. After cooling, the reaction mixture was filtered through celite/silica pad and the solvent was evaporated. The residue was then purified by column chromatography using DCM:hexane (1:4, v/v) as the eluent. The solid was recrystallized from methanol, yielding 0.16 g (47%) of Compound 9-H.

A.C. Example of Synthesis of Compound 82-H Using Precursor dibenzo[f,h]quinolin-2-yl trifluoromethanesulfonate

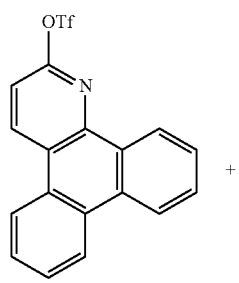

+

-continued

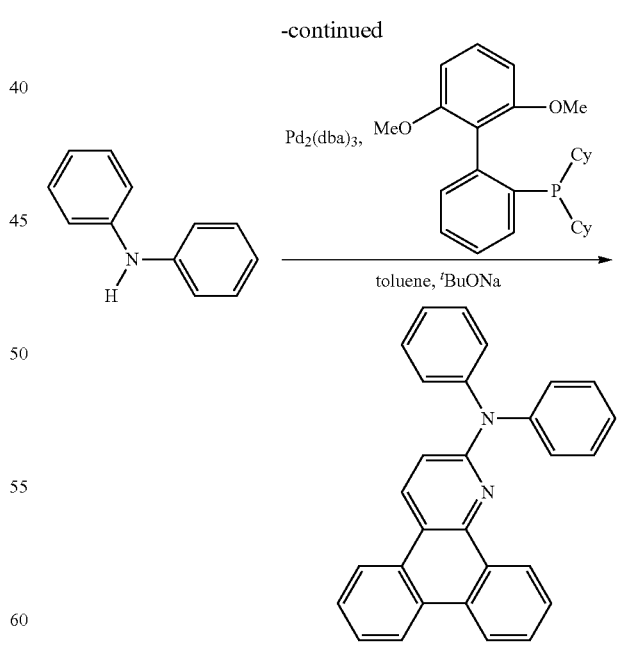

Diphenylamine (0.08 g, 0.48 mmol) and dibenzo[f,h]quinolin-2-yl trifluoromethanesulfonate (0.2 g, 0.49 mmol) were mixed in 70 mL of dry toluene. The resulting solution was bubbled with nitrogen for 15 min. Pd$_2$(dba)$_3$ (0.02 g, 0.02 mmol), 2-dicyclohexylphosphino-2',6'-dimethoxybiphenyl (0.04 g, 0.08 mmol) and 'BuONa (0.15 g, 1.5 mmol) were added. The mixture was refluxed overnight under nitrogen. After cooling, the reaction mixture was filtered through celite/silica pad and the solvent was evaporated. The residue was then purified by column chromatography using DCM:hexane (1:4, v/v) as the eluent. The solid was recrystallized from methanol, yielding 0.09 g (47%) of Compound 82-H.

B. Synthesis of Compound 129-H

B.1. Synthesis of 5-([1,1'-biphenyl]-2-yl)-2-methoxypyrimidine

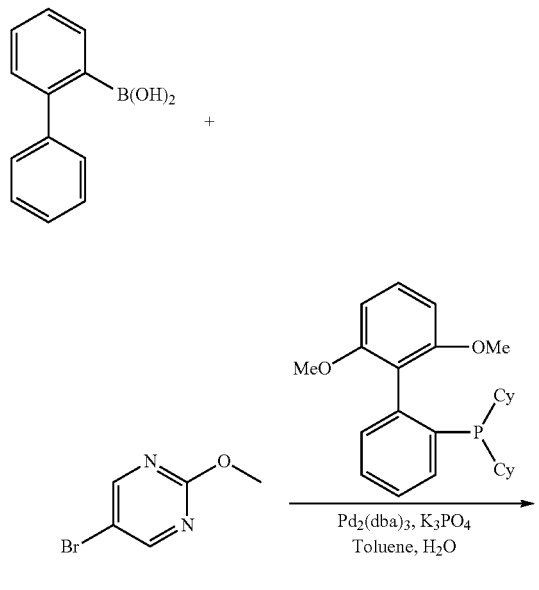

2-biphenylboronic acid (4.0 g, 20.0 mol), and 5-bromo-2-methoxypyrimidine (2.4 g, 20.0 mmol) were mixed in 250 mL of toluene and 30 mL of deionized water. The solution was bubbled with nitrogen for 15 min. Pd$_2$(dba)$_3$ (0.3 g, 0.3 mmol), 2-dicyclohexylphosphino-2',6'-dimethoxybiphenyl (0.6 g, 1.5 mmol) and K$_3$PO$_4$ (13.6 g, 64 mmol) were added in sequence. The mixture was refluxed overnight under nitrogen. After cooling, the aqueous layer was removed from the reaction mixture, the organic layer was dried over magnesium sulfate, filtered and concentrated. The residue was then purified by column chromatography using DCM:hexane (1:4, v/v) as the eluent. The white solid obtained was recrystallized from hexane, yielding 4.2 g (80%) of product.

B.2. Synthesis of 2-methoxydibenzo[f,h]quinazoline

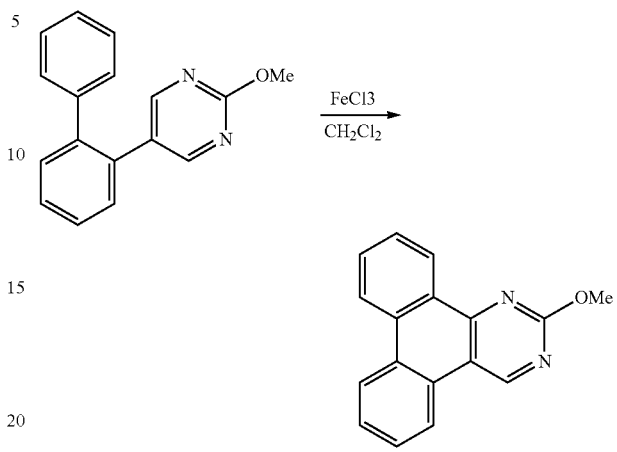

In a 250 mL round-bottom flask equipped with a nitrogen inlet and a stir bar, 5-([1,1'-biphenyl]-2-yl)-2-methoxypyrimidine (4.0 g, 15.3 mmol) was dissolved in anhydrous methylene chloride (100 mL). Iron(III) chloride (5.0 g, 30.6 mmol) was then added, and the mixture was stirred overnight. An additional two equivalents of iron(III) chloride were added, and the reaction reached completion within one hour. Methanol and water were added to the mixture and the organic layer was separated, dried over magnesium sulfate, and concentrated. The residue was purified by silica gel column chromatography with 60/40 methlyene chloride/hexane as the eluent to give 3.5 g of a light yellow solid which was recyrstallized from 700 mL of methanol, yielding 3 g of 2-methoxydibenzo[f,h]quinazoline.

B.3. Synthesis of 2-hydroxydibenzo[f,h]quinazoline

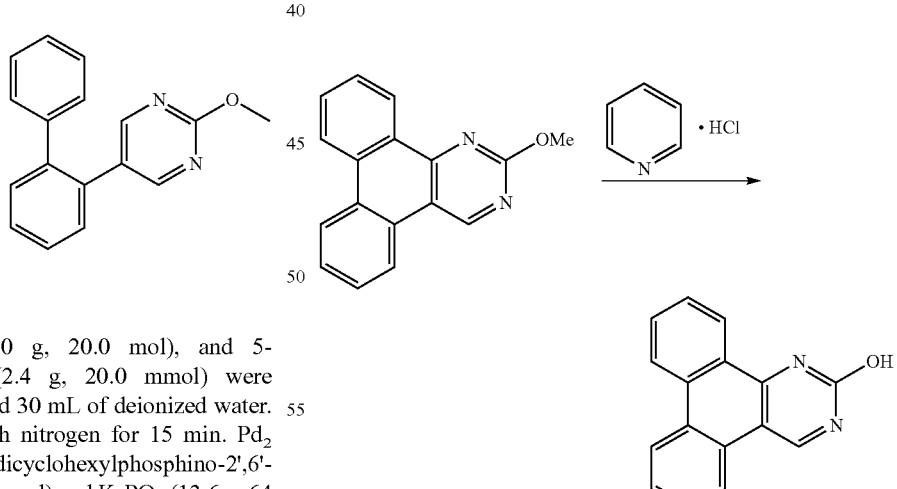

A mixture of 2-methoxydibenzo[f,h]quinazoline (1.0 g, 3.8 mmol) and pyridine hydrochloride (4.5 g, 38.0 mmol) was heated at 220° C. for 2 h under nitrogen. The solution was cooled and water was added, resulting in the formation of a white precipitate, which was collected by vacuum filtration, washed with water, and dried in vacuo to yield 0.9 g (96%) of 2-hydroxydibenzo[f,h]quinazoline.

B.4. Synthesis of precursor dibenzo[f,h]quinazolin-2-yl trifluoromethanesulfonate

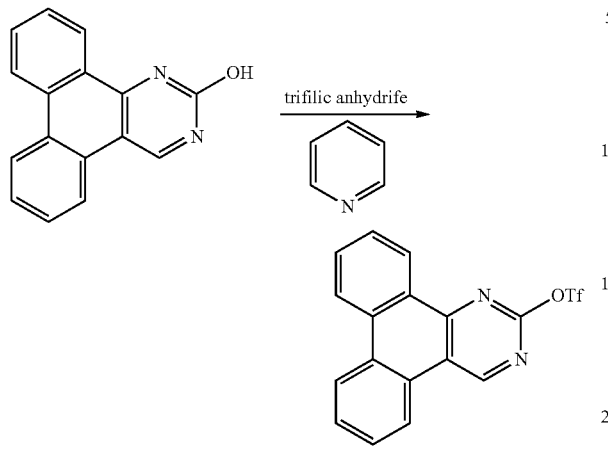

To a cooled solution (0° C.) of 2-hydroxydibenzo[f,h]quinazoline (0.9 g, 3.6 mmol), pyridine (1.2 mL) and 200 mL of dy dichloromethane was added dropwise trifluoromethanesulfonyl anhydride (3.5 mL). The reaction mixture was allowed to stir overnight at room temperature. The reaction mixture was cooled to 0° C. and quenched by water. The organic layer was dried over magnesium sulfate and filtered. The solvent was evaporated and the residue was purified by column chromatography using DCM:hexane (1:4, v/v) as the eluent. The white solid obtained was recrystallized from methanol, yielding 1.2 g (88%) of product.

B.A. Synthesis of Compound 129-H Using Precursor dibenzo[f,h]quinazolin-2-yl trifluoromethanesulfonate

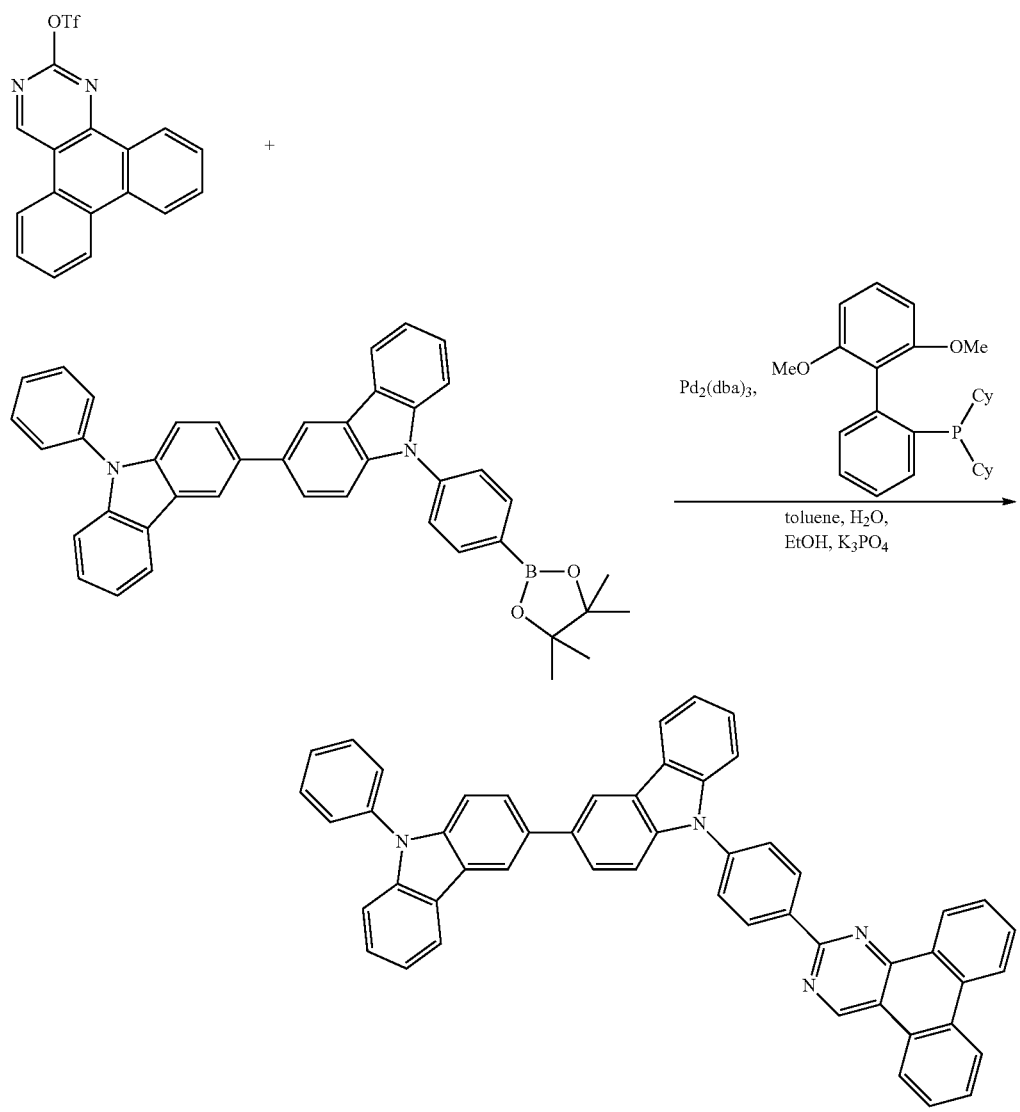

9-phenyl-9'-(4-(4,4,5,5-tetramethyl-1,3,2-dioxaborolan-2-yl)phenyl)-9H,9'H-3,3'-bicarbazole (0.5 g, 0.8 mmol), potassium phosphate tribasic (0.5 g, 2.4 mmol) and dibenzo[f,h]quinazolin-2-yl trifluoromethanesulfonate (0.3 g, 0.8 mmol) were mixed in 70 mL of toluene, 10 mL of deionized water and 10 mL of ethanol. To the solution was bubbled nitrogen for 15 min. Pd$_2$(dba)$_3$ (0.3 g, 0.3 mmol) and 2-dicyclohexylphosphino-2',6'-dimethoxybiphenyl (0.6 g, 1.4 mmol) were added. The mixture was refluxed for 2 days under nitrogen. After cooling, the aqueous layer was discarded. The organic layer was filtered through celite/silica pad and concentrated. The residue was purified by column chromatography using THF:hexane (1:9, v/v) as the eluent. The residue was purified by column chromatography using DCM:hexane (1:1, v/v) as the eluent. The solid obtained was recrystallized from methanol, yielding 0.12 g (21%) of product.

C. Synthesis of Compound 15-H

C.1. Synthesis of 5-([1,1'-biphenyl]-2-yl)-2-chloropyrimidine

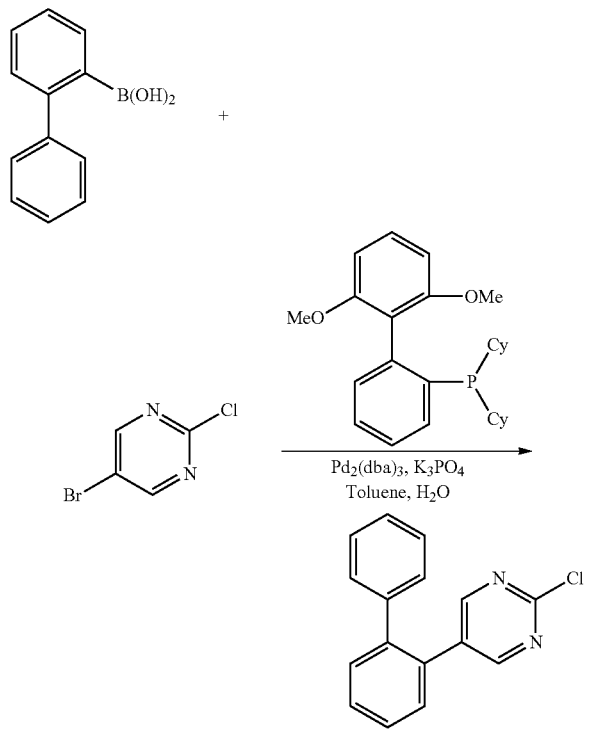

2-biphenylboronic acid (4.0 g, 20.0 mol), and 5-bromo-2-chloropyrimidine (2.4 g, 20.0 mmol) were mixed in 250 mL of toluene and 30 mL of deionized water. To the solution was bubbled nitrogen while 15 min. Pd$_2$(dba)$_3$ (0.3 g, 0.3 mmol), 2-dicyclohexylphosphino-2',6'-dimethoxybiphenyl (0.6 g, 1.5 mmol) and K$_3$PO$_4$ (13.6 g, 64 mmol) were added. The mixture was refluxed overnight under nitrogen. After cooling, the aqueous layer was removed from the reaction mixture. The organic layer was dried over magnesium sulfate, filtered and concentrated. The residue was purified by column chromatography using DCM:hexane (1:4, v/v) as eluent. The white solid obtained was recrystallized from hexane, yielding 4.2 g (80%) of product.

C.2. Synthesis of Precursor 2-chlorodibenzo[f,h]quinazoline

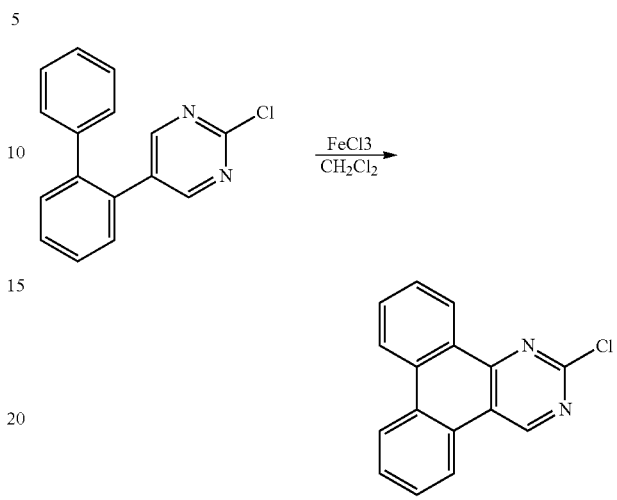

A Iron(III) chloride (5.0 g, 30.6 mmol) was then added to 5-([1,1'-biphenyl]-2-yl)-2-chloropyrimidine (4.0 g, 15.3 mmol) in anhydrous methylene chloride (100 mL). and the mixture was stirred overnight. An additional two equivalents of iron(III) chloride were added, and the reaction reached completion within one hour. Methanol and water were added to the mixture and the organic layer was separated, dried over magnesium sulfate, and concentrated. The crude product was purified by column chromatography with 60/40 methylene chloride/hexane as the eluent to give 3.5 g of a light yellow solid which was recyrstallized from 700 mL of methanol, yielding 3.0 g of 2-chlorodibenzo[f,h]quinazoline.

C.A. Synthesis of Compound 15-H Using the Precursor 2-chlorodibenzo[f,h]quinazoline

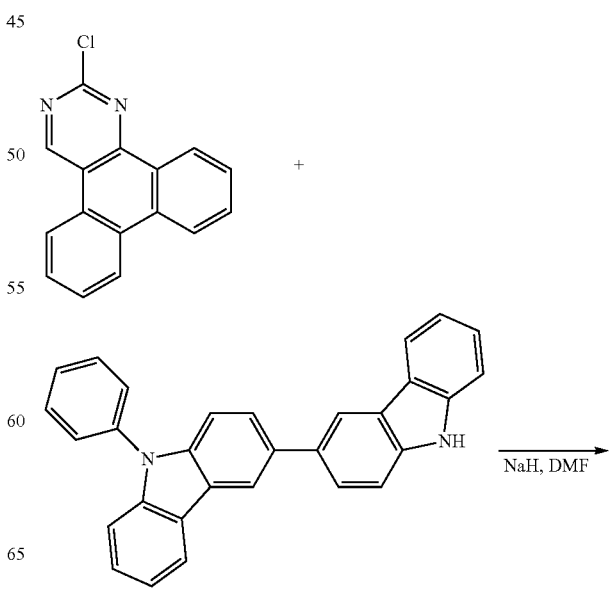

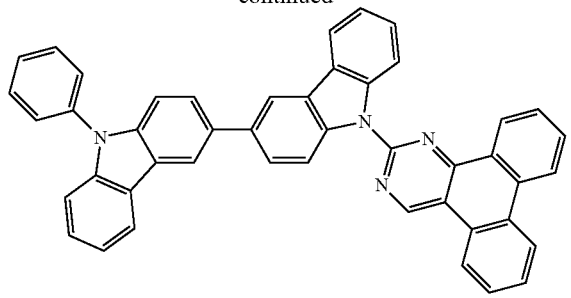

9-phenyl-9H,9'H-3,3'-bicarbazole (0.31 g, 0.76 mmol) and sodium hydride (0.05 g, 1.2 mmol) were mixed in 30 mL of dry dimethylformamide. The mixture was stirred for 1 h. 2-chlorodibenzo[f,h]quinazoline (0.2 g, 0.75 mmol) were added and the mixture was stirred overnight. The solvent was removed and the residue was then purified by column chromatography using THF:hexane (1:4, v/v) as the eluent. The solid obtained was recrystallized from methanol, yielding 0.15 g (32%) of product.

D. Synthesis of Compound 4-H

D.1. Synthesis of 2-([1,1'-biphenyl]-2-yl)-5-methoxypyrazine

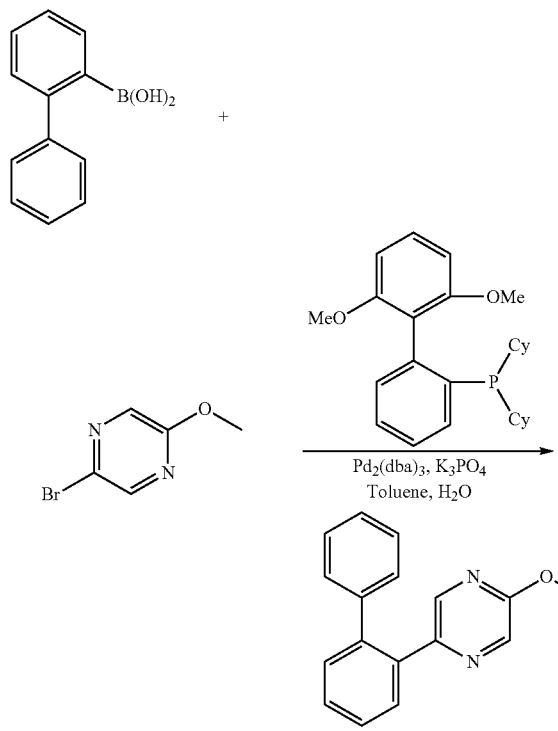

2-biphenylboronic acid (4.0 g, 20 mol), and 2-bromo-5-methoxypyrazine (3.1 g, 16.2 mmol) were mixed in 150 mL of toluene and 50 mL of ethanol. The solution was bubbled with nitrogen for 15 min. Pd$_2$(dba)$_3$ (0.46 g, 0.5 mmol), 2-dicyclohexylphosphino-2',6'-dimethoxybiphenyl (0.6 g, 1.5 mmol) and K$_3$PO$_4$ (12.9 g, 60.6 mmol) were added. The mixture was refluxed overnight under nitrogen. After cooling, the aqueous layer was removed from the reaction mixture. The organic layer was dried over magnesium sulfate, filtered and concentrated. The residue was purified by column chromatography using EA:hexane (1:1, v/v) as the eluent, yielding 2.7 g (64%) of a white solid as the product.

D.2. Synthesis of 2-methoxydibenzo[f,h]quinoxaline

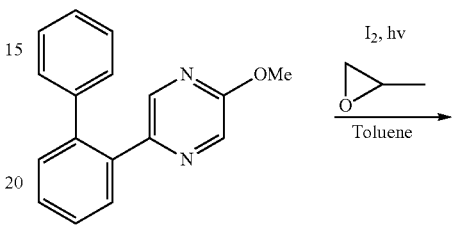

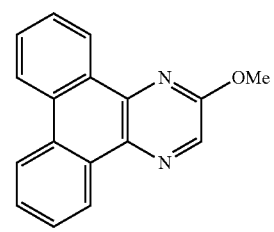

2-([1,1'-biphenyl]-2-yl)-5-methoxypyrazine (2.5 g, 9.6 mmol), iodine (3.6 g, 14.4 mmol), propylene oxide (25 ml) and 250 mL toluene were charged into a double-walled quartz photochemical reactor equipped with a medium pressure mercury lamp. The solution was bubbled with nitrogen for 15 min. It was then irradiated for 24 h. After cooling, the reaction mixture was quenched with sodium sulfite and the organic layer was dried over magnesium sulfate and filtered. The solvent was then evaporated and the residue was purified by column chromatography using EA:hexane (1:1, v/v) as the eluent, yielding 1.89 g (76%) of 2-methoxydibenzo[f,h]quinoxaline.

D.3. Synthesis of dibenzo[f,h]quinoxalin-2-ol

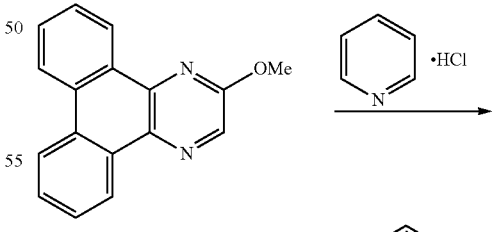

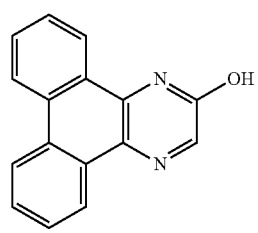

A mixture of 2-methoxydibenzo[f,h]quinazoline (1.3 g, 5.1 mmol) and pyridine hydrochloride (5.8 g, 50.6 mol) was heated at 220° C. for 2 hours under nitrogen. The solution was cooled and water was added, resulting in the formation of a white precipitate, which was collected by vacuum filtration, washed with water, and dried in vacuo, yielding 1.2 g (97%) of dibenzo[f,h]quinoxalin-2-ol.

D.4. Synthesis of Precursor dibenzo[f,h]quinoxalin-2-yl trifluoromethanesulfonate

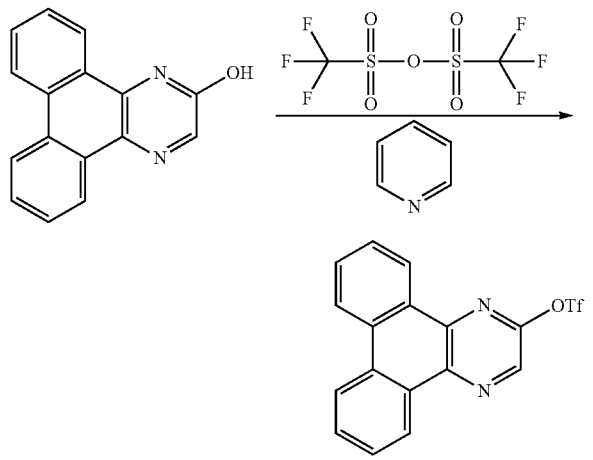

To a cooled solution (0° C.) of dibenzo[f,h]quinoxalin-2-ol (1.2 g, 4.9 mmol), pyridine (60 mL) and 15 mL of anhydrous dichloromethane was added dropwise trifluoromethanesulfonic anhydride (2 mL) under nitrogen. The reaction mixture was allowed to stir overnight at room temperature. The reaction mixture was cooled to 0° C. and quenched by deionized water. The organic layer was dried over magnesium sulfate, filtered and concentrated and the residue was then purified by column chromatography using toluene:hexane (1:4, v/v) as the eluent, yielding 0.6 g (32%) of dibenzo[f,h]quinoxalin-2-yl trifluoromethanesulfonate.

D.A. Synthesis of Compound 4-H Using Precursor dibenzo[f,h]quinoxalin-2-yl trifluoromethanesulfonate

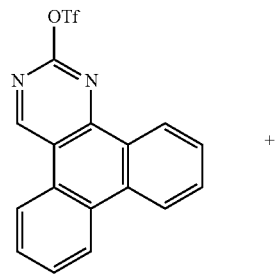

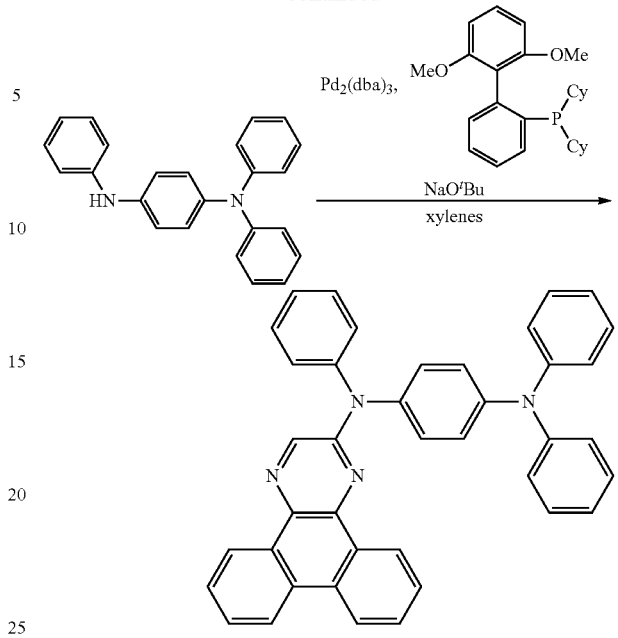

$N^1,N^1,N^4$-triphenylbenzene-1,4-diamine (0.089 g, 0.3 mmol), and dibenzo[f,h]quinoxalin-2-yl trifluoromethanesulfonate (0.1 g, 0.3 mmol) were mixed in 10 mL of xylene. The solution was bubbled with nitrogen for 15 min. $Pd_2(dba)_3$ (0.012 g, 0.01 mmol), 2-dicyclohexylphosphino-2',6'-dimethoxybiphenyl (0.011 g, 0.03 mmol) and sodium t-butoxide (0.025 g, 0.3 mmol) were added. The mixture was refluxed for 2 days under nitrogen. After cooling, the reaction mixture was filtered and the solvent was evaporated. The residue was then purified by column chromatography using gradient from hexane to toluene:hexane (1:1, v/v) as eluent, yielding 0.86 g (58%) of Compound 4-H.

E. Synthesis of Compound 16-H and 457-H

E.1. Synthesis of Precursor 2-bromodibenzo[f,h]quinoxaline

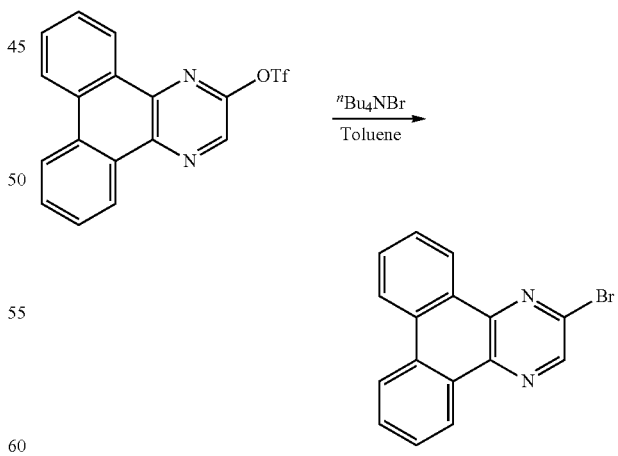

Dibenzo[f,h]quinoxalin-2-yl trifluoromethanesulfonate (0.49 g, 1.2 mmol) and tetrabutylammonium bromide (0.83 g, 25.8 mmol) were refluxed in 20 ml toluene under nitrogen for 24 h. The solution was dried and column chromatographed using toluene:hexane (1:4, v/v) as the eluent, yielding 0.35 g (87%) of 2-bromodibenzo[f,h]quinoxaline.

E.A. Example of Synthesis of Compound 16-H
Using Precursor 2-bromodibenzo[f,h]quinoxaline

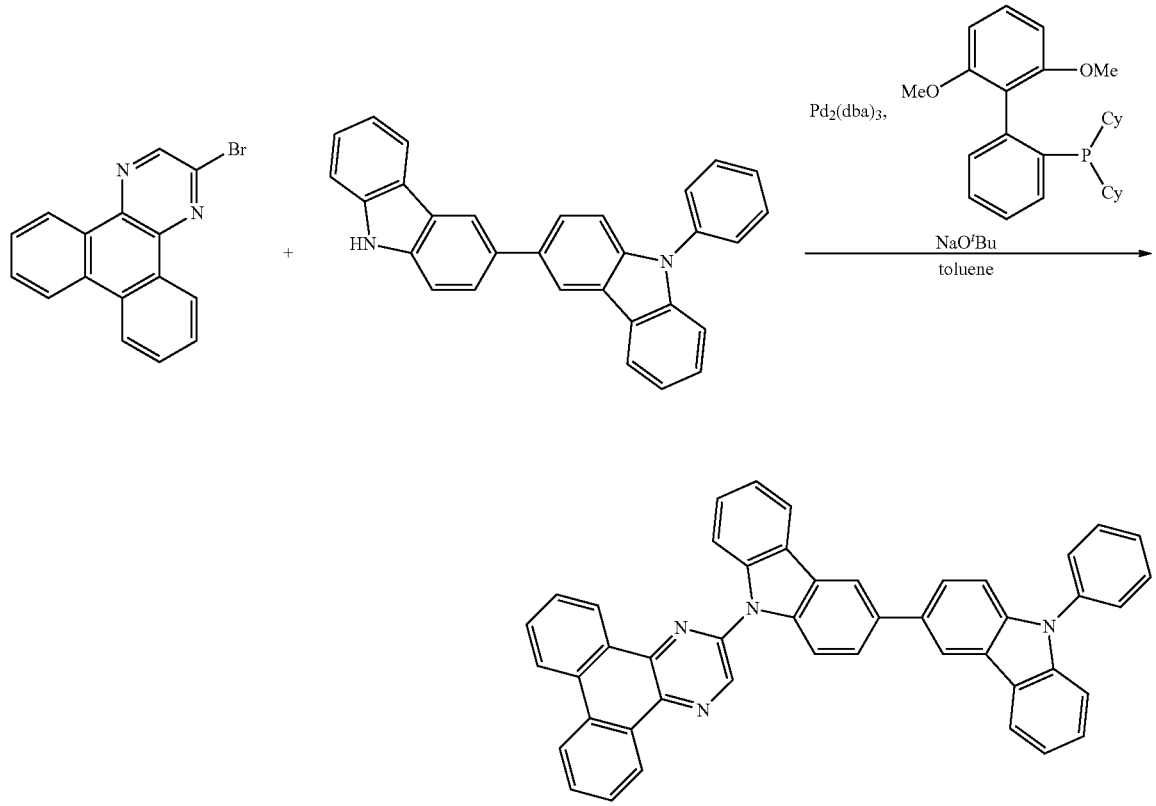

9-phenyl-9H,9'H-3,3'-bicarbazole (0.15 g, 0.4 mmol), and 2-bromodibenzo[f,h]quinoxaline (0.1 g, 0.3 mmol) were mixed in 5 mL toluene. The solution was bubbled with nitrogen for 15 min. Pd$_2$(dba)$_3$ (0.016 g, 0.02 mmol), 2-dicyclohexylphosphino-2',6'-dimethoxybiphenyl (0.015 g, 0.04 mmol) and sodium t-butoxide (0.035 g, 0.4 mmol) were added. The mixture was refluxed overnight under nitrogen. After cooling, the reaction mixture was filtered through celite/silica pad and the filtrate was concentrated under vacuum. The residue was then purified by column chromatography using THF:hexane (1:1, v/v) as the eluent, yielding 0.13 g (57%) of Compound 16-H.

E.B. Example of Synthesis of Compound 457-H
Using Precursor 2-bromodibenzo[f,h]quinoxaline

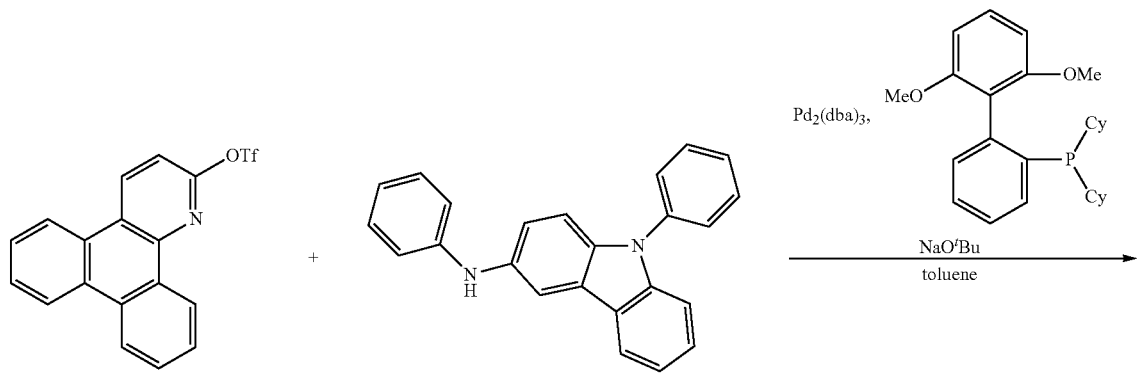

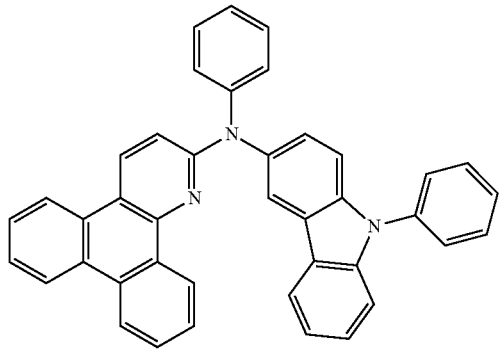

N,9-diphenyl-9H-carbazol-3-amine (0.52 g, 1.6 mmol), and dibenzo[f,h]quinolin-2-yl trifluoromethanesulfonate (0.53 g, 1.6 mmol) were mixed in 15 mL toluene. The solution was bubbled with nitrogen for 15 min. $Pd_2(dba)_3$ (0.071 g, 0.08 mmol), 2-dicyclohexylphosphino-2',6'-dimethoxybiphenyl (0.064 g, 0.16 mmol) and sodium t-butoxide (3.3 g, 3.4 mmol) were added. The mixture was refluxed overnight under nitrogen. After cooling, the reaction mixture was filtered through celite/silica pad and the filtrated was concentrated under vacuum. The residue was purified by column using toluene:hexane (2:3, v/v) as the eluent, yielding 0.28 g (32%) of Compound 457-H.

Alternate Novel Method for Synthesis of Compounds of Formula 1

As disclosed herein, Formula 1 is represented by

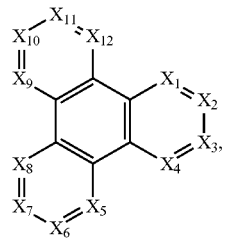

wherein $X_1$ to $X_{12}$ is independently selected from the group consisting of C—R and N, wherein each R is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. The inventors have also discovered that the syntheses of compounds of Formula 1 by ring closing of compounds of Formula Y

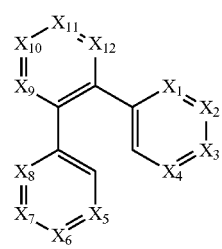

can be achieved by an improved novel method instead of using the traditional method using UV, iodine and propylene oxide.

In the novel method, the ring closure is achieved by the use of light (UV) and cyclohexene. Although light (UV) and cyclohexene was shown to be effective in ring closure of stilbenes to form phenanthrenes (Bull. Chem. Soc. Jpn. Vol. 82, No. 9, 1182), it was unexpected that such a mild system would work for the ring closure of compounds of Formula Y to form compounds of Formula 1. Because of the steric effect, the two rings where the C—C bond formation occurs are more out of plane of each other in compounds of Formula Y than in stilbenes (unsubstituted at the double bond as reported in Bull. Chem. Soc. Jpn. Vol. 82, No. 9, 1182). As a result, only strong oxidants such as iodine and oxygen have been shown to be effective in photocyclization of compounds of Formula Y to form compounds of Formula 1. In this discovery, it was unexpectedly found that cyclohexene, although a weak oxidant, was effective in photocyclization of compounds of Formula Y to form compounds of Formula 1.

F.1. Synthesis of Precursor 2-methoxydibenzo[f,h]quinolone Using the Novel Method

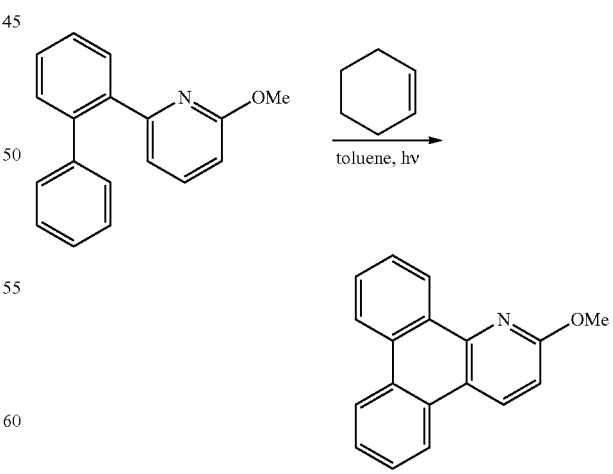

2-([1,1'-biphenyl]-2-yl)-6-methoxypyridine (1.0 g, 3.7 mmol), cyclohexene (2 mL) and toluene (250 mL) were charged into a double-walled quartz photochemical reactor equipped with a medium pressure mercury lamp. The solution was bubbled with nitrogen for 15 min. It was then irradiated with UV for 24 hrs. After cooling, the solvent was evaporated and the residue was then purified by column chromatography using DCM:hexane (1:4, v/v) as the eluent. The white solid obtained was recrystallized from methanol, yielding 0.7 g (75%) of product.

F.2. Synthesis of 4,4'-(4-methoxy-1,2-phenylene)dipyridine

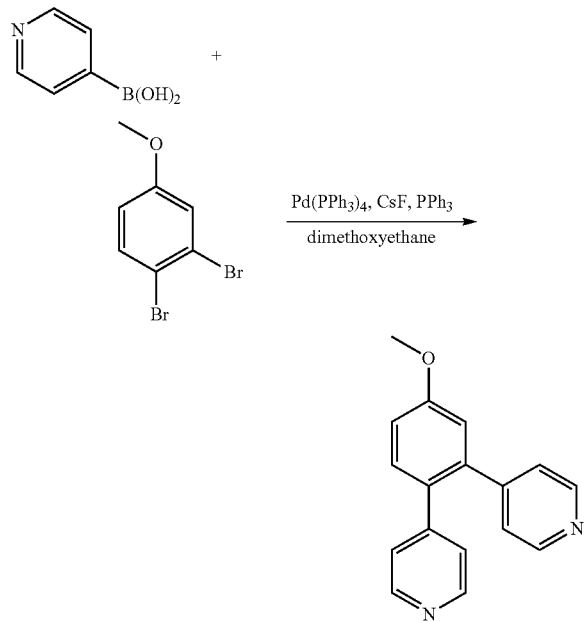

Pyridine-4-ylboronic acid (7.5 g, 61.0 mmol), and 1,2-dibromo-4-methoxybenzene (4.1 g, 15.3 mmol) were mixed in 80 mL of dimethoxyethane. The solution was bubbled with nitrogen for 15 min. Pd(PPh$_3$)$_4$ (3.5 g, 3.1 mmol), triphenylphosphine (2.5 g, 6.1 mmol) and cesium fluoride (9.7 g, 45.8 mmol) were added. The mixture was refluxed overnight under nitrogen. After cooling, the aqueous layer was removed from the reaction mixture. The organic layer was dried over magnesium sulfate, filtered and concentrated. The residue was purified by column chromatography using THF:hexane (7:3, v/v) as the eluent. The white solid obtained was recrystallized from hexane, yielding 3.3 g (82%) of product.

G.1. Synthesis of Precursor 6-methoxybenzo[f][2,9]phenanthroline

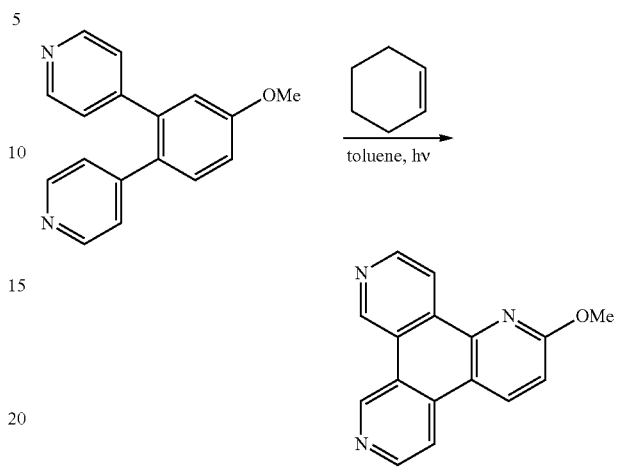

4,4'-(4-methoxy-1,2-phenylene)dipyridine (0.5 g, 1.9 mmol), cyclohexene (2 ml) and toluene (250 mL) were charged into a double-walled quartz photochemical reactor equipped a medium pressure mercury lamp. The solution was bubbled with nitrogen for 15 min. It was then irradiated for 2 days. After cooling, the solvent was then evaporated and the residue was purified by column chromatography using THF:hexane (7:3, v/v) as the eluent. The white solid was recrystallized from methanol, yielding 0.3 g (69%) of product.

This new method avoids light absorption by iodine, eliminates the formation of acidic HI and polymerized propylene oxide. Furthermore, propylene oxide evaporates easily due to its low boiling point of (b.p.=34° C.), making the control of exact equivalents in the reaction difficult. One the other hand, cyclohexene has a much high boiling point (b.p.=83° C.) and does not evaporate easily, allowing the control of exact equivalents in the reaction.

Experimental Data:

Electrochemistry, photoluminescence, photoluminescence quantum yield (PLQY) and solvatochromism experiments were carried out for samples of the donor-acceptor compound samples Compound 9, 13 and 82. The data is summarized below in Table 2. Small molecule host (Compound B and Compound D) doped films were fabricated by vacuum thermal evaporation on quartz substrates. Poly (methyl methacrylate) (PMMA) and polystyrene (PS) doped film were fabricated by solution drop casting on quartz substrates.

TABLE 2

| Cmpd | Oxidation and Reduction potential, vs Fc/Fc$^+$ [V] | PLQY, 5% doping (host) | Em$_{max}$ (host) [nm] | Em$_{max}$ at RT in 2Me—THF [nm] | Em$_{max}$ at RT in toluene [nm] | Em$_{max}$ at RT in hexane [nm] |
|---|---|---|---|---|---|---|
| 9-H | $E_{ox}$ = 0.13 (R) $E_{red}$ = 2.70 (R) | 76% (Cmpd B) 69% (Cmpd D) | 473 (Cmpd B) 477 (Cmpd D) | 536 | 507 | 474 |
| 457-H | $E_{ox}$ = 0.45 (R) $E_{red}$ = −2.70 (R) | 52% (PMMA) 41% (PS) 36% (Cmpd D) | 455 (PMMA) 455 (PMMA) 450 (Cmpd D) | 430 | 420 | 406 |
| 4-H | $E_{ox}$ = 0.34 (R) $E_{red}$ = −2.23 (R) | 45% (PMMA) | 539 (PMMA) | 626 | 597 | 536 |
| 129-H | $E_{ox}$ = 0.59 (IR) $E_{red}$ = −2.23 (IR) | 34% (PMMA) 63% (Cmpd D) | 448 (PMMA) 437 (Cmpd D) | 481 | 432 | 392 |

TABLE 2-continued

| Cmpd | Oxidation and Reduction potential, vs Fc/Fc+ [V] | PLQY, 5% doping (host) | Em$_{max}$ (host) [nm] | Em$_{max}$ at RT in 2Me—THF [nm] | Em$_{max}$ at RT in toluene [nm] | Em$_{max}$ at RT in hexane [nm] |
|---|---|---|---|---|---|---|
| 15-H | E$_{ox}$ = 0.64 (R) E$_{red}$ = −2.13 (R) | 44% (PMMA) | 467 (PMMA) | 504 | 475 | 444 |
| 16-H | E$_{ox}$ = 0.65 (R) E$_{red}$ = −2.03 (R) | 69% (PMMA) | 494 (PMMA) | 515 | 483 | 436 |

(R = reversible, IR = irreversible)

Table 2 shows that the emission of the donor-acceptor compounds of Formula 1 consists of charge transfer origins as evidenced by the solvatochromism. Donor-acceptor emitters of Formula 1 can be efficient luminescent compounds. The PLQY of Compound 9-H in mCBP is 69%. When Compound 9-His doped in Compound B, the PLQY is 76%. Compound 9-H shows reversible redox, a desirable feature for stable OLEDs. The PLQY of Compound 129-H in mCBP is 63%. The compounds can produce blue luminescence as shown. The acceptor strength in the donor-acceptor compounds can be tuned by varying the position and number of nitrogens in the triphenylene such as in Formulae 2-19 whereas the donor strength can be tuned by using various electron donating groups such as in D1-D140. Consequently, the CT emission can be tuned.

Device Examples:

In the OLED experiment, all device examples were fabricated by high vacuum (<10-7 Torr) thermal evaporation. The anode electrode is ~800 Å of indium tin oxide (ITO). The cathode consisted of 10 Å of LiF followed by 1,000 Å of Al. All devices were encapsulated with a glass lid sealed with an epoxy resin in a nitrogen glove box (<1 ppm of H2O and O2) and a moisture getter was incorporated inside the package.

The organic stack of the Device Example 1 consists of sequentially, from the ITO surface, 100 Å of LG101 (purchased from LG Chem, Korea) as the hole injection layer (HIL), 300 Å of Compound A as the hole transporting layer (HTL), 300 Å of Compound B doped with 5% of Compound 9-H as the emissive layer (EML), 50 Å of Compound C as the ETL2 and 400 Å of LG-201 as the ETL1. The maximum external quantum efficiency is 9.6%. CIE is 0.171, 0.317.

Device Example 2 is the same as Device Example 1 except that Compound B is replaced with Compound D. The maximum external quantum efficiency is 8.0%. CIE is 0.173, 0.335.

The high device external quamtum efficiency (EQE) of Device Examples 1 and 2 shows that donor-acceptor compounds of Formula 1 are efficient emitters for OLEDs. The high device external quamtum efficiency also suggests that triplet excition may be converted into emissive singlet excition via the delayed fluorescence mechanism.

Compound A

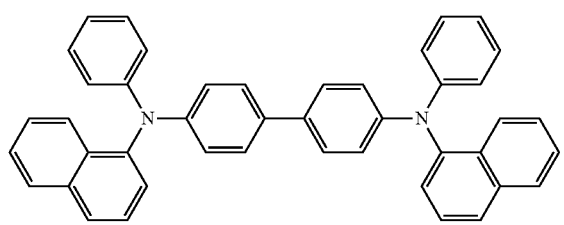

-continued

Compound B

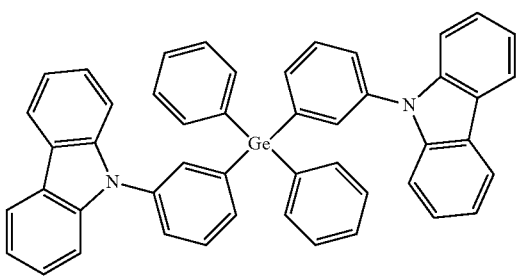

Compound C

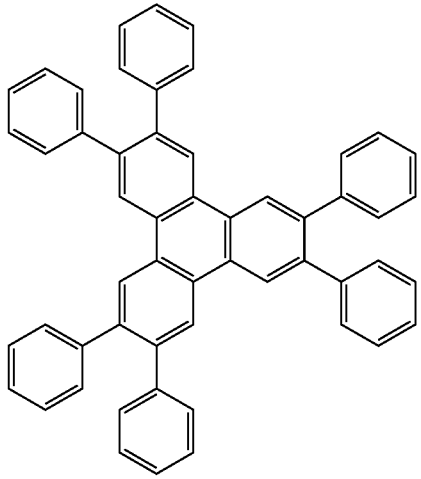

Compound D

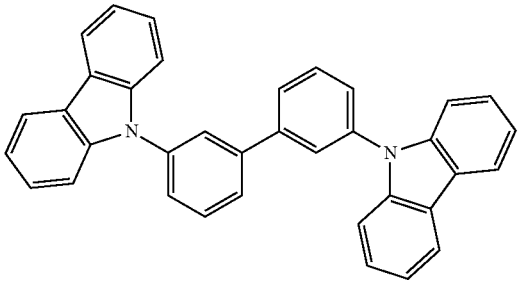

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore include variations from the particular examples and preferred embodiments described herein, as

We claim:

1. A compound having the formula:

Formula 1 wherein $X_1$ to $X_{12}$ is independently selected from the group consisting of C—R and N;

wherein at least one of $X_1$ to $X_{12}$ is N;

wherein each R is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;

wherein at least one of the R is $(L)_m$($Donor)_n$;

wherein L is an organic aromatic group linker,
m is 1 or 0,
n≥1;

wherein Donor is an electron donating group containing at least two electron-donating nitrogens and Donors can be different when n>1; and wherein at least one electron-donating nitrogen in the Donor is directly bonded to L.

2. The compound of claim 1, wherein the compound is selected from the group consisting of Formula 2

Formula 3

Formula 4

Formula 5

Formula 6

Formula 7

Formula 8
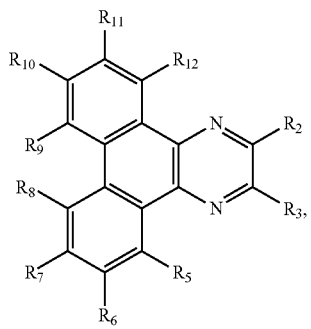
Formula 9
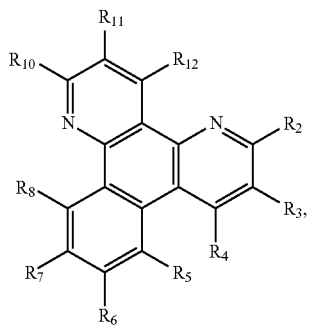
Formula 10
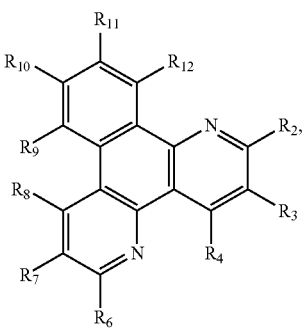
Formula 11
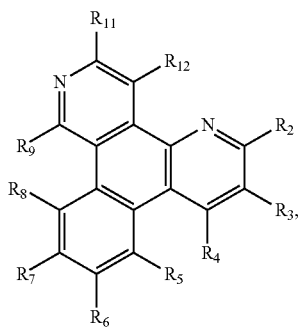
Formula 12
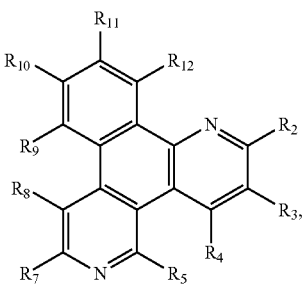
Formula 13
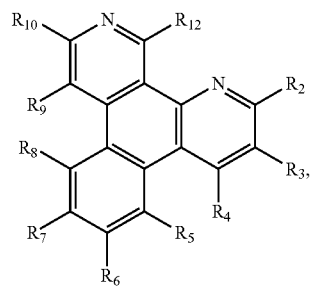
Formula 14
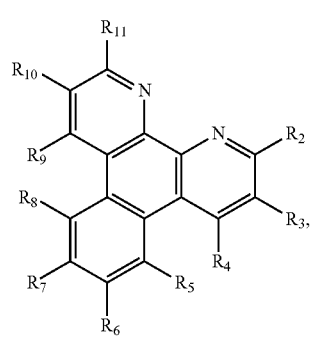
Formula 15
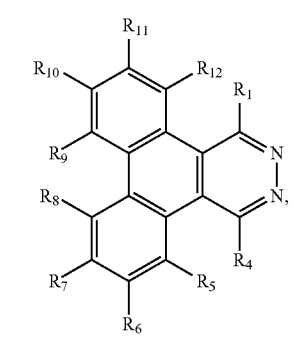
Formula 16
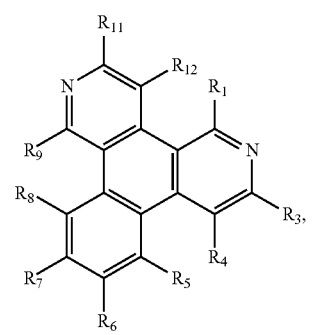
Formula 17
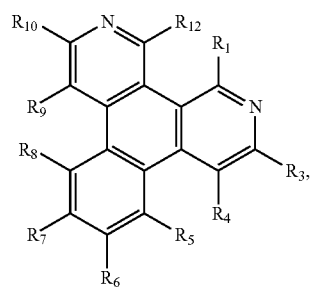

Formula 18

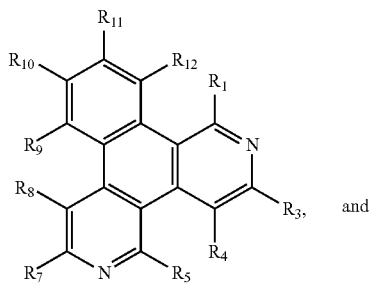

and

Formula 19

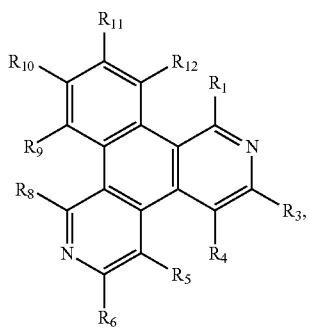

wherein $R_1$ to $R_{12}$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;

at least one of $R_1$ to $R_{12}$ is

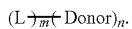

3. The compound of claim 2, wherein Donor is selected from the group consisting of:

D1

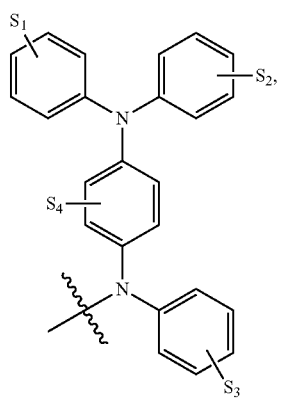

D2

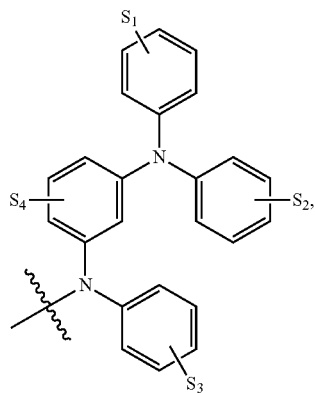

D3

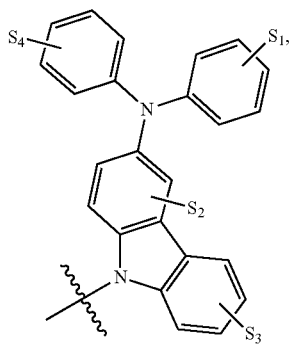

D4

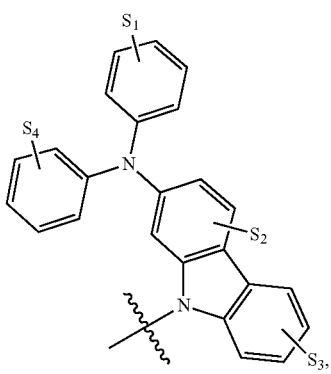

D5

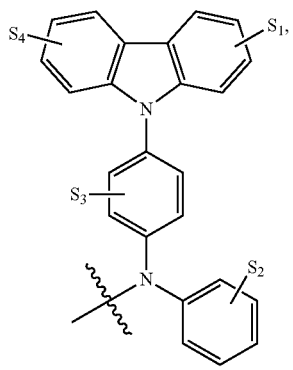

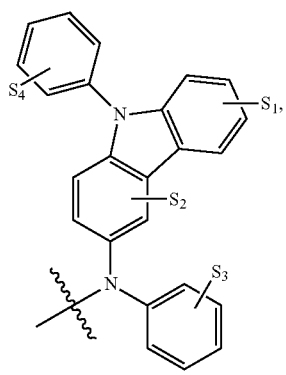
D6
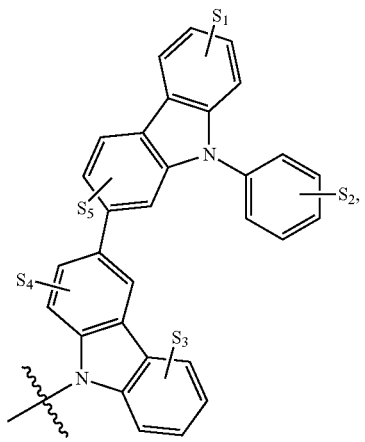
D9
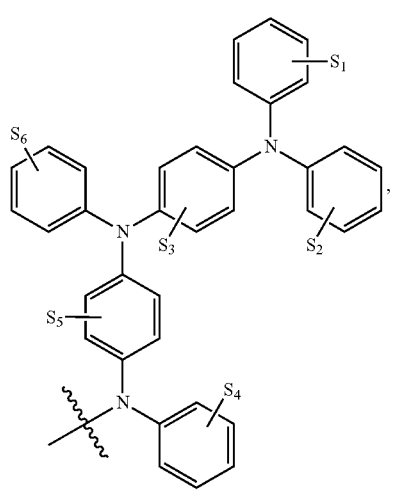
D7
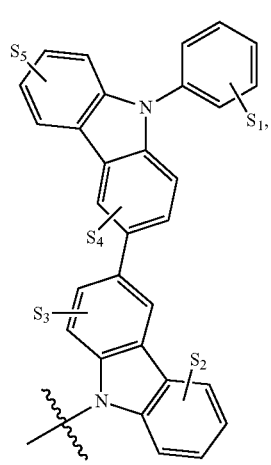
D10
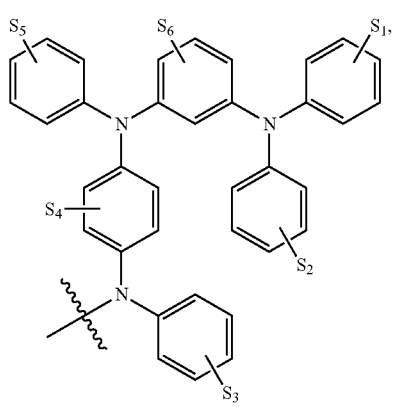
D8
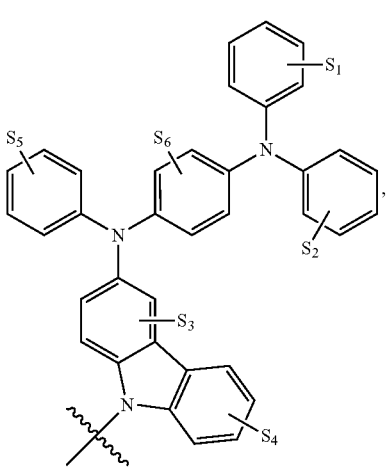
D11

361
-continued
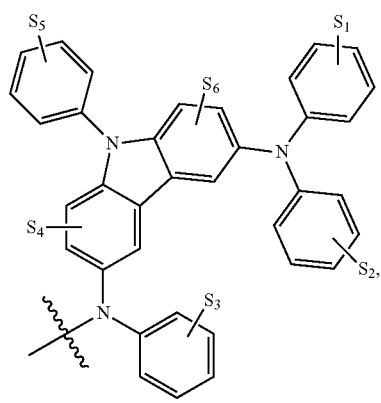
D12
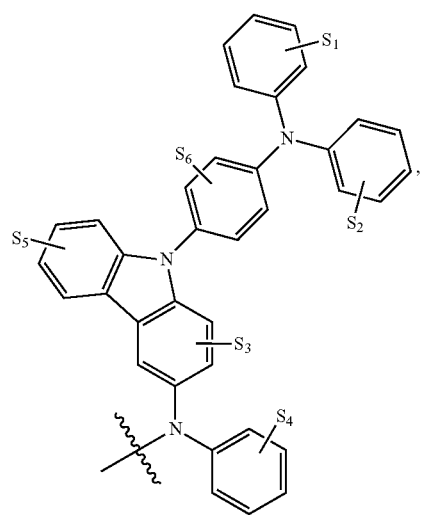
D13
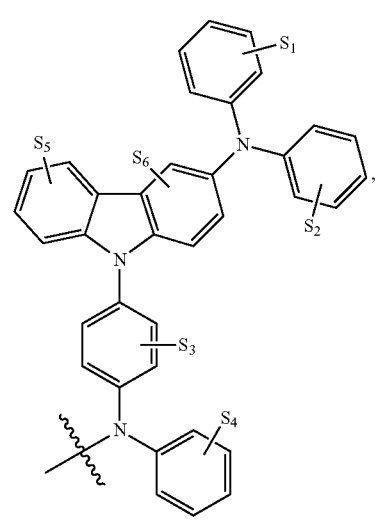
D14
362
-continued
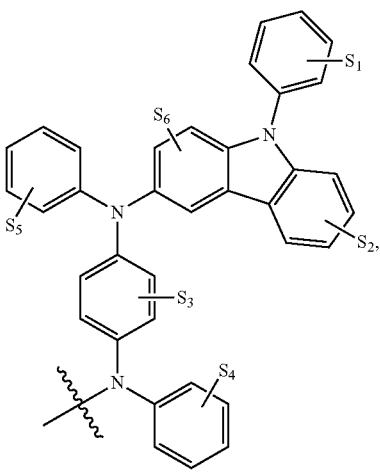
D15
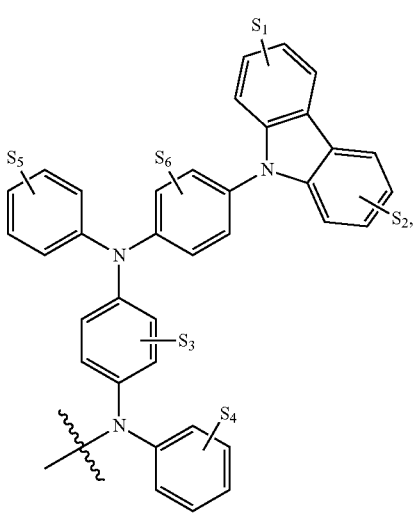
D16
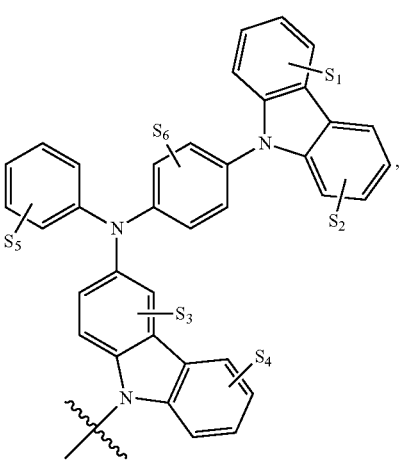
D17

-continued
D18
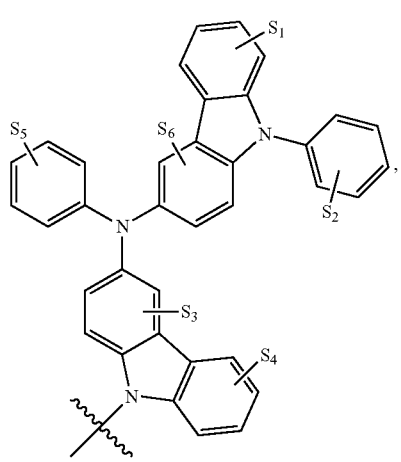
D19
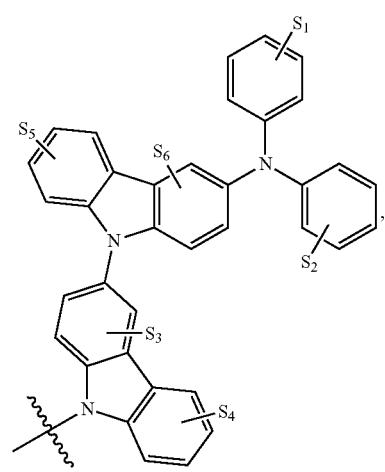
D20
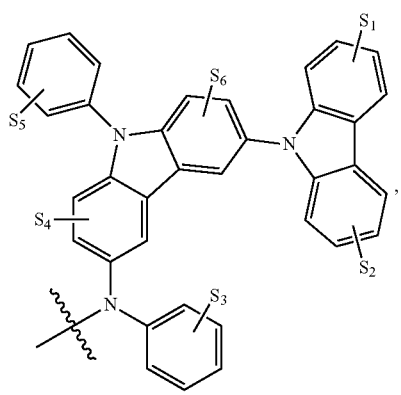
-continued
D21
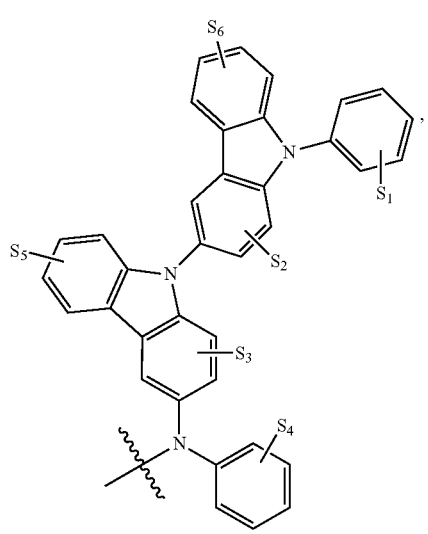
D22
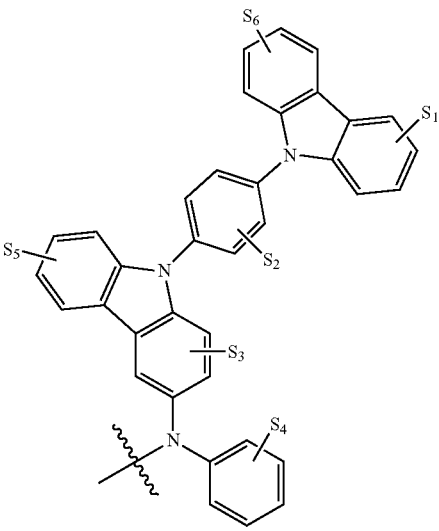
D23
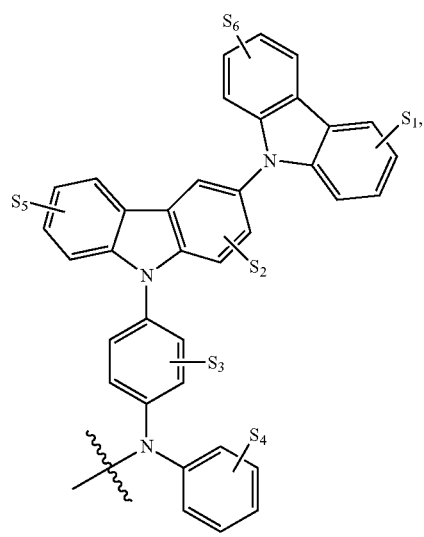

-continued
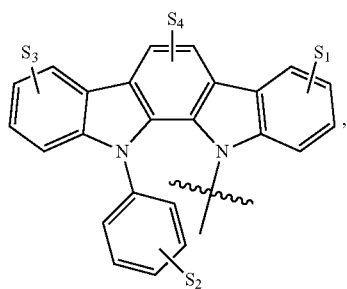
D24
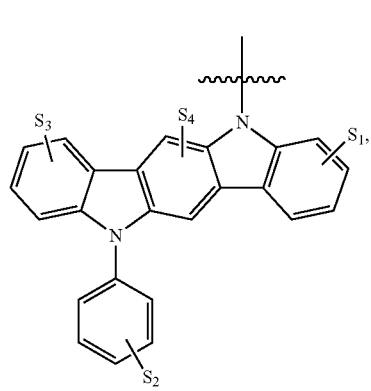
D25
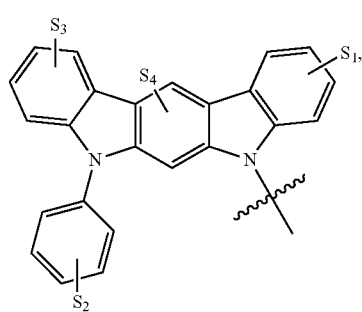
D26
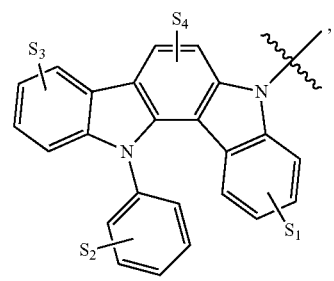
D27
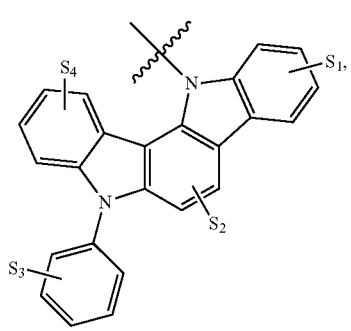
D28
-continued
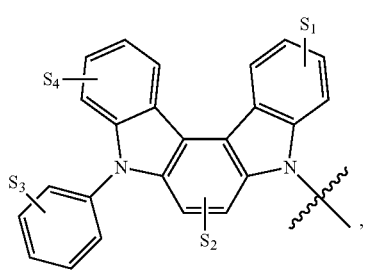
D29
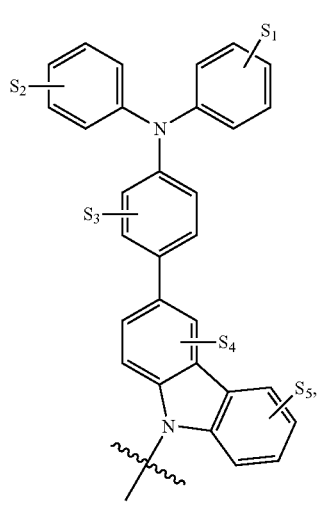
D33
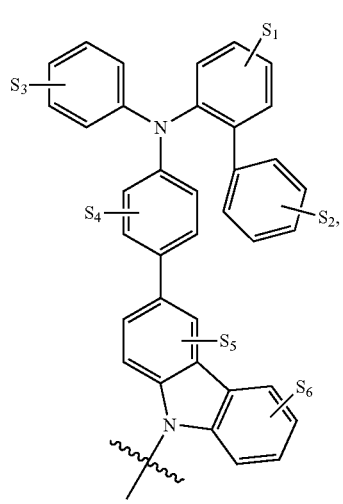
D34

-continued
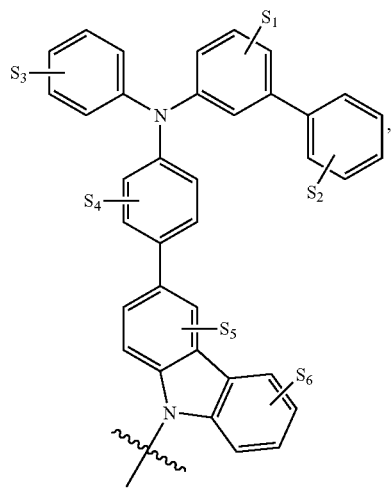
D35
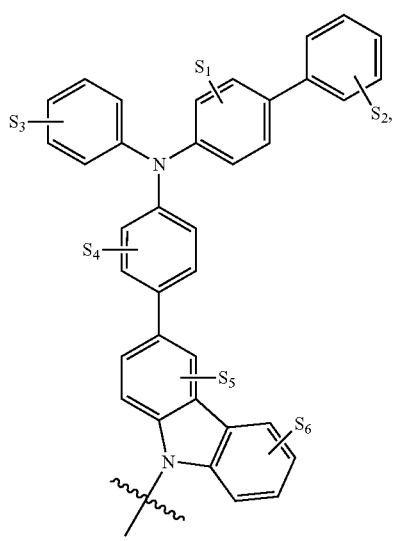
D36
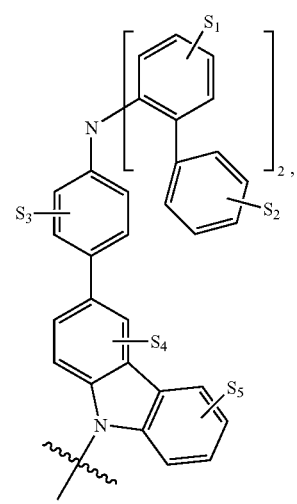
D37
-continued
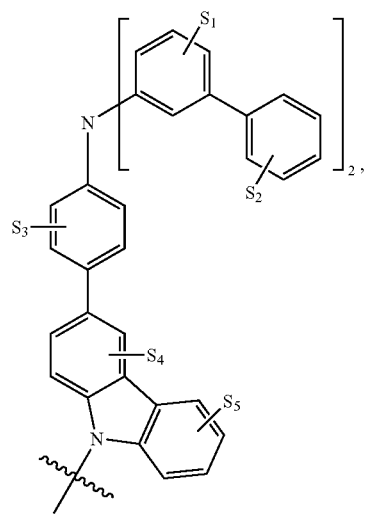
D38
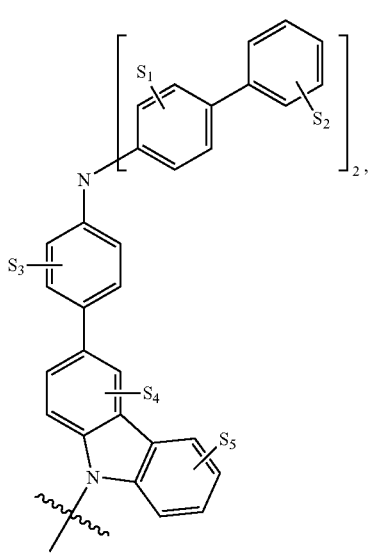
D39
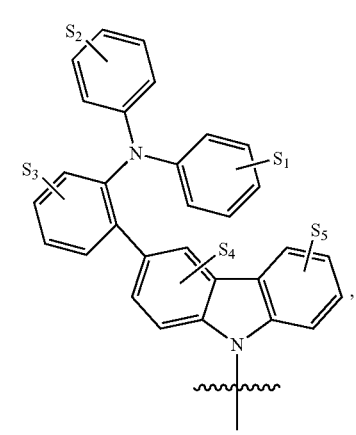
D40

369
-continued
D41
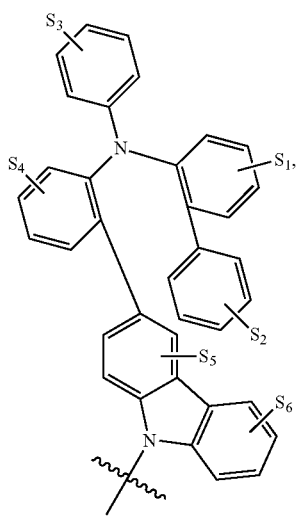
D42
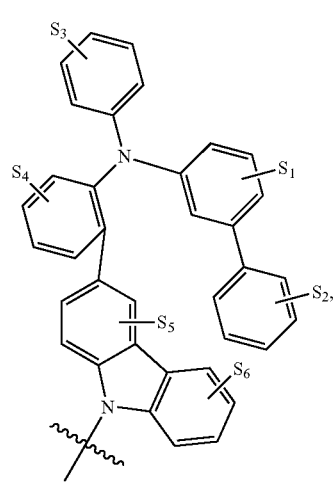
D43
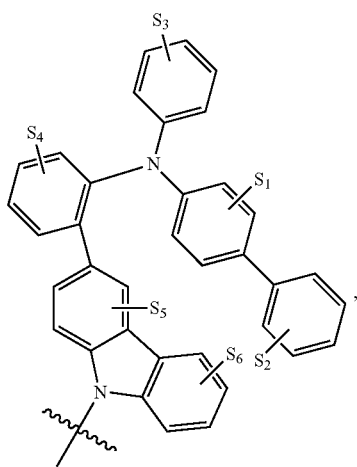
370
-continued
D44
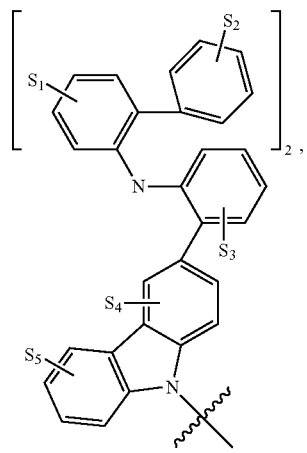
D45
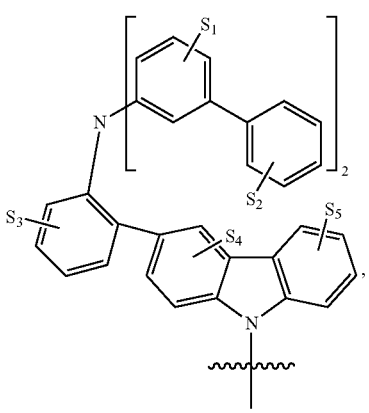
D46
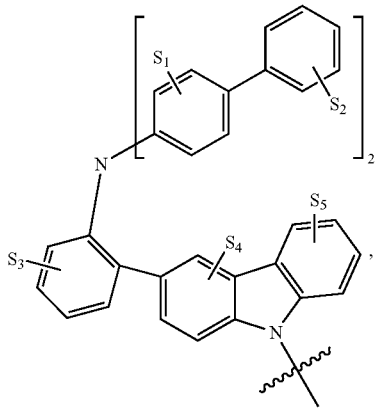

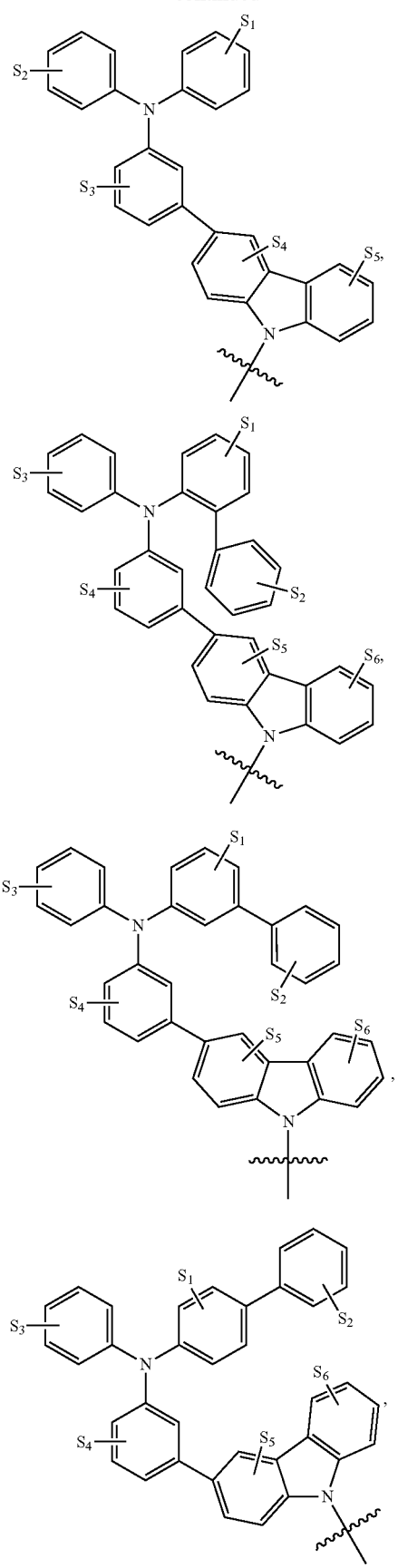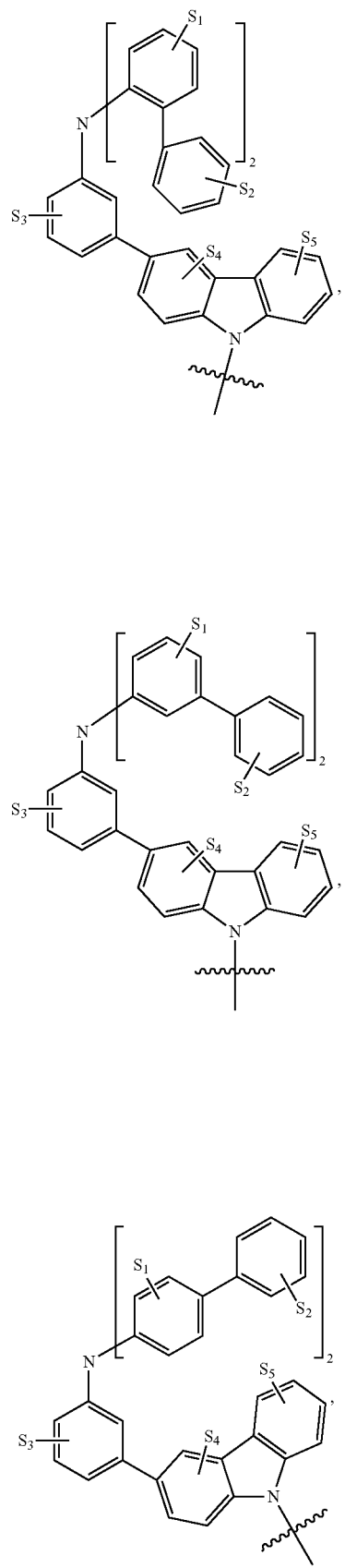

D54
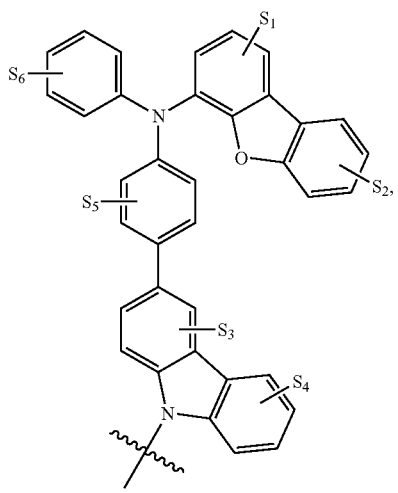
D55
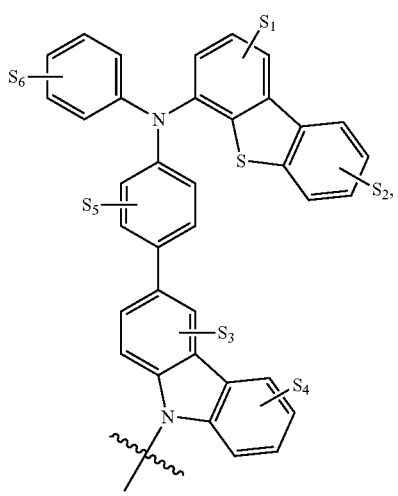
D56
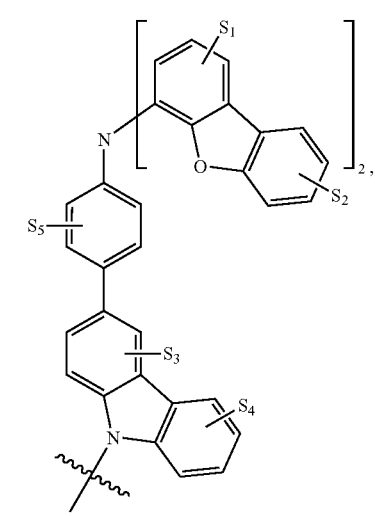
D57
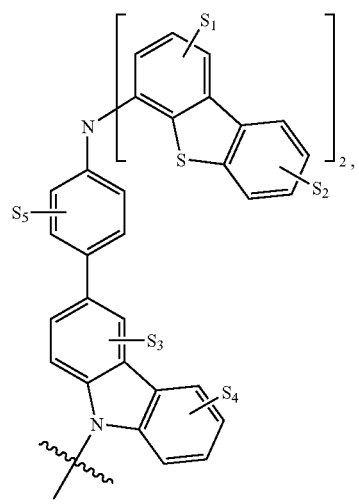
D58
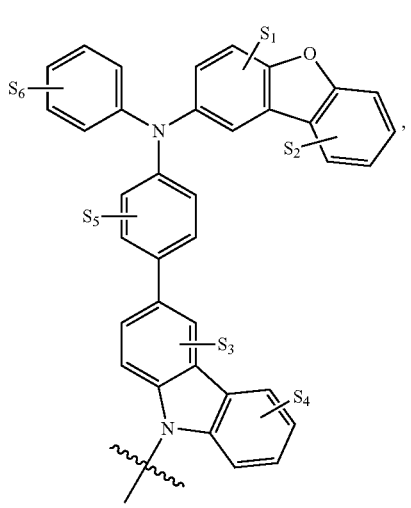
D59
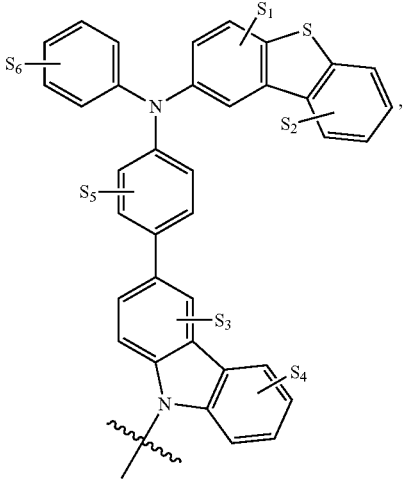

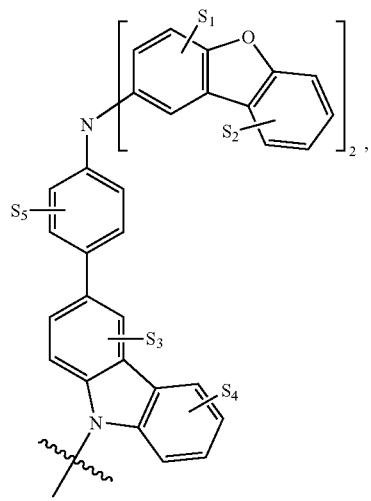
D60
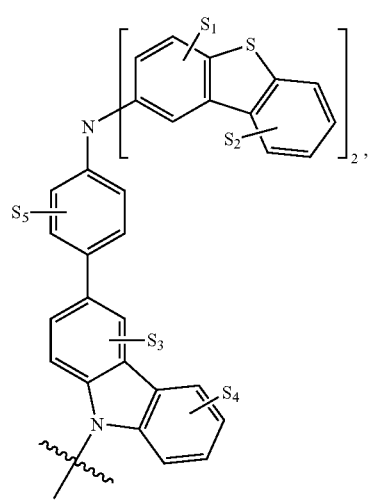
D61
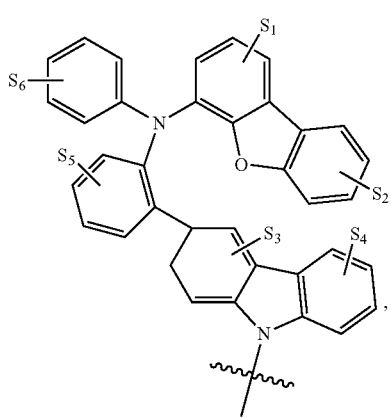
D62
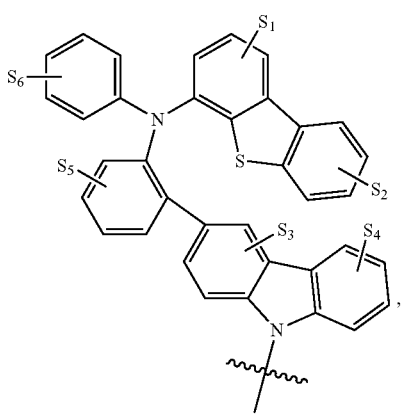
D63
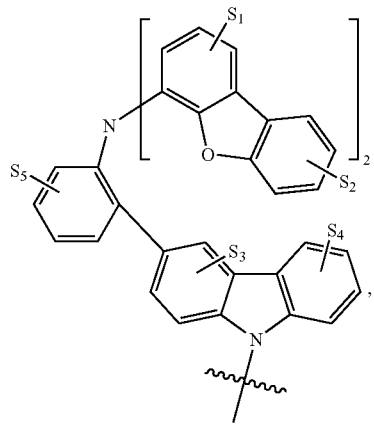
D64
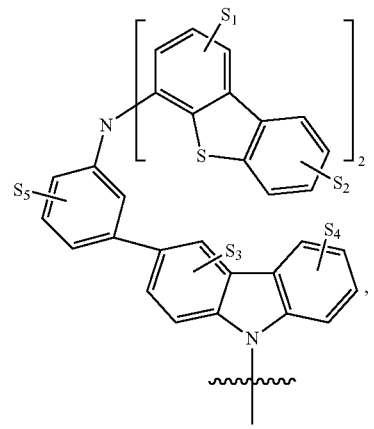
D65
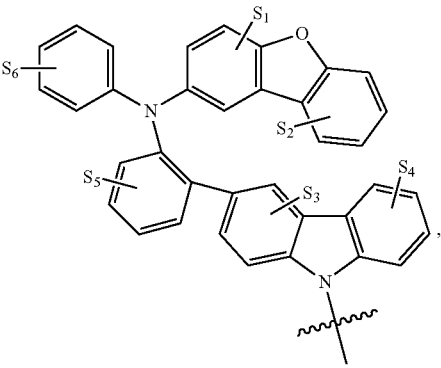
D66

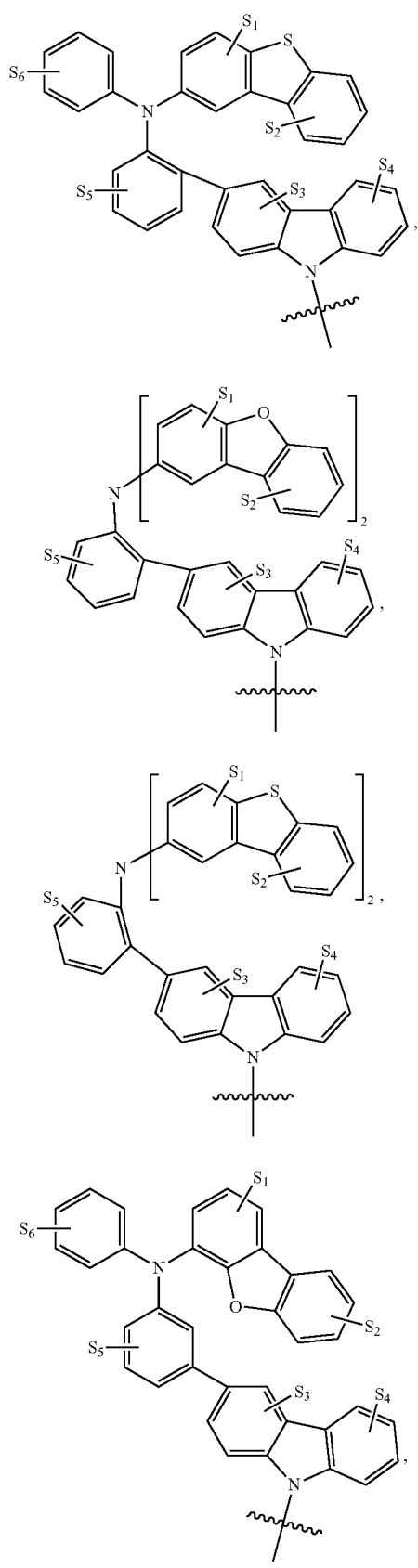
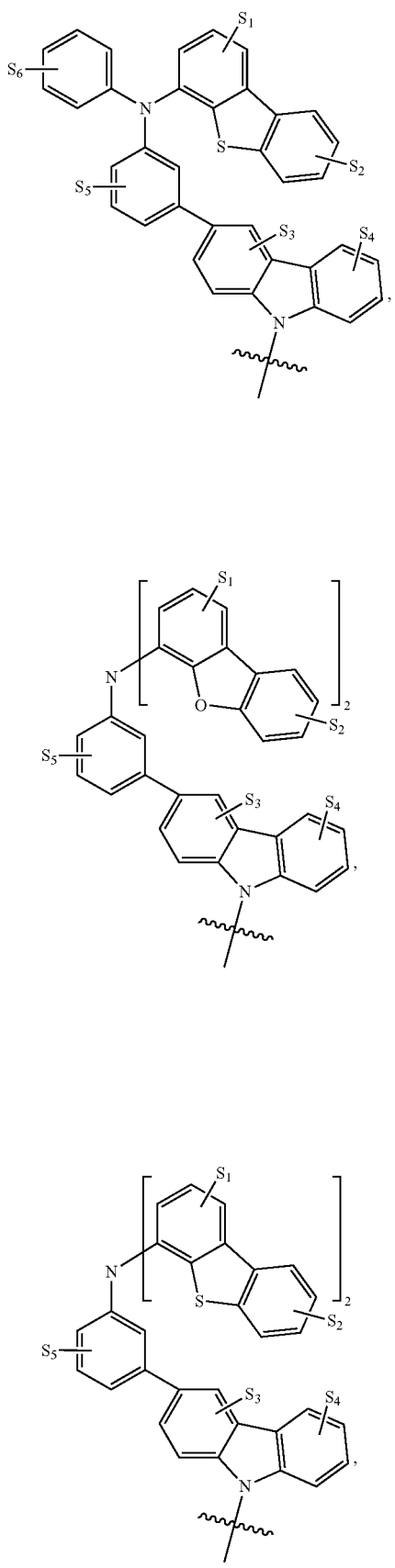

D74

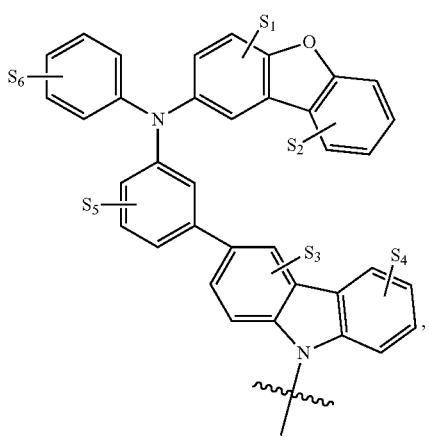

D75

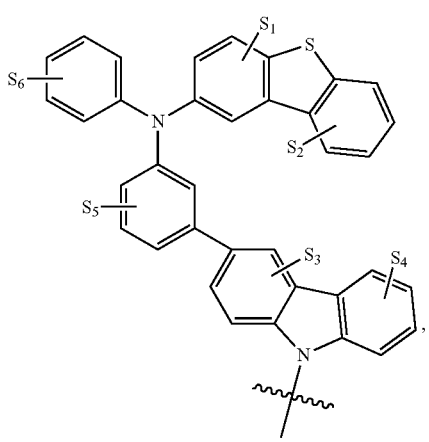

D76

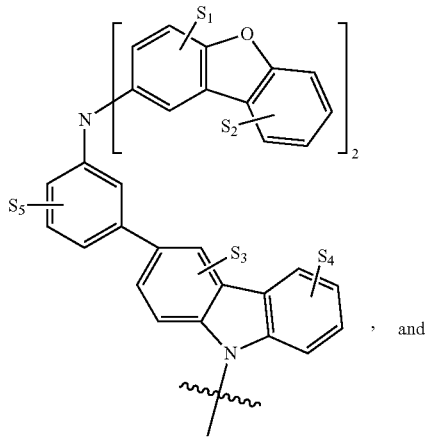, and

D77

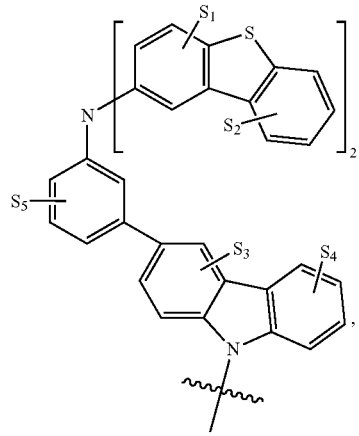, wherein $S_1$ to $S_6$ represent mono, di, tri, tetra or penta substitutions with hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

4. The compound of claim 2, wherein L is one of

L1

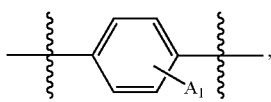

L2

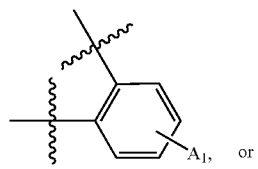, or

L3

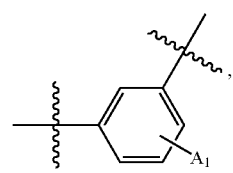, wherein $A_1$ to $A_2$ represent mono, di, tri or tetra substitutions with hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

5. The compound of claim 4, wherein the compound is one of

Compound 1

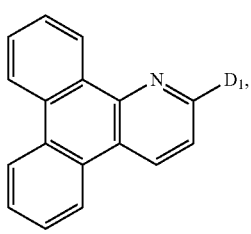

-continued
Compound 2
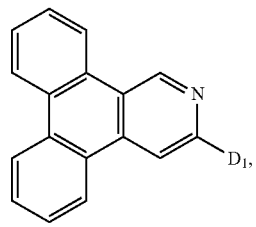
Compound 3
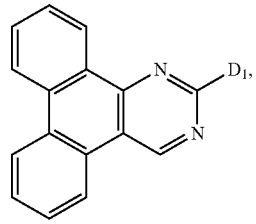
Compound 4
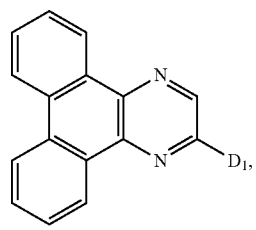
Compound 5
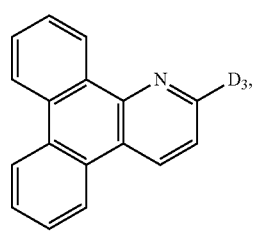
Compound 6
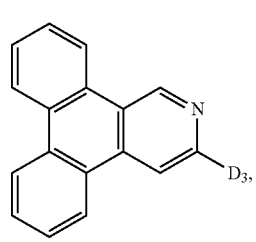
Compound 7
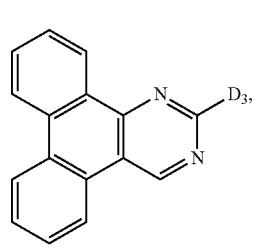
Compound 8
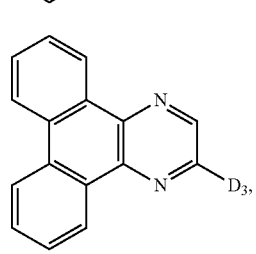
-continued
Compound 9
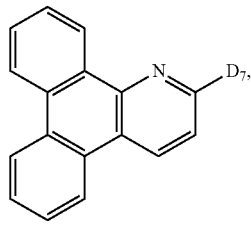
Compound 10
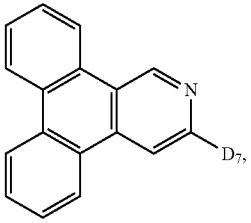
Compound 11
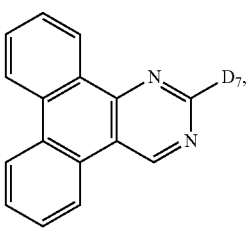
Compound 12
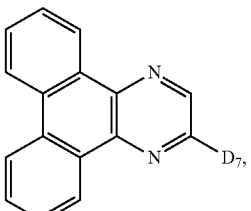
Compound 13
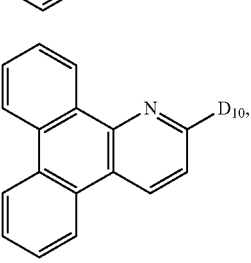
Compound 14
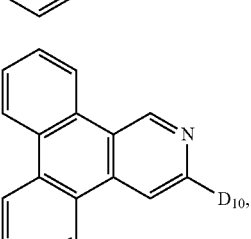
Compound 15
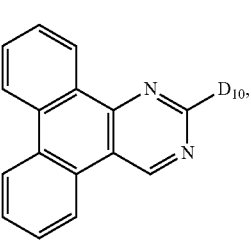

Compound 16
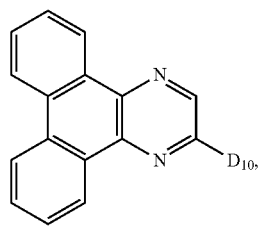
Compound 17
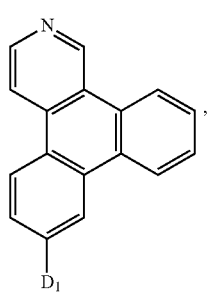
Compound 18
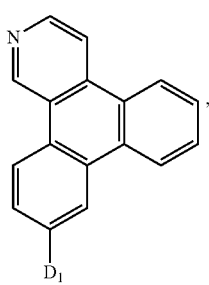
Compound 19
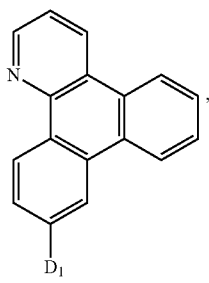
Compound 20
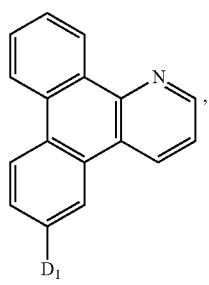
Compound 21
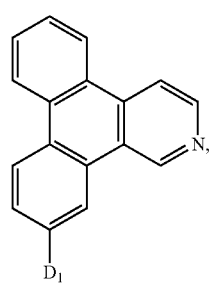
Compound 22
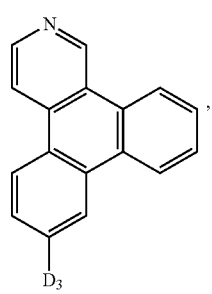
Compound 23
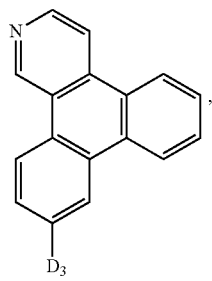
Compound 24
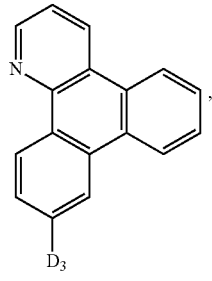
Compound 25
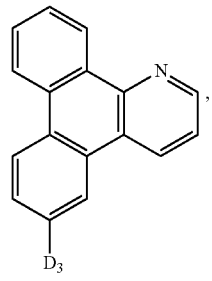

Compound 26
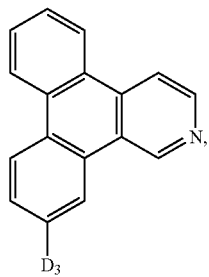
Compound 27
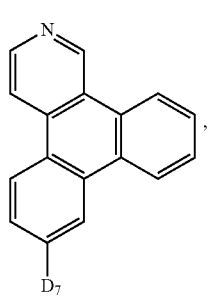
Compound 28
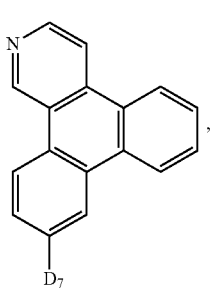
Compound 29
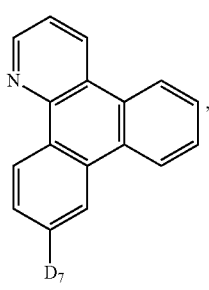
Compound 30
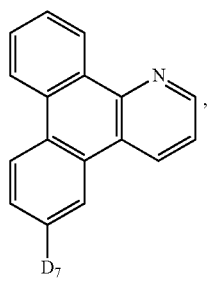
Compound 31
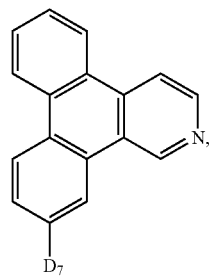
Compound 32
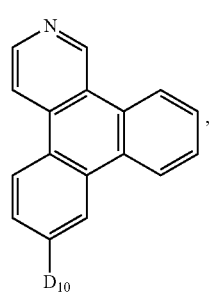
Compound 33
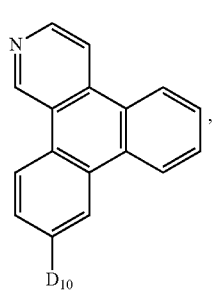
Compound 34
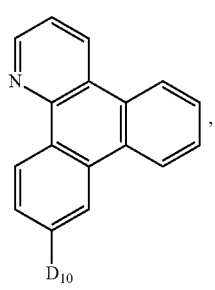
Compound 35
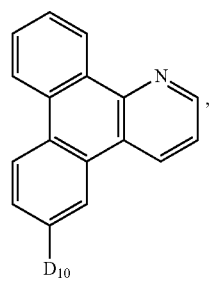

Compound 36
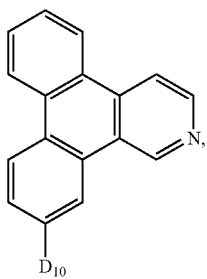
Compound 37
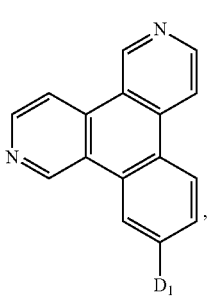
Compound 38
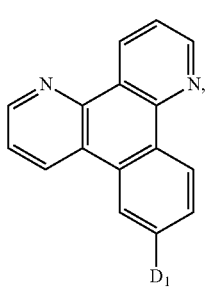
Compound 39
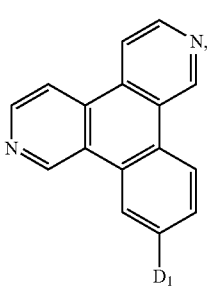
Compound 40
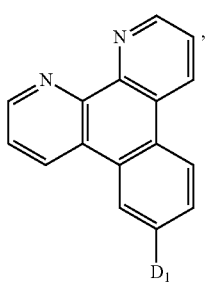
Compound 41
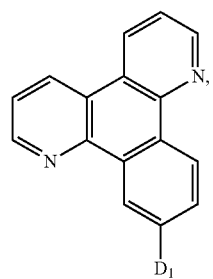
Compound 42
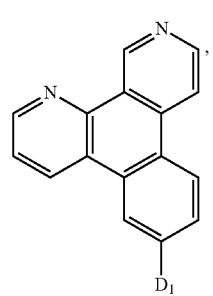
Compound 43
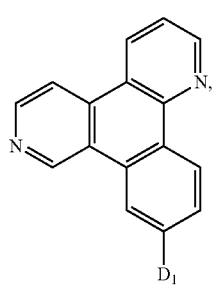
Compound 44
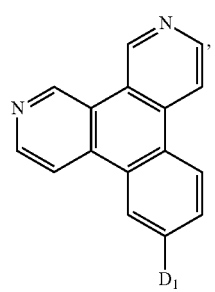
Compound 45
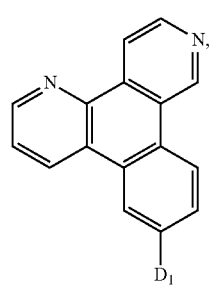

Compound 46
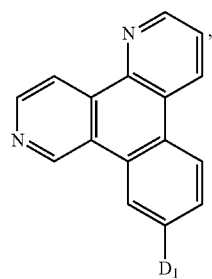
Compound 47
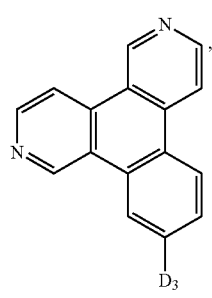
Compound 48
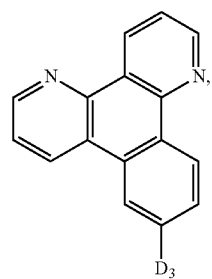
Compound 49
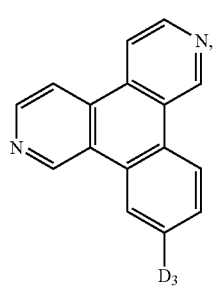
Compound 50
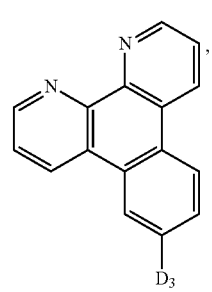
Compound 51
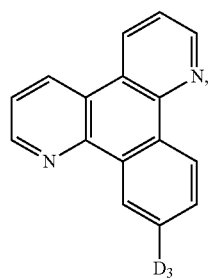
Compound 52
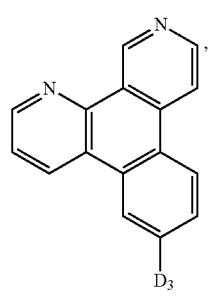
Compound 53
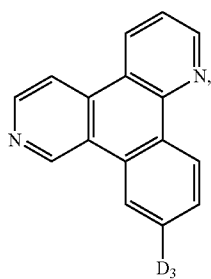
Compound 54
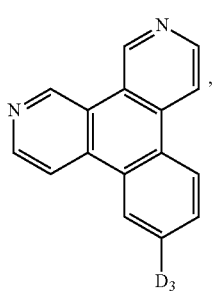
Compound 55
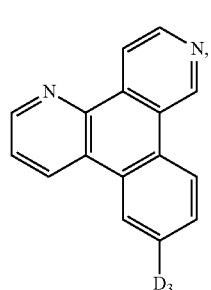

Compound 56
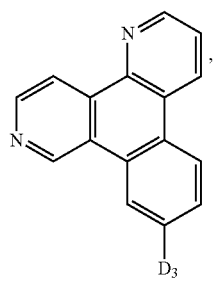
Compound 57
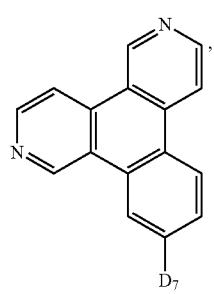
Compound 58
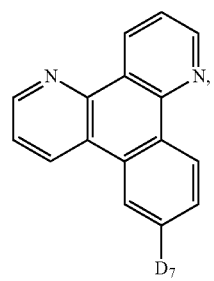
Compound 59
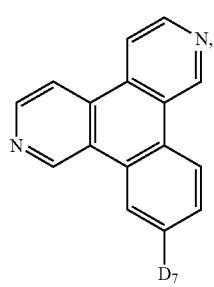
Compound 60
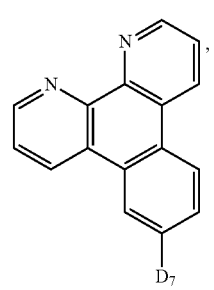
Compound 61
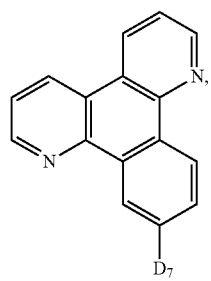
Compound 62
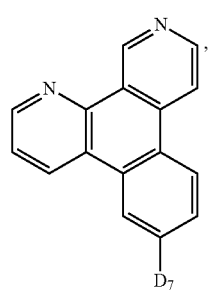
Compound 63
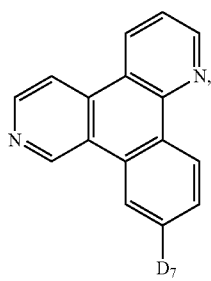
Compound 64
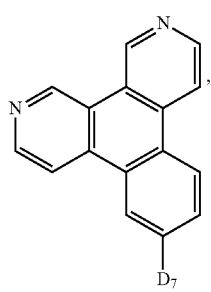
Compound 65
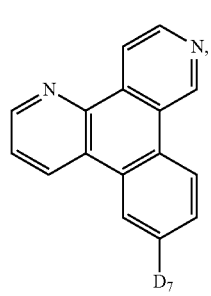

Compound 66
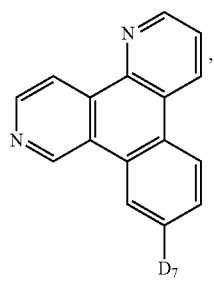
Compound 67
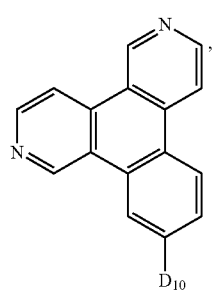
Compound 68
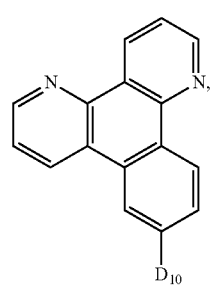
Compound 69
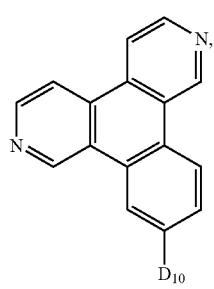
Compound 70
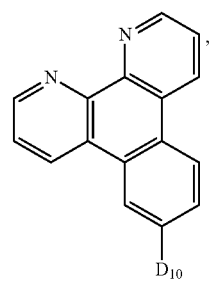
Compound 71
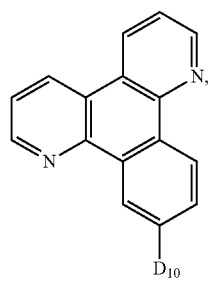
Compound 72
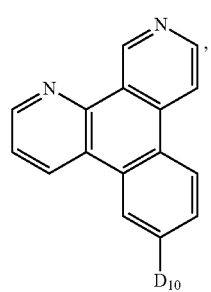
Compound 73
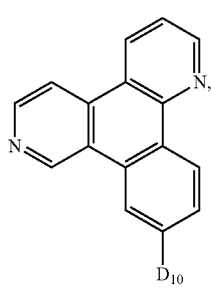
Compound 74
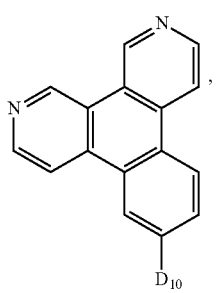
Compound 75
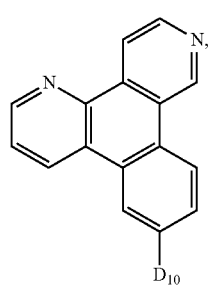

Compound 76
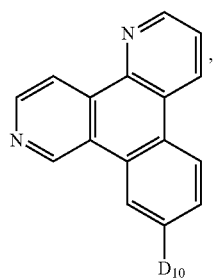
Compound 115
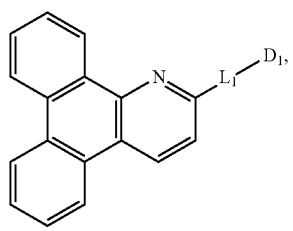
Compound 116
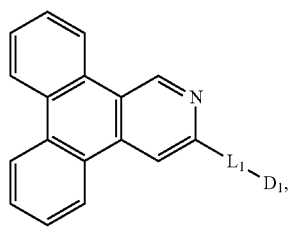
Compound 117
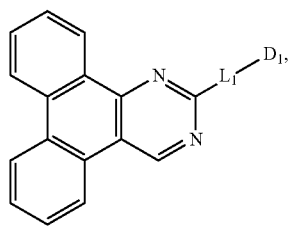
Compound 118
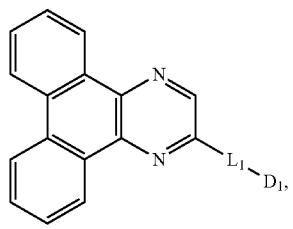
Compound 119
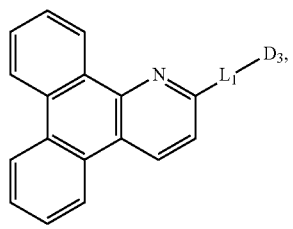
Compound 120
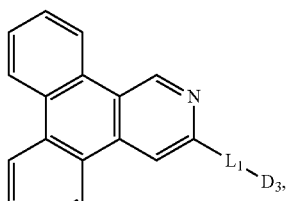
Compound 121
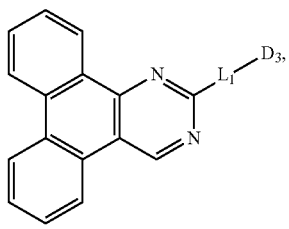
Compound 122
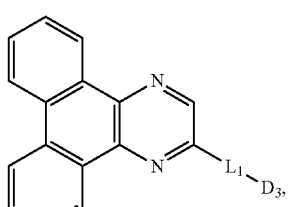
Compound 123
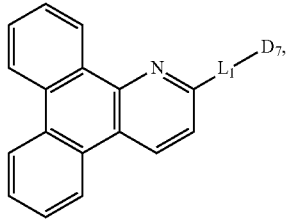
Compound 124
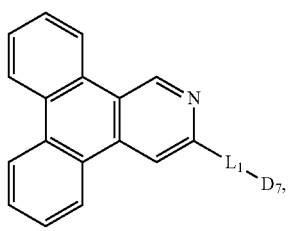
Compound 125
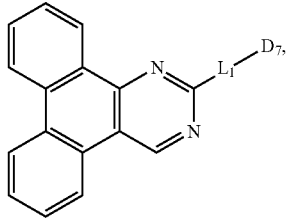
Compound 126

Compound 127
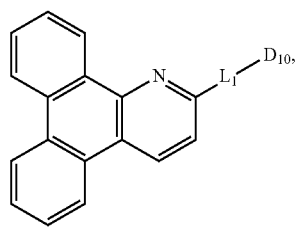
Compound 128
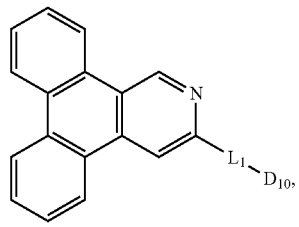
Compound 129
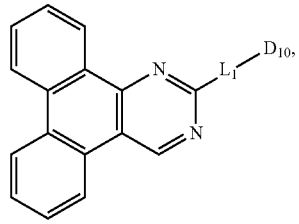
Compound 130
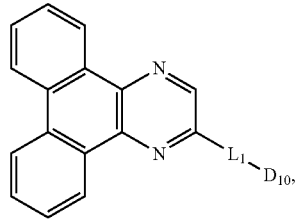
Compound 131
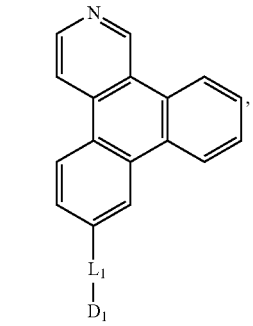
Compound 132
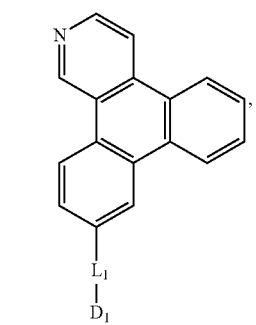
Compound 133
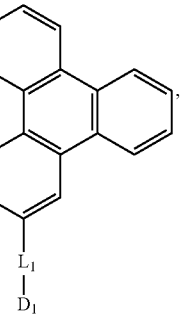
Compound 134
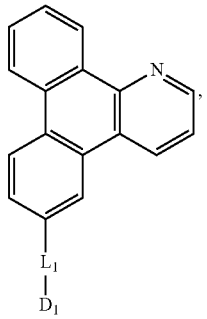
Compound 135
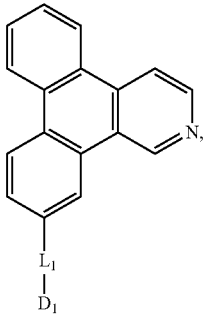
Compound 136
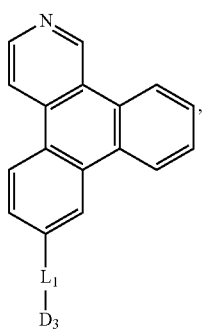
Compound 137
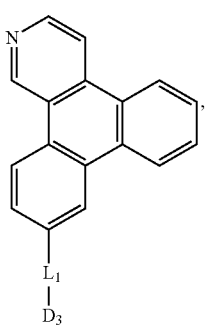

Compound 138
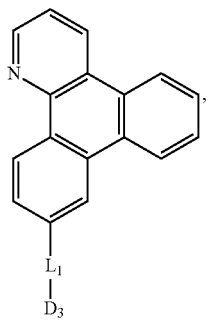
Compound 143
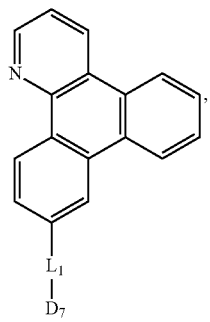
Compound 139
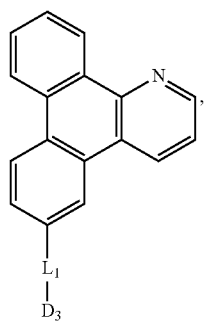
Compound 144
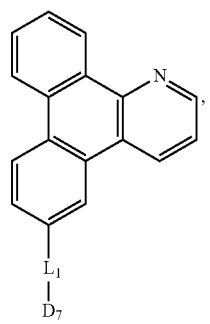
Compound 140
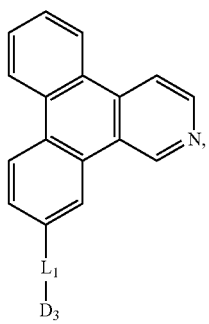
Compound 145
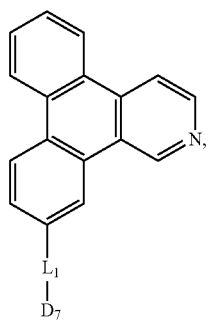
Compound 141
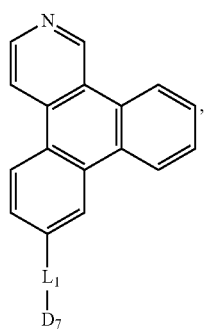
Compound 146
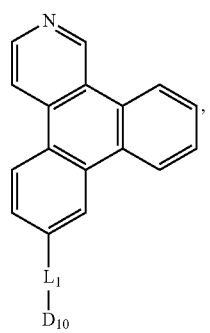
Compound 142
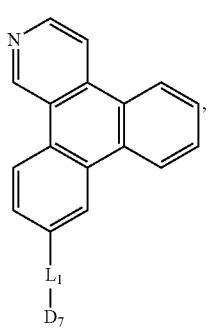
Compound 147
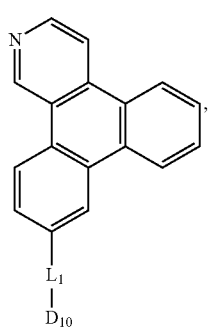

-continued
Compound 148
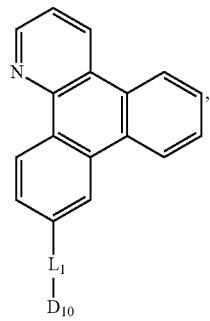
Compound 149
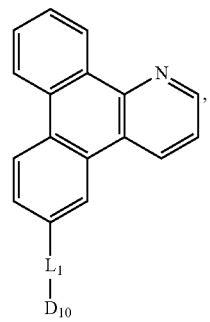
Compound 150
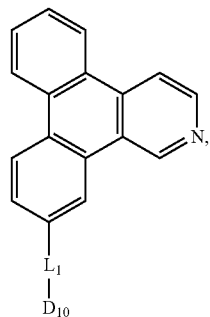
Compound 151
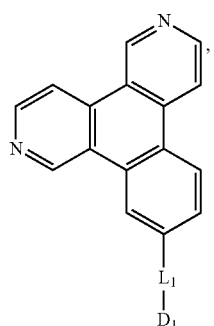
Compound 152
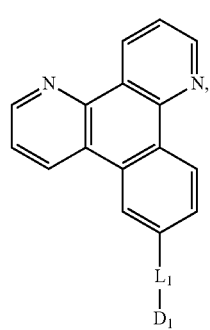
-continued
Compound 153
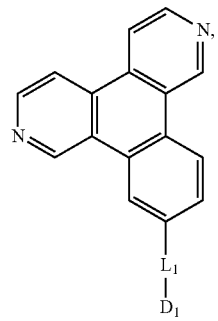
Compound 154
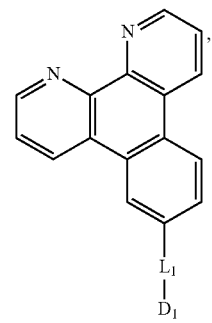
Compound 155
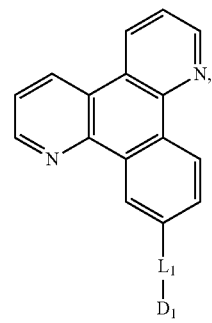
Compound 156
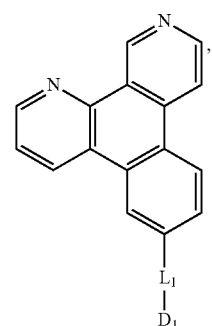
Compound 157
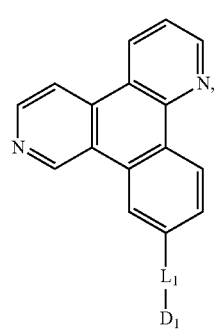

Compound 158
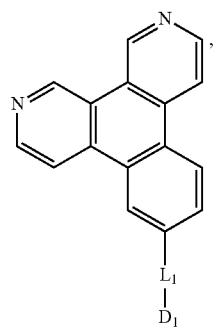
Compound 159
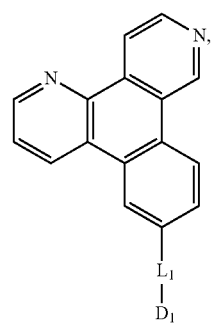
Compound 160
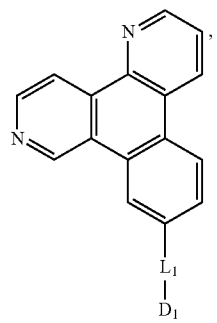
Compound 161
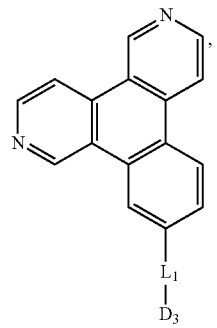
Compound 162
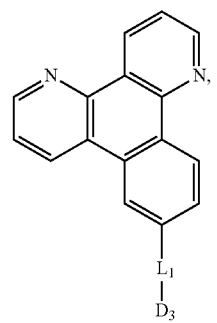
Compound 163
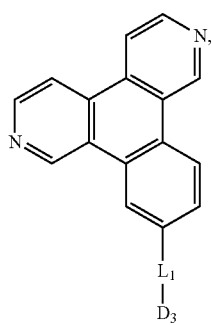
Compound 164
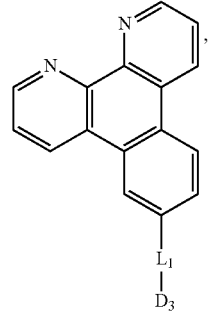
Compound 165
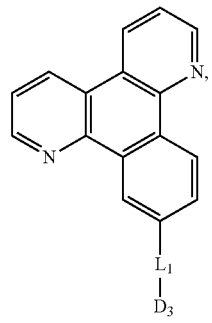
Compound 166
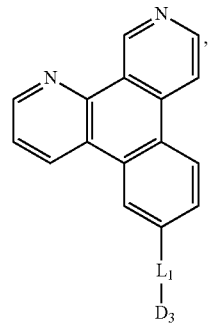
Compound 167
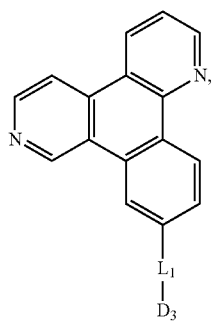

Compound 168
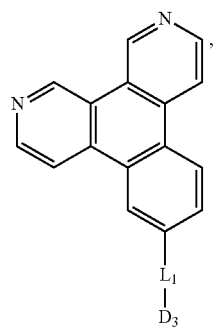
Compound 169
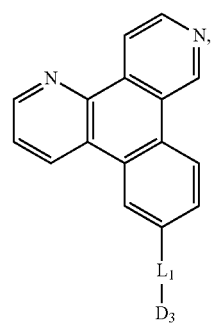
Compound 170
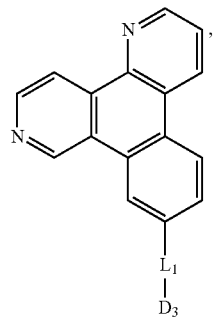
Compound 171
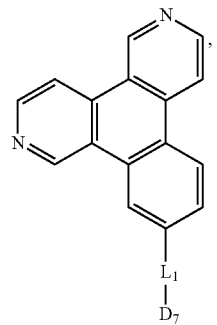
Compound 172
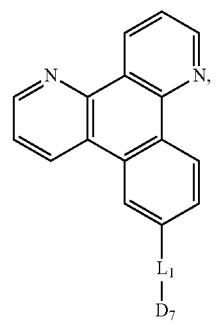
Compound 173
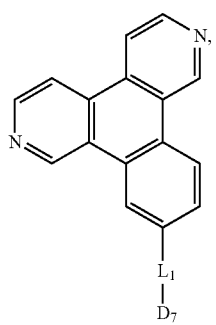
Compound 174
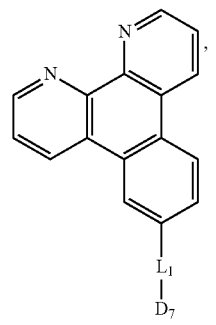
Compound 175
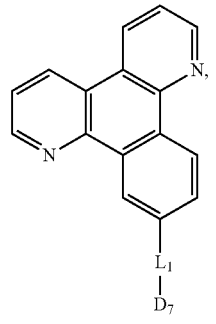
Compound 176
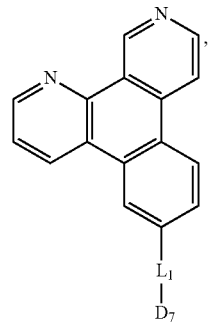
Compound 177
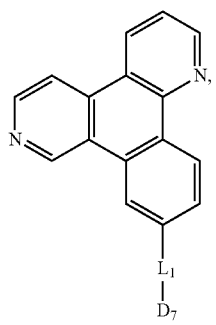

| Compound 178 | Compound 183 |
|---|---|
| 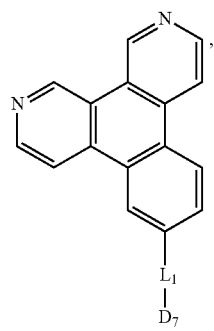 | 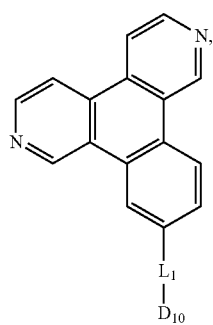 |
| Compound 179 | Compound 184 |
| 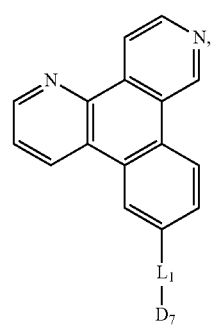 | 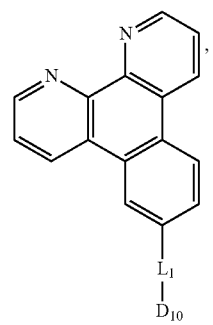 |
| Compound 180 | Compound 185 |
| 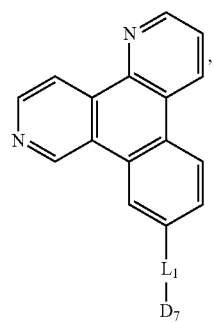 | 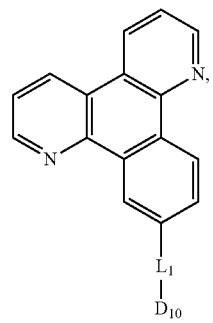 |
| Compound 181 | Compound 186 |
| 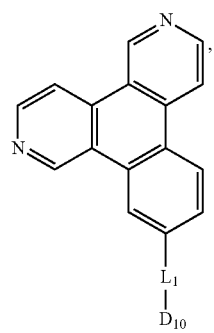 | 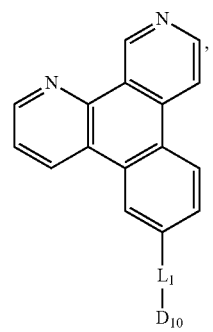 |
| Compound 182 | Compound 187 |
| 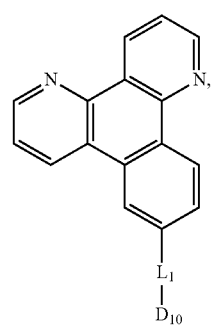 | 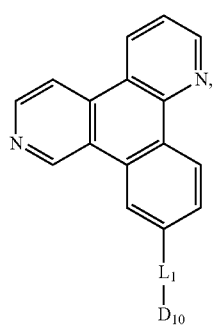 |

Compound 188
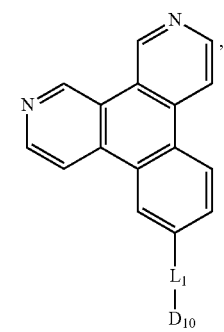
Compound 189
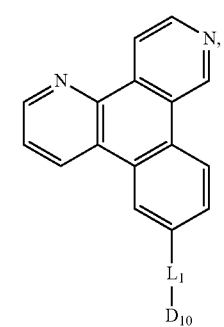
Compound 190
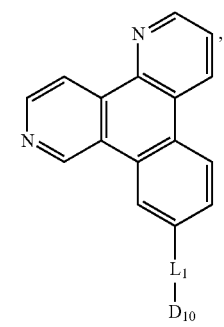
Compound 229
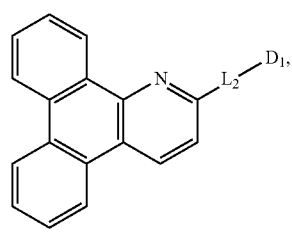
Compound 230
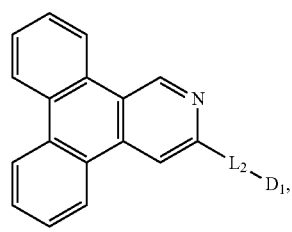
Compound 231
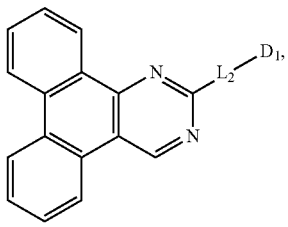
Compound 232
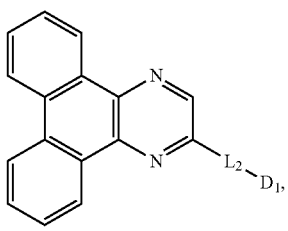
Compound 233
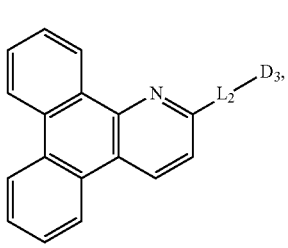
Compound 234
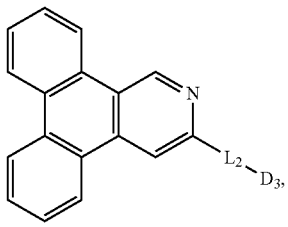
Compound 235
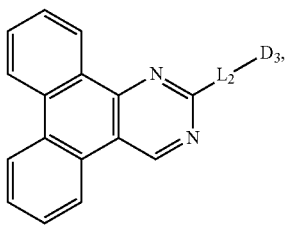
Compound 236
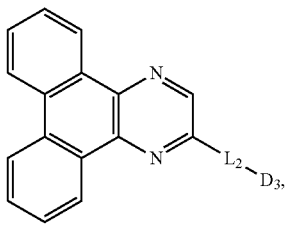
Compound 237

Compound 238
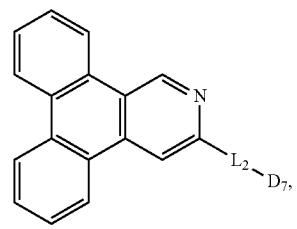
Compound 239
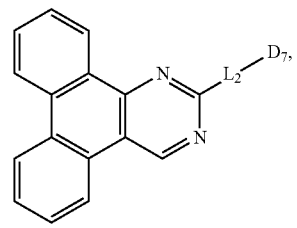
Compound 240
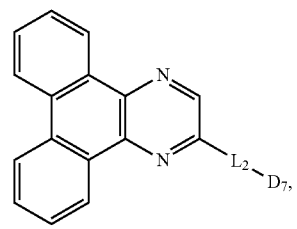
Compound 241
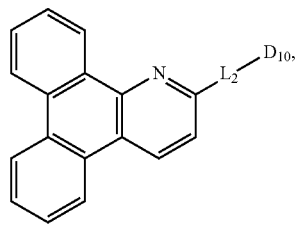
Compound 242
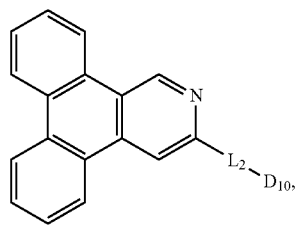
Compound 243
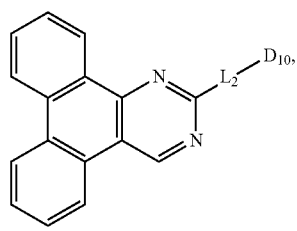
Compound 244
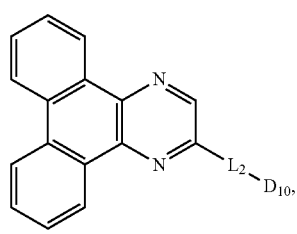
Compound 245
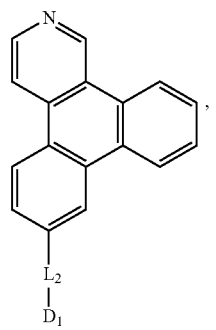
Compound 246
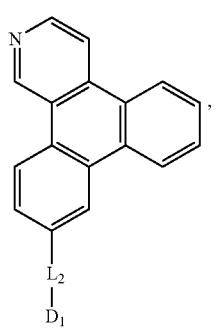
Compound 247
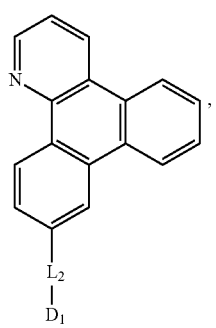
Compound 248
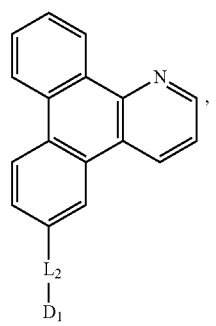
Compound 249
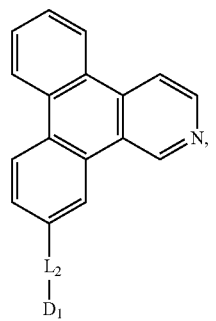

-continued
Compound 250
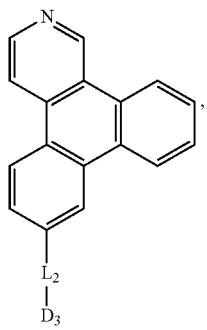
Compound 251
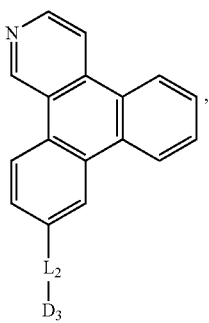
Compound 252
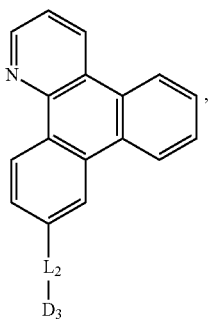
Compound 253
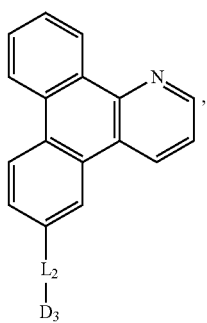
Compound 254
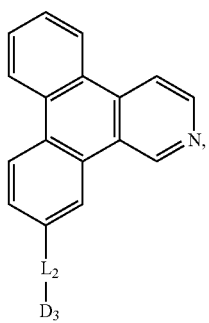
-continued
Compound 255
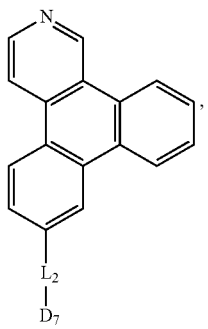
Compound 256
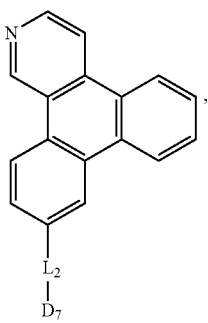
Compound 257
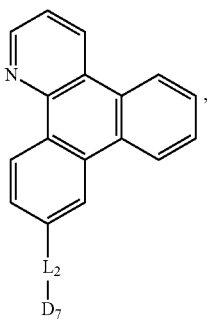
Compound 258
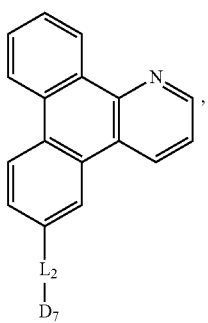
Compound 259
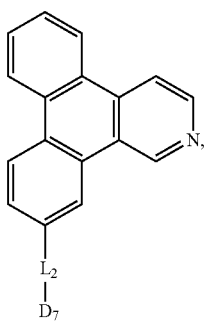

-continued
Compound 260
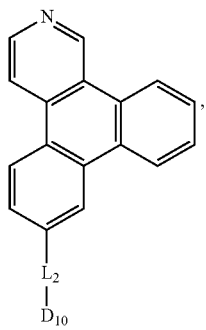
Compound 261
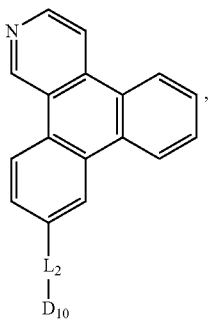
Compound 262
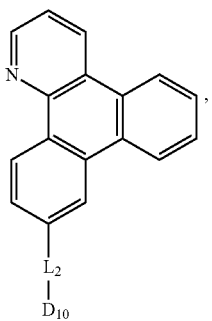
Compound 263
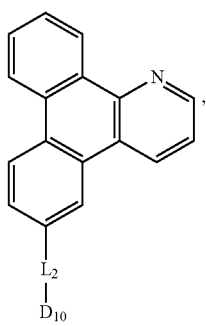
Compound 264
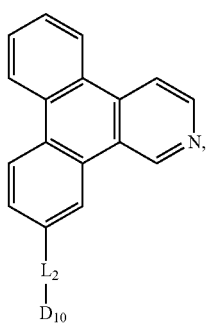
-continued
Compound 265
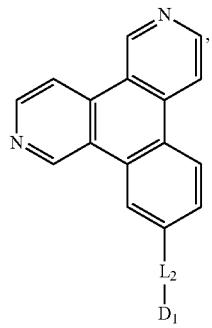
Compound 266
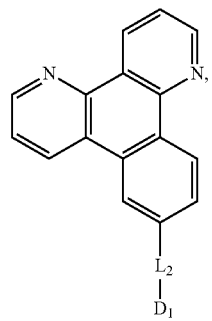
Compound 267
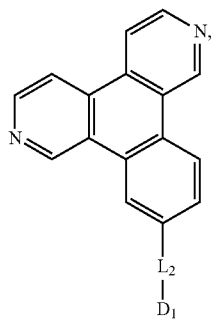
Compound 268
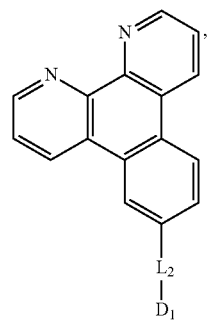
Compound 269
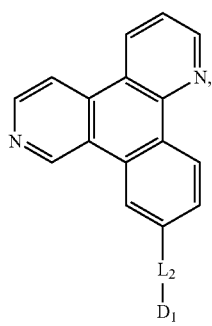

Compound 270
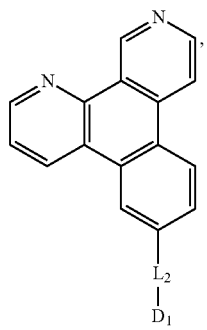
Compound 271
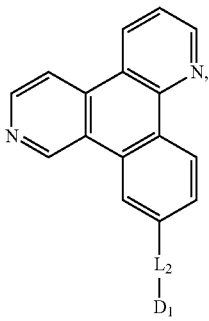
Compound 272
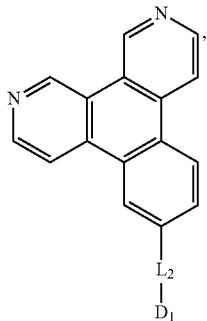
Compound 273
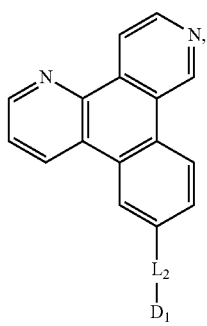
Compound 274
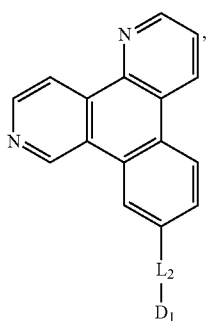
Compound 275
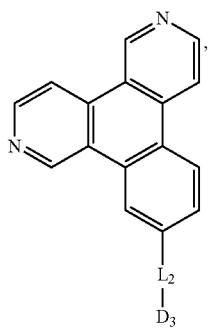
Compound 276
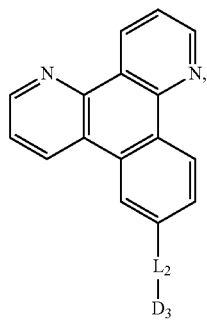
Compound 277
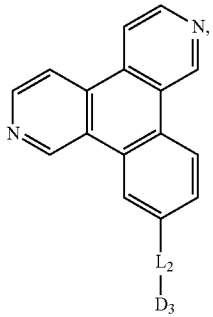
Compound 278
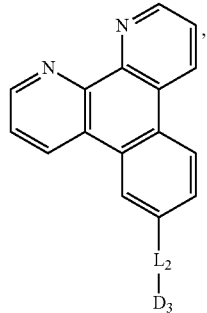
Compound 279
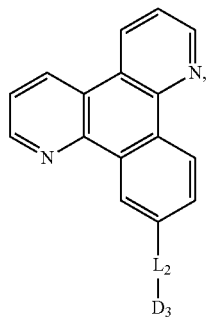

Compound 280
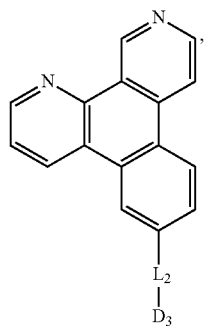
Compound 281
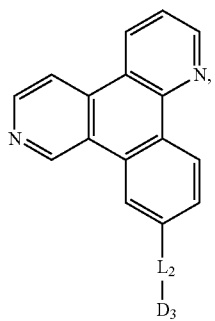
Compound 282
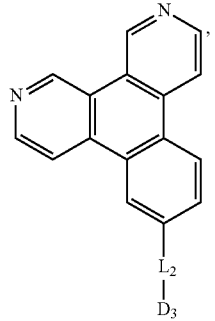
Compound 283
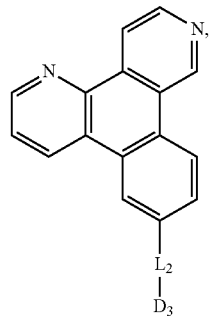
Compound 284
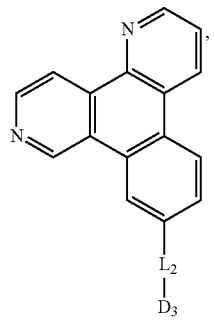
Compound 285
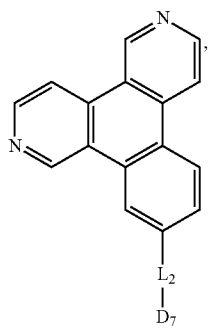
Compound 286
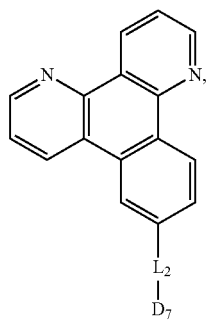
Compound 287
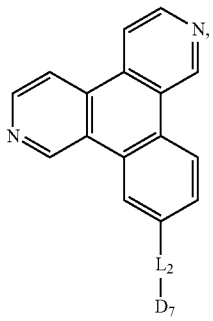
Compound 288
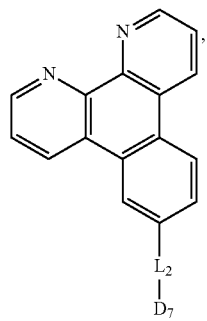
Compound 289
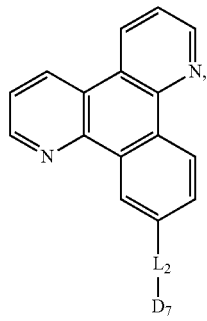

-continued
Compound 290
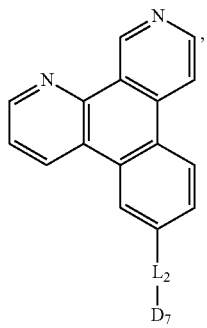
Compound 291
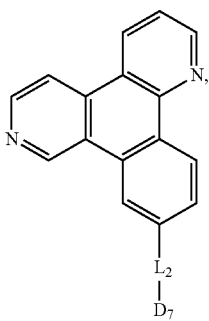
Compound 292
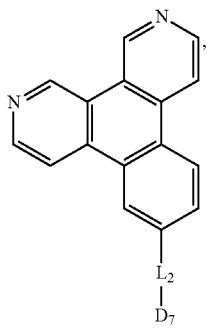
Compound 293
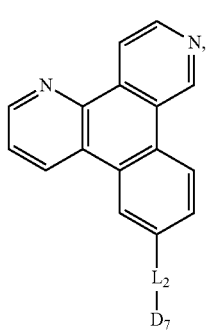
Compound 294
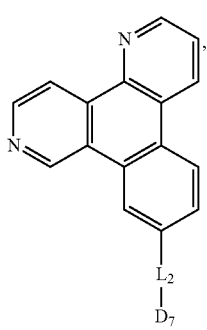
-continued
Compound 295
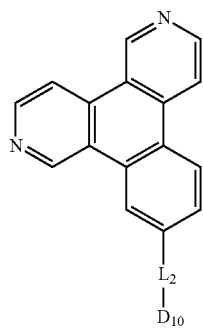
Compound 296
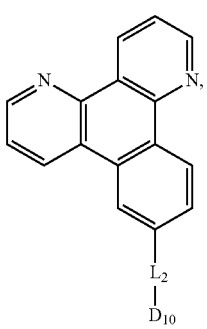
Compound 297
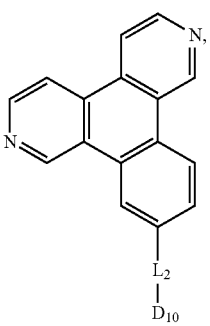
Compound 298
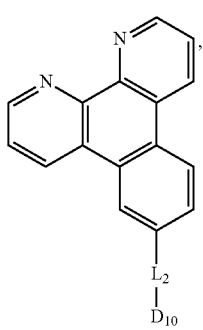
Compound 299
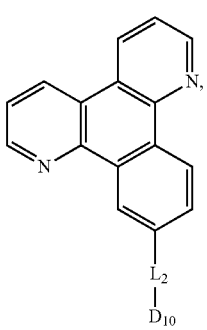

Compound 300
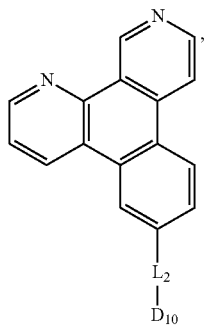
Compound 301
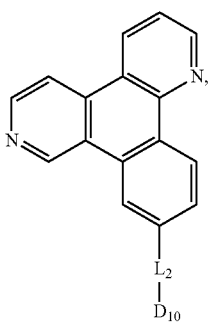
Compound 302
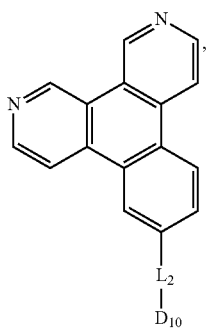
Compound 303
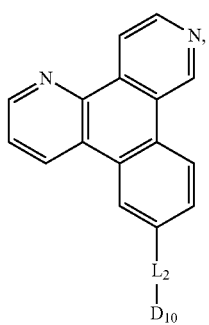
Compound 304
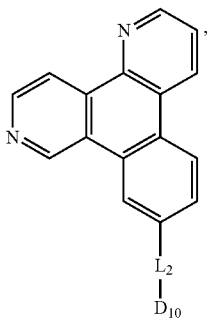
Compound 343
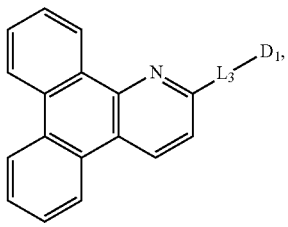
Compound 344
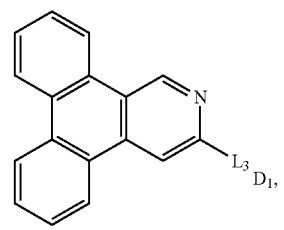
Compound 345
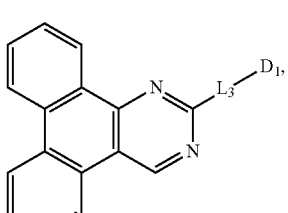
Compound 346
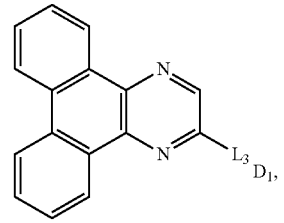
Compound 347
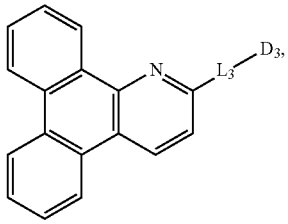
Compound 348
Compound 349
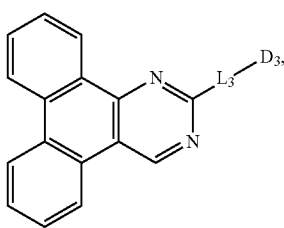

425
-continued
Compound 350
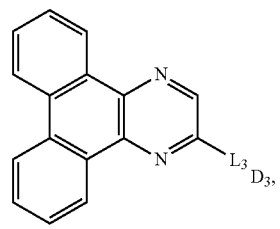
Compound 351
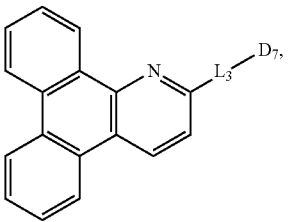
Compound 352
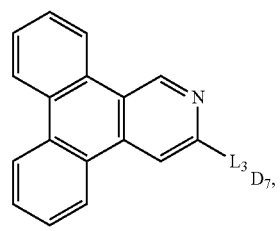
Compound 353
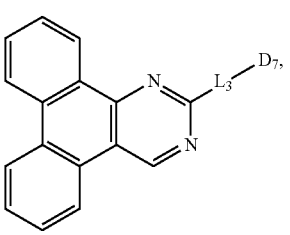
Compound 354
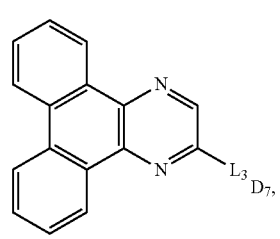
Compound 355
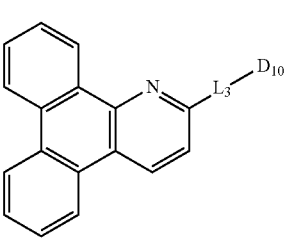
Compound 356
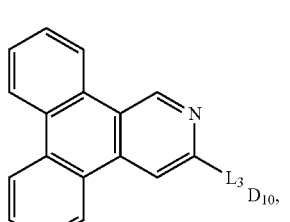
426
-continued
Compound 357
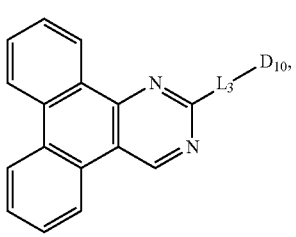
Compound 358
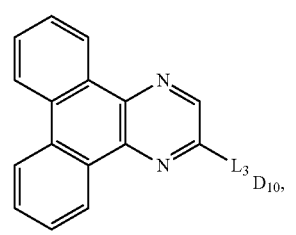
Compound 359
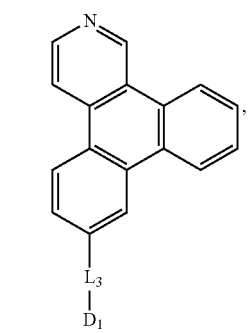
Compound 360
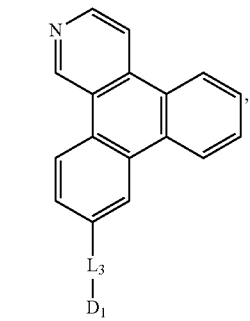
Compound 361
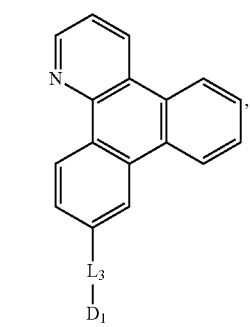

427
-continued
Compound 362
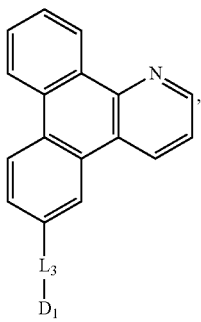
Compound 363
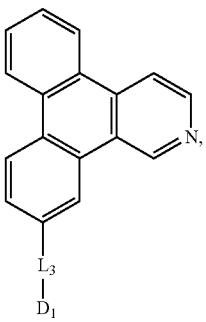
Compound 364
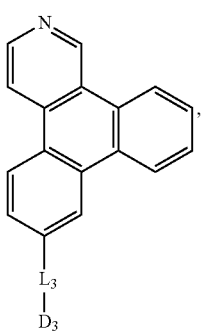
Compound 365
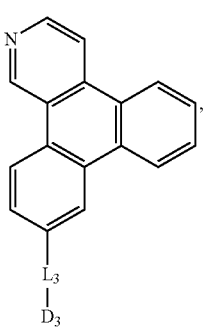
Compound 366
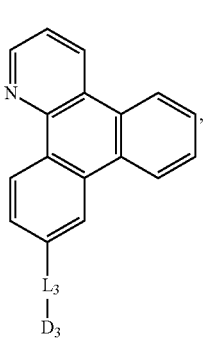
428
-continued
Compound 367
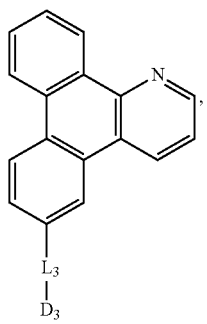
Compound 368
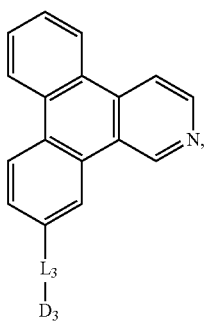
Compound 369
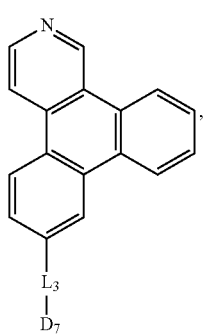
Compound 370
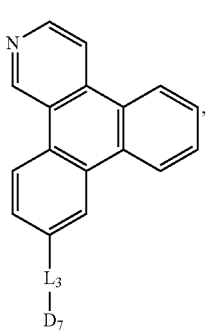
Compound 371

| | |
|---|---|
| Compound 372 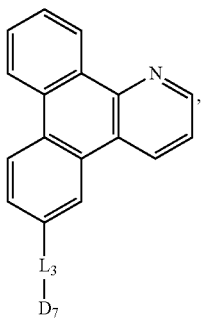 | Compound 377 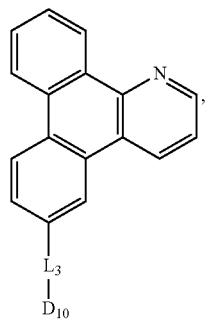 |
| Compound 373 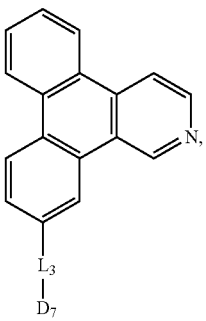 | Compound 378 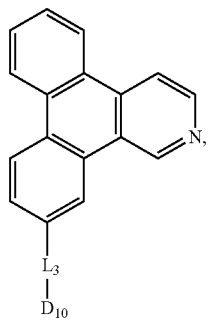 |
| Compound 374 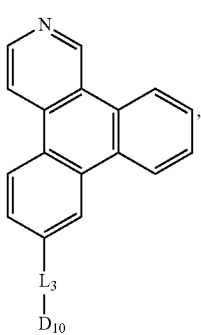 | Compound 379 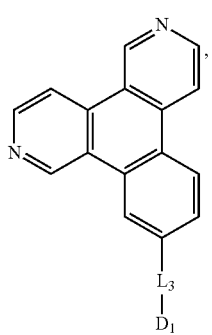 |
| Compound 375 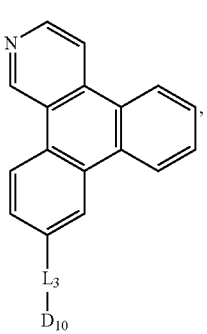 | Compound 380 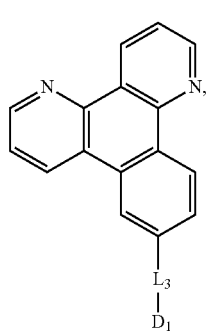 |
| Compound 376 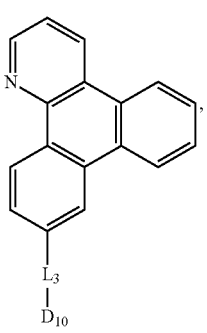 | Compound 381 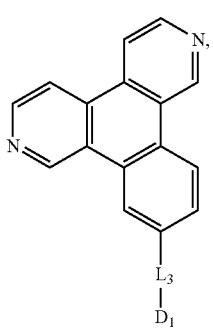 |

-continued
Compound 382
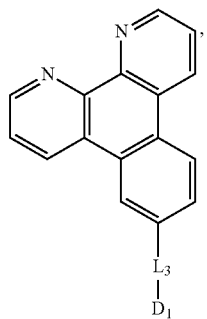
Compound 383
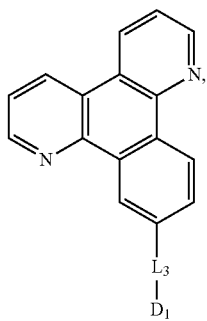
Compound 384
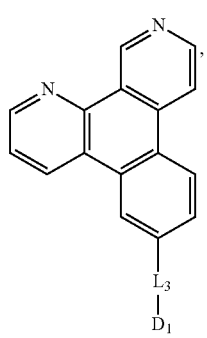
Compound 385
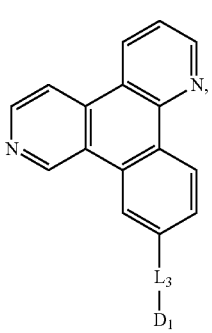
Compound 386
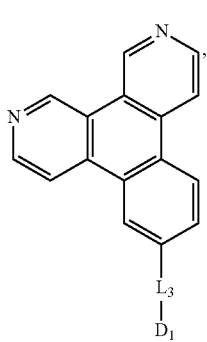
-continued
Compound 387
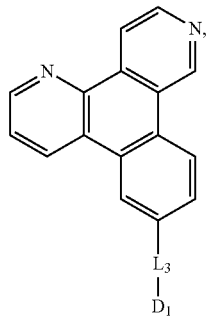
Compound 388
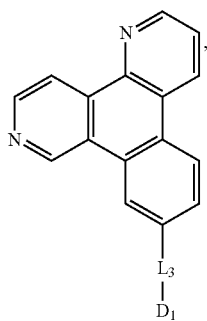
Compound 389
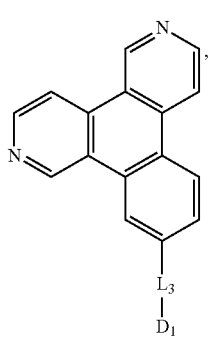
Compound 390
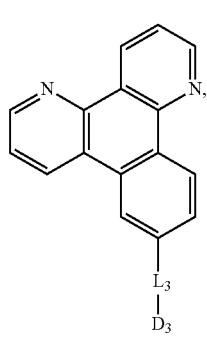
Compound 391
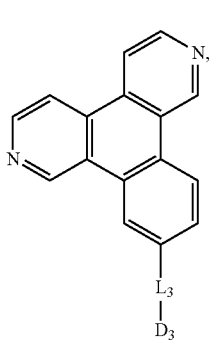

-continued
Compound 392
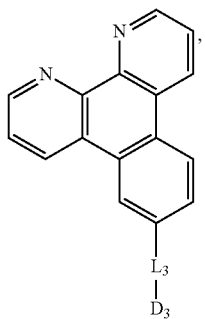
Compound 393
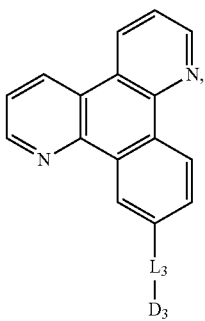
Compound 394
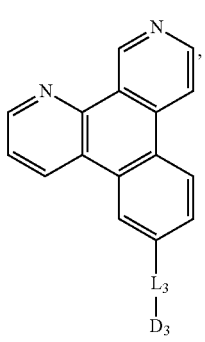
Compound 395
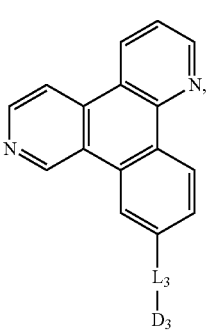
Compound 396
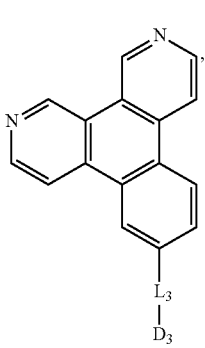
-continued
Compound 397
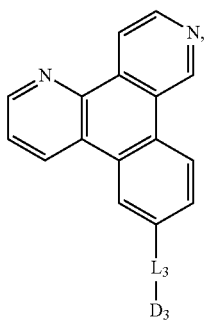
Compound 398
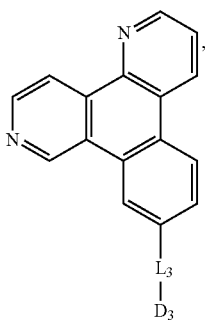
Compound 399
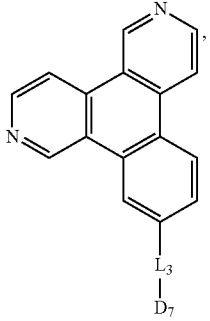
Compound 400
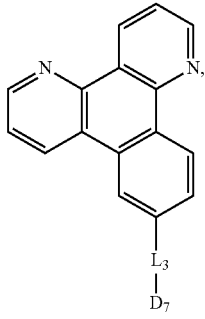
Compound 401
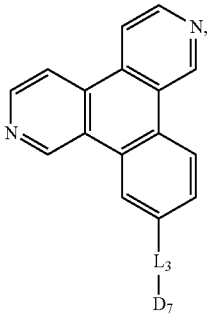

Compound 402
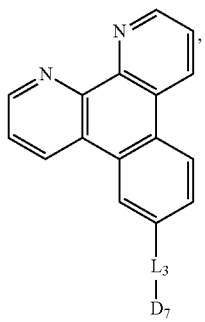
Compound 403
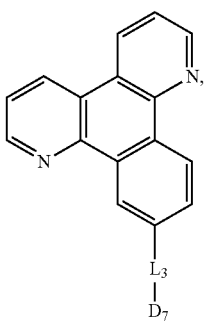
Compound 404
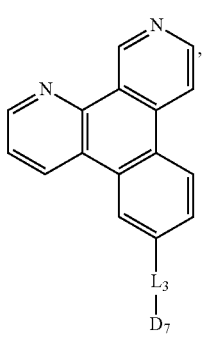
Compound 405
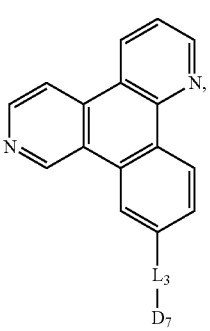
Compound 406
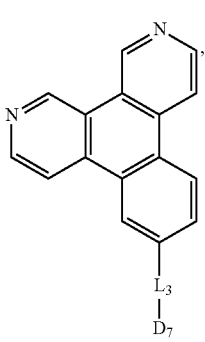
Compound 407
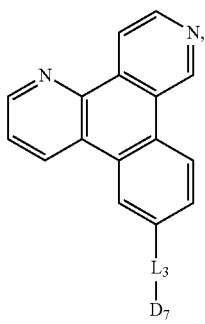
Compound 408
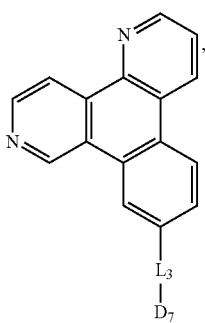
Compound 409
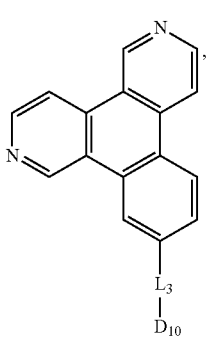
Compound 410
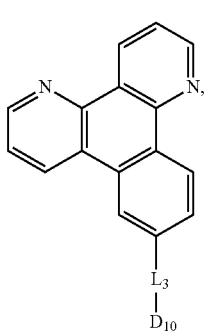
Compound 411
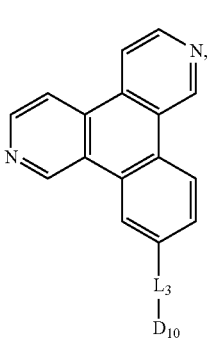

Compound 412
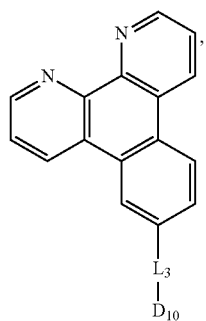
Compound 413
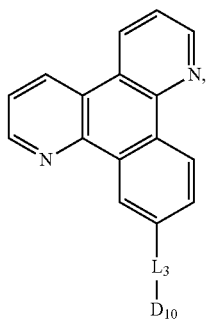
Compound 414
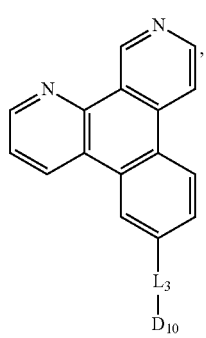
Compound 415
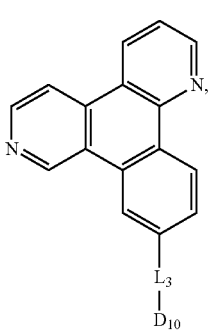
Compound 416
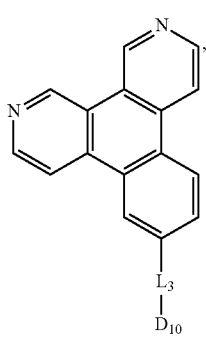
Compound 417
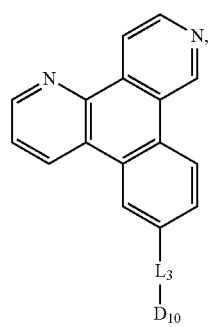
Compound 418
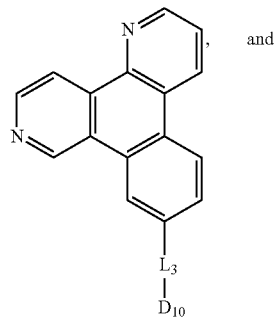
and
Compound 457
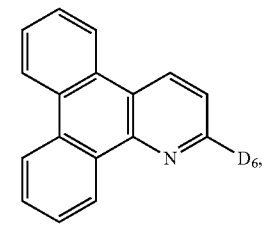
wherein D1, D2, D6, D7, and D10 are
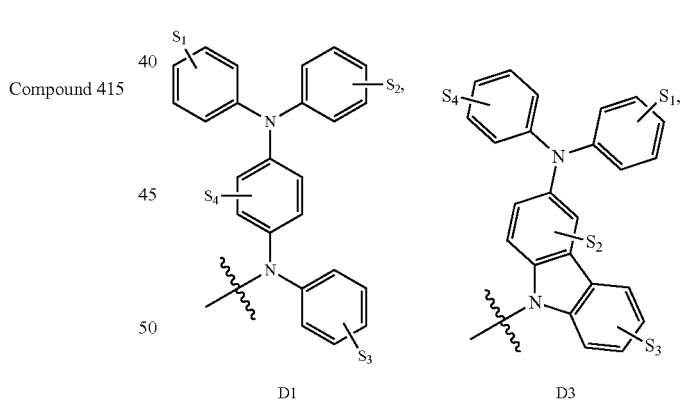
D1        D3
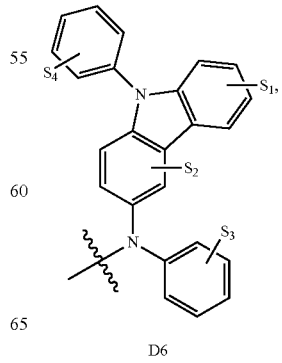
D6

-continued

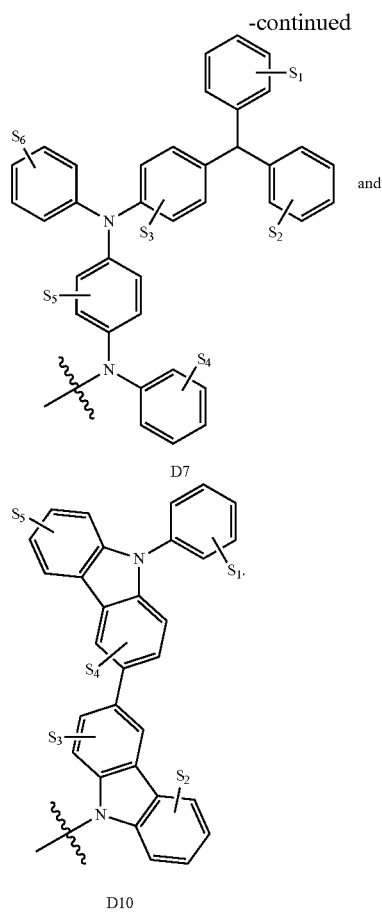

D7

D10

6. The compound of claim 5, wherein $S_1$ to $S_6$ and $A_1$-$A_2$ are H.

7. A first device comprising a first organic light emitting device,
further comprising:
an anode;
a cathode; and
an organic emissive layer, disposed between the anode and the cathode;
wherein the organic emissive layer comprises a first emitting compound having a structure according to Formula 1

Formula 1

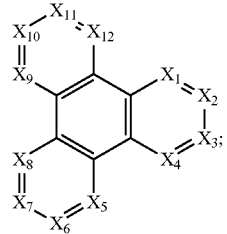

wherein $X_1$ to $X_{12}$ is independently selected from the group consisting of C—R and N;
at least one of $X_1$ to $X_{12}$ is N;
each R is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;
wherein at least one of the R is $$(L)_m(\text{Donor})_n;$$

wherein L is an organic aromatic group linker,
m is 1 or 0,
n≥1;
wherein Donor is an electron donating group containing at least two electron-donating nitrogens and Donors can be different when n>1; and
wherein at least one electron-donating nitrogen in the Donor is directly bonded to L.

8. The first device of claim 7, wherein the first emitting compound is selected from the group consisting of Formula 2

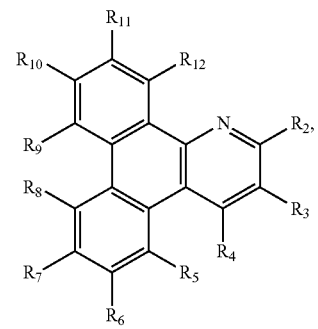

Formula 3

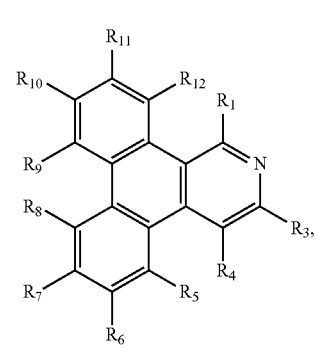

Formula 4

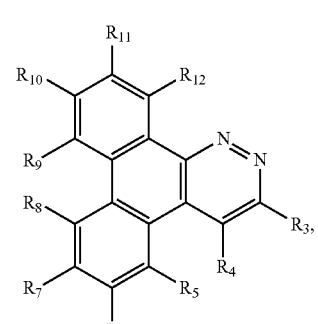

-continued
Formula 5
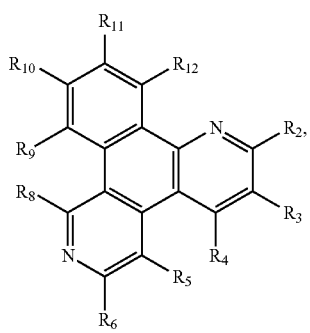
Formula 6
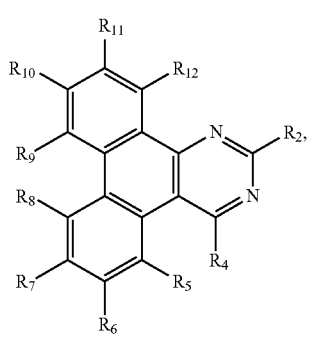
Formula 7
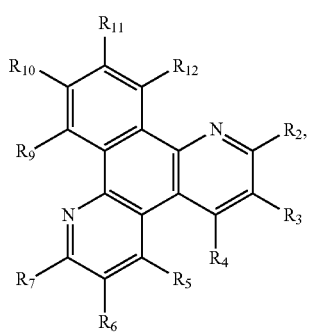
Formula 8
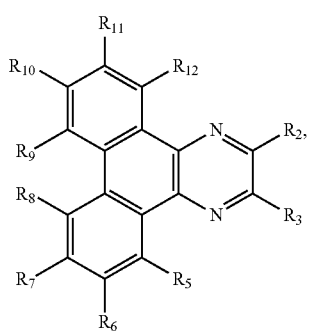
Formula 9
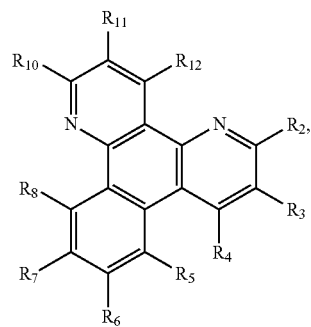
Formula 10
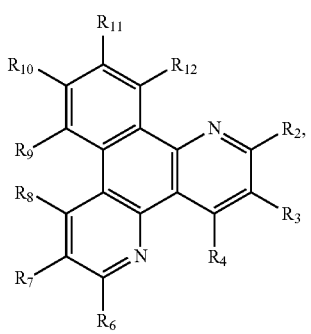
Formula 11
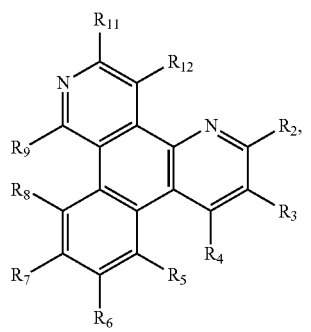
Formula 12
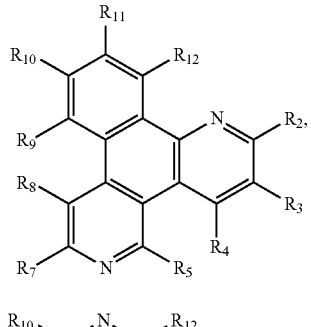
Formula 13
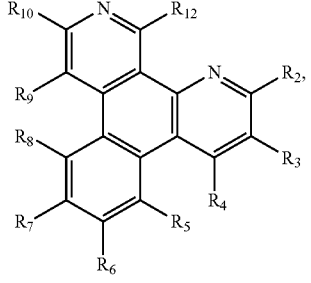

443
-continued

Formula 14
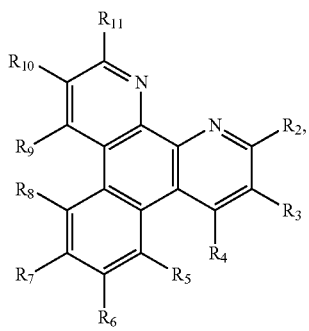

Formula 15
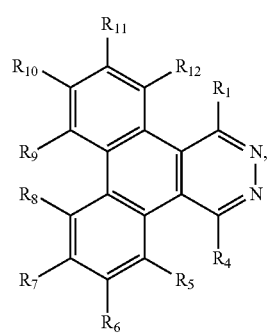

Formula 16
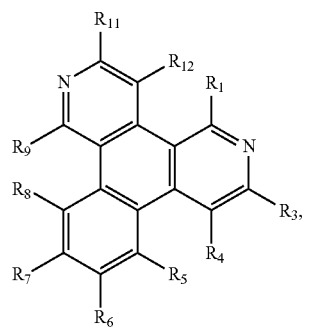

Formula 17
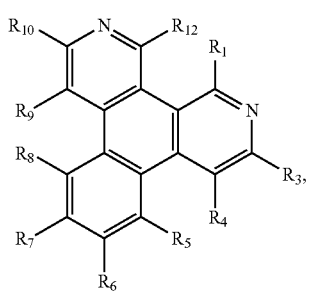

Formula 18
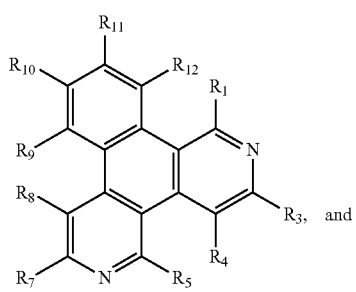 and

444
-continued

Formula 19
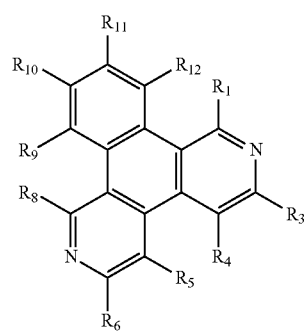

wherein $R_1$ to $R_{12}$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;

at least one of $R_1$ to $R_{12}$ is $(L)_m(\text{Donor})_n$.

9. The first device of claim 8, wherein Donor is selected from the group consisting of:

D1
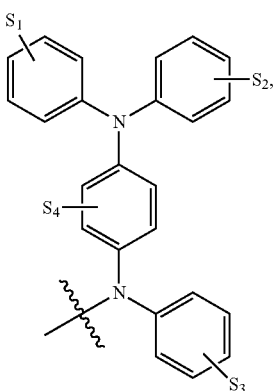

D2
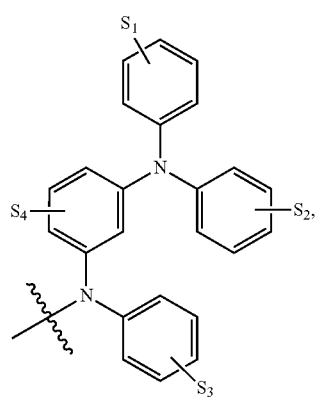

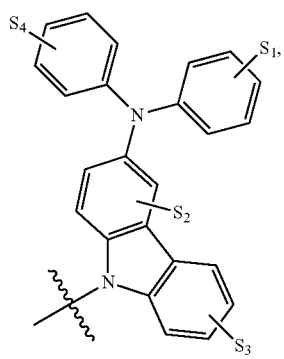 D3
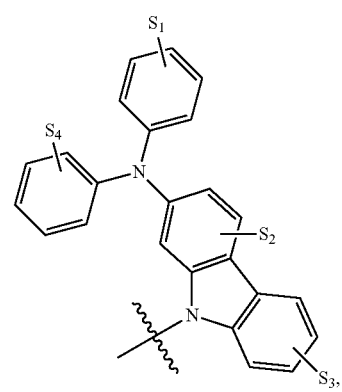 D4
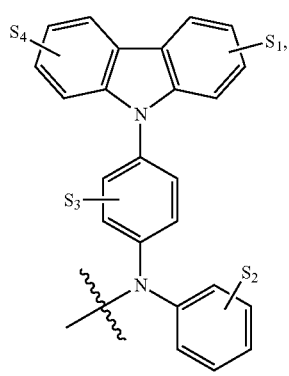 D5
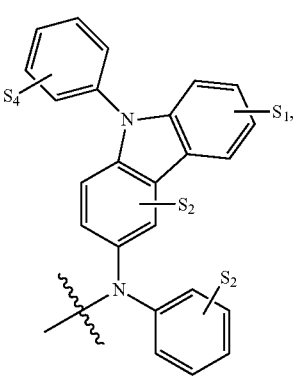 D6
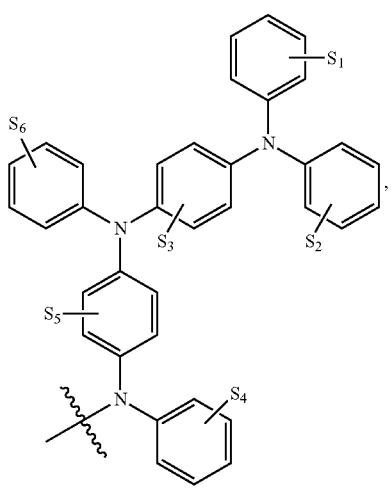 D7
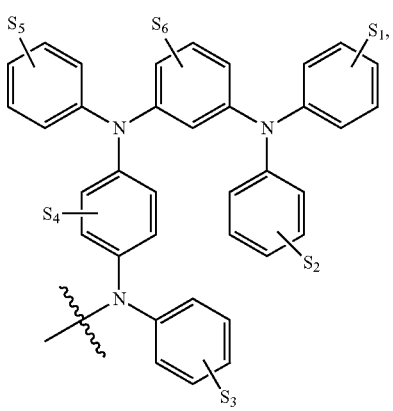 D8
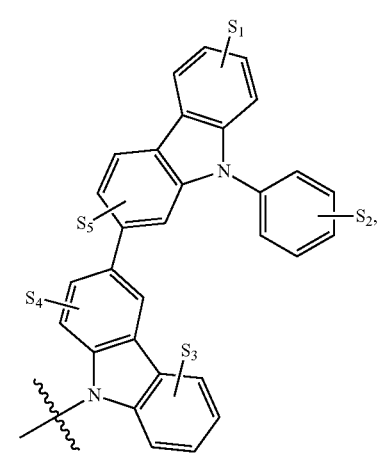 D9

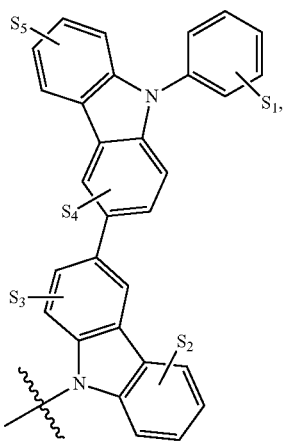
D10
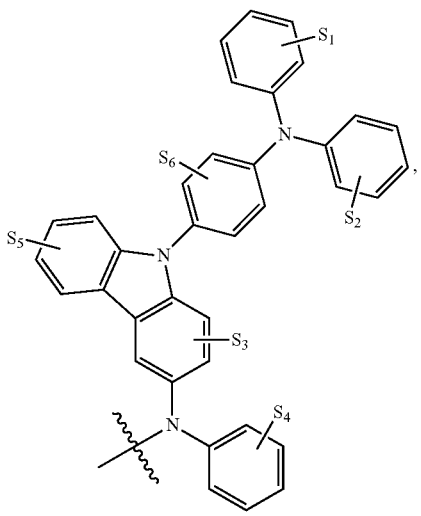
D13
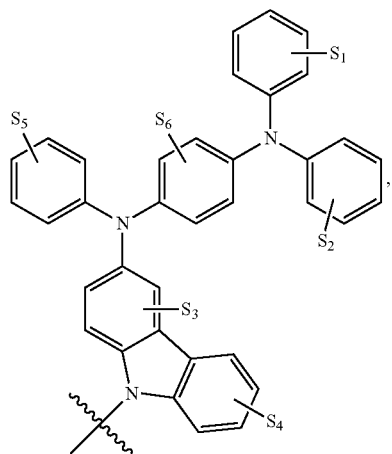
D11
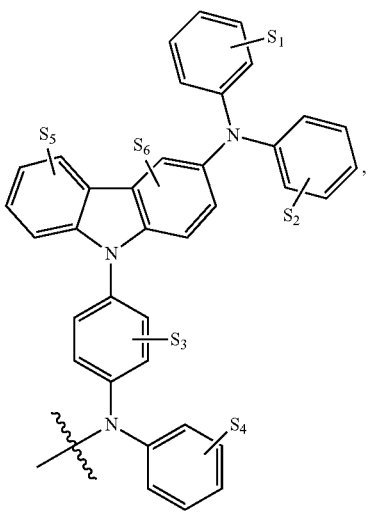
D14
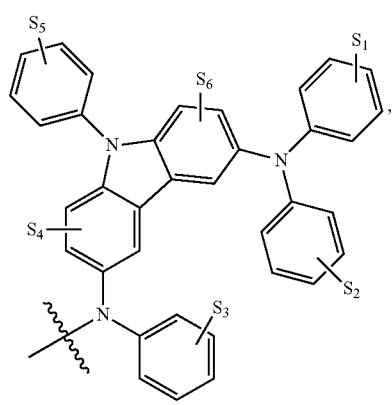
D12
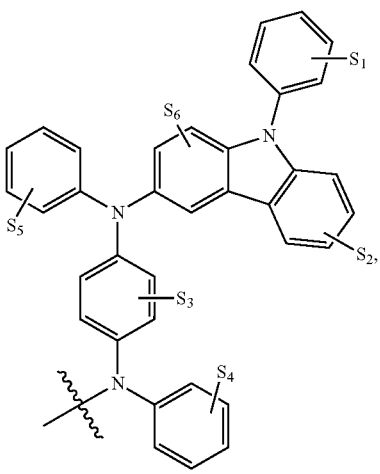
D15

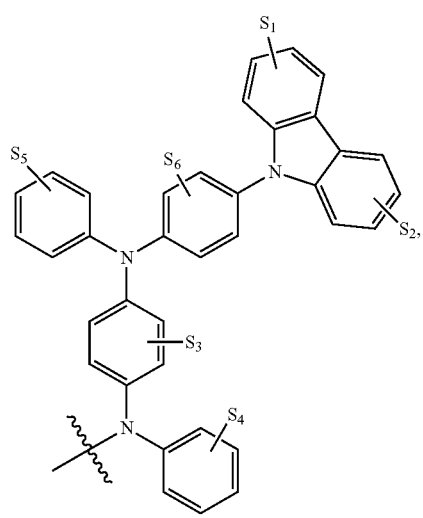
D16
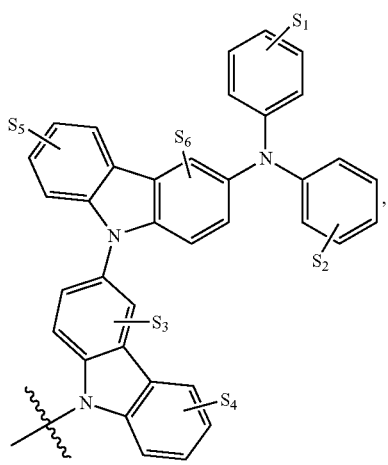
D19
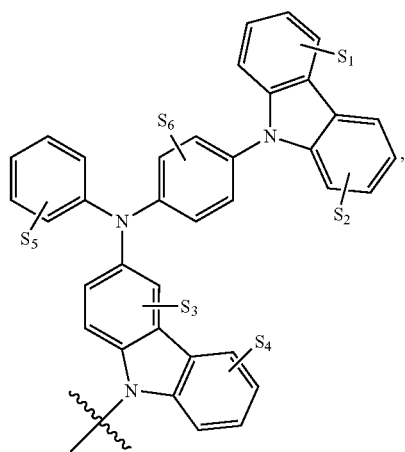
D17
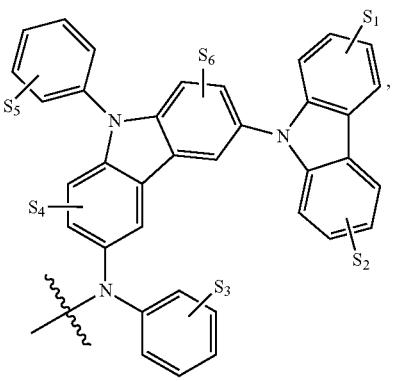
D20
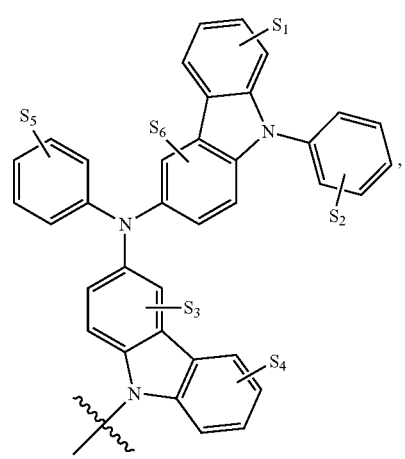
D18
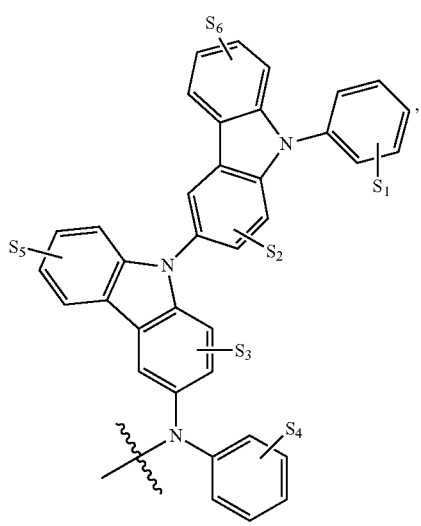
D21

D22 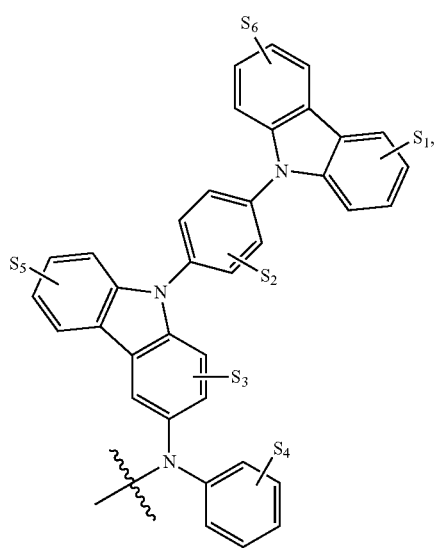
D23 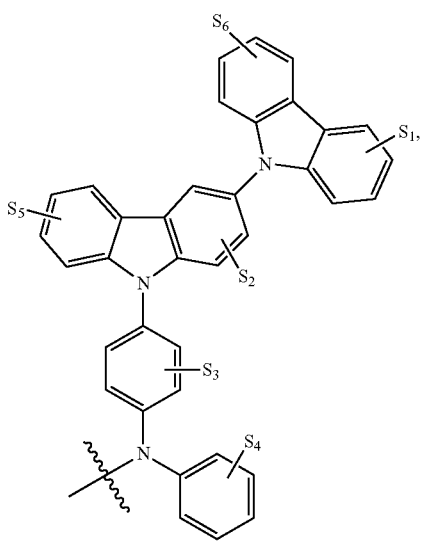
D24 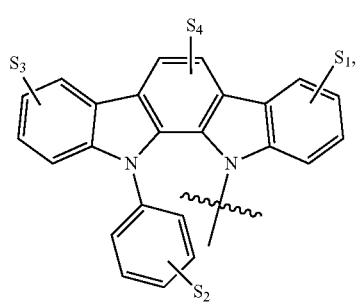
D25 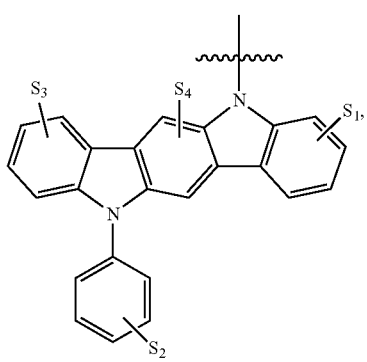
D26 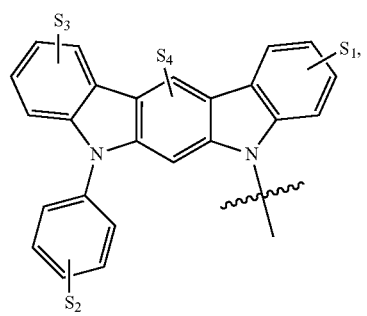
D27 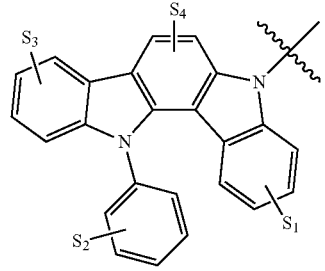
D28 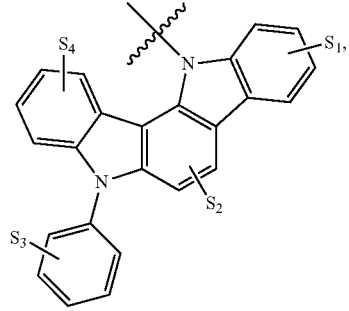
D29 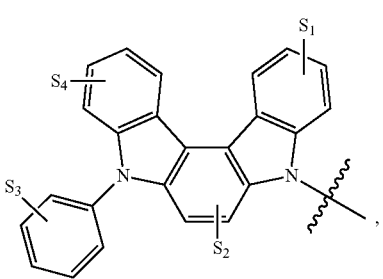

-continued
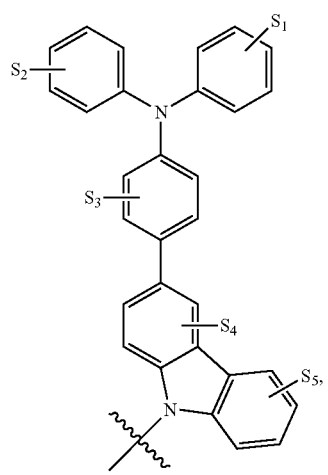
D33
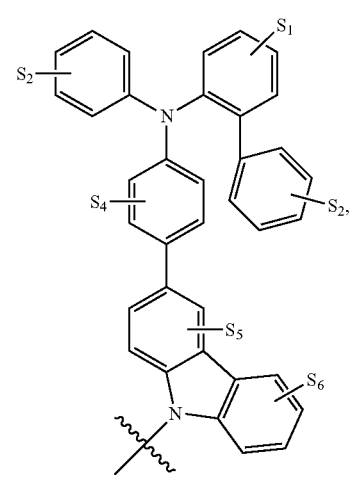
D34
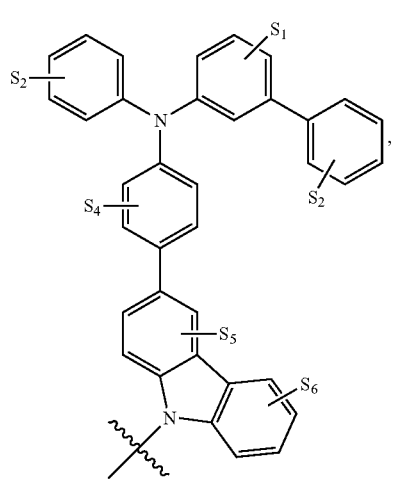
D35
-continued
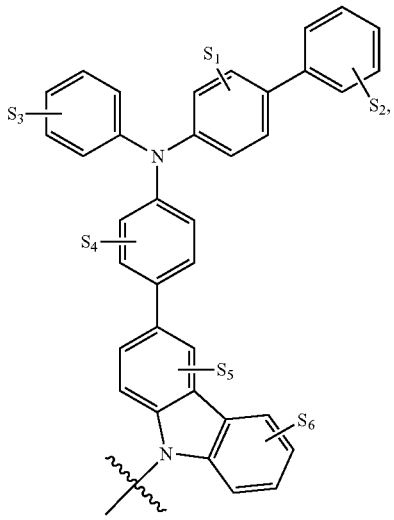
D36
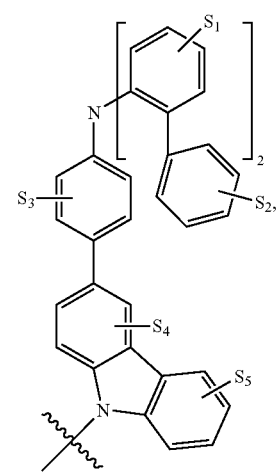
D37
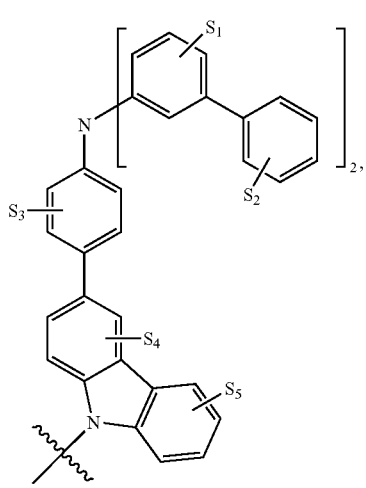
D38

D39
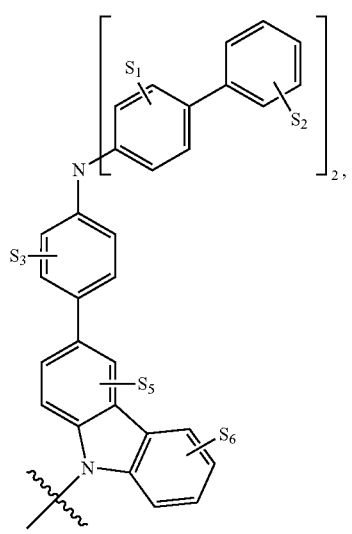
D40
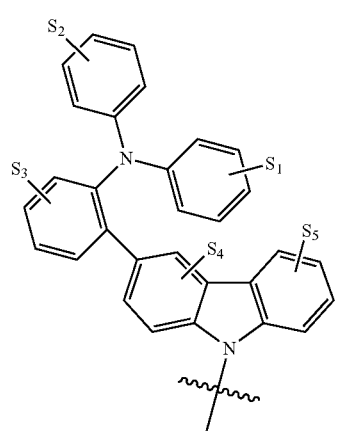
D41
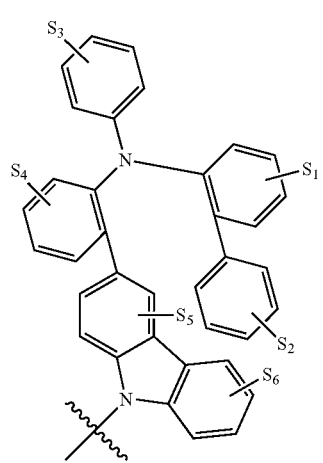
D42
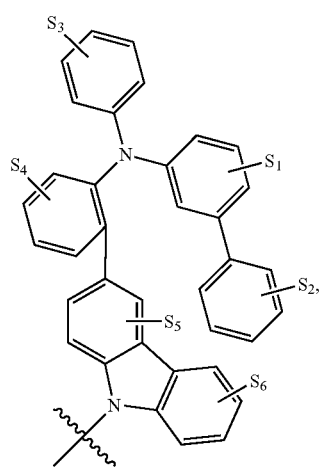
D43
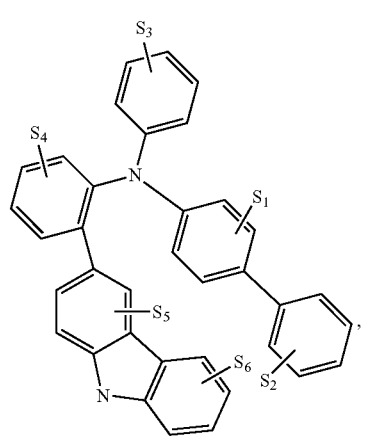
D44
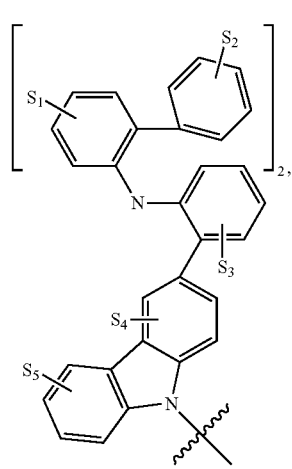

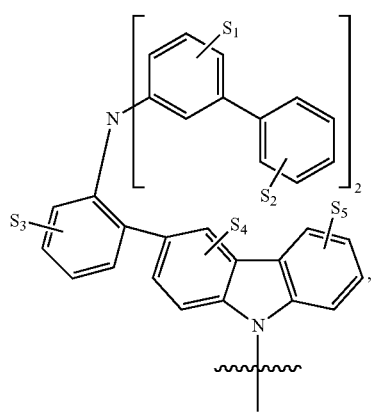
D45
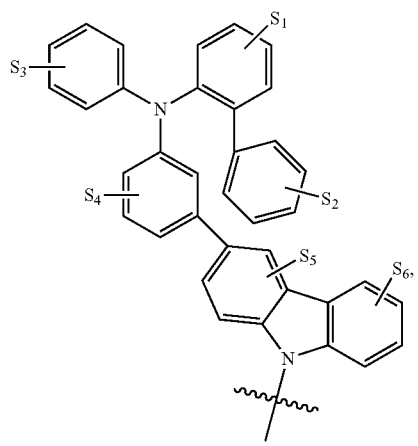
D48
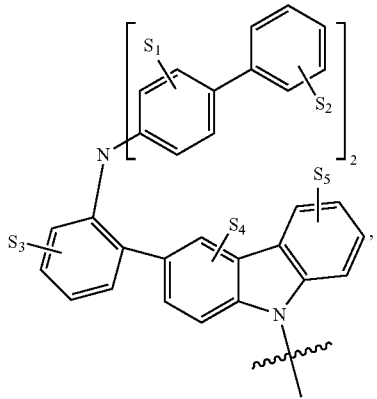
D46
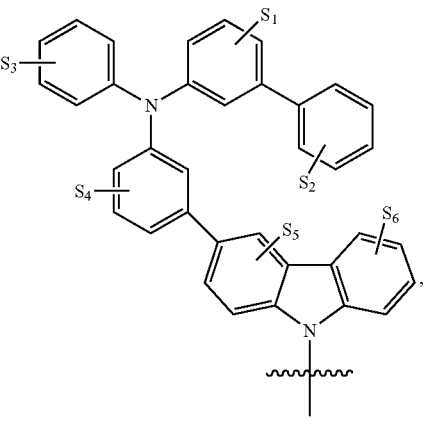
D49
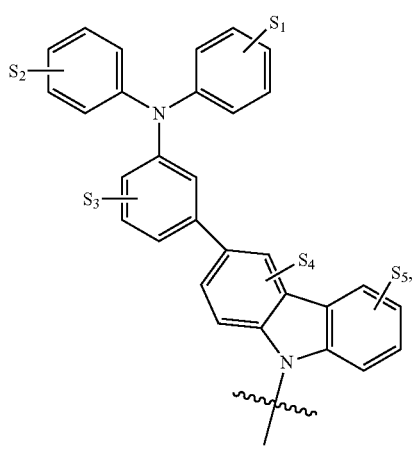
D47
D50

D51
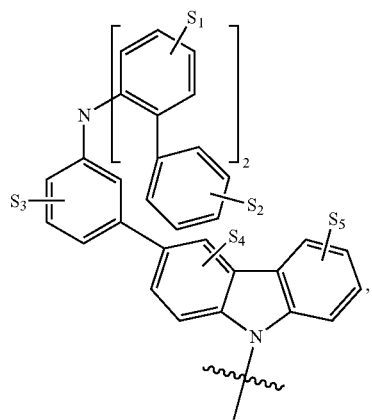
D52
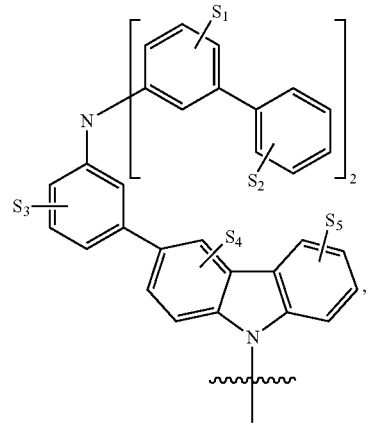
D53
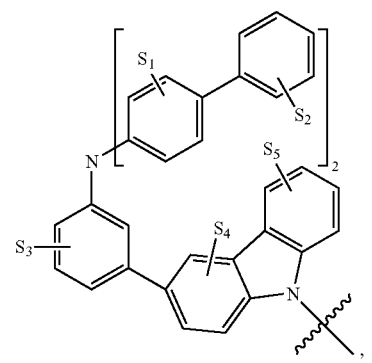
D54
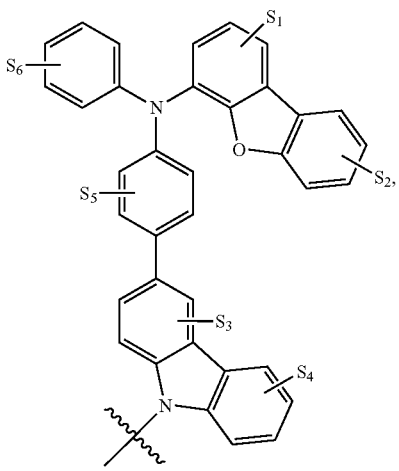
D55
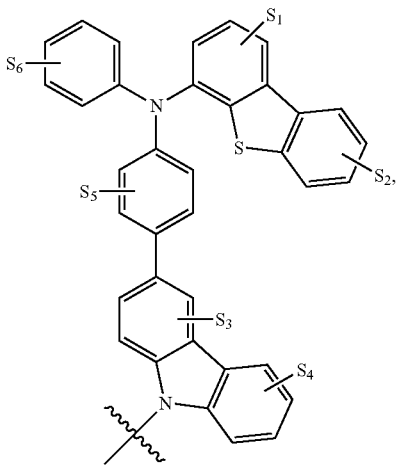
D56
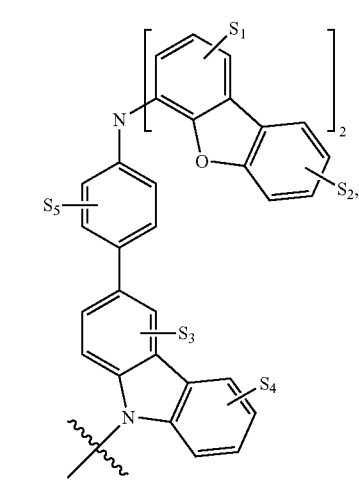

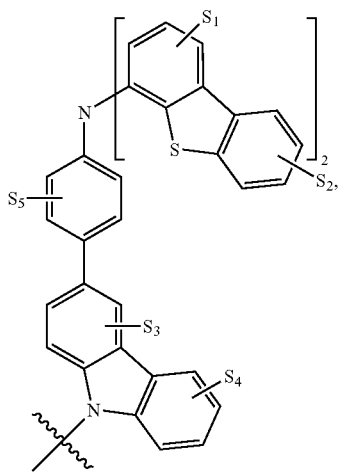
D57
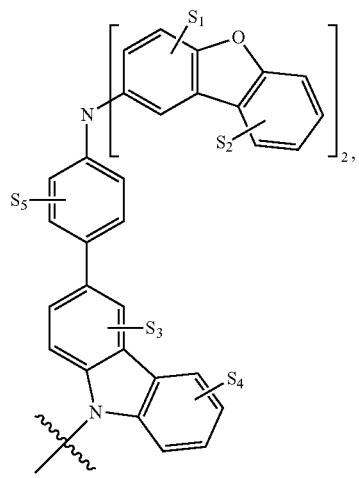
D60
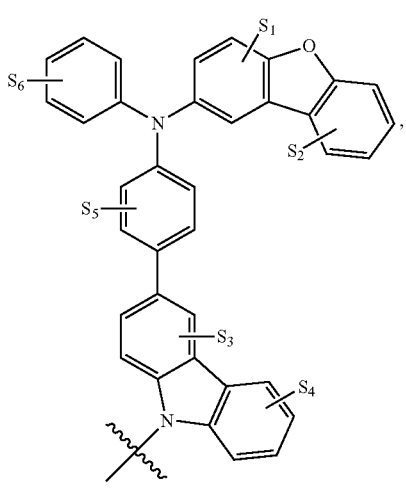
D58
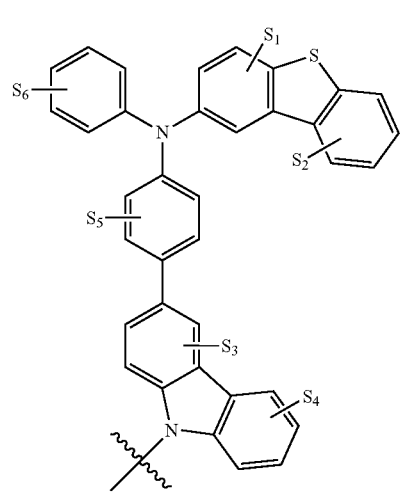
D59

-continued
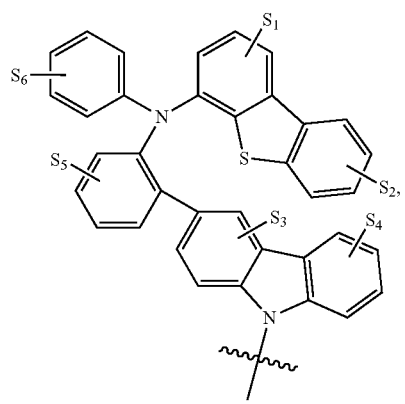
D63
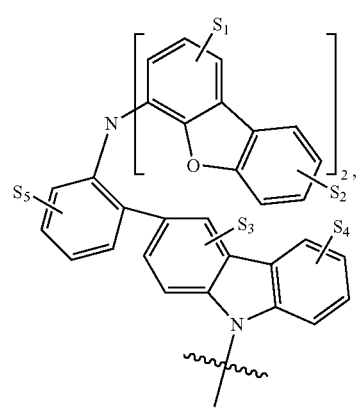
D64
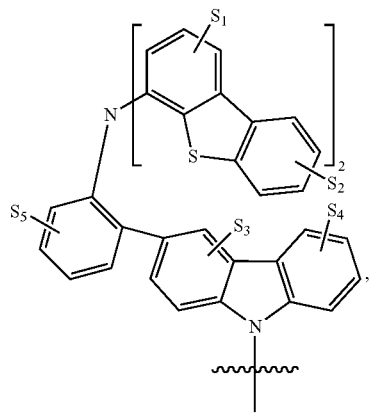
D65
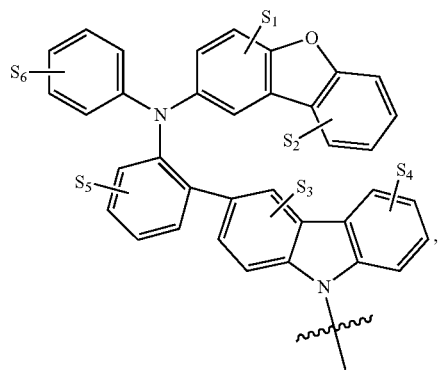
D66
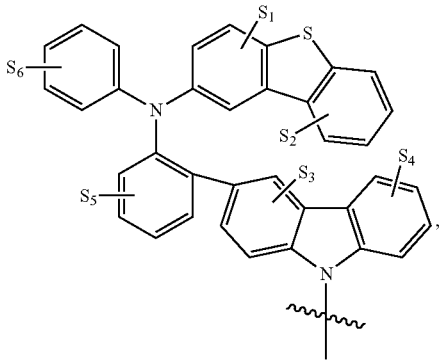
D67
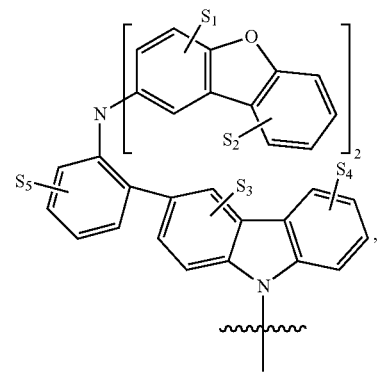
D68
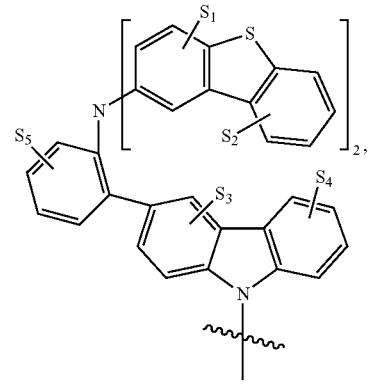
D69
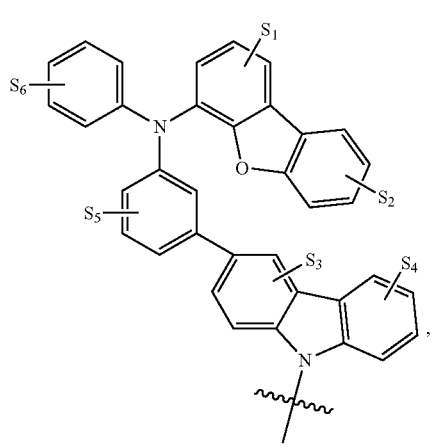
D70

-continued
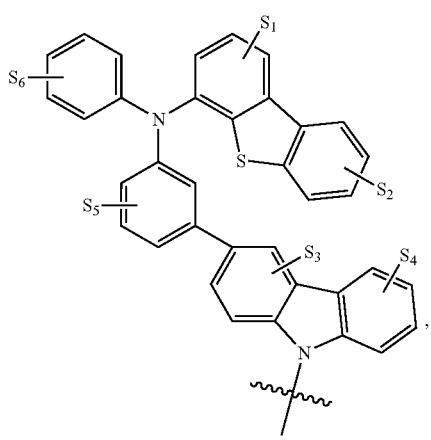
D71
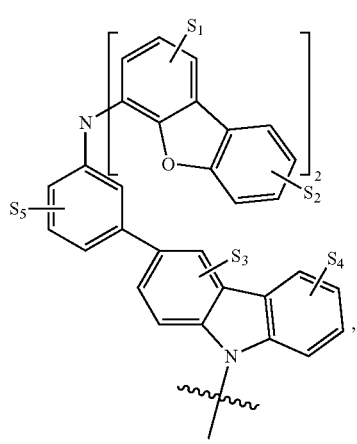
D72
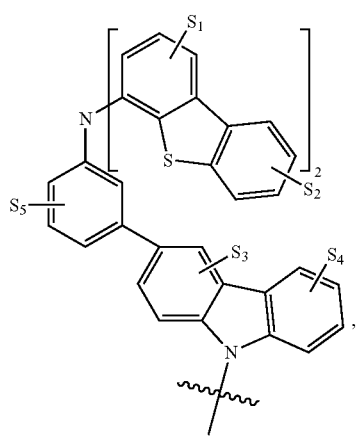
D73
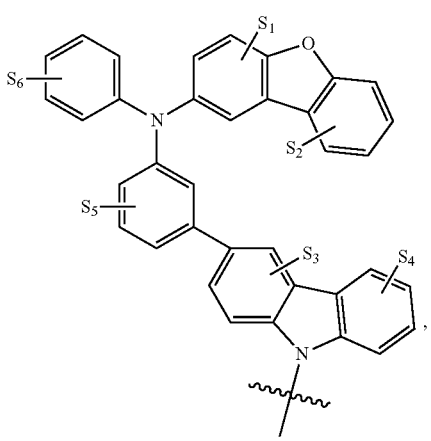
D74
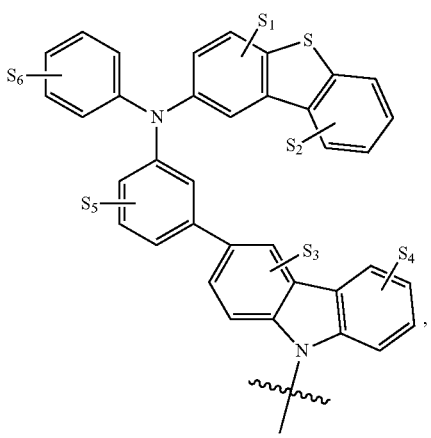
D75
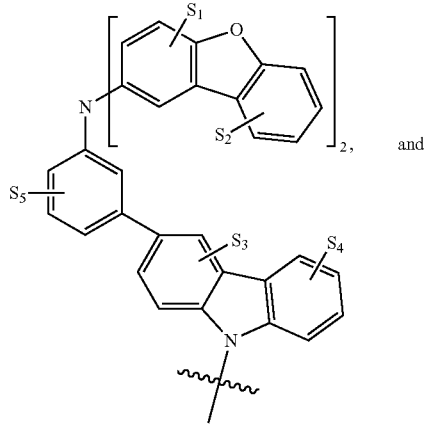
D76
and -continued

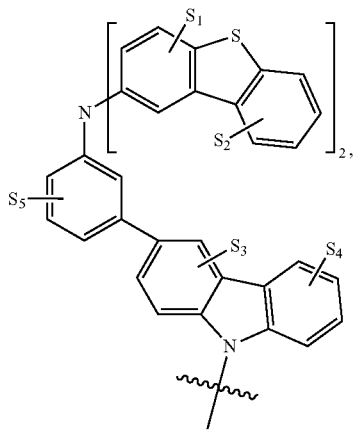

D77 wherein $S_1$ to $S_6$ represent mono, di, tri, tetra or penta substitutions with hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

10. The first device of claim 9, wherein L is one of

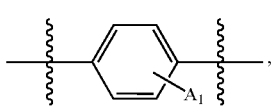 L1

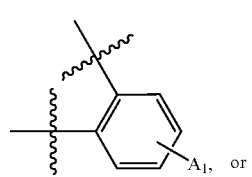 L2

, or

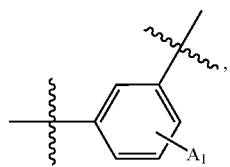 L3 wherein $A_1$ to $A_2$ represent mono, di, tri or tetra substitutions with hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

11. The first device of claim 10, wherein the first emitting compound is one of

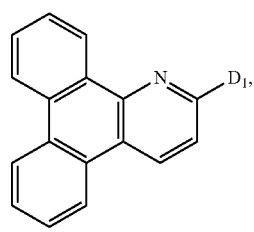 Compound 1

-continued

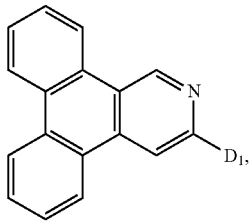 Compound 2

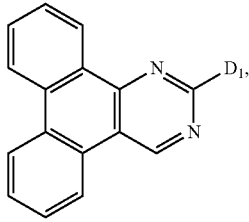 Compound 3

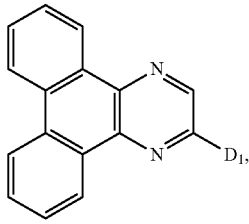 Compound 4

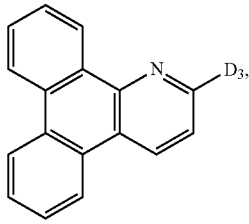 Compound 5

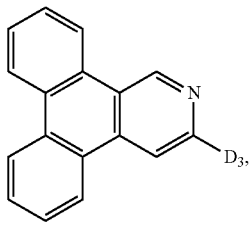 Compound 6

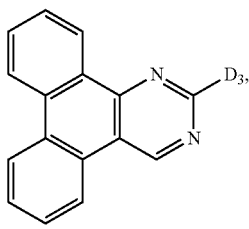 Compound 7

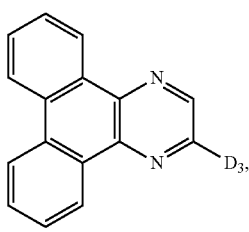 Compound 8

Compound 9
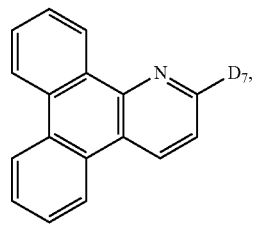
Compound 10
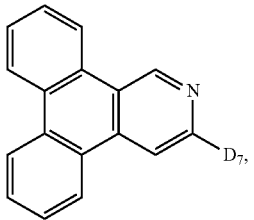
Compound 11
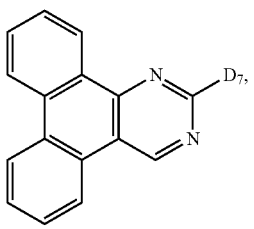
Compound 12
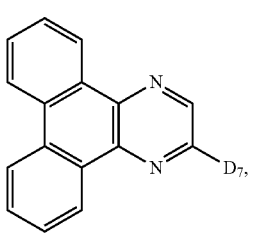
Compound 13
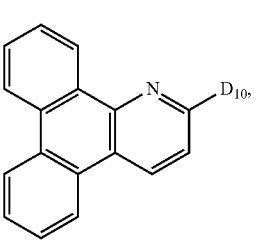
Compound 14
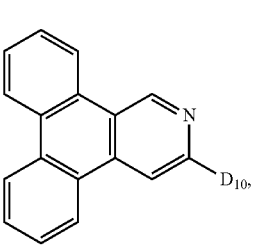
Compound 15
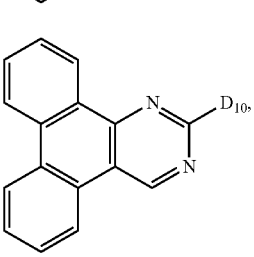
Compound 16
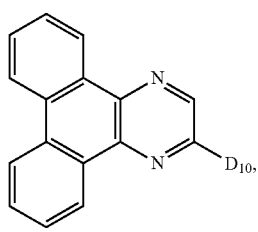
Compound 17
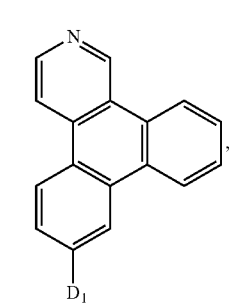
Compound 18
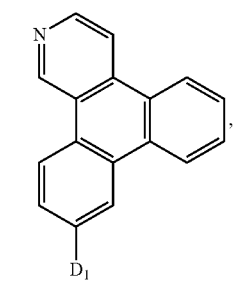
Compound 19
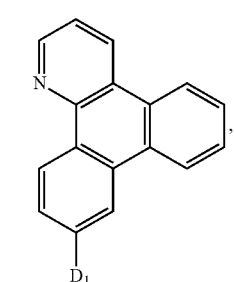
Compound 20
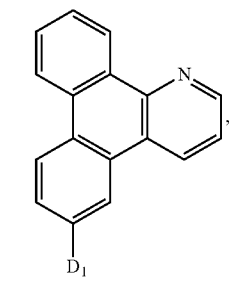

-continued
Compound 21
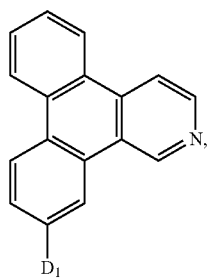
D₁
Compound 22
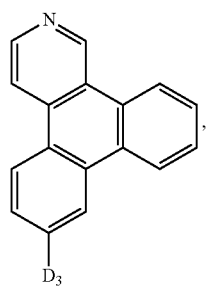
D₃
Compound 23
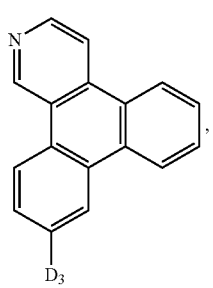
D₃
Compound 24
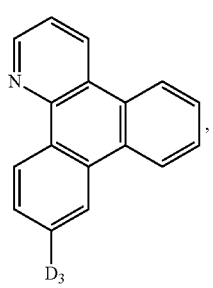
D₃
Compound 25
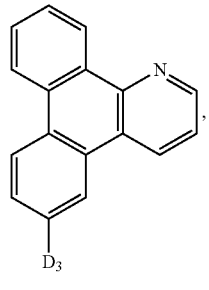
D₃
-continued
Compound 26
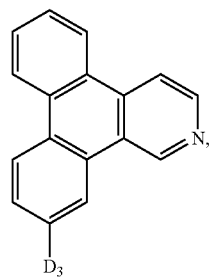
D₃
Compound 27
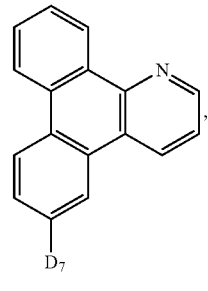
D₇
Compound 28
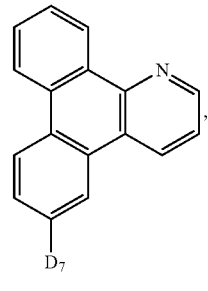
D₇
Compound 29
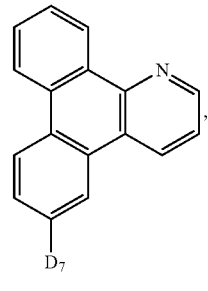
D₇
Compound 30
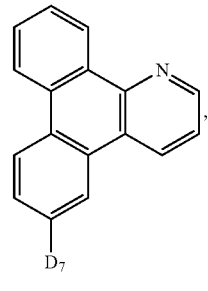
D₇

Compound 31
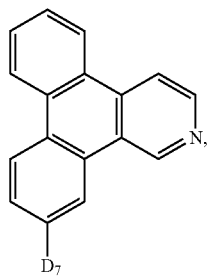
Compound 32
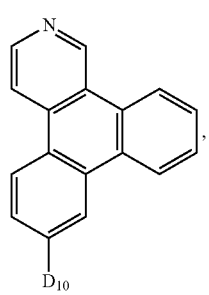
Compound 33
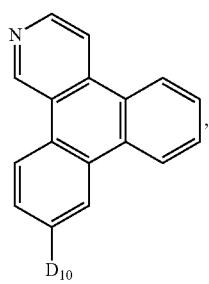
Compound 34
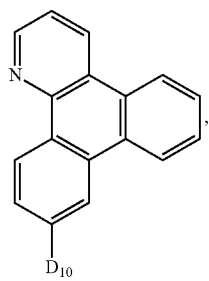
Compound 35
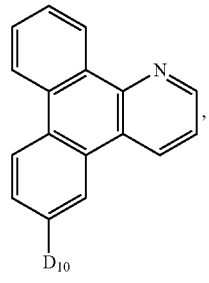
Compound 36
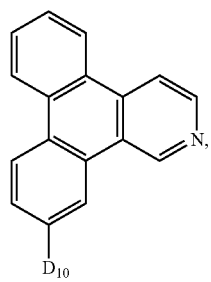
Compound 37
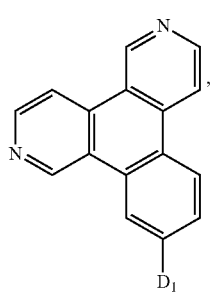
Compound 38
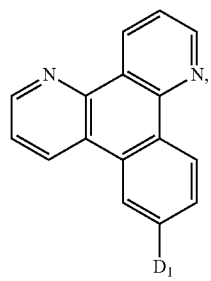
Compound 39
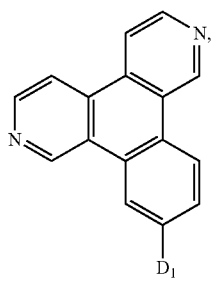
Compound 40
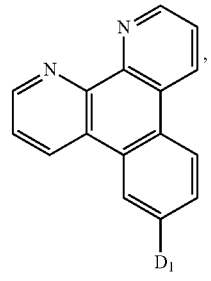

Compound 41
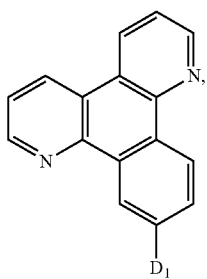
Compound 42
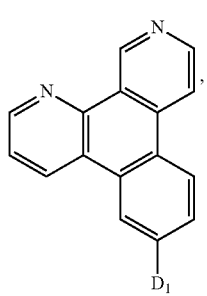
Compound 43
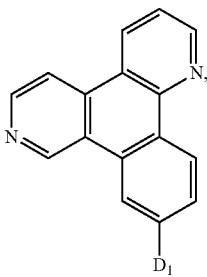
Compound 44
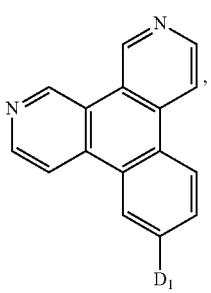
Compound 45
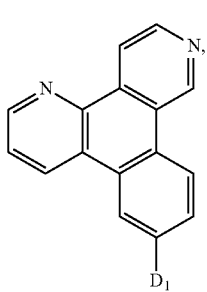
Compound 46
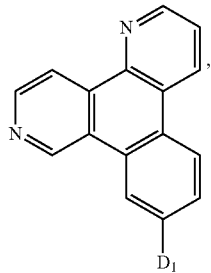
Compound 47
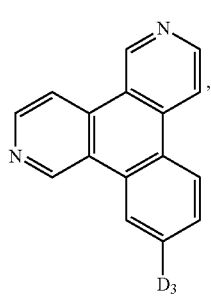
Compound 48
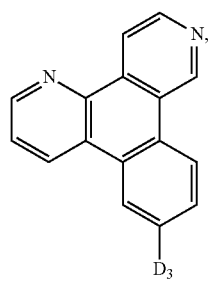
Compound 49
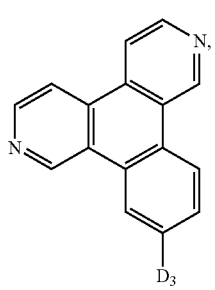
Compound 50
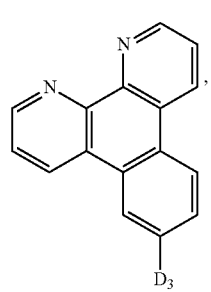

Compound 51
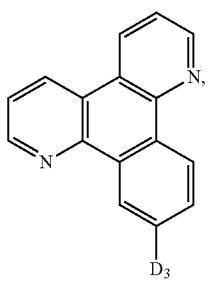
Compound 52
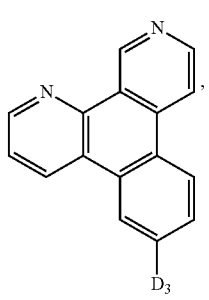
Compound 53
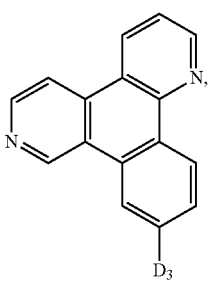
Compound 54
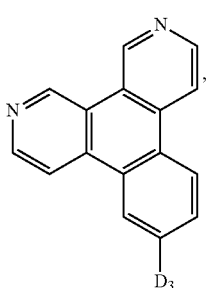
Compound 55
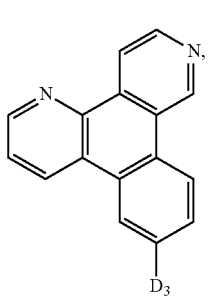
Compound 56
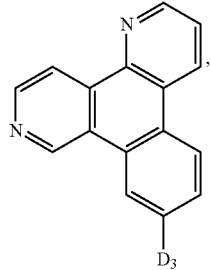
Compound 57
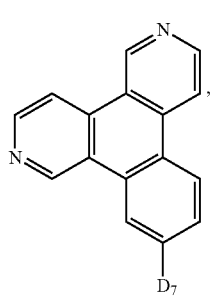
Compound 58
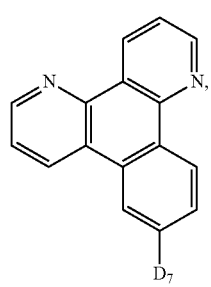
Compound 59
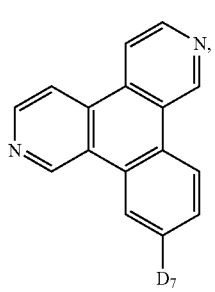
Compound 60
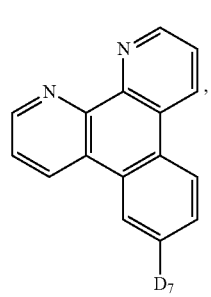

Compound 61
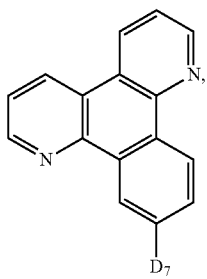
Compound 62
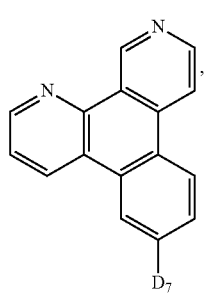
Compound 63
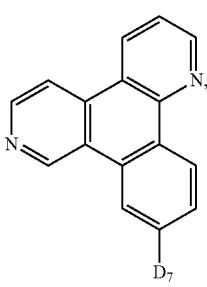
Compound 64
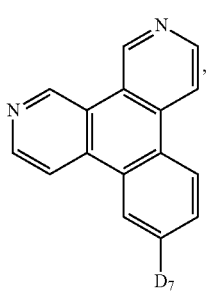
Compound 65
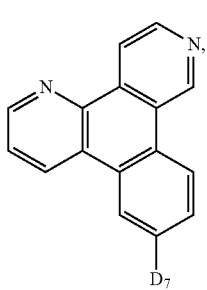
Compound 66
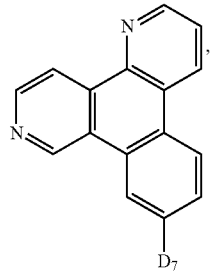
Compound 67
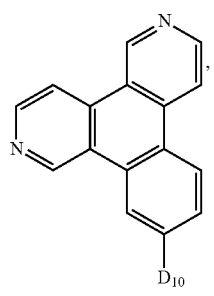
Compound 68
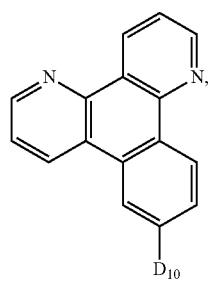
Compound 69
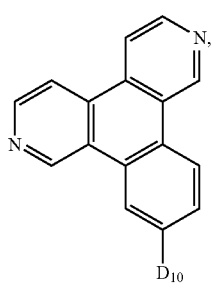
Compound 70
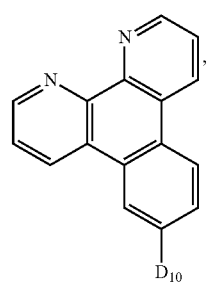

Compound 71
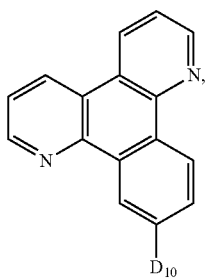
Compound 72
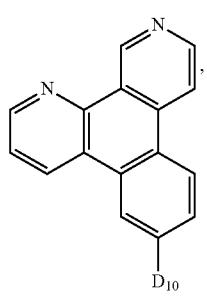
Compound 73
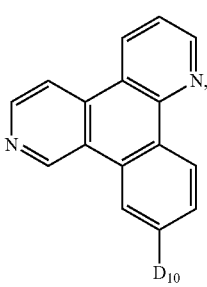
Compound 74
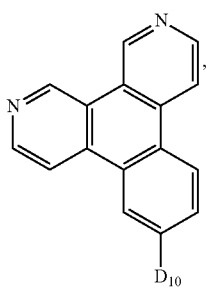
Compound 75
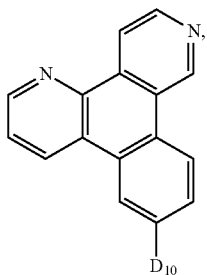
Compound 76
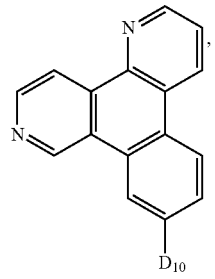
Compound 115
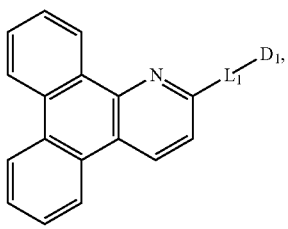
Compound 116
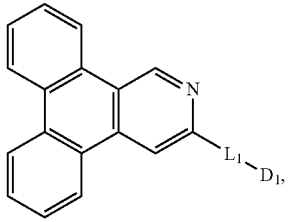
Compound 117
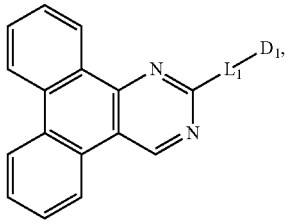
Compound 118
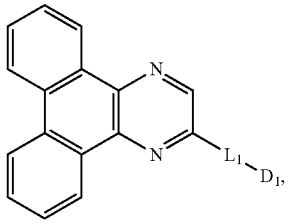
Compound 119
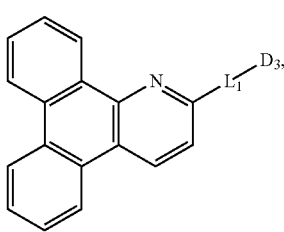

-continued
Compound 120
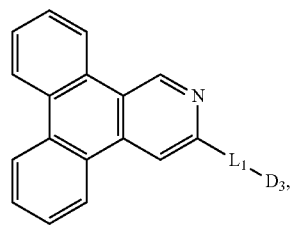
Compound 121
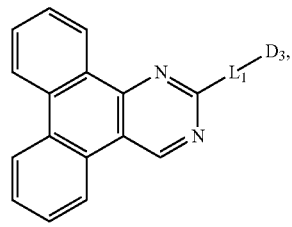
Compound 122
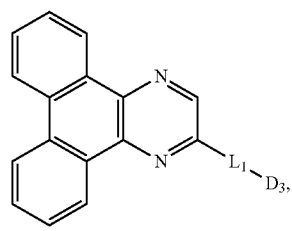
Compound 123
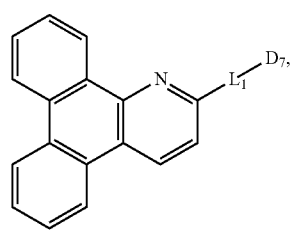
Compound 124
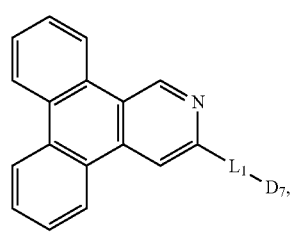
Compound 125
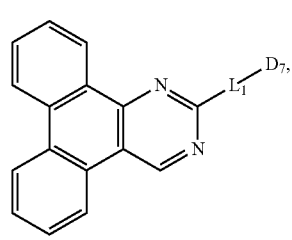
Compound 126
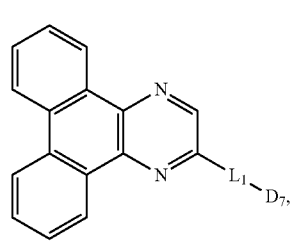
-continued
Compound 127
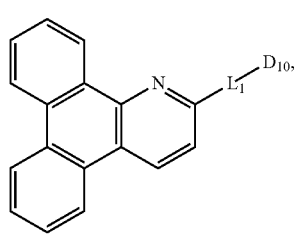
Compound 128
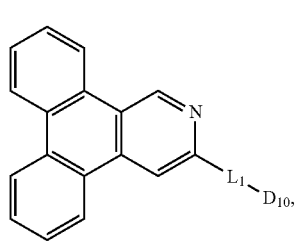
Compound 129
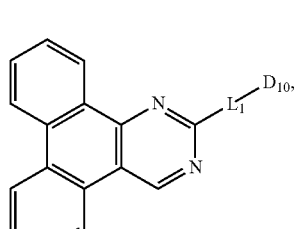
Compound 130
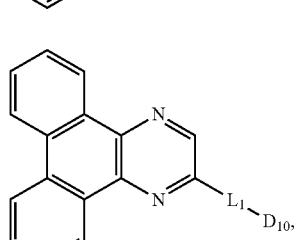
Compound 131
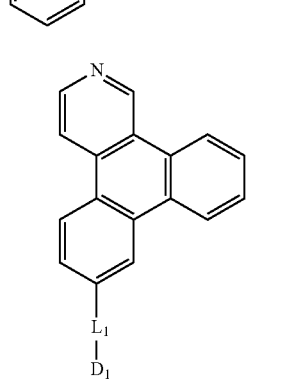
Compound 132
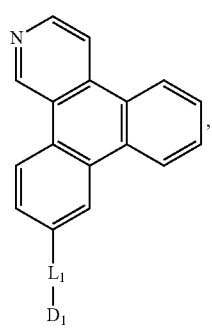

Compound 133
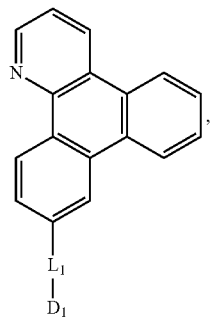
Compound 134
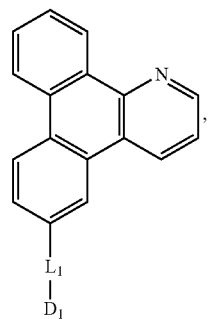
Compound 135
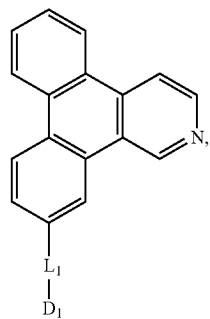
Compound 136
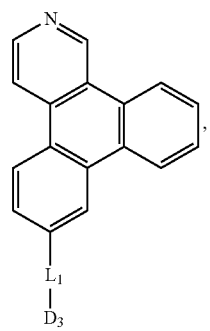
Compound 137
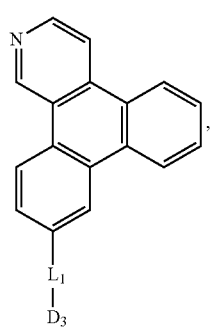
Compound 138
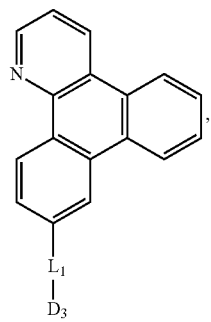
Compound 139
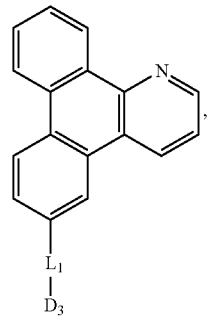
Compound 140
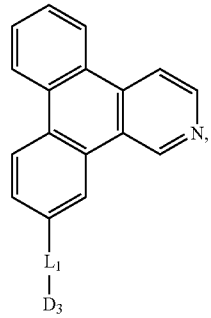
Compound 141
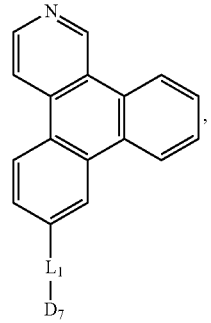
Compound 142
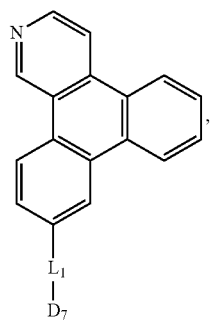

487
-continued
Compound 143
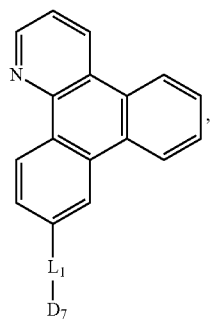
Compound 144
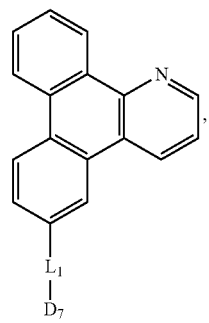
Compound 145
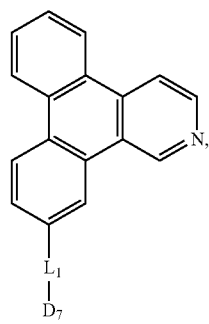
Compound 146
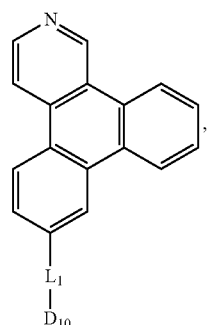
Compound 147
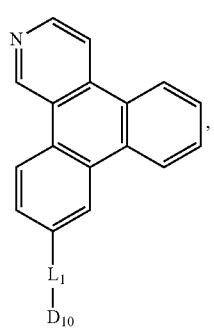
488
-continued
Compound 148
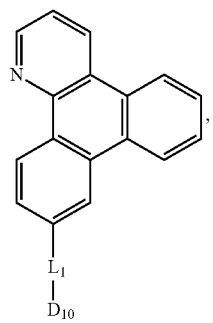
Compound 149
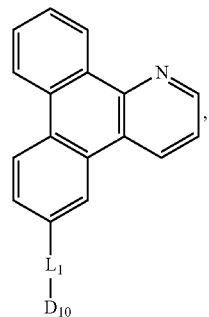
Compound 150
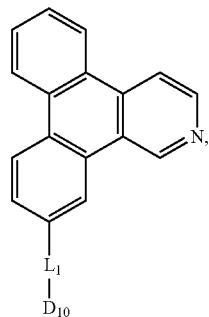
Compound 151
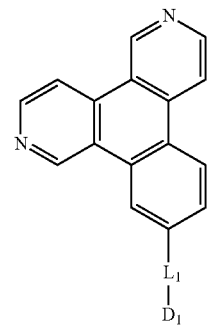
Compound 152
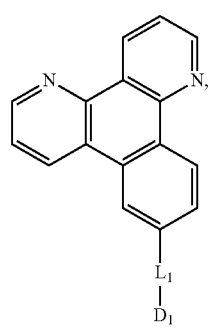

Compound 153
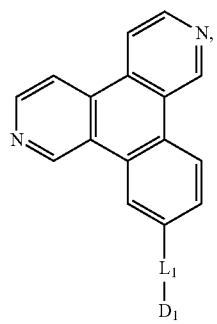
Compound 154
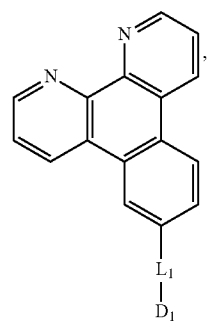
Compound 155
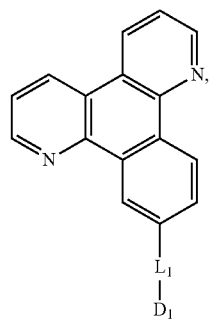
Compound 156
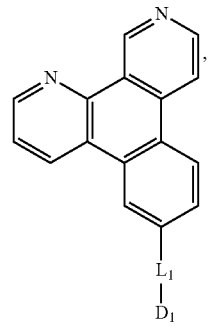
Compound 157
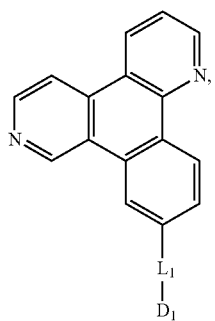
Compound 158
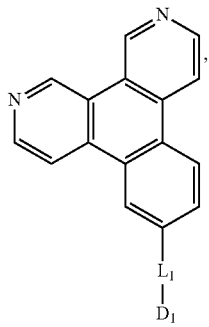
Compound 159
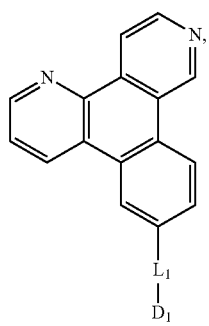
Compound 160
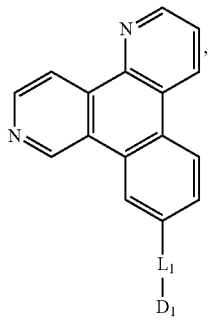
Compound 161
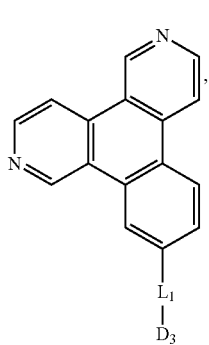
Compound 162
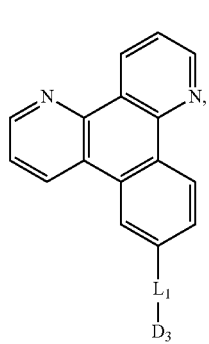

Compound 163
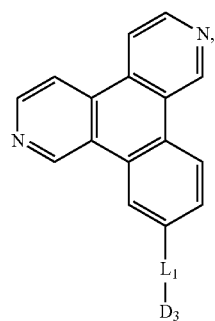
Compound 164
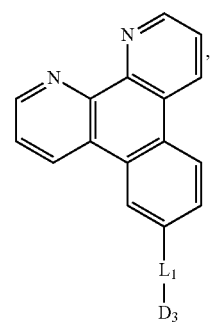
Compound 165
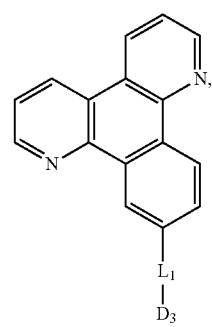
Compound 166
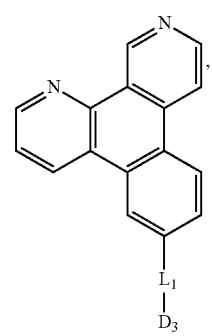
Compound 167
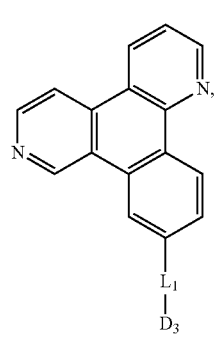
Compound 168
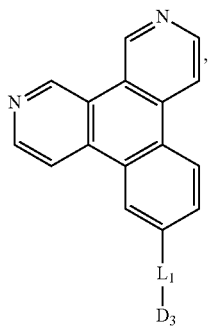
Compound 169
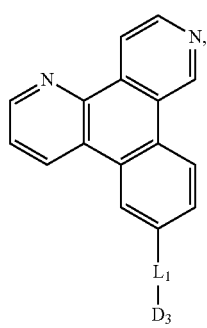
Compound 170
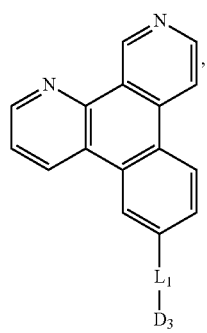
Compound 171
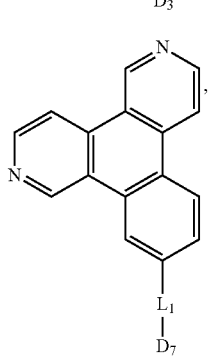
Compound 172
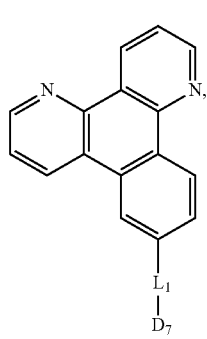

Compound 173
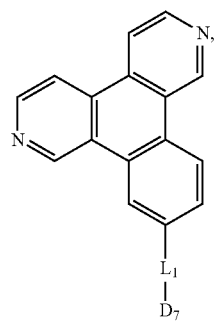
Compound 174
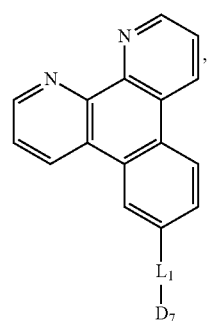
Compound 175
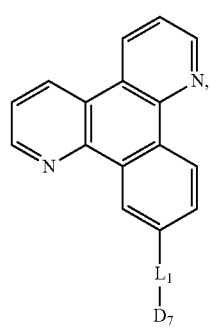
Compound 176
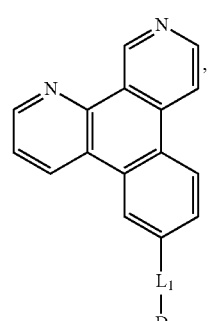
Compound 177
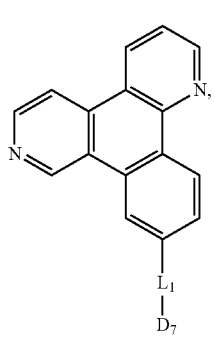
Compound 178
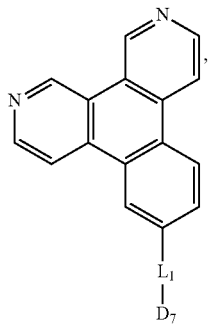
Compound 179
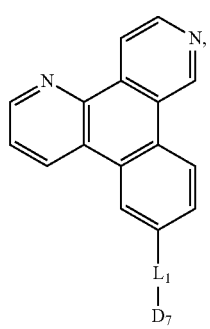
Compound 180
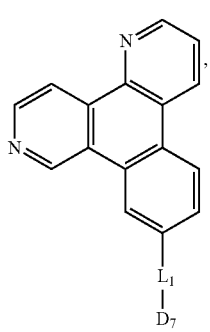
Compound 181
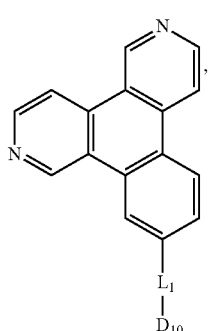
Compound 182
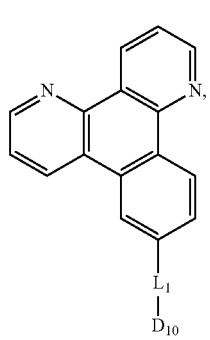

Compound 183
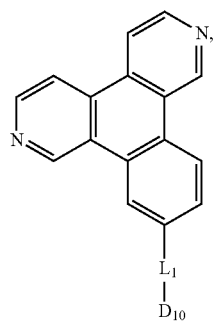
Compound 184
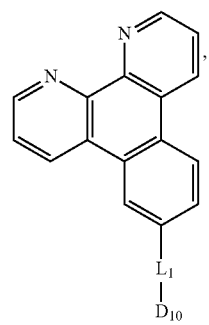
Compound 185
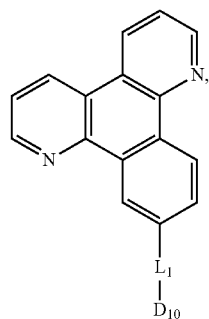
Compound 186
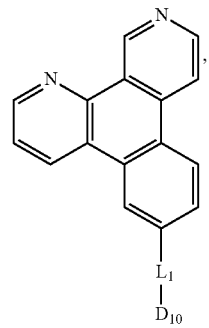
Compound 187
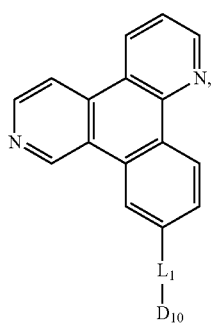
Compound 188
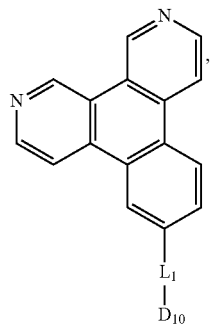
Compound 189
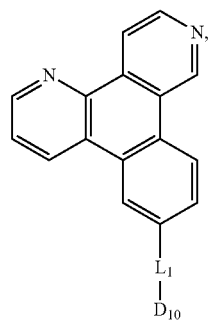
Compound 190
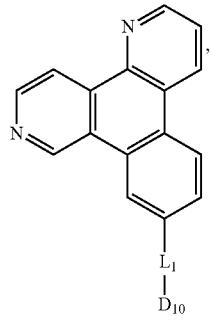
Compound 229
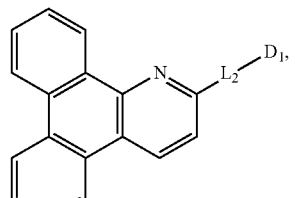
Compound 230
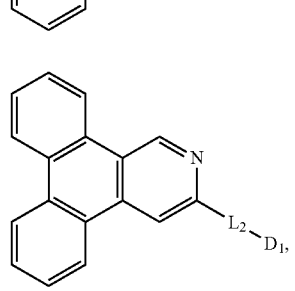

| Compound 231 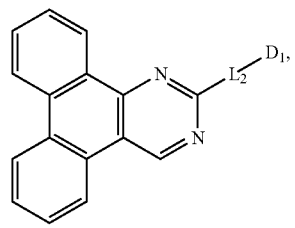 | Compound 238 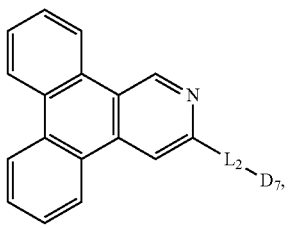 |
| Compound 232 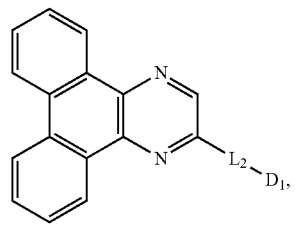 | Compound 239 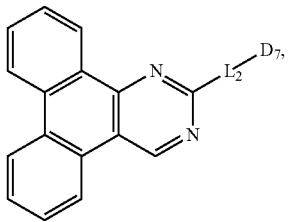 |
| Compound 233 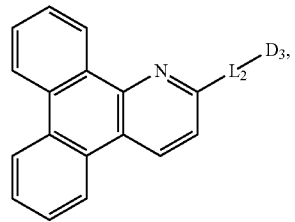 | Compound 240 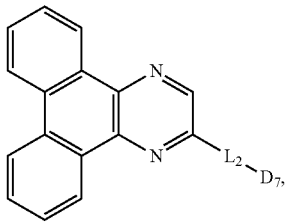 |
| Compound 234 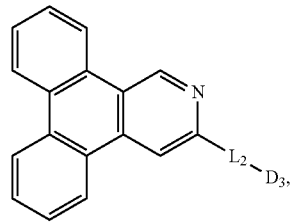 | Compound 241 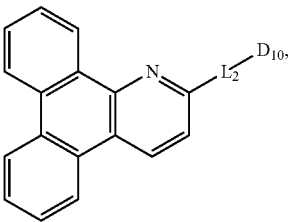 |
| Compound 235 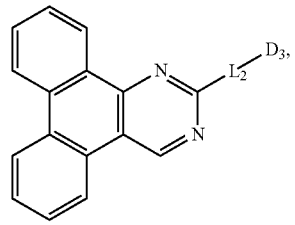 | Compound 242 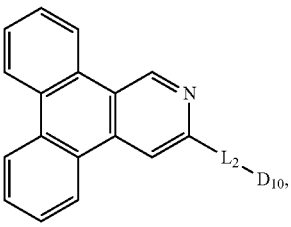 |
| Compound 236 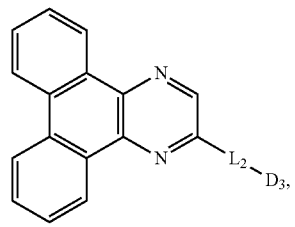 | Compound 243 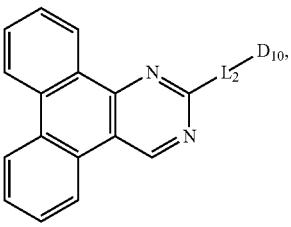 |
| Compound 237 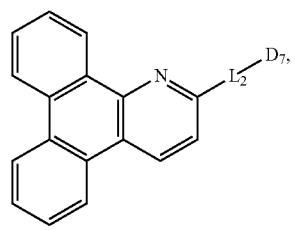 | Compound 244 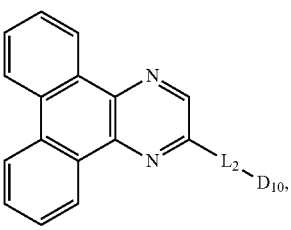 |

| Compound 245 | Compound 250 |
|---|---|
| 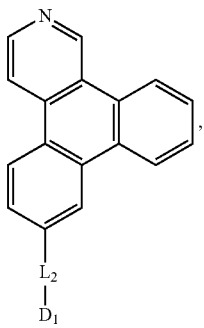 | 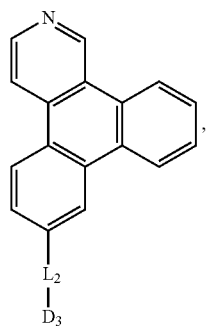 |
| Compound 246 | Compound 251 |
| 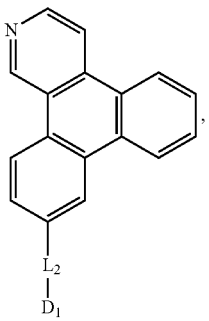 | 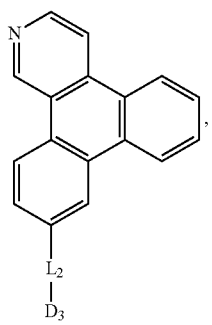 |
| Compound 247 | Compound 252 |
| 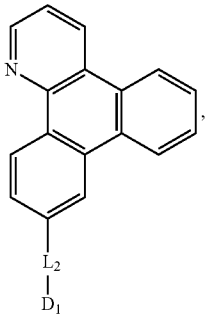 | 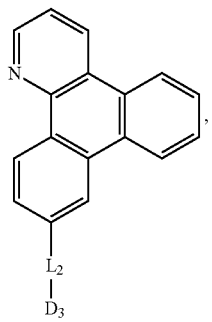 |
| Compound 248 | Compound 253 |
| 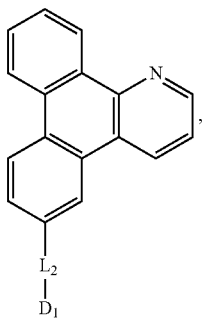 | 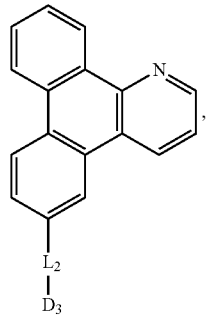 |
| Compound 249 | Compound 254 |
| 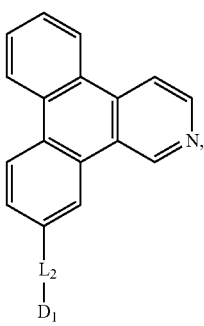 | 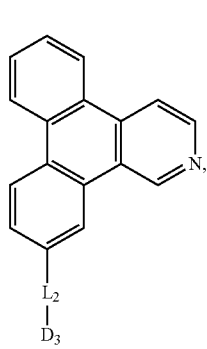 |

501
-continued
Compound 255
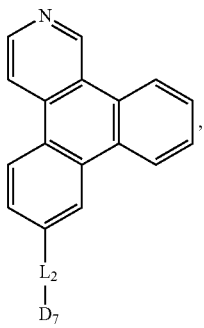
Compound 256
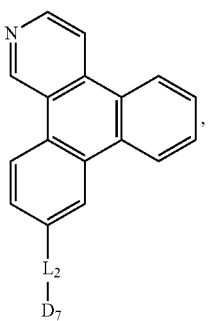
Compound 257
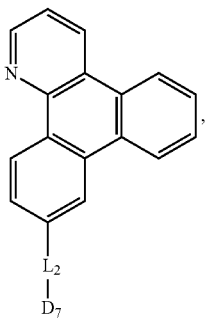
Compound 258
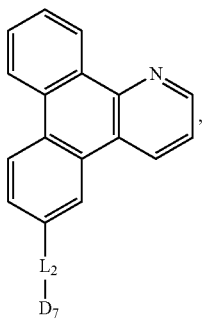
Compound 259
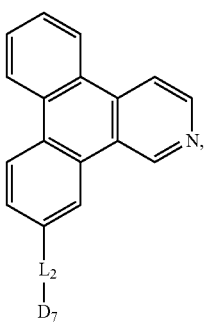
502
-continued
Compound 260
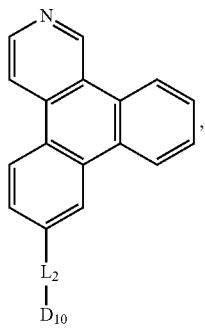
Compound 261
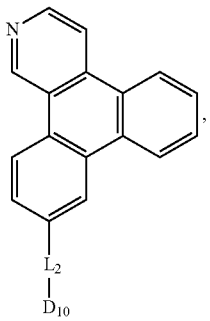
Compound 262
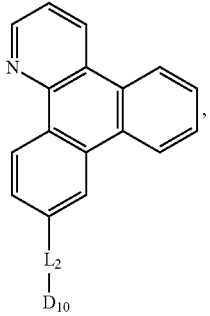
Compound 263
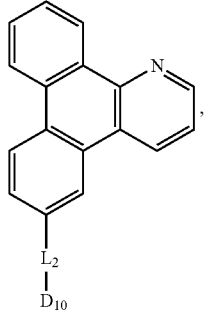
Compound 264
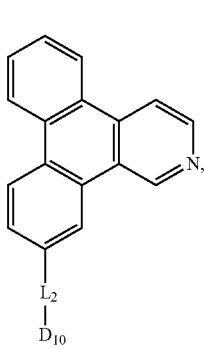

Compound 265
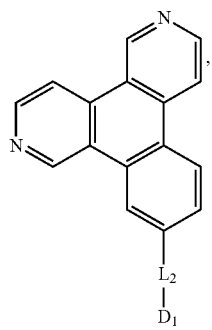
Compound 266
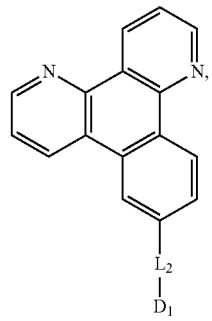
Compound 267
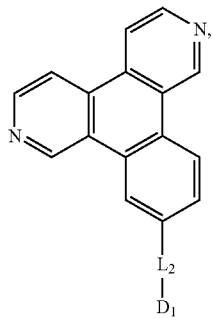
Compound 268
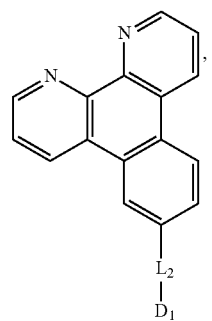
Compound 269
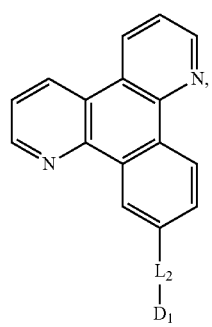
Compound 270
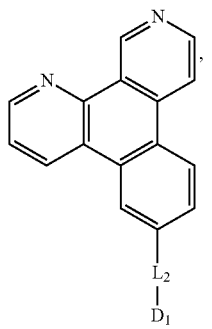
Compound 271
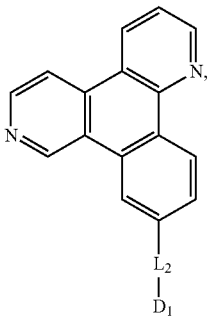
Compound 272
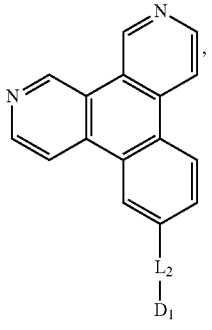
Compound 273
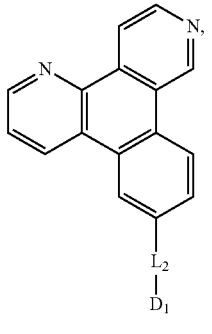
Compound 274
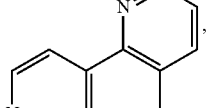
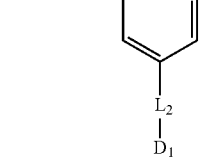

Compound 275
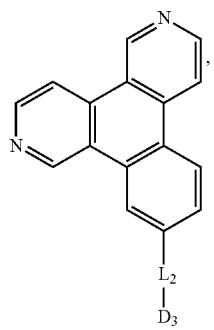
Compound 276
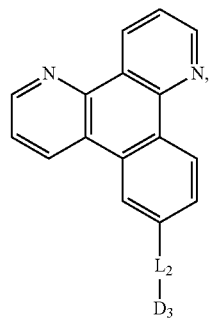
Compound 277
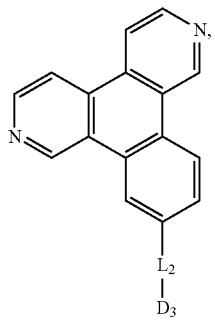
Compound 278
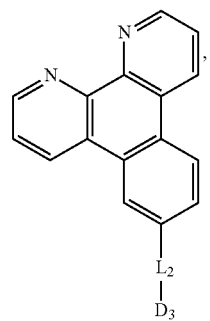
Compound 279
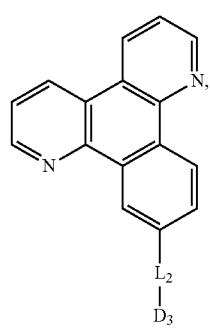
Compound 280
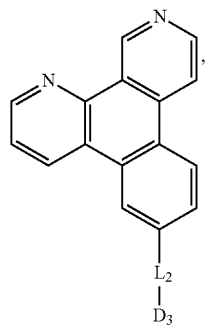
Compound 281
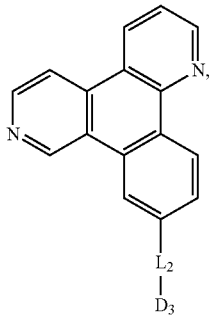
Compound 282
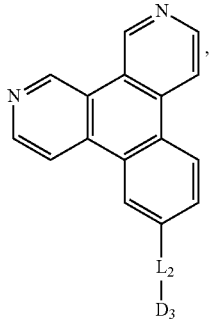
Compound 283
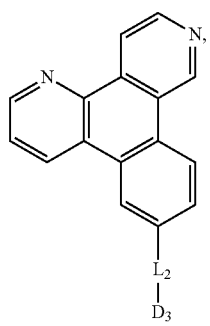
Compound 284
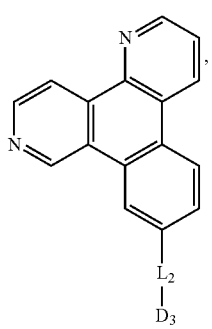

-continued
Compound 285
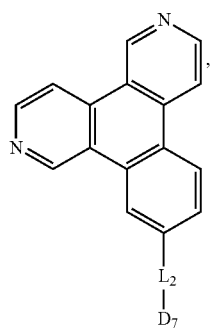
Compound 286
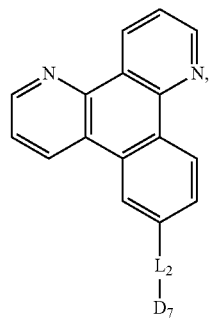
Compound 287
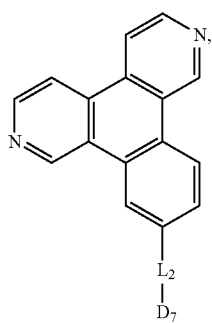
Compound 288
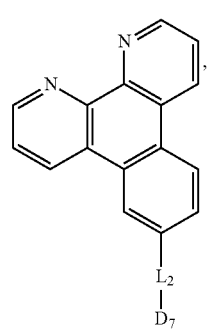
Compound 289
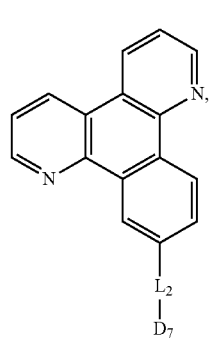
-continued
Compound 290
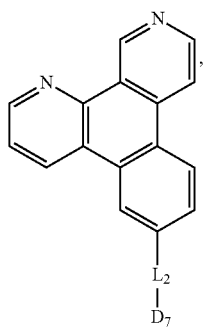
Compound 291
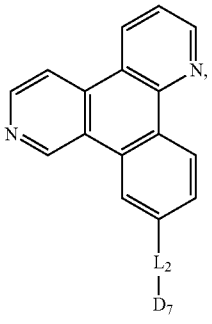
Compound 292
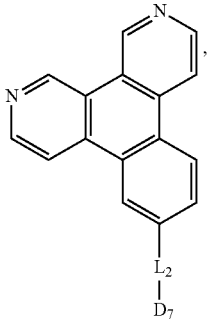
Compound 293
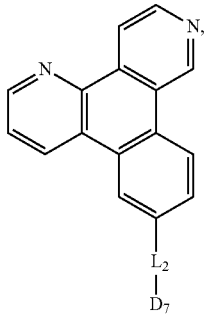
Compound 294
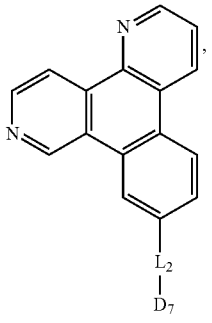

Compound 295
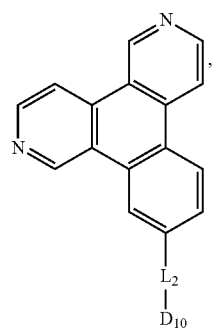
Compound 296
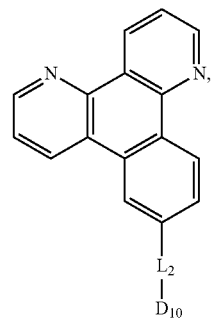
Compound 297
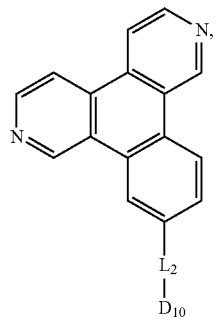
Compound 298
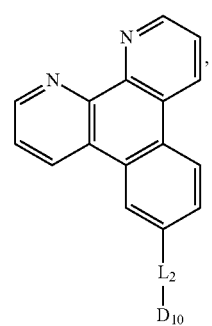
Compound 299
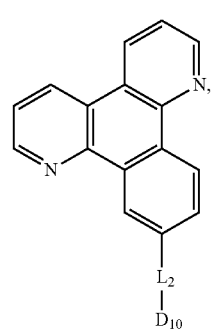
Compound 300
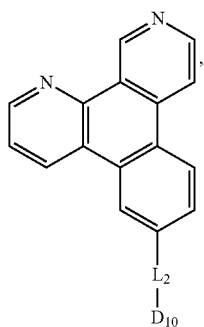
Compound 301
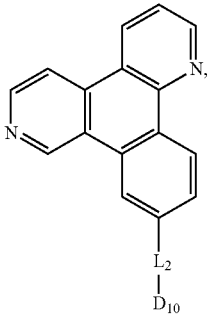
Compound 302
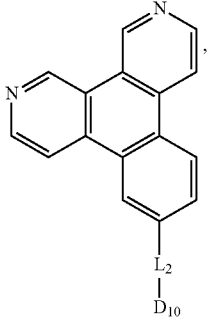
Compound 303
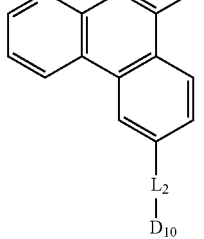
Compound 304
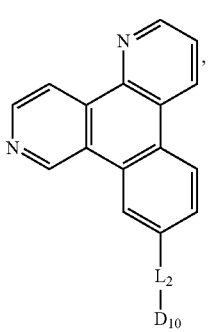

-continued
Compound 343
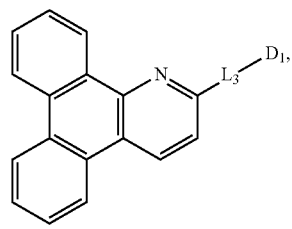
Compound 344
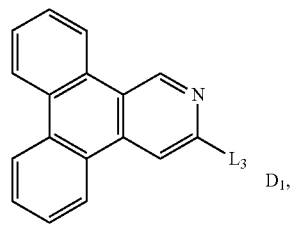
Compound 345
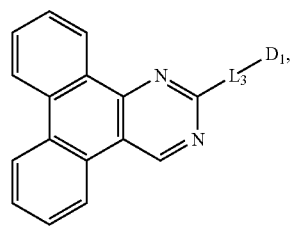
Compound 346
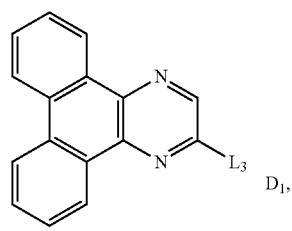
Compound 347
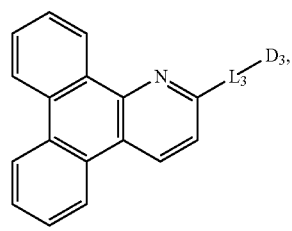
Compound 348
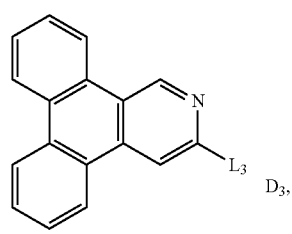
Compound 349
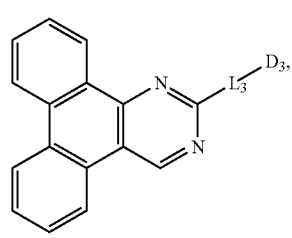
-continued
Compound 350
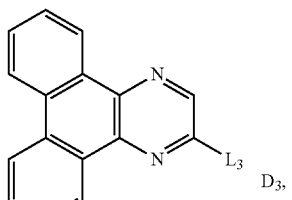
Compound 351
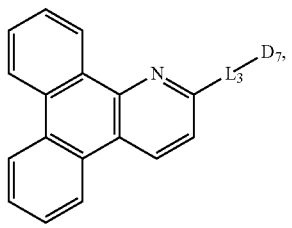
Compound 352
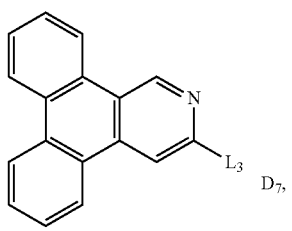
Compound 353
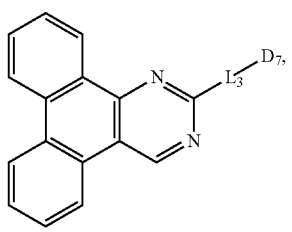
Compound 354
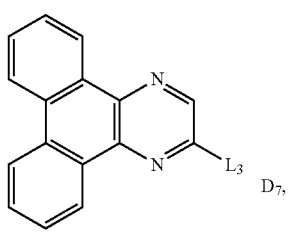
Compound 355
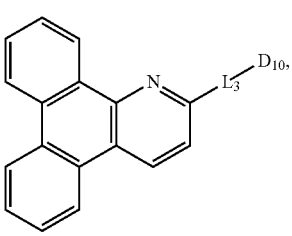
Compound 356
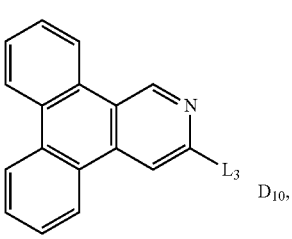

Compound 357
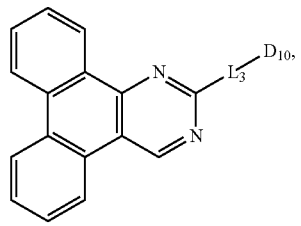
Compound 358
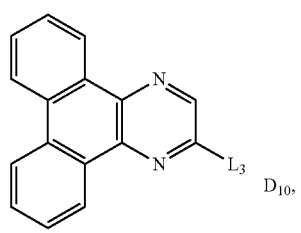
Compound 359
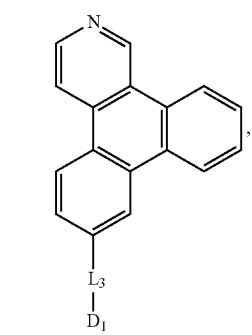
Compound 360
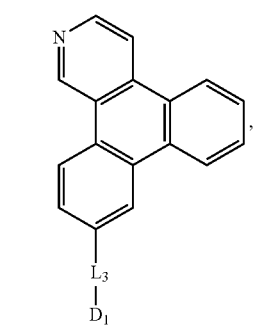
Compound 361
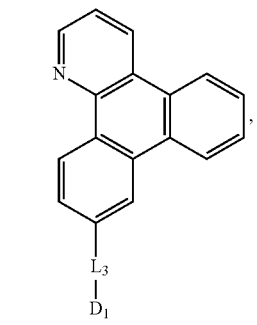
Compound 362
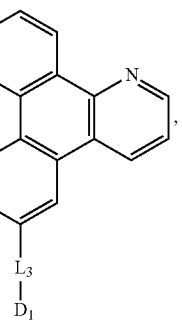
Compound 363
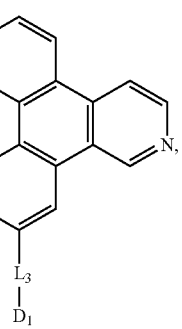
Compound 364
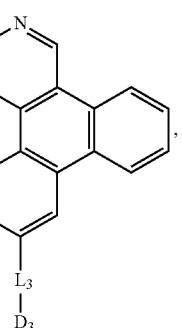
Compound 365
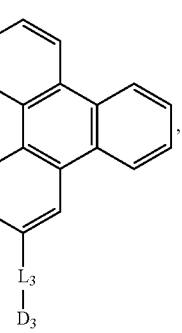
Compound 366
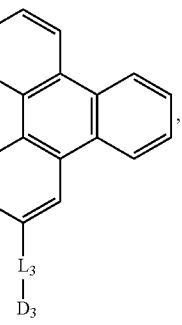

-continued
Compound 367
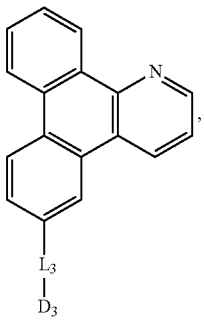
Compound 368
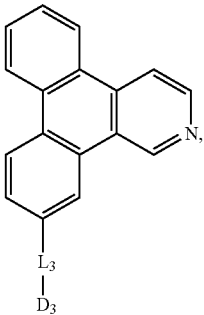
Compound 369
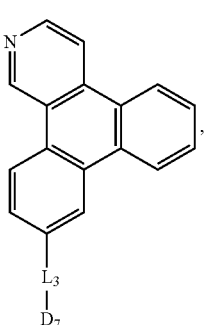
Compound 370
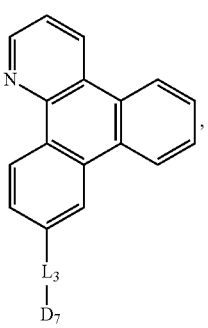
Compound 371
-continued
Compound 372
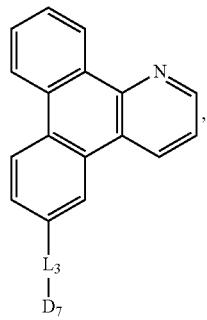
Compound 373
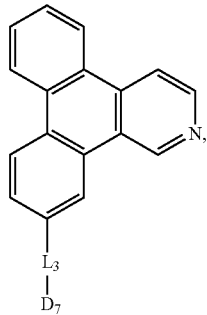
Compound 374
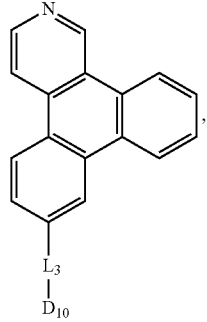
Compound 375
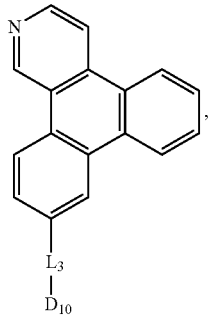
Compound 376
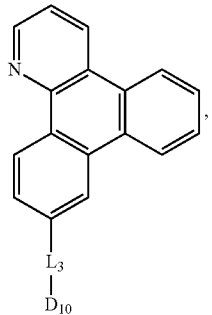

-continued
Compound 377
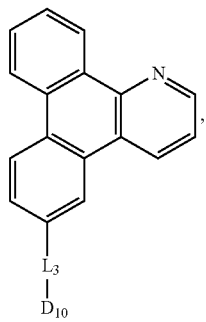
Compound 378
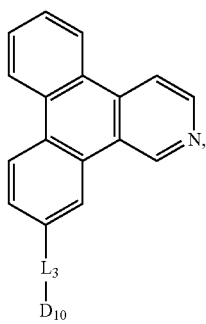
Compound 379
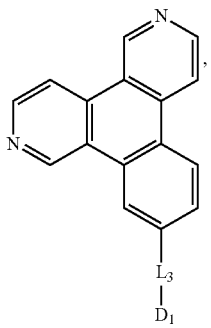
Compound 380
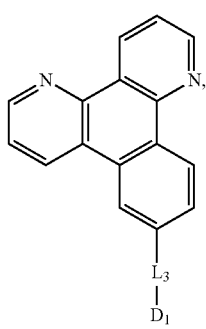
Compound 381
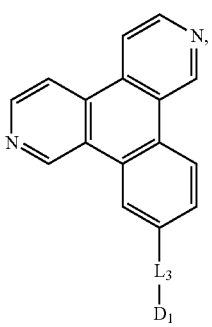
-continued
Compound 382
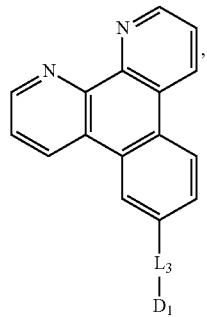
Compound 383
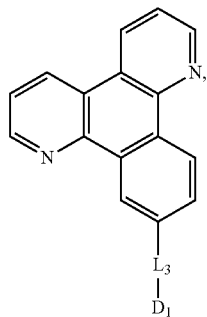
Compound 384
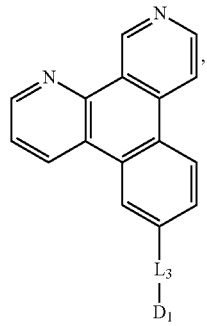
Compound 385
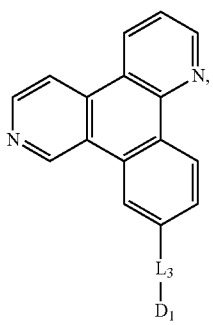
Compound 386
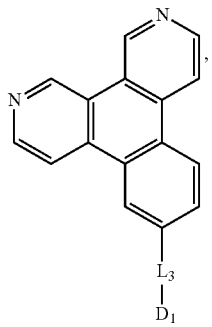

Compound 387
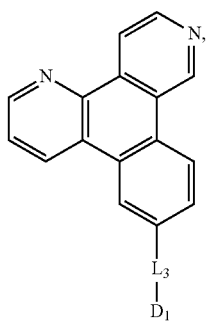
Compound 388
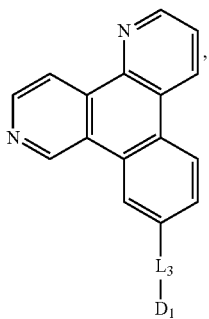
Compound 389
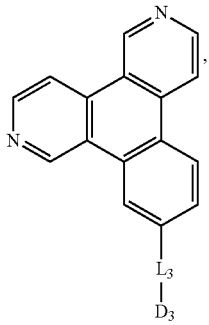
Compound 390
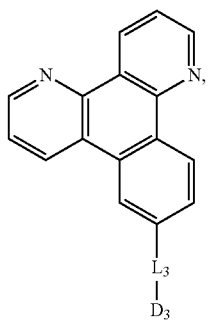
Compound 391
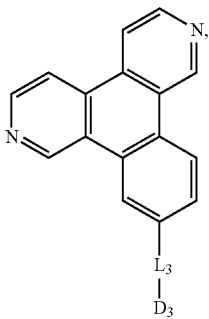
Compound 392
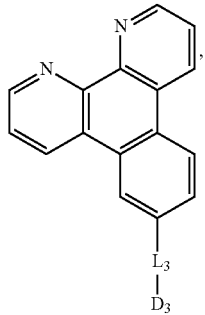
Compound 393
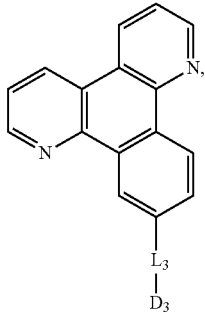
Compound 394
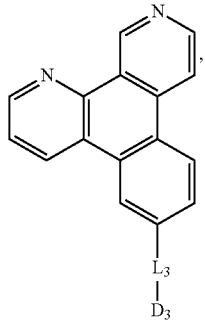
Compound 395
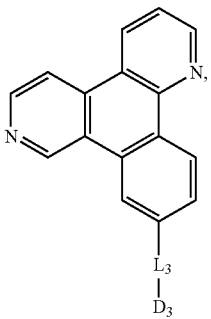
Compound 396
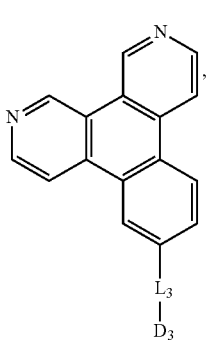

-continued
Compound 397
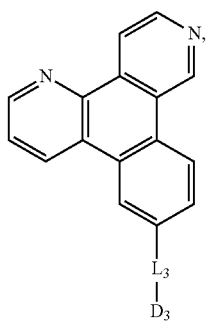
Compound 398
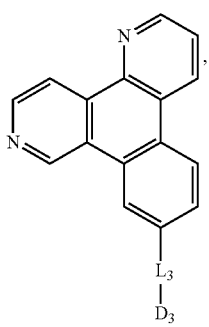
Compound 399
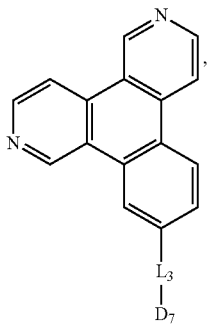
Compound 400
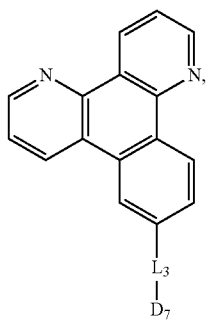
Compound 401
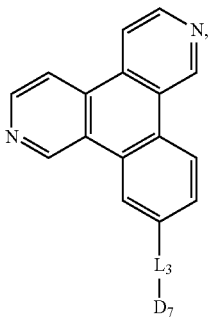
-continued
Compound 402
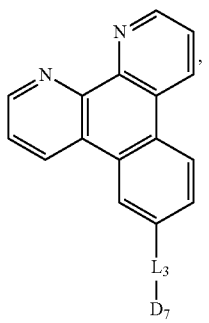
Compound 403
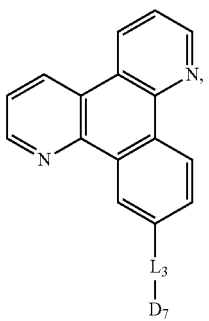
Compound 404
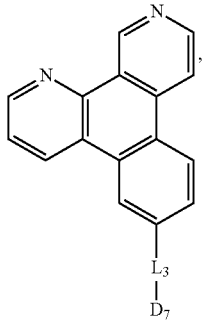
Compound 405
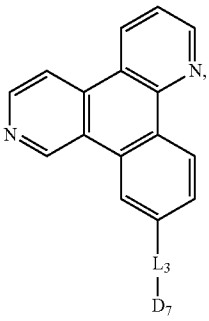
Compound 406
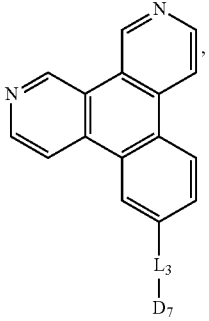

Compound 407
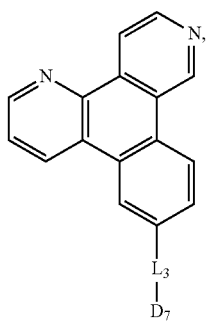
Compound 408
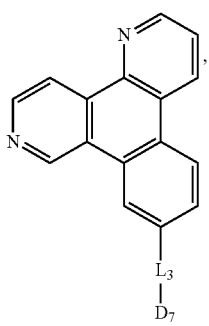
Compound 409
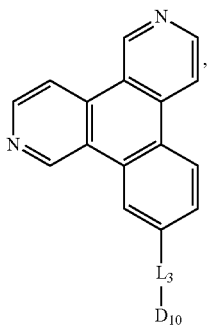
Compound 410
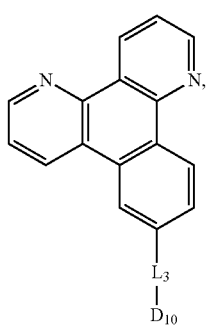
Compound 411
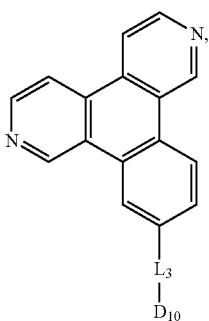
Compound 412
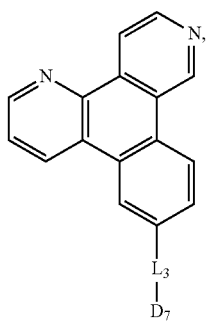
Compound 413
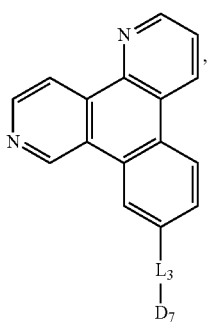
Compound 414
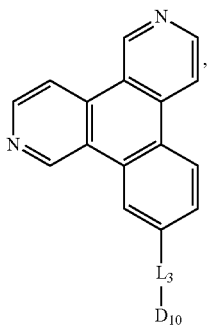
Compound 415
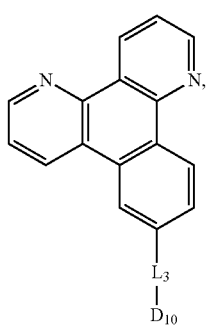
Compound 416
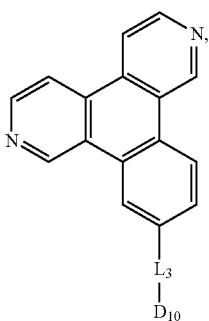

Compound 417

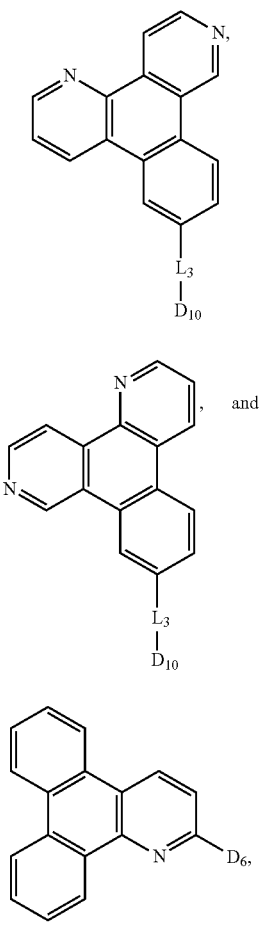

Compound 418

Compound 457

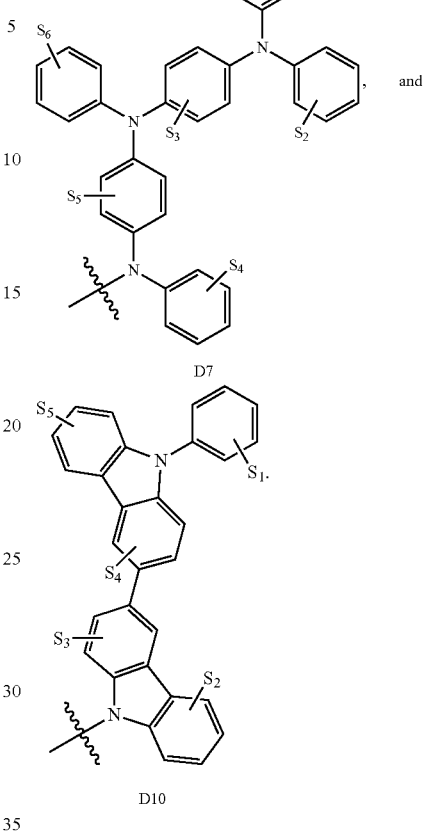

wherein D1, D3, D6, D7, D10 and D31 are

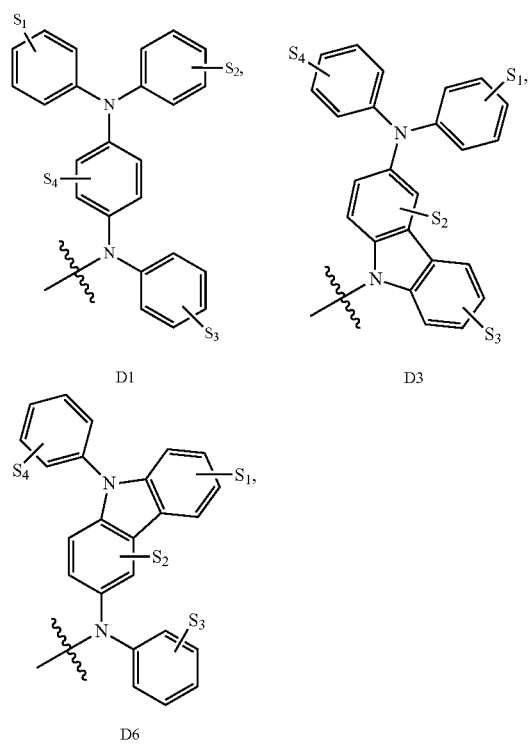

12. The first device of 11, wherein $S_1$ to $S_6$ and $A_1$-$A_2$ are H.

13. The first device of claim 7, wherein the first device emits a luminescent radiation at room temperature when a voltage is applied across the organic light emitting device; wherein the luminescent radiation comprises a delayed fluorescence process.

14. The first device of claim 7, wherein the emissive layer further comprises a first phosphorescent emitting material.

15. The first device of claim 14, wherein the emissive layer further comprises a second phosphorescent emitting material.

16. The first device of claim 7, wherein the emissive layer further comprises a host material.

17. The first device of claim 14, wherein the first device emits a white light at room temperature when a voltage is applied across the organic light emitting device.

18. The first device of claim 17, wherein the first emitting compound emits a blue light with a peak wavelength of about 400 nm to about 500 nm.

19. The first device of claim 17, wherein the first emitting compound emits a yellow light with a peak wavelength of about 530 nm to about 580 nm.

20. The first device of claim 7, wherein the first device comprises a second organic light emitting device; wherein the second organic light emitting device is stacked on the first organic light emitting device.

21. The first device of claim 7, wherein the first device is a consumer product.

22. The first device of claim 7, wherein the first device is an organic light-emitting device.

23. The first device of claim 7, wherein the first device is a lighting panel.

24. The first device of claim 7, wherein at least one of the R comprises a donor group with at least two electron-donating nitrogens.

25. A formulation comprising a compound according to claim 1.

* * * * *